US010046046B2

(12) United States Patent
Anderson et al.

(10) Patent No.: US 10,046,046 B2
(45) Date of Patent: Aug. 14, 2018

(54) AMINO SPHINGOGLYCOLIPID ANALOGUES

(71) Applicant: Victoria Link Limited, Wellington (NZ)

(72) Inventors: Regan James Anderson, Lower Hutt (NZ); Benjamin Jason Compton, Lower Hutt (NZ); Colin Malcolm Hayman, Lower Hutt (NZ); Ian Francis Hermans, Wellington (NZ); Karen Anne Johnston, Lower Hutt (NZ); Gavin Frank Painter, Lower Hutt (NZ)

(73) Assignee: Victoria Link Limited, Wellington (NZ)

( * ) Notice: Subject to any disclaimer, the term of this patent is extended or adjusted under 35 U.S.C. 154(b) by 0 days.

(21) Appl. No.: 15/316,124

(22) PCT Filed: Jun. 5, 2015

(86) PCT No.: PCT/NZ2015/050070
§ 371 (c)(1),
(2) Date: Dec. 2, 2016

(87) PCT Pub. No.: WO2015/187040
PCT Pub. Date: Dec. 10, 2015

(65) Prior Publication Data
US 2017/0119875 A1 May 4, 2017

(30) Foreign Application Priority Data
Jun. 5, 2014 (NZ) ....................... 625895

(51) Int. Cl.
| A61K 39/00 | (2006.01) |
| A61K 39/39 | (2006.01) |
| A61K 39/385 | (2006.01) |
| C07H 15/04 | (2006.01) |
| C07H 15/18 | (2006.01) |
| A61K 47/48 | (2006.01) |

(52) U.S. Cl.
CPC ........ *A61K 39/385* (2013.01); *A61K 39/0011* (2013.01); *A61K 39/39* (2013.01); *A61K 47/48092* (2013.01); *C07H 15/04* (2013.01); *C07H 15/18* (2013.01); *A61K 2039/55511* (2013.01); *A61K 2039/60* (2013.01)

(58) Field of Classification Search
CPC .. A61K 39/385; A61K 39/0011; A61K 39/39; A61K 47/48092; A61K 2039/60; A61K 2039/55511; C07H 15/04; C07H 15/18
USPC ........................................................ 514/23
See application file for complete search history.

(56) References Cited

U.S. PATENT DOCUMENTS 8,227,581 B2 * 7/2012 Savage .................. C07H 15/06
424/184.1

FOREIGN PATENT DOCUMENTS

| WO | 2004/094444 A1 | 11/2004 | |
| WO | WO 2004/094444 A1 * | 11/2004 | ............... C07H 7/00 |
| WO | 2007/118234 A2 | 10/2007 | |
| WO | WO2007/118234 A2 * | 10/2007 | ........... A61K 31/739 |
| WO | 2009/060086 A2 | 5/2009 | |
| WO | WO 2009/060086 A2 * | 5/2009 | ............. A61K 47/48 |
| WO | 2014/017928 A1 | 1/2014 | |
| WO | 2014/088432 A1 | 6/2014 | |
| WO | 2014/200363 A1 | 12/2014 | |

OTHER PUBLICATIONS

Zhou et al, Organic Letters, 2002, 4(8), 1267-1270.*
Alexander et al., "Development of High Potency Universal DR-Restricted Helper Epitopes by Modification of High Affinity DR-Blocking Peptides," *Immunity* 1(9):751-761, 1994.
Alexander et al., "(Acyloxy)alkyl Carbamates as Novel Bioreversible Prodrugs for Amines: Increased Permeation through Biological Membranes," *Journal of Medicinal Chemistry* 31(2):318-322, 1988.
Amblard et al., "Methods and Protocols of Modern Solid Phase Peptide Synthesis," *Molecular Biotechnology* 33(3):239-254, 2006.
Amsberry et al., "Amine Prodrugs Which Utilize Hydroxy Amide Lactonization. I. A Potential Redox-Sensitive Amide Prodrug," *Pharmaceutical Research* 8(3):323-330, 1991.
Amsberry et al., "Amine Prodrugs Which Utilize Hydroxy Amide Lactonization. II. A Potential Esterase-Sensitive Amide Prodrug," *Pharmaceutical Research* 8(4):455-461, 1991.
Anderson et al., "A self-adjuvanting vaccine induces cytotoxic T lymphocytes that suppress allergy," *Nature Chemical Biology* 10(11):943-949, 2014. (9 pages).
Atherton et al., "A Mild Procedure for Solid Phase Peptide Synthesis: Use of Fluorenylmethoxycarbonylamino-acids," *Journal of the Chemical Society, Chemical Communications* 0(13):537-539, 1978.
Atwell et al., "Relationships between Structure and Kinetics of Cyclization of 2-Aminoaryl Amides: Potential Prodrugs of Cyclization-Activated Aromatic Mustards," *Journal of Medicinal Chemistry* 37(3):371-380, 1994.
Baek et al., "The 3-Deoxy Analogue of α-GalCer: Disclosing the Role of the 4-Hydroxyl Group for CD1d-Mediated NKT Cell Activation," *ACS Medicinal Chemistry Letters* 2(7):544-548, 2011.
Banchet-Cadeddu et al., "The stimulating adventure of KRN 7000," *Organic & Biomolecular Chemistry*(9):3080-3104, 2011.
Bendelac et al., "The Biology of NKT Cells," *Annual Review of Immunology* 25:297-336, 2007.
Berinstein et al., "First-in-man application of a novel therapeutic cancer vaccine formulation with the capacity to induce multifunctional T cell responses in ovarian, breast and prostate cancer patients," *Journal of Translational Medicine* 10:156, 2012.

(Continued)

*Primary Examiner* — Ganapathy Krishnan
(74) *Attorney, Agent, or Firm* — Seed IP Law Group LLP

(57) ABSTRACT

The invention relates to amino sphingoglycolipid analogues and peptide derivatives thereof, compositions comprising these compounds and methods of treating or preventing diseases or conditions using such compounds, especially diseases or conditions relating to cancer, infection, atopic disorders, autoimmune disease or diabetes.

21 Claims, 3 Drawing Sheets

(56) References Cited

OTHER PUBLICATIONS

Bettinotti et al., "Stringent Allele/Epitope Requirements for MART-1/Melan A Immunodominance: Implications for Peptide-Based Immunotherapy," *The Journal of Immunology* 161(2):877-889, 1998.
Borg et al., "CD1d-lipid-antigen recognition by the semi-invariant NKT T-cell receptor," *Nature* 448(7149):44-49, 2007.
Brossart et al., "Identification of HLA-A2-Restricted T-Cell Epitopes Derived From the MUC1 Tumor Antigen for Broadly Applicable Vaccine Therapies," *Blood* 93(12):4309-4317, 1999.
Cai et al., "Towards a Fully Synthetic MUC1-Based Anticancer Vaccine: Efficient Conjugation of Glycopeptides with Mono-, Di-, and Tetravalent Lipopeptides Using Click Chemistry," *Chemistry—A European Journal* 17(23):6396-6406, 2011.
Campos et al., "Development of Thermal and Photochemical Strategies for Thiol-Ene Click Polymer Functionalization," *Macromolecules* 41(19):7063-7070, 2008.
Carpino et al., "Reductive Lactonization of Strategically Methylated Quinone Propionic Acid Esters and Amides," *The Journal of Organic Chemistry* 54(14):3303-3310, 1989.
Chang, "Efficient amplification of melanoma-specific CD8$^+$T cells using artificial antigen presenting complex," *Experimental and Molecular Medicine* 38(6):591-598, 2006.
Chaudhary et al., "Using mixed anhydrides from amino acids and isobutyl chloroformate in N-acylations: a case study on the elucidation of mechanism of urethane formation and starting amino acid liberation using carbon dioxide as the probe," *Tetrahedron Letters* 44(29):5543-5546, 2003.
Chen et al., "Efficient Synthesis of a-C-Galactosyl Ceramide Immunostimulants: Use of Ethylene-Promoted Olefin Cross-Metathesis," *Organic Letters* 6(22):4077-4080, 2004.
Choi et al., "α-Acylamino Radical Cyclizations: Application to the Synthesis of a Tetracyclic Substructure of Gelsemine," *The Journal of Organic Chemistry* 54(2):279-290, 1989.
Ciesielski et al., "Therapeutic Effect of a T Helper Cell Supported CTL Response Induced by a Survivin Peptide Vaccine against Murine Cerebral Glioma," *Cancer Immunology, Immunotherapy* 57(12):1827-1835, 2008.
Davidson et al., "Effect of TA-CIN (HPV 16 L2E6E7) booster immunisation in vulval intraepithelial neoplasia patients previously vaccinated with TA-HPV (vaccinia virus encoding HPV 16/18 E6E7)," *Vaccine* 22(21-22):2722-2729, 2004.
De Araújo et al., "Diels-Alder Ligation and Surface Immobilization of Proteins," *Angewandte Chemie International Edition* 45(2):296-301, 2006.
Deng et al., "Impact of sugar stereochemistry on natural killer T cell stimulation by bacterial glycolipids," *Organic & Biomolecular Chemistry* 9(22):7659-7662, 2011.
Dere et al., "The First Synthesis of a Thioglycoside Analogue of the Immunostimulant KRN7000," *Organic Letters* 10(20):4641-4644, 2008.
Dirksen et al., "Nucleophilic Catalysis of Oxime Ligation," *Angewandte Chemie International Edition* 45(45):7581-7584, 2006.
Dondoni, "The Emergence of Thiol-Ene Coupling as a Click Process for Materials and Bioorganic Chemistry," *Angewandte Chemie International Edition* 47(47):8995-8997, 2008.
Du et al., "Efficient, one-pot syntheses of biologically active α-linked glycolipids," *Chemical Communications* 0(23):2336-2338, 2007.
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," *Bioconjugate Chemistry* 13(4):855-869, 2002.
Ebensen et al., "A Pegylated Derivative of α-Galactosylceramide Exhibits Improved Biological Properties," *The Journal of Immunology* 179(4):2065-2073, 2007.
Fang et al., "Convergent Chemical Synthesis of Proteins by Ligation of Peptide Hydrazides," *Angewandte Chemie International Edition* 51(41):10347-10350, 2012.
Fields et al., "Solid phase peptide synthesis utilizing 9-fluorenylmethoxycarbonyl amino acids," *International Journal of Peptide & Protein Research* 35(3):161-214, 1990.
Friedrichs et al., "Survivin-derived peptide epitopes and their role for induction of antitumor immunity in hematological malignancies," *Leukemia & Lymphoma* 47(6):978-985, 2006.
Fujii et al., "Activation of Natural Killer T Cells by α-Galactosylceramide Rapidly Induces the Full Maturation of Dendritic Cells In Vivo and Thereby Acts as an Adjuvant for Combined CD4 and CD8 T Cell Immunity to a Coadministered Protein," *The Journal of Experimental Medicine* 198(2):267-279, 2003.
Wang et al., "Synthesis of a Novel Esterase-Sensitive Cyclic Prodrug System for Peptides That Utilizes a "Trimethyl Lock"-Facilitated Lactonization Reaction," *The Journal of Organic Chemistry* 62(5):1363-1367, 1997.
Geoghegan et al., "Site-Directed Conjugation of Nonpeptide Groups to Peptides and Proteins via Periodate Oxidation of a 2-Amino Alcohol. Application to Modification at N-Terminal Serine," *Bioconjugate Chemistry* 3(2):138-146, 1992.
Giaccone et al., "A Phase I Study of the Natural Killer T-Cell Ligand α-Galactosylceramide (KRN7000) in Patients with Solid Tumors," *Clinical Cancer Research* 8(12):3702-3709, 2002.
Greenwald et al., "Drug Delivery Systems Based on Trimethyl Lock Lactonization: Poly(ethylene glycol) Prodrugs of Amino-Containing Compounds," *Journal of Medicinal Chemistry* 43(3):475-487, 2000.
Greenwald et al., "Drug Delivery Systems Employing 1,4- or 1,6-Elimination: Poly(ethylene glycol) Prodrugs of Amine-Containing Compounds," *Journal of Medicinal Chemistry* 42(18):3657-3667, 1999.
Hackenberger et al., "Chemoselective Ligation and Modification Strategies for Peptides and Proteins," *Angewandte Chemie International Edition* 47(52):10030-10074, 2008.
Hatakeyama et al., "Iron-Catalyzed Negishi Coupling Toward an Effective Olefin Synthesis," *Organic Letters* 11(20):4496-4499, 2009.
Hermans et al., "NKT Cells Enhance CD4$^+$and CD8$^+$T Cell Responses to Soluble Antigen In Vivo Cells through Direct Interaction with Dendritic Cells," *The Journal of Immunology* 171(10):5140-5147, 2003.
Hong et al., "The natural killer T-cell ligand α-galactosylceramide prevents autoimmune diabetes in non-obese diabetic mice," *Nature Medicine* 7(9):1052-1056, 2001.
Howell et al., "Approaches to the preparation of sphinganines," *Tetrahedron* 60(50):11327-11347, 2004.
Huarte et al., "Enhancing Immunogenicity of a CTL Epitope from Carcinoembryonic Antigen by Selective Amino Acid Replacements," *Clinical Cancer Research* 8(7):2336-2344, 2002.
Hudlicky et al., "Cyclopentene Annulation via Intramolecular Addition of Diazo Ketones to 1,3-Dienes. Applications to the Synthesis of Cyclopentanoid Terpenes," *The Journal of Organic Chemistry* 45(25):5020-5027, 1980.
Iha et al., "Complex, Degradable Polyester Materials via Ketoxime Ether-Based Functionalization: Amphiphilic, Multifunctional Graft Copolymers and Their Resulting Solution-State Aggregates," *Journal of Polymer Science Part A: Polymer Chemistry* 48(16):3553-3563, 2010.
Isidro-Llobet et al., "Amino Acid-Protecting Groups," *Chemical Reviews* 109(6):2455-2504, 2009.
Jäger et al., "Peptide-Specific CD8+ T-Cell Evolution In Vivo: Response to Peptide Vaccination with Melan-A/MART-1," *International Journal of Cancer* 98(3):376-388, 2002.
Jervis et al., "Synthesis of a Versatile Building Block for the Preparation of 6-N-Derivatized α-Galactosyl Ceramides: Rapid Access to Biologically Active Glycolipids," *The Journal of Organic Chemistry* 76(1):320-323, 2011.
Karbach et al., "Tumor-reactive CD8$^+$T-cell responses after vaccination with NT-ESO-1 peptide, CpG 7909 and Montanide® ISA-51: association with survival," *International Journal of Cancer* 126(4):909-919, 2010.

(56) References Cited

OTHER PUBLICATIONS

Kawano et al., "CD1d-Restricted and TCR-Mediated Activation of $V_\alpha 14$ NKT Cells by Glycosylceramides," *Science* 278(5343):1626-1629, 1997.
Kinjo et al., "Invariant natural killer T cells recognize glycolipids from pathogenic Gram-positive bacteria," *Nature Immunology* 12(10):966-975, 2011.
Kiick et al., "Incorporation of azides into recombinant proteins for chemoselective modification by the Staudinger ligation," *Proceedings of the National Academy of Sciences of the United States of America* 99(1):19-24, 2002.
Kreiter et al., "Mutant MHC class II epitopes drive therapeutic immune responses to cancer," *Nature* 520(7549):692-696, 2015.
Lee et al., "Novel synthesis of a-galactosyl-ceramides and confirmation of their powerful NKT cell agonist activity," *Carbohydrate Research* 341(17):2785-2798, 2006.
Lennerz et al., "The response of autologous T cells to a human melanoma is dominated by mutated neoantigens," *Proceedings of the National Academy of Sciences of the United States of America* 102(44):16013-16018, 2005.
Levy et al., "A melanoma multiepitope polypeptide induces specific CD8+ T-cell response," *Cellular Immunology* 250(1-2):24-30, 2008.
Li et al., "Design of a potent CD1d-binding NKT cell ligand as a vaccine adjuvant," *Proceedings of the National Academy of Sciences of the United States of America* 107(29):13010-13015, 2010.
Li et al., "The Vα14 invariant natural killer T cell TCR forces microbial glycolipids and CD1d into a conserved binding mode," *The Journal of Experimental Medicine* 207(11):2383-2393, 2010.
Li et al., "Identification of a WT1 protein-derived peptide, $WT1_{187}$, as a HLA-A*0206-restricted, WT1-specific CTL epitope," *Microbiology and Immunology* 52(11):551-558, 2008.
Liu et al., "Orthogonal Ligation of Unprotected Peptide Segments through Pseudoproline Formation for the Synthesis of HIV-1 Protease Analogs," *Journal of the American Chemical Society* 118(2):307-312, 1996.
Liu et al., "Chemical Ligation Approach to Form a Peptide Bond between Unprotected Peptide Segments. Concept and Model Study," *Journal of the American Chemical Society* 116(10):4149-4153, 1994.
Liu et al., "Synthesis of diglycosylceramides and evaluation of their iNKT cell stimulatory properties," *Bioorganic & Medicinal Chemistry Letters* 18(10):3052-3055, 2008.
Lu et al., "Induction of the Epstein-Barr Virus Latent Membrane Protein 2 Antigen-specific Cytotoxic T Lymphocytes Using Human Leukocyte Antigen Tetramer-based Artificial Antigen-presenting Cells," *Acta Biochimica et Biophysica Sinica* 38(3):157-163, 2006.
Majireck et al., "A Study of the Scope and Regioselectivity of the Ruthenium-Catalyzed [3+2]-Cycloaddition of Azides with Internal Alkynes," *The Journal of Organic Chemistry* 71(22):8680-8683, 2006.
Morita et al., "Structure-Activity Relationship of α-Galactosylceramides against B16-Bearing Mice," *Journal of Medicinal Chemistry* 38(12):2176-2187, 1995.
Motoki et al., "Immunostimulatory and Antitumor Activities of Monoglycosylceramides Having Various Sugar Moieties," *Biological and Pharmaceutical Bulletin* 18(11):1487-1491, 1995.
Nicolaou et al., "Phosphate Prodrugs for Amines Utilizing a Fast Intramolecular Hydroxy Amide Lactonization," *The Journal of Organic Chemistry* 61(24):8636-8641, 1996.
Noppen et al., "Naturally Processed and Concealed HLA-A2.1-Restricted Epitopes from Tumor-Associated Antigen Tyrosinase-related Protein-2," *International Journal of Cancer* 87(2):241-246, 2000.
O'Reilly et al., "Synthesis of α-S-Glycosphingolipids Based on Uronic Acids," *Organic Letters* 13(19):5168-5171, 2011.
Parekh et al., "Glycolipid antigen induces long-term natural killer T cell anergy in mice," *The Journal of Clinical Investigation* 115(9):2572-2583, 2005.
Park et al., "Synthesis of all stereoisomers of KRN7000, the CD1d-binding NKT cell ligand," *Bioorganic & Medicinal Chemistry Letters* 18(14):3906-3909, 2008.
Pauwels et al., "Synthesis of 6"-triazole-substituted α-GalCer analogues as potent iNKT cell stimulating ligands," *Bioorganic & Medicinal Chemistry* 20(24):7149-7154, 2012.
Petersen et al., "Potent anti-tumor responses to immunization with dendritic cells loaded with tumor tissue and an NKT cell ligand," *Immunology and Cell Biology* 88(5):596-604, 2010.
Plettenburg et al., "Synthesis of α-Galactosyl Ceramide, a Potent Immunostimulatory Agent," *The Journal of Organic Chemistry* 67(13):4559-4564, 2002.
Presolski et al., "Tailored Ligand Acceleration of the Cu-Catalyzed Azide-Alkyne Cycloaddition Reaction: Practical and Mechanistic Implications," *Journal of the American Chemical Society* 132(41):14570-14576, 2010. (15 pages).
Raju et al., "Synthesis and evaluation of 3"- and 4"-deoxy and -fluoro analogs of the immunostimulatory glycolipid, KRN7000," *Bioorganic & Medicinal Chemistry Letters* 19(15):4122-4125, 2009.
Rostovtsev et al., "A Stepwise Huisgen Cycloaddition Process: Copper(I)-Catalyzed Regioselective "Ligation" of Azides and Terminal Alkynes," *Angewandte Chemie* 114(14):2708-2711, 2002.
Saxon et al., "Cell Surface Engineering by a Modified Staudinger Reaction," *Science* 287(5460):2007-2010, 2000.
Schmitz et al., "Generation of Survivin-specific $CD8^+T$ Effector Cells by Dendritic Cells Pulsed with Protein or Selected Peptides," *Cancer Research* 60(17):4845-4849, 2000. (6 pages).
Semmling et al., "Alternative cross-priming through CCL17-CCR4-mediated attraction of CTLs toward NKT cell-licensed DCs," *Nature Immunology* 11(4):313-320, 2010.
Silk et al., "Utilizing the adjuvant properties of CD1d-dependent NKT cells in T cell-mediated immunotherapy," *The Journal of Clinical Investigation* 114(12):1800-1811, 2004.
Soellner et al., "Staudinger Ligation of Peptides at Non-Glycyl Residues," *The Journal of Organic Chemistry* 71(26):9824-9830, 2006.
Speiser et al., "Molecularly defined vaccines for cancer immunotherapy, and protective T cell immunity," *Seminars in Immunology* 22(3):144-154, 2010.
Tam et al., "Water-Soluble Phosphinothiols for Traceless Staudinger Ligation and Integration with Expressed Protein Ligation," *Journal of the American Chemical Society* 129(37):11421-11430, 2007.
Trappeniers et al., "Synthesis and in vitro Evaluation of α-GalCer Epimers," *ChemMedChem* 3(7):1061-1070, 2008.
Trappeniers et al., "6'-Derivatised α-GalCer Analogues Capable of Inducing Strong CD1d-Mediated Th1-Biased NKT Cell Responses in Mice," *Journal of the American Chemical Society* 130(49):16468-16469, 2008.
Tupin et al., "CD1d-dependent Activation of NKT Cells Aggravates Atherosclerosis," *The Journal of Experimental Medicine* 199(3):417-422, 2004.
Veerapen et al., "Synthesis and biological activity of α-galactosyl ceramide KRN7000 and galactosyl (a1→2) galactosyl ceramide," *Bioorganic & Medicinal Chemistry Letters* 19(15):4288-4291, 2009.
Widdison et al., "Semisynthetic Maytansine Analogues for the Targeted Treatment of Cancer," *Journal of Medicinal Chemistry* 49(14):4392-4408, 2006.
Wingender et al., "Invariant NKT cells are required for airway inflammation induced by environmental antigens," *The Journal of Experimental Medicine* 208(6):1151-1162, 2011.
Wu et al., "Avidity of CD1d-ligand-receptor ternary complex contributes to T-helper 1 (Th1) polarization and anticancer efficacy," *Proceedings of the National Academy of Sciences of the United States of America* 108(42):17275-17280, 2011.
Zeng et al., "Activation of natural killer T cells in NZB/W mice induces Th1-type immune responses exacerbating lupus," *The Journal of Clinical Investigation* 112(8):1211-1222, 2003.
Zhang et al., "Ruthenium-Catalyzed Cycloaddition of Alkynes and Organic Azides," *Journal of the American Chemical Society* 127(46):15998-15999, 2005.

(56) References Cited

OTHER PUBLICATIONS

Zhou et al., "Synthesis and NKT Cell Stimulating Properties of Fluorophore- and Biotin-Appended 6"-Amino-6"-deoxy-galactosylceramides," *Organic Letters* 4(8):1267-1270, 2002.

* cited by examiner

SEQUENCE LISTING

```
<160> NUMBER OF SEQ ID NOS: 415

<210> SEQ ID NO 1
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 1

Ala Met Leu Gly Thr His Thr Met Glu Val
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 2

Met Leu Gly Thr His Thr Met Glu Val
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 3

Glu Ala Ala Gly Ile Gly Ile Leu Thr Val
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 4

Ala Ala Gly Ile Gly Ile Leu Thr Val
1               5

<210> SEQ ID NO 5
<211> LENGTH: 18
<212> TYPE: PRT
<213> ORGANISM: Artificial Sequence
<220> FEATURE:
<223> OTHER INFORMATION: Synthetic Immunogen

<400> SEQUENCE: 5

Ala Ala Asp His Arg Gln Leu Gln Leu Ser Ile Ser Ser Cys Leu Gln
1               5                   10                  15

Gln Leu
```

<210> SEQ ID NO 6
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 6

```
Ala Ala Gly Ile Gly Ile Leu Thr Val Ile Leu Gly Val Leu
1               5                   10
```

<210> SEQ ID NO 7
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 7

```
Ala Ala Arg Ala Val Phe Leu Ala Leu
1               5
```

<210> SEQ ID NO 8
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 8

```
Ala Cys Asp Pro His Ser Gly His Phe Val
1               5                   10
```

<210> SEQ ID NO 9
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 9

```
Ala Cys Tyr Glu Phe Leu Trp Gly Pro Arg Ala Leu Val Glu Thr Ser
1               5                   10                  15
```

<210> SEQ ID NO 10
<211> LENGTH: 17
<212> TYPE: PRT
<213> ORGANISM: Artificial Sequence
<220> FEATURE:
<223> OTHER INFORMATION: Synthetic Immunogen

<400> SEQUENCE: 10

```
Ala Asp His Arg Gln Leu Gln Leu Ser Ile Ser Ser Cys Leu Gln Gln
1               5                   10                  15

Leu
```

<210> SEQ ID NO 11
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 11

```
Ala Glu Glu Ala Ala Gly Ile Gly Ile Leu Thr
```

```
1               5                  10

<210> SEQ ID NO 12
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 12

Ala Glu Glu Ala Ala Gly Ile Gly Ile Leu
1               5                  10

<210> SEQ ID NO 13
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 13

Ala Glu Leu Val His Phe Leu Leu Leu
1               5

<210> SEQ ID NO 14
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 14

Ala Glu Leu Val His Phe Leu Leu Leu Lys Tyr Arg Ala Arg
1               5                  10

<210> SEQ ID NO 15
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 15

Ala Glu Pro Ile Asn Ile Gln Thr Trp
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 16

Ala Phe Leu Pro Trp His Arg Leu Phe
1               5

<210> SEQ ID NO 17
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 17

Ala Gly Ala Thr Gly Gly Arg Gly Pro Arg Gly Ala Gly Ala
1               5                  10
```

-continued

```
<210> SEQ ID NO 18
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 18

Ala Leu Cys Arg Trp Gly Leu Leu Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 19

Ala Leu Asp Val Tyr Asn Gly Leu Leu
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 20

Ala Leu Phe Asp Ile Glu Ser Lys Val
1               5

<210> SEQ ID NO 21
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 21

Ala Leu Gly Gly His Pro Leu Leu Gly Val
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 22

Ala Leu Ile His His Asn Thr His Leu
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 23

Ala Leu Lys Asp Val Glu Glu Arg Val
1               5
```

```
<210> SEQ ID NO 24
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 24

Ala Leu Leu Ala Val Gly Ala Thr Lys
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 25

Ala Leu Leu Glu Ile Ala Ser Cys Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 26

Ala Leu Asn Phe Pro Gly Ser Gln Lys
1               5

<210> SEQ ID NO 27
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 27

Ala Leu Pro Tyr Trp Asn Phe Ala Thr Gly
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 28

Ala Leu Ser Val Met Gly Val Tyr Val
1               5

<210> SEQ ID NO 29
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 29

Ala Leu Trp Pro Trp Leu Leu Met Ala Thr
1               5                   10
```

```
<210> SEQ ID NO 30
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 30

Ala Leu Trp Pro Trp Leu Leu Met Ala
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 31

Ala Leu Tyr Val Asp Ser Leu Phe Phe Leu
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 32

Ala Asn Asp Pro Ile Phe Val Val Leu
1               5

<210> SEQ ID NO 33
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 33

Ala Pro Pro Ala Tyr Glu Lys Leu Ser Ala Glu Gln
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 34

Ala Pro Arg Gly Pro His Gly Gly Ala Ala Ser Gly Leu
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 35

Ala Pro Arg Gly Val Arg Met Ala Val
1               5

<210> SEQ ID NO 36
```

<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 36

Ala Arg Gly Pro Glu Ser Arg Leu Leu
1               5

<210> SEQ ID NO 37
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 37

Ala Ser Gly Pro Gly Gly Gly Ala Pro Arg
1               5                   10

<210> SEQ ID NO 38
<211> LENGTH: 17
<212> TYPE: PRT
<213> ORGANISM: Artificial Sequence
<220> FEATURE:
<223> OTHER INFORMATION: Synthetic Immunogen

<400> SEQUENCE: 38

Ala Thr Gly Phe Lys Gln Ser Ser Lys Ala Leu Gln Arg Pro Val Ala
1               5                   10                  15

Ser

<210> SEQ ID NO 39
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 39

Ala Val Cys Pro Trp Thr Trp Leu Arg
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 40

Ala Trp Ile Ser Lys Pro Pro Gly Val
1               5

<210> SEQ ID NO 41
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 41

Ala Tyr Val Cys Gly Ile Gln Asn Ser Val Ser Ala Asn Arg Ser
1               5                   10                  15

```
<210> SEQ ID NO 42
<211> LENGTH: 17
<212> TYPE: PRT
<213> ORGANISM: Artificial Sequence
<220> FEATURE:
<223> OTHER INFORMATION: Synthetic Immunogen

<400> SEQUENCE: 42

Cys Ala Thr Trp Lys Val Ile Cys Lys Ser Cys Ile Ser Gln Thr Pro
1               5                   10                  15

Gly

<210> SEQ ID NO 43
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 43

Cys Glu Phe His Ala Cys Trp Pro Ala Phe Thr Val Leu Gly Glu
1               5                   10                  15

<210> SEQ ID NO 44
<211> LENGTH: 22
<212> TYPE: PRT
<213> ORGANISM: Artificial Sequence
<220> FEATURE:
<223> OTHER INFORMATION: Synthetic Immunogen

<400> SEQUENCE: 44

Cys Leu Ser Arg Arg Pro Trp Lys Arg Ser Trp Ser Ala Gly Ser Cys
1               5                   10                  15

Pro Gly Met Pro His Leu
            20

<210> SEQ ID NO 45
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 45

Cys Met Thr Trp Asn Gln Met Asn Leu
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 46

Cys Gln Trp Gly Arg Leu Trp Gln Leu
1               5

<210> SEQ ID NO 47
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 47
```

Cys Thr Ala Cys Arg Trp Lys Lys Ala Cys Gln Arg
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 48

Asp Pro Ala Arg Tyr Glu Phe Leu Trp
1               5

<210> SEQ ID NO 49
<211> LENGTH: 25
<212> TYPE: PRT
<213> ORGANISM: Artificial Sequence
<220> FEATURE:
<223> OTHER INFORMATION: Synthetic Immunogen

<400> SEQUENCE: 49

Asp Thr Gly Phe Tyr Thr Leu His Val Ile Lys Ser Asp Leu Val Asn
1               5                   10                  15

Glu Glu Ala Thr Gly Gln Phe Arg Val
            20                  25

<210> SEQ ID NO 50
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 50

Asp Val Thr Phe Asn Ile Ile Cys Lys Lys Cys Gly
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 51

Glu Ala Ala Gly Ile Gly Ile Leu Thr Val
1               5                   10

<210> SEQ ID NO 52
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 52

Glu Ala Asp Pro Thr Gly His Ser Tyr
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic Immunogen

```
<400> SEQUENCE: 53

Glu Ala Phe Ile Gln Pro Ile Thr Arg
1               5

<210> SEQ ID NO 54
<211> LENGTH: 29
<212> TYPE: PRT
<213> ORGANISM: Artificial Sequence
<220> FEATURE:
<223> OTHER INFORMATION: Synthetic Immunogen

<400> SEQUENCE: 54

Glu Asp Leu Thr Val Lys Ile Gly Asp Phe Gly Leu Ala Thr Glu Lys
1               5                   10                  15

Ser Arg Trp Ser Gly Ser His Gln Phe Glu Gln Leu Ser
            20                  25

<210> SEQ ID NO 55
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 55

Glu Glu Ala Ala Gly Ile Gly Ile Leu Thr Val Ile
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 56

Glu Glu Lys Leu Ile Val Val Leu Phe
1               5

<210> SEQ ID NO 57
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 57

Glu Phe Tyr Leu Ala Met Pro Phe Ala Thr Pro Met
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 58

Glu Gly Asp Cys Ala Pro Glu Glu Lys
1               5

<210> SEQ ID NO 59
<211> LENGTH: 13
<212> TYPE: PRT
<213> ORGANISM: Artificial Sequence
<220> FEATURE:
```

-continued

<223> OTHER INFORMATION: Synthetic Immunogen

<400> SEQUENCE: 59

Glu Ile Ile Tyr Pro Asn Ala Ser Leu Leu Ile Gln Asn
1               5                   10

<210> SEQ ID NO 60
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 60

Glu Lys Ile Gln Lys Ala Phe Asp Asp Ile Ala Lys Tyr Phe Ser Lys
1               5                   10                  15

<210> SEQ ID NO 61
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 61

Glu Leu Thr Leu Gly Glu Phe Leu Lys Leu
1               5                   10

<210> SEQ ID NO 62
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 62

Glu Leu Val Arg Arg Ile Leu Ser Arg
1               5

<210> SEQ ID NO 63
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 63

Glu Ser Arg Leu Leu Glu Phe Tyr Leu Ala Met Pro Phe
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 64

Glu Thr Val Ser Glu Gln Ser Asn Val
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic Immunogen

```
<400> SEQUENCE: 65

Glu Val Asp Pro Ala Ser Asn Thr Tyr
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 66

Glu Val Asp Pro Ile Gly His Leu Tyr
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 67

Glu Val Asp Pro Ile Gly His Val Tyr
1               5

<210> SEQ ID NO 68
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 68

Glu Val Ile Ser Cys Lys Leu Ile Lys Arg
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 69

Glu Val Tyr Asp Gly Arg Glu His Ser Ala
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 70

Glu Tyr Leu Gln Leu Val Phe Gly Ile
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic Immunogen
```

```
<400> SEQUENCE: 71

Glu Tyr Leu Ser Leu Ser Asp Lys Ile
1               5

<210> SEQ ID NO 72
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 72

Glu Tyr Ser Lys Glu Cys Leu Lys Glu Phe
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 73

Glu Tyr Val Ile Lys Val Ser Ala Arg Val Arg Phe
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 74

Phe Ile Ala Ser Asn Gly Val Lys Leu Val
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 75

Phe Ile Asn Asp Glu Ile Phe Val Glu Leu
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 76

Phe Leu Asp Glu Phe Met Glu Gly Val
1               5

<210> SEQ ID NO 77
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 77
```

```
Phe Leu Glu Gly Asn Glu Val Gly Lys Thr Tyr
1               5                   10

<210> SEQ ID NO 78
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 78

Phe Leu Phe Leu Leu Phe Phe Trp Leu
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 79

Phe Leu Ile Ile Trp Gln Asn Thr Met
1               5

<210> SEQ ID NO 80
<211> LENGTH: 21
<212> TYPE: PRT
<213> ORGANISM: Artificial Sequence
<220> FEATURE:
<223> OTHER INFORMATION: Synthetic Immunogen

<400> SEQUENCE: 80

Phe Leu Leu His His Ala Phe Val Asp Ser Ile Phe Glu Gln Trp Leu
1               5                   10                  15

Gln Arg His Arg Pro
            20

<210> SEQ ID NO 81
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 81

Phe Leu Leu Leu Lys Tyr Arg Ala Arg Glu Pro Val Thr Lys Ala Glu
1               5                   10                  15

<210> SEQ ID NO 82
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 82

Phe Leu Thr Pro Lys Lys Leu Gln Cys Val
1               5                   10

<210> SEQ ID NO 83
<211> LENGTH: 9
<212> TYPE: PRT
<213> ORGANISM: Artificial Sequence
<220> FEATURE:
<223> OTHER INFORMATION: Synthetic Immunogen
```

<400> SEQUENCE: 83

Phe Leu Trp Gly Pro Arg Ala Leu Val
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 84

Phe Met Asn Lys Phe Ile Tyr Glu Ile
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 85

Phe Met Val Glu Asp Glu Thr Val Leu
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 86

Phe Pro Ser Asp Ser Trp Cys Tyr Phe
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 87

Phe Arg Ser Gly Leu Asp Ser Tyr Val
1               5

<210> SEQ ID NO 88
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 88

Phe Ser Trp Ala Met Asp Leu Asp Pro Lys Gly Ala
1               5                   10

<210> SEQ ID NO 89
<211> LENGTH: 38
<212> TYPE: PRT
<213> ORGANISM: Artificial Sequence
<220> FEATURE:
<223> OTHER INFORMATION: Synthetic Immunogen

```
<400> SEQUENCE: 89

Gly Ala Arg Gly Pro Glu Ser Arg Leu Leu Glu Phe Tyr Leu Ala Met
1               5                   10                  15

Pro Phe Ala Thr Pro Met Glu Ala Glu Leu Ala Arg Arg Ser Leu Ala
                20                  25                  30

Gln Asp Ala Pro Pro Leu
            35

<210> SEQ ID NO 90
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 90

Gly Asp Asn Gln Ile Met Pro Lys Ala Gly Leu Leu Ile Ile Val
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 91

Gly Glu Leu Ile Gly Ile Leu Asn Ala Ala Lys Val Pro Ala Asp
1               5                   10                  15

<210> SEQ ID NO 92
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 92

Gly Phe Lys Gln Ser Ser Lys Ala Leu
1               5

<210> SEQ ID NO 93
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 93

Gly Leu Ala Ser Phe Lys Ser Phe Leu Lys
1               5                   10

<210> SEQ ID NO 94
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 94

Gly Leu Cys Thr Leu Val Ala Met Leu
1               5

<210> SEQ ID NO 95
<211> LENGTH: 9
```

```
<212> TYPE: PRT
<213> ORGANISM: Artificial Sequence
<220> FEATURE:
<223> OTHER INFORMATION: Synthetic Immunogen

<400> SEQUENCE: 95

Gly Leu Pro Pro Asp Val Gln Arg Val
1               5

<210> SEQ ID NO 96
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 96

Gly Leu Tyr Asp Gly Met Glu His Leu Leu
1               5                   10

<210> SEQ ID NO 97
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 97

Gly Arg Ala Met Leu Gly Thr His Thr Met Glu Val Thr Val Tyr
1               5                   10                  15

<210> SEQ ID NO 98
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 98

Gly Val Ala Leu Gln Thr Met Lys Gln
1               5

<210> SEQ ID NO 99
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 99

Gly Val Gly Ser Pro Tyr Val Ser Arg Leu Leu Gly Ile Cys Leu
1               5                   10                  15

<210> SEQ ID NO 100
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 100

Ala Lys Phe Val Ala Ala Trp Thr Leu Lys Ala Ala Ala
1               5                   10

<210> SEQ ID NO 101
<211> LENGTH: 19
<212> TYPE: PRT
```

```
<213> ORGANISM: Artificial Sequence
<220> FEATURE:
<223> OTHER INFORMATION: Synthetic Immunogen

<400> SEQUENCE: 101

Gly Val Leu Leu Lys Glu Phe Thr Val Ser Gly Asn Ile Leu Thr Ile
1               5                   10                  15

Arg Leu Thr

<210> SEQ ID NO 102
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 102

Gly Val Leu Val Gly Val Ala Leu Ile
1               5

<210> SEQ ID NO 103
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 103

Gly Val Tyr Asp Gly Arg Glu His Thr Val
1               5                   10

<210> SEQ ID NO 104
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 104

His Leu Phe Gly Tyr Ser Trp Tyr Lys
1               5

<210> SEQ ID NO 105
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 105

His Leu Ile Arg Val Glu Gly Asn Leu Arg Val Glu
1               5                   10

<210> SEQ ID NO 106
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 106

His Leu Ser Thr Ala Phe Ala Arg Val
1               5

<210> SEQ ID NO 107
<211> LENGTH: 9
```

```
<212> TYPE: PRT
<213> ORGANISM: Artificial Sequence
<220> FEATURE:
<223> OTHER INFORMATION: Synthetic Immunogen

<400> SEQUENCE: 107

His Leu Tyr Gln Gly Cys Gln Val Val
1               5

<210> SEQ ID NO 108
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 108

His Gln Gln Tyr Phe Tyr Lys Ile Pro Ile Leu Val Ile Asn Lys
1               5                   10                  15

<210> SEQ ID NO 109
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 109

His Thr Met Glu Val Thr Val Tyr His Arg
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 110

Ile Ala Leu Asn Phe Pro Gly Ser Gln Lys
1               5                   10

<210> SEQ ID NO 111
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 111

Ile Gly Arg Ile Ala Glu Cys Ile Leu Gly Met Asn Pro Ser Arg
1               5                   10                  15

<210> SEQ ID NO 112
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 112

Ile Ile Ser Ala Val Val Gly Ile Leu
1               5

<210> SEQ ID NO 113
<211> LENGTH: 9
<212> TYPE: PRT
```

```
<213> ORGANISM: Artificial Sequence
<220> FEATURE:
<223> OTHER INFORMATION: Synthetic Immunogen

<400> SEQUENCE: 113

Ile Leu Ala Lys Phe Leu His Trp Leu
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 114

Ile Leu Asp Ser Ser Glu Glu Asp Lys
1               5

<210> SEQ ID NO 115
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 115

Ile Leu Asp Thr Ala Gly Arg Glu Glu Tyr
1               5                   10

<210> SEQ ID NO 116
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 116

Ile Leu His Asn Gly Ala Tyr Ser Leu
1               5

<210> SEQ ID NO 117
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 117

Ile Leu Ser Arg Asp Ala Ala Pro Leu Pro Arg Pro Gly
1               5                   10

<210> SEQ ID NO 118
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 118

Ile Leu Thr Val Ile Leu Gly Val Leu
1               5

<210> SEQ ID NO 119
<211> LENGTH: 9
<212> TYPE: PRT
<213> ORGANISM: Artificial Sequence
```

```
<220> FEATURE:
<223> OTHER INFORMATION: Synthetic Immunogen

<400> SEQUENCE: 119

Ile Met Asp Gln Val Pro Phe Phe Ser
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 120

Ile Met Asp Gln Val Pro Phe Ser Val
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 121

Ile Met Ile Gly Val Leu Val Gly Val
1               5

<210> SEQ ID NO 122
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 122

Ile Asn Lys Thr Ser Gly Pro Lys Arg Gly Lys His Ala Trp Thr His
1               5                   10                  15

Arg Leu Arg Glu
            20

<210> SEQ ID NO 123
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 123

Ile Ser Gly Gly Pro Arg Ile Ser Tyr
1               5

<210> SEQ ID NO 124
<211> LENGTH: 21
<212> TYPE: PRT
<213> ORGANISM: Artificial Sequence
<220> FEATURE:
<223> OTHER INFORMATION: Synthetic Immunogen

<400> SEQUENCE: 124

Ile Ser Pro Asn Ser Val Phe Ser Gln Trp Arg Val Val Cys Asp Ser
1               5                   10                  15

Leu Glu Asp Tyr Asp
            20
```

<210> SEQ ID NO 125
<211> LENGTH: 17
<212> TYPE: PRT
<213> ORGANISM: Artificial Sequence
<220> FEATURE:
<223> OTHER INFORMATION: Synthetic Immunogen

<400> SEQUENCE: 125

Ile Ser Gln Ala Val His Ala Ala His Ala Glu Ile Asn Glu Ala Gly
1               5                   10                  15
Arg

<210> SEQ ID NO 126
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 126

Ile Thr Asp Gln Val Pro Phe Ser Val
1               5

<210> SEQ ID NO 127
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 127

Ile Thr Lys Lys Val Ala Asp Leu Val Gly Phe
1               5                   10

<210> SEQ ID NO 128
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 128

Lys Ala Ser Glu Lys Ile Phe Tyr Val
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 129

Lys Ala Val Tyr Asn Phe Ala Thr Met
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 130

Lys Cys Asp Ile Cys Thr Asp Glu Tyr
1               5

<210> SEQ ID NO 131
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 131

Lys Glu Phe Thr Val Ser Gly Asn Ile Leu Thr
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 132

Lys Glu Phe Thr Val Ser Gly Asn Ile Leu Thr Ile
1               5                   10

<210> SEQ ID NO 133
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 133

Lys Glu Leu Glu Gly Ile Leu Leu Leu
1               5

<210> SEQ ID NO 134
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 134

Lys His Ala Trp Thr His Arg Leu Arg Glu Arg Lys Gln Leu Val Val
1               5                   10                  15

Tyr Glu Glu Ile
            20

<210> SEQ ID NO 135
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 135

Lys Ile Phe Gly Ser Leu Ala Phe Leu
1               5

<210> SEQ ID NO 136
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 136

```
Lys Ile Phe Ser Glu Val Thr Leu Lys
1               5

<210> SEQ ID NO 137
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 137

Lys Ile Phe Tyr Val Tyr Met Lys Arg Lys Tyr Glu Ala Met
1               5                   10

<210> SEQ ID NO 138
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 138

Lys Ile Phe Tyr Val Tyr Met Lys Arg Lys Tyr Glu Ala Met Thr
1               5                   10                  15

<210> SEQ ID NO 139
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 139

Lys Ile Leu Asp Ala Val Val Ala Gln Lys
1               5                   10

<210> SEQ ID NO 140
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 140

Lys Ile Asn Lys Asn Pro Lys Tyr Lys
1               5

<210> SEQ ID NO 141
<211> LENGTH: 31
<212> TYPE: PRT
<213> ORGANISM: Artificial Sequence
<220> FEATURE:
<223> OTHER INFORMATION: Synthetic Immunogen

<400> SEQUENCE: 141

Lys Ile Ser Gln Ala Val His Ala Ala His Ala Glu Ile Asn Glu Ala
1               5                   10                  15

Gly Arg Glu Ser Ile Ile Asn Phe Glu Lys Leu Thr Glu Trp Thr
                20                  25                  30

<210> SEQ ID NO 142
<211> LENGTH: 16
<212> TYPE: PRT
<213> ORGANISM: Artificial Sequence
<220> FEATURE:
<223> OTHER INFORMATION: Synthetic Immunogen
```

```
<400> SEQUENCE: 142

Lys Lys Leu Leu Thr Gln His Phe Val Gln Glu Asn Tyr Leu Glu Tyr
1               5                   10                  15

<210> SEQ ID NO 143
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 143

Lys Met Asp Ala Glu His Pro Glu Leu
1               5

<210> SEQ ID NO 144
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 144

Lys Asn Cys Glu Pro Val Val Pro Asn Ala Pro Pro Ala Tyr Glu Lys
1               5                   10                  15

Leu Ser Ala Glu
            20

<210> SEQ ID NO 145
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 145

Lys Arg Tyr Phe Lys Leu Ser His Leu Gln Met His Ser Arg Lys His
1               5                   10                  15

<210> SEQ ID NO 146
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 146

Lys Ser Ser Glu Lys Ile Val Tyr Val Tyr Met Lys Leu Asn Tyr Glu
1               5                   10                  15

Val Met Thr Lys
            20

<210> SEQ ID NO 147
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 147

Lys Thr Trp Gly Gln Tyr Trp Gln Val
1               5

<210> SEQ ID NO 148
<211> LENGTH: 9
```

```
<212> TYPE: PRT
<213> ORGANISM: Artificial Sequence
<220> FEATURE:
<223> OTHER INFORMATION: Synthetic Immunogen

<400> SEQUENCE: 148

Lys Val Ala Glu Leu Val His Phe Leu
1               5

<210> SEQ ID NO 149
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 149

Lys Val His Pro Val Ile Trp Ser Leu
1               5

<210> SEQ ID NO 150
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 150

Lys Val Leu Glu Tyr Val Ile Lys Val
1               5

<210> SEQ ID NO 151
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 151

Lys Tyr Asp Cys Phe Leu His Pro Phe
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 152

Lys Tyr Val Gly Ile Glu Arg Glu Met
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 153

Leu Ala Ala Leu Pro His Ser Cys Leu
1               5

<210> SEQ ID NO 154
<211> LENGTH: 10
<212> TYPE: PRT
```

<213> ORGANISM: Artificial Sequence
<220> FEATURE:
<223> OTHER INFORMATION: Synthetic Immunogen

<400> SEQUENCE: 154

Leu Ala Ala Gln Glu Arg Arg Val Pro Arg
1               5                   10

<210> SEQ ID NO 155
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 155

Leu Ala Gly Ile Gly Ile Leu Thr Val
1               5

<210> SEQ ID NO 156
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 156

Leu Ala Met Pro Phe Ala Thr Pro Met
1               5

<210> SEQ ID NO 157
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 157

Leu Gly Phe Lys Val Thr Leu Pro Pro Phe Met Arg Ser Lys Arg Ala
1               5                   10                  15

Ala Asp Phe His
            20

<210> SEQ ID NO 158
<211> LENGTH: 8
<212> TYPE: PRT
<213> ORGANISM: Artificial Sequence
<220> FEATURE:
<223> OTHER INFORMATION: Synthetic Immunogen

<400> SEQUENCE: 158

Leu Gly Pro Gly Arg Pro Tyr Arg
1               5

<210> SEQ ID NO 159
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 159

Leu His His Ala Phe Val Asp Ser Ile Phe
1               5                   10

<210> SEQ ID NO 160

```
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 160

Leu Ile Tyr Arg Arg Arg Leu Met Lys
1               5

<210> SEQ ID NO 161
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 161

Leu Lys Glu Phe Thr Val Ser Gly Asn Ile Leu Thr Ile Arg Leu
1               5                   10                  15

<210> SEQ ID NO 162
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 162

Leu Lys Leu Ser Gly Val Val Arg Leu
1               5

<210> SEQ ID NO 163
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 163

Leu Leu Ala Asn Gly Arg Met Pro Thr Val Leu Gln Cys Val Asn
1               5                   10                  15

<210> SEQ ID NO 164
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 164

Leu Leu Asp Gly Thr Ala Thr Leu Arg Leu
1               5                   10

<210> SEQ ID NO 165
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 165

Leu Leu Glu Phe Tyr Leu Ala Met Pro Phe Ala Thr Pro Met
1               5                   10

<210> SEQ ID NO 166
<211> LENGTH: 25
```

```
<212> TYPE: PRT
<213> ORGANISM: Artificial Sequence
<220> FEATURE:
<223> OTHER INFORMATION: Synthetic Immunogen

<400> SEQUENCE: 166

Leu Leu Glu Phe Tyr Leu Ala Met Pro Phe Ala Thr Pro Met Glu Ala
1               5                   10                  15

Glu Leu Ala Arg Arg Ser Leu Ala Gln
            20                  25

<210> SEQ ID NO 167
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 167

Leu Leu Phe Gly Leu Ala Leu Ile Glu Val
1               5                   10

<210> SEQ ID NO 168
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 168

Leu Leu Gly Ala Thr Cys Met Phe Val
1               5

<210> SEQ ID NO 169
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 169

Leu Leu Gly Pro Gly Arg Pro Tyr Arg
1               5

<210> SEQ ID NO 170
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 170

Leu Leu Gly Arg Asn Ser Phe Glu Val
1               5

<210> SEQ ID NO 171
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 171

Leu Leu Lys Tyr Arg Ala Arg Glu Pro Val Thr Lys Ala Glu
1               5                   10
```

```
<210> SEQ ID NO 172
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 172

Leu Leu Leu Asp Asp Leu Leu Val Ser Ile
1               5                   10

<210> SEQ ID NO 173
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 173

Leu Leu Leu Leu Thr Val Leu Thr Val
1               5

<210> SEQ ID NO 174
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 174

Leu Leu Trp Ser Phe Gln Thr Ser Ala
1               5

<210> SEQ ID NO 175
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 175

Leu Leu Tyr Lys Leu Ala Asp Leu Ile
1               5

<210> SEQ ID NO 176
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 176

Leu Met Leu Gln Asn Ala Leu Thr Thr Met
1               5                   10

<210> SEQ ID NO 177
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 177

Leu Pro Ala Val Val Gly Leu Ser Pro Gly Glu Gln Glu Tyr
1               5                   10

<210> SEQ ID NO 178
```

```
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 178

Leu Pro His Ser Ser Ser His Trp Leu
1               5

<210> SEQ ID NO 179
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 179

Leu Pro Arg Trp Pro Pro Pro Gln Leu
1               5

<210> SEQ ID NO 180
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 180

Leu Pro Ser Ser Ala Asp Val Glu Phe
1               5

<210> SEQ ID NO 181
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 181

Leu Ser His Leu Gln Met His Ser Arg Lys His
1               5                   10

<210> SEQ ID NO 182
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 182

Leu Ser Arg Leu Ser Asn Arg Leu Leu
1               5

<210> SEQ ID NO 183
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 183

Leu Thr Asp Leu Gln Pro Tyr Met Arg Gln Phe Val Ala His Leu
1               5                   10                  15

<210> SEQ ID NO 184
<211> LENGTH: 13
```

```
<212> TYPE: PRT
<213> ORGANISM: Artificial Sequence
<220> FEATURE:
<223> OTHER INFORMATION: Synthetic Immunogen

<400> SEQUENCE: 184

Leu Trp Trp Val Asn Asn Gln Ser Leu Pro Val Ser Pro
1               5                   10

<210> SEQ ID NO 185
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 185

Leu Tyr Ala Thr Val Ile His Asp Ile
1               5

<210> SEQ ID NO 186
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 186

Leu Tyr Ser Ala Cys Phe Trp Trp Leu
1               5

<210> SEQ ID NO 187
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 187

Leu Tyr Val Asp Ser Leu Phe Phe Leu
1               5

<210> SEQ ID NO 188
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 188

Met Glu Val Asp Pro Ile Gly His Leu Tyr
1               5                   10

<210> SEQ ID NO 189
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 189

Met Ile Ala Val Phe Leu Pro Ile Val
1               5

<210> SEQ ID NO 190
<211> LENGTH: 14
<212> TYPE: PRT
```

-continued

```
<213> ORGANISM: Artificial Sequence
<220> FEATURE:
<223> OTHER INFORMATION: Synthetic Immunogen

<400> SEQUENCE: 190

Met Ile Phe Glu Lys His Gly Phe Arg Arg Thr Thr Pro Pro
1               5                   10

<210> SEQ ID NO 191
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 191

Met Lys Leu Asn Tyr Glu Val Met Thr Lys Leu Gly Phe Lys Val Thr
1               5                   10                  15

Leu Pro Pro Phe
            20

<210> SEQ ID NO 192
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 192

Met Leu Ala Val Ile Ser Cys Ala Val
1               5

<210> SEQ ID NO 193
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 193

Met Leu Leu Ala Val Leu Tyr Cys Leu
1               5

<210> SEQ ID NO 194
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 194

Met Leu Met Ala Gln Glu Ala Leu Ala Phe Leu
1               5                   10

<210> SEQ ID NO 195
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 195

Met Pro Phe Ala Thr Pro Met Glu Ala
1               5

<210> SEQ ID NO 196
```

```
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 196

Met Pro Arg Glu Asp Ala His Phe Ile Tyr Gly Tyr Pro Lys Lys Gly
1               5                   10                  15

His Gly His Ser
            20

<210> SEQ ID NO 197
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 197

Met Ser Leu Gln Arg Gln Phe Leu Arg
1               5

<210> SEQ ID NO 198
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 198

Met Val Lys Ile Ser Gly Gly Pro Arg
1               5

<210> SEQ ID NO 199
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 199

Asn Leu Val Pro Met Val Ala Thr Val
1               5

<210> SEQ ID NO 200
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 200

Asn Pro Pro Ser Met Val Ala Ala Gly Ser Val Val Ala Ala Val
1               5                   10                  15

<210> SEQ ID NO 201
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 201

Asn Ser Ile Val Lys Ser Ile Thr Val Ser Ala Ser Gly
1               5                   10
```

<210> SEQ ID NO 202
<211> LENGTH: 25
<212> TYPE: PRT
<213> ORGANISM: Artificial Sequence
<220> FEATURE:
<223> OTHER INFORMATION: Synthetic Immunogen

<400> SEQUENCE: 202

Asn Ser Asn His Val Ala Ser Gly Ala Gly Glu Ala Ala Ile Glu Thr
1               5                   10                  15

Gln Ser Ser Ser Ser Glu Glu Ile Val
            20                  25

<210> SEQ ID NO 203
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 203

Asn Ser Gln Pro Val Trp Leu Cys Leu
1               5

<210> SEQ ID NO 204
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 204

Asn Thr Tyr Ala Ser Pro Arg Phe Lys
1               5

<210> SEQ ID NO 205
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 205

Asn Tyr Ala Arg Thr Glu Asp Phe Phe
1               5

<210> SEQ ID NO 206
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 206

Asn Tyr Lys Arg Cys Phe Pro Val Ile
1               5

<210> SEQ ID NO 207
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 207

Asn Tyr Asn Asn Phe Tyr Arg Phe Leu 1          5

<210> SEQ ID NO 208
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 208

Pro Asp Thr Arg Pro Ala Pro Gly Ser Thr Ala Pro Pro Ala His Gly
1               5                   10                  15

Val Thr Ser Ala
            20

<210> SEQ ID NO 209
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 209

Pro Phe Ala Thr Pro Met Glu Ala Glu Leu Ala Arg Arg
1               5                   10

<210> SEQ ID NO 210
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 210

Pro Gly Ser Thr Ala Pro Pro Ala His Gly Val Thr
1               5                   10

<210> SEQ ID NO 211
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 211

Pro Gly Thr Arg Val Arg Ala Met Ala Ile Tyr Lys Gln
1               5                   10

<210> SEQ ID NO 212
<211> LENGTH: 25
<212> TYPE: PRT
<213> ORGANISM: Artificial Sequence
<220> FEATURE:
<223> OTHER INFORMATION: Synthetic Immunogen

<400> SEQUENCE: 212

Pro Gly Val Leu Leu Lys Glu Phe Thr Val Ser Gly Asn Ile Leu Thr
1               5                   10                  15

Ile Arg Leu Thr Ala Ala Asp His Arg
            20                  25

<210> SEQ ID NO 213
<211> LENGTH: 9
<212> TYPE: PRT
<213> ORGANISM: Artificial Sequence
<220> FEATURE:

<223> OTHER INFORMATION: Synthetic Immunogen

<400> SEQUENCE: 213

Pro Leu Leu Glu Asn Val Ile Ser Lys
1               5

<210> SEQ ID NO 214
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 214

Pro Leu Pro Pro Ala Arg Asn Gly Gly Leu
1               5                   10

<210> SEQ ID NO 215
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 215

Pro Leu Gln Pro Glu Gln Leu Gln Val
1               5

<210> SEQ ID NO 216
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 216

Pro Leu Thr Ser Ile Ile Ser Ala Val
1               5

<210> SEQ ID NO 217
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 217

Pro Arg Ala Leu Ala Glu Thr Ser Tyr Val Lys Val Leu Glu Tyr
1               5                   10                  15

<210> SEQ ID NO 218
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 218

Pro Val Thr Trp Arg Arg Ala Pro Ala
1               5

<210> SEQ ID NO 219
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 219

Pro Tyr Tyr Phe Ala Ala Glu Leu Pro Pro Arg Asn Leu Pro Glu Pro
1               5                   10                  15

<210> SEQ ID NO 220
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 220

Gln Cys Ser Gly Asn Phe Met Gly Phe
1               5

<210> SEQ ID NO 221
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 221

Gln Cys Thr Glu Val Arg Ala Asp Thr Arg Pro Trp Ser Gly Pro
1               5                   10                  15

<210> SEQ ID NO 222
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 222

Gln Gly Ala Met Leu Ala Ala Gln Glu Arg Arg Val Pro Arg Ala Ala
1               5                   10                  15

Glu Val Pro Arg
            20

<210> SEQ ID NO 223
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 223

Gln Gly Gln His Phe Leu Gln Lys Val
1               5

<210> SEQ ID NO 224
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 224

Gln Leu Ala Val Ser Val Ile Leu Arg Val
1               5                   10

<210> SEQ ID NO 225
<211> LENGTH: 15
<212> TYPE: PRT
<213> ORGANISM: Artificial Sequence

```
<220> FEATURE:
<223> OTHER INFORMATION: Synthetic Immunogen

<400> SEQUENCE: 225

Gln Asn Ile Leu Leu Ser Asn Ala Pro Leu Gly Pro Gln Phe Pro
1               5                   10                  15

<210> SEQ ID NO 226
<211> LENGTH: 8
<212> TYPE: PRT
<213> ORGANISM: Artificial Sequence
<220> FEATURE:
<223> OTHER INFORMATION: Synthetic Immunogen

<400> SEQUENCE: 226

Gln Gln Ile Thr Lys Thr Glu Val
1               5

<210> SEQ ID NO 227
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 227

Gln Arg Pro Tyr Gly Tyr Asp Gln Ile Met
1               5                   10

<210> SEQ ID NO 228
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 228

Gln Tyr Ser Trp Phe Val Asn Gly Thr Phe
1               5                   10

<210> SEQ ID NO 229
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 229

Arg Ala Gly Leu Gln Val Arg Lys Asn Lys
1               5                   10

<210> SEQ ID NO 230
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 230

Arg Glu Pro Phe Thr Lys Ala Glu Met Leu Gly Ser Val Ile Arg
1               5                   10                  15

<210> SEQ ID NO 231
<211> LENGTH: 10
<212> TYPE: PRT
<213> ORGANISM: Artificial Sequence
<220> FEATURE:
```

<223> OTHER INFORMATION: Synthetic Immunogen

<400> SEQUENCE: 231

Arg Glu Pro Val Thr Lys Ala Glu Met Leu
1               5                   10

<210> SEQ ID NO 232
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 232

Arg Ile Ala Glu Cys Ile Leu Gly Met
1               5

<210> SEQ ID NO 233
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 233

Arg Lys Val Ala Glu Leu Val His Phe Leu Leu Leu Lys Tyr Arg
1               5                   10                  15

<210> SEQ ID NO 234
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 234

Arg Lys Val Ala Glu Leu Val His Phe Leu Leu Leu Lys Tyr Arg Ala
1               5                   10                  15

<210> SEQ ID NO 235
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 235

Arg Leu Leu Glu Phe Tyr Leu Ala Met Pro Phe Ala
1               5                   10

<210> SEQ ID NO 236
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 236

Arg Leu Leu Gln Glu Thr Glu Leu Val
1               5

<210> SEQ ID NO 237
<211> LENGTH: 9
<212> TYPE: PRT
<213> ORGANISM: Artificial Sequence
<220> FEATURE:
<223> OTHER INFORMATION: Synthetic Immunogen

```
<400> SEQUENCE: 237

Arg Leu Met Lys Gln Asp Phe Ser Val
1               5

<210> SEQ ID NO 238
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 238

Arg Leu Pro Arg Ile Phe Cys Ser Cys
1               5

<210> SEQ ID NO 239
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 239

Arg Leu Ser Ser Cys Val Pro Val Ala
1               5

<210> SEQ ID NO 240
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 240

Arg Leu Val Asp Asp Phe Leu Leu Val
1               5

<210> SEQ ID NO 241
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 241

Arg Met Pro Glu Ala Ala Pro Pro Val
1               5

<210> SEQ ID NO 242
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 242

Arg Met Pro Thr Val Leu Gln Cys Val Asn Val Ser Val Val Ser
1               5                   10                  15

<210> SEQ ID NO 243
<211> LENGTH: 11
<212> TYPE: PRT
<213> ORGANISM: Artificial Sequence
<220> FEATURE:
<223> OTHER INFORMATION: Synthetic Immunogen
```

```
<400> SEQUENCE: 243

Arg Asn Gly Tyr Arg Ala Leu Met Asp Lys Ser
1               5                   10

<210> SEQ ID NO 244
<211> LENGTH: 23
<212> TYPE: PRT
<213> ORGANISM: Artificial Sequence
<220> FEATURE:
<223> OTHER INFORMATION: Synthetic Immunogen

<400> SEQUENCE: 244

Arg Asn Gly Tyr Arg Ala Leu Met Asp Lys Ser Leu His Val Gly Thr
1               5                   10                  15

Gln Cys Ala Leu Thr Arg Arg
            20

<210> SEQ ID NO 245
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 245

Arg Pro Gly Leu Leu Gly Ala Ser Val Leu Gly Leu Asp Asp Ile
1               5                   10                  15

<210> SEQ ID NO 246
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 246

Arg Pro His Val Pro Glu Ser Ala Phe
1               5

<210> SEQ ID NO 247
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 247

Arg Gln Lys Arg Ile Leu Val Asn Leu
1               5

<210> SEQ ID NO 248
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 248

Arg Ser Asp Ser Gly Gln Gln Ala Arg Tyr
1               5                   10

<210> SEQ ID NO 249
<211> LENGTH: 9
<212> TYPE: PRT
<213> ORGANISM: Artificial Sequence
<220> FEATURE:
```

<223> OTHER INFORMATION: Synthetic Immunogen

<400> SEQUENCE: 249

Arg Thr Lys Gln Leu Tyr Pro Glu Trp
1               5

<210> SEQ ID NO 250
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 250

Arg Val Ile Lys Asn Ser Ile Arg Leu Thr Leu
1               5                   10

<210> SEQ ID NO 251
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 251

Arg Val Arg Phe Phe Phe Pro Ser Leu
1               5

<210> SEQ ID NO 252
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 252

Arg Tyr Gln Leu Asp Pro Lys Phe Ile
1               5

<210> SEQ ID NO 253
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 253

Ser Ala Phe Pro Thr Thr Ile Asn Phe
1               5

<210> SEQ ID NO 254
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 254

Ser Ala Trp Ile Ser Lys Pro Pro Gly Val
1               5                   10

<210> SEQ ID NO 255
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 255

Ser Ala Tyr Gly Glu Pro Arg Lys Leu
1               5

<210> SEQ ID NO 256
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 256

Ser Glu Ile Trp Arg Asp Ile Asp Phe
1               5

<210> SEQ ID NO 257
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 257

Ser Glu Leu Phe Arg Ser Gly Leu Asp Ser Tyr
1               5                   10

<210> SEQ ID NO 258
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 258

Ser Glu Ser Ile Lys Lys Lys Val Leu
1               5

<210> SEQ ID NO 259
<211> LENGTH: 8
<212> TYPE: PRT
<213> ORGANISM: Artificial Sequence
<220> FEATURE:
<223> OTHER INFORMATION: Synthetic Immunogen

<400> SEQUENCE: 259

Ser Glu Ser Leu Lys Met Ile Phe
1               5

<210> SEQ ID NO 260
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 260

Ser Phe Ser Tyr Thr Leu Leu Ser Leu
1               5

<210> SEQ ID NO 261
<211> LENGTH: 9
<212> TYPE: PRT
<213> ORGANISM: Artificial Sequence
<220> FEATURE:
<223> OTHER INFORMATION: Synthetic Immunogen

```
<400> SEQUENCE: 261

Ser His Glu Thr Val Ile Ile Glu Leu
1               5

<210> SEQ ID NO 262
<211> LENGTH: 8
<212> TYPE: PRT
<213> ORGANISM: Artificial Sequence
<220> FEATURE:
<223> OTHER INFORMATION: Synthetic Immunogen

<400> SEQUENCE: 262

Ser Ile Ile Asn Phe Glu Lys Leu
1               5

<210> SEQ ID NO 263
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 263

Ser Leu Ala Asp Thr Asn Ser Leu Ala Val
1               5                   10

<210> SEQ ID NO 264
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 264

Ser Leu Phe Glu Gly Ile Asp Ile Tyr Thr
1               5                   10

<210> SEQ ID NO 265
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 265

Ser Leu Phe Pro Asn Ser Pro Lys Trp Thr Ser Lys
1               5                   10

<210> SEQ ID NO 266
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 266

Ser Leu Phe Arg Ala Val Ile Thr Lys
1               5

<210> SEQ ID NO 267
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 267
```

```
Ser Leu Gly Trp Leu Phe Leu Leu Leu
1               5

<210> SEQ ID NO 268
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 268

Ser Leu Leu Met Trp Ile Thr Gln Cys
1               5

<210> SEQ ID NO 269
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 269

Ser Leu Leu Met Trp Ile Thr Gln Cys Phe Leu Pro Val Phe
1               5                   10

<210> SEQ ID NO 270
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 270

Ser Leu Leu Gln His Leu Ile Gly Leu
1               5

<210> SEQ ID NO 271
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 271

Ser Leu Pro Tyr Trp Asn Phe Ala Thr Gly
1               5                   10

<210> SEQ ID NO 272
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 272

Ser Leu Ser Lys Ile Leu Asp Thr Val
1               5

<210> SEQ ID NO 273
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 273
```

```
Ser Leu Tyr Lys Phe Ser Pro Phe Pro Leu
1               5                   10

<210> SEQ ID NO 274
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 274

Ser Leu Tyr Ser Phe Pro Glu Pro Glu Ala
1               5                   10

<210> SEQ ID NO 275
<211> LENGTH: 8
<212> TYPE: PRT
<213> ORGANISM: Artificial Sequence
<220> FEATURE:
<223> OTHER INFORMATION: Synthetic Immunogen

<400> SEQUENCE: 275

Ser Asn Asp Gly Pro Thr Leu Ile
1               5

<210> SEQ ID NO 276
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 276

Ser Pro Arg Trp Trp Pro Thr Cys Leu
1               5

<210> SEQ ID NO 277
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 277

Ser Pro Ser Ser Asn Arg Ile Arg Asn Thr
1               5                   10

<210> SEQ ID NO 278
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 278

Ser Gln Lys Thr Tyr Gln Gly Ser Tyr
1               5

<210> SEQ ID NO 279
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 279

Ser Arg Phe Gly Gly Ala Val Val Arg
```

```
<210> SEQ ID NO 280
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 280

Ser Ser Ala Leu Leu Ser Ile Phe Gln Ser Ser Pro Glu
1               5                   10

<210> SEQ ID NO 281
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 281

Ser Ser Asp Tyr Val Ile Pro Ile Gly Thr Tyr
1               5                   10

<210> SEQ ID NO 282
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 282

Ser Ser Lys Ala Leu Gln Arg Pro Val
1               5

<210> SEQ ID NO 283
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 283

Ser Ser Pro Gly Cys Gln Pro Pro Ala
1               5

<210> SEQ ID NO 284
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 284

Ser Thr Ala Pro Pro Val His Asn Val
1               5

<210> SEQ ID NO 285
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 285

Ser Val Ala Ser Thr Ile Thr Gly Val
1               5
```

<210> SEQ ID NO 286
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 286

Ser Val Asp Tyr Phe Phe Val Trp Leu
1               5

<210> SEQ ID NO 287
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 287

Ser Val Ser Glu Ser Asp Thr Ile Arg Ser Ile Ser Ile Ala Ser
1               5                   10                  15

<210> SEQ ID NO 288
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 288

Ser Val Tyr Asp Phe Phe Val Trp Leu
1               5

<210> SEQ ID NO 289
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 289

Ser Tyr Leu Asp Ser Gly Ile His Phe
1               5

<210> SEQ ID NO 290
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 290

Ser Tyr Leu Gln Asp Ser Asp Pro Asp Ser Phe Gln Asp
1               5                   10

<210> SEQ ID NO 291
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 291

Thr Phe Pro Asp Leu Glu Ser Glu Phe
1               5

```
<210> SEQ ID NO 292
<211> LENGTH: 17
<212> TYPE: PRT
<213> ORGANISM: Artificial Sequence
<220> FEATURE:
<223> OTHER INFORMATION: Synthetic Immunogen

<400> SEQUENCE: 292

Thr Gly Arg Ala Met Leu Gly Thr His Thr Met Glu Val Thr Val Tyr
1               5                   10                  15

His

<210> SEQ ID NO 293
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 293

Thr Leu Asp Ser Gln Val Met Ser Leu
1               5

<210> SEQ ID NO 294
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 294

Thr Leu Asp Trp Leu Leu Gln Thr Pro Lys
1               5                   10

<210> SEQ ID NO 295
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 295

Thr Leu Glu Glu Ile Thr Gly Tyr Leu
1               5

<210> SEQ ID NO 296
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 296

Thr Leu Met Ser Ala Met Thr Asn Leu
1               5

<210> SEQ ID NO 297
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 297

Thr Leu Asn Asp Glu Cys Trp Pro Ala
1               5
```

```
<210> SEQ ID NO 298
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 298

Thr Leu Pro Gly Tyr Pro Pro His Val
1               5

<210> SEQ ID NO 299
<211> LENGTH: 14
<212> TYPE: PRT
<213> ORGANISM: Artificial Sequence
<220> FEATURE:
<223> OTHER INFORMATION: Synthetic Immunogen

<400> SEQUENCE: 299

Thr Leu Tyr Gln Asp Asp Thr Leu Thr Leu Gln Ala Ala Gly
1               5                   10

<210> SEQ ID NO 300
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 300

Thr Met Lys Gln Ile Cys Lys Lys Glu Ile Arg Arg Leu His Gln Tyr
1               5                   10                  15

<210> SEQ ID NO 301
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 301

Thr Met Asn Gly Ser Lys Ser Pro Val
1               5

<210> SEQ ID NO 302
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 302

Thr Pro Arg Leu Pro Ser Ser Ala Asp Val Glu Phe
1               5                   10

<210> SEQ ID NO 303
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 303

Thr Ser Cys Ile Leu Glu Ser Leu Phe Arg Ala Val Ile Thr Lys
1               5                   10                  15
```

```
<210> SEQ ID NO 304
<211> LENGTH: 11
<212> TYPE: PRT
<213> ORGANISM: Artificial Sequence
<220> FEATURE:
<223> OTHER INFORMATION: Synthetic Immunogen

<400> SEQUENCE: 304

Thr Ser Glu Lys Arg Pro Phe Met Cys Ala Tyr
1               5                   10

<210> SEQ ID NO 305
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 305

Thr Ser Tyr Val Lys Val Leu His His Met Val Lys Ile Ser Gly
1               5                   10                  15

<210> SEQ ID NO 306
<211> LENGTH: 18
<212> TYPE: PRT
<213> ORGANISM: Artificial Sequence
<220> FEATURE:
<223> OTHER INFORMATION: Synthetic Immunogen

<400> SEQUENCE: 306

Thr Thr Glu Trp Val Glu Thr Thr Ala Arg Glu Leu Pro Ile Pro Glu
1               5                   10                  15

Pro Glu

<210> SEQ ID NO 307
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 307

Thr Val Ser Gly Asn Ile Leu Thr Ile Arg
1               5                   10

<210> SEQ ID NO 308
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 308

Thr Tyr Ala Cys Phe Val Ser Asn Leu
1               5

<210> SEQ ID NO 309
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 309

Thr Tyr Leu Pro Thr Asn Ala Ser Leu
1               5
```

<210> SEQ ID NO 310
<211> LENGTH: 13
<212> TYPE: PRT
<213> ORGANISM: Artificial Sequence
<220> FEATURE:
<223> OTHER INFORMATION: Synthetic Immunogen

<400> SEQUENCE: 310

Thr Tyr Tyr Arg Pro Gly Val Asn Leu Ser Leu Ser Cys
1               5                   10

<210> SEQ ID NO 311
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 311

Val Ala Glu Leu Val His Phe Leu Leu
1               5

<210> SEQ ID NO 312
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 312

Val Phe Gly Ile Glu Leu Met Glu Val Asp Pro Ile Gly His Leu
1               5                   10                  15

<210> SEQ ID NO 313
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 313

Val Gly Gln Asp Val Ser Val Leu Phe Arg Val Thr Gly Ala Leu Gln
1               5                   10                  15

<210> SEQ ID NO 314
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 314

Val Ile Phe Ser Lys Ala Ser Ser Ser Leu Gln Leu
1               5                   10

<210> SEQ ID NO 315
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 315

Val Ile Ser Asn Asp Val Cys Ala Gln Val
1               5                   10

<210> SEQ ID NO 316
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 316

Val Leu Asp Gly Leu Asp Val Leu Leu
1               5

<210> SEQ ID NO 317
<211> LENGTH: 8
<212> TYPE: PRT
<213> ORGANISM: Artificial Sequence
<220> FEATURE:
<223> OTHER INFORMATION: Synthetic Immunogen

<400> SEQUENCE: 317

Val Leu Phe Tyr Leu Gly Gln Tyr
1               5

<210> SEQ ID NO 318
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 318

Val Leu His Trp Asp Pro Glu Thr Val
1               5

<210> SEQ ID NO 319
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 319

Val Leu Leu Lys Glu Phe Thr Val Ser Gly
1               5                   10

<210> SEQ ID NO 320
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 320

Val Leu Leu Gln Ala Gly Ser Leu His Ala
1               5                   10

<210> SEQ ID NO 321
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 321

Val Leu Pro Asp Val Phe Ile Arg Cys Val
1               5                   10

```
<210> SEQ ID NO 322
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 322

Val Leu Pro Asp Val Phe Ile Arg Cys
1               5

<210> SEQ ID NO 323
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 323

Val Leu Arg Glu Asn Thr Ser Pro Lys
1               5

<210> SEQ ID NO 324
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 324

Val Leu Tyr Arg Tyr Gly Ser Phe Ser Val
1               5                   10

<210> SEQ ID NO 325
<211> LENGTH: 26
<212> TYPE: PRT
<213> ORGANISM: Artificial Sequence
<220> FEATURE:
<223> OTHER INFORMATION: Synthetic Immunogen

<400> SEQUENCE: 325

Val Pro Gly Val Leu Leu Lys Glu Phe Thr Val Ser Gly Asn Ile Leu
1               5                   10                  15

Thr Ile Arg Leu Thr Ala Ala Asp His Arg
            20                  25

<210> SEQ ID NO 326
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 326

Val Pro Leu Asp Cys Val Leu Tyr Arg Tyr
1               5                   10

<210> SEQ ID NO 327
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 327

Val Arg Ile Gly His Leu Tyr Ile Leu
1               5
```

```
<210> SEQ ID NO 328
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 328

Val Ser Ser Phe Phe Ser Tyr Thr Leu
1               5

<210> SEQ ID NO 329
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 329

Val Val Leu Gly Val Val Phe Gly Ile
1               5

<210> SEQ ID NO 330
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 330

Val Val Pro Cys Glu Pro Pro Glu Val
1               5

<210> SEQ ID NO 331
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 331

Val Val Val Gly Ala Val Gly Val Gly
1               5

<210> SEQ ID NO 332
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 332

Val Tyr Phe Phe Leu Pro Asp His Leu
1               5

<210> SEQ ID NO 333
<211> LENGTH: 18
<212> TYPE: PRT
<213> ORGANISM: Artificial Sequence
<220> FEATURE:
<223> OTHER INFORMATION: Synthetic Immunogen

<400> SEQUENCE: 333

Trp Glu Lys Met Lys Ala Ser Glu Lys Ile Phe Tyr Val Tyr Met Lys
1               5                   10                  15
```

Arg Lys

<210> SEQ ID NO 334
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 334

Trp Leu Pro Phe Gly Phe Ile Leu Ile
1               5

<210> SEQ ID NO 335
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 335

Trp Asn Arg Gln Leu Tyr Pro Glu Trp Thr Glu Ala Gln Arg Leu Asp
1               5                   10                  15

<210> SEQ ID NO 336
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 336

Trp Gln Tyr Phe Phe Pro Val Ile Phe
1               5

<210> SEQ ID NO 337
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 337

Trp Arg Arg Ala Pro Ala Pro Gly Ala
1               5

<210> SEQ ID NO 338
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 338

Tyr Ala Cys Phe Val Ser Asn Leu Ala Thr Gly Arg Asn Asn Ser
1               5                   10                  15

<210> SEQ ID NO 339
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 339

Tyr Phe Ser Lys Lys Glu Trp Glu Lys Met Lys Ser Ser Glu Lys Ile
1               5                   10                  15

Val Tyr Val Tyr
            20

<210> SEQ ID NO 340
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 340

Tyr Leu Glu Pro Gly Pro Val Thr Ala
1               5

<210> SEQ ID NO 341
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 341

Tyr Leu Glu Pro Gly Pro Val Thr Val
1               5

<210> SEQ ID NO 342
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 342

Tyr Leu Asn Asp His Leu Glu Pro Trp Ile
1               5                   10

<210> SEQ ID NO 343
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 343

Tyr Leu Gln Leu Val Phe Gly Ile Glu Val
1               5                   10

<210> SEQ ID NO 344
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 344

Tyr Leu Ser Gly Ala Asn Leu Asn Leu
1               5

<210> SEQ ID NO 345
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 345

```
Tyr Leu Val Pro Gln Gln Gly Phe Phe Cys
1               5                   10
```

<210> SEQ ID NO 346
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 346

```
Tyr Met Asp Gly Thr Met Ser Gln Val
1               5
```

<210> SEQ ID NO 347
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 347

```
Tyr Met Ile Met Val Lys Cys Trp Met Ile
1               5                   10
```

<210> SEQ ID NO 348
<211> LENGTH: 8
<212> TYPE: PRT
<213> ORGANISM: Artificial Sequence
<220> FEATURE:
<223> OTHER INFORMATION: Synthetic Immunogen

<400> SEQUENCE: 348

```
Tyr Arg Pro Arg Pro Arg Arg Tyr
1               5
```

<210> SEQ ID NO 349
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 349

```
Tyr Ser Val Tyr Phe Asn Leu Pro Ala Asp Thr Ile Tyr Thr Asn
1               5                   10                  15
```

<210> SEQ ID NO 350
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 350

```
Tyr Ser Trp Arg Ile Asn Gly Ile Pro Gln Gln His Thr Gln Val
1               5                   10                  15
```

<210> SEQ ID NO 351
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 351

```
Tyr Val Asp Phe Arg Glu Tyr Glu Tyr Tyr
```

```
1               5               10
```

<210> SEQ ID NO 352
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 352

Tyr Tyr Trp Pro Arg Pro Arg Arg Tyr
1               5

<210> SEQ ID NO 353
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 353

Ile Met Asp Gln Val Pro Phe Phe Ser
1               5

<210> SEQ ID NO 354
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 354

Ser Val Asp Tyr Phe Phe Val Trp Leu
1               5

<210> SEQ ID NO 355
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 355

Ala Leu Phe Asp Ile Glu Ser Lys Val
1               5

<210> SEQ ID NO 356
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 356

Asn Leu Val Pro Met Val Ala Thr Val
1               5

<210> SEQ ID NO 357
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 357

Gly Leu Cys Thr Leu Val Ala Met Leu
1               5

```
<210> SEQ ID NO 358
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 358

Ser Val Ala Ser Thr Ile Thr Gly Val
1               5

<210> SEQ ID NO 359
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 359

Val Met Ala Gly Asp Ile Tyr Ser Val
1               5

<210> SEQ ID NO 360
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 360

Ala Leu Ala Asp Gly Val Gln Lys Val
1               5

<210> SEQ ID NO 361
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 361

Leu Leu Gly Ala Thr Cys Met Phe Val
1               5

<210> SEQ ID NO 362
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 362

Ser Val Phe Ala Gly Val Val Gly Val
1               5

<210> SEQ ID NO 363
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 363

Ala Leu Phe Asp Gly Asp Pro His Leu
1               5
```

<210> SEQ ID NO 364
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 364

Tyr Val Asp Pro Val Ile Thr Ser Ile
1               5

<210> SEQ ID NO 365
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 365

Ser Thr Ala Pro Pro Val His Asn Val
1               5

<210> SEQ ID NO 366
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 366

Leu Ala Ala Leu Pro His Ser Cys Leu
1               5

<210> SEQ ID NO 367
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 367

Ser Gln Asp Asp Ile Lys Gly Ile Gln Lys Leu Tyr Gly Lys Arg Ser
1               5                   10                  15

<210> SEQ ID NO 368
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 368

Phe Leu Pro Ser Asp Phe Phe Pro Ser Val
1               5                   10

<210> SEQ ID NO 369
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 369

Phe Leu Pro Ser Asp Phe Phe Pro Ser Val
1               5                   10

-continued

```
<210> SEQ ID NO 370
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 370

Thr Leu Gly Glu Phe Leu Lys Leu Asp Arg Glu Arg Ala Lys Asn
1               5                   10                  15

<210> SEQ ID NO 371
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 371

Thr Phe Ser Tyr Val Asp Pro Val Ile Thr Ser Ile Ser Pro Lys Tyr
1               5                   10                  15

Gly Met Glu Thr
            20

<210> SEQ ID NO 372
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 372

Ala Met Thr Gln Leu Leu Ala Gly Val
1               5

<210> SEQ ID NO 373
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 373

Lys Val Phe Ala Gly Ile Pro Thr Val
1               5

<210> SEQ ID NO 374
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 374

Ala Ile Ile Asp Gly Val Glu Ser Val
1               5

<210> SEQ ID NO 375
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 375

Gly Leu Trp His His Gln Thr Glu Val
1               5
```

<210> SEQ ID NO 376
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 376

Asn Leu Asp Thr Leu Met Thr Tyr Val
1               5

<210> SEQ ID NO 377
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 377

Lys Ile Gln Glu Ile Leu Thr Gln Val
1               5

<210> SEQ ID NO 378
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 378

Leu Thr Phe Gly Asp Val Val Ala Val
1               5

<210> SEQ ID NO 379
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 379

Thr Met Leu Ala Arg Leu Ala Ser Ala
1               5

<210> SEQ ID NO 380
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 380

Ile Met Asp Gln Val Pro Phe Ser Val
1               5

<210> SEQ ID NO 381
<211> LENGTH: 32
<212> TYPE: PRT
<213> ORGANISM: Artificial Sequence
<220> FEATURE:
<223> OTHER INFORMATION: Synthetic Immunogen

<400> SEQUENCE: 381

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

<210> SEQ ID NO 382
<211> LENGTH: 12
<212> TYPE: PRT
<213> ORGANISM: Artificial Sequence
<220> FEATURE:
<223> OTHER INFORMATION: Synthetic Immunogen

<400> SEQUENCE: 382

Leu Pro Gln Leu Cys Thr Glu Leu Gln Thr Thr Ile
1               5                   10

<210> SEQ ID NO 383
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 383

His Asp Ile Ile Leu Glu Cys Val Tyr Cys Lys Gln Gln Leu Leu Arg
1               5                   10                  15

Arg Glu Val Tyr
            20

<210> SEQ ID NO 384
<211> LENGTH: 25
<212> TYPE: PRT
<213> ORGANISM: Artificial Sequence
<220> FEATURE:
<223> OTHER INFORMATION: Synthetic Immunogen

<400> SEQUENCE: 384

Lys Gln Gln Leu Leu Arg Arg Glu Val Tyr Asp Phe Ala Phe Arg Asp
1               5                   10                  15

Leu Cys Ile Val Tyr Arg Asp Gly Asn
            20                  25

<210> SEQ ID NO 385
<211> LENGTH: 26
<212> TYPE: PRT
<213> ORGANISM: Artificial Sequence
<220> FEATURE:
<223> OTHER INFORMATION: Synthetic Immunogen

<400> SEQUENCE: 385

Arg Asp Leu Cys Ile Val Tyr Arg Asp Gly Asn Pro Tyr Ala Val Cys
1               5                   10                  15

Asp Lys Cys Leu Lys Phe Tyr Ser Lys Ile
            20                  25

<210> SEQ ID NO 386
<211> LENGTH: 25
<212> TYPE: PRT
<213> ORGANISM: Artificial Sequence
<220> FEATURE:
<223> OTHER INFORMATION: Synthetic Immunogen

<400> SEQUENCE: 386

Asp Lys Cys Leu Lys Phe Tyr Ser Lys Ile Ser Glu Tyr Arg His Tyr
1               5                   10                  15

Cys Tyr Ser Leu Tyr Gly Thr Thr Leu
            20                  25

<210> SEQ ID NO 387
<211> LENGTH: 25
<212> TYPE: PRT
<213> ORGANISM: Artificial Sequence
<220> FEATURE:
<223> OTHER INFORMATION: Synthetic Immunogen

<400> SEQUENCE: 387

His Tyr Cys Tyr Ser Leu Tyr Gly Thr Thr Leu Glu Gln Gln Tyr Asn
1               5                   10                  15

Lys Pro Leu Cys Asp Leu Leu Ile Arg
            20                  25

<210> SEQ ID NO 388
<211> LENGTH: 32
<212> TYPE: PRT
<213> ORGANISM: Artificial Sequence
<220> FEATURE:
<223> OTHER INFORMATION: Synthetic Immunogen

<400> SEQUENCE: 388

Tyr Gly Thr Thr Leu Glu Gln Gln Tyr Asn Lys Pro Leu Cys Asp Leu
1               5                   10                  15

Leu Ile Arg Cys Ile Asn Cys Gln Lys Pro Leu Cys Pro Glu Glu Lys
            20                  25                  30

<210> SEQ ID NO 389
<211> LENGTH: 32
<212> TYPE: PRT
<213> ORGANISM: Artificial Sequence
<220> FEATURE:
<223> OTHER INFORMATION: Synthetic Immunogen

<400> SEQUENCE: 389

Arg Cys Ile Asn Cys Gln Lys Pro Leu Cys Pro Glu Glu Lys Gln Arg
1               5                   10                  15

His Leu Asp Lys Lys Gln Arg Phe His Asn Ile Arg Gly Arg Trp Thr
            20                  25                  30

<210> SEQ ID NO 390
<211> LENGTH: 32
<212> TYPE: PRT
<213> ORGANISM: Artificial Sequence
<220> FEATURE:
<223> OTHER INFORMATION: Synthetic Immunogen

<400> SEQUENCE: 390

Asp Lys Lys Gln Arg Phe His Asn Ile Arg Gly Arg Trp Thr Gly Arg
1               5                   10                  15

Cys Met Ser Cys Cys Arg Ser Ser Arg Thr Arg Arg Glu Thr Gln Leu
            20                  25                  30

<210> SEQ ID NO 391
<211> LENGTH: 35
<212> TYPE: PRT
<213> ORGANISM: Artificial Sequence
<220> FEATURE:
<223> OTHER INFORMATION: Synthetic Immunogen

<400> SEQUENCE: 391

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser

-continued

```
                20                  25                  30
Glu Glu Glu
        35

<210> SEQ ID NO 392
<211> LENGTH: 35
<212> TYPE: PRT
<213> ORGANISM: Artificial Sequence
<220> FEATURE:
<223> OTHER INFORMATION: Synthetic Immunogen

<400> SEQUENCE: 392

Leu Tyr Cys Tyr Glu Gln Leu Asn Asp Ser Ser Glu Glu Glu Asp Glu
1               5                   10                  15

Ile Asp Gly Pro Ala Gly Gln Ala Glu Pro Asp Arg Ala His Tyr Asn
                20                  25                  30

Ile Val Thr
        35

<210> SEQ ID NO 393
<211> LENGTH: 35
<212> TYPE: PRT
<213> ORGANISM: Artificial Sequence
<220> FEATURE:
<223> OTHER INFORMATION: Synthetic Immunogen

<400> SEQUENCE: 393

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
                20                  25                  30

Asp Ile Arg
        35

<210> SEQ ID NO 394
<211> LENGTH: 35
<212> TYPE: PRT
<213> ORGANISM: Artificial Sequence
<220> FEATURE:
<223> OTHER INFORMATION: Synthetic Immunogen

<400> SEQUENCE: 394

Thr Leu Arg Leu Cys Val Gln Ser Thr His Val Asp Ile Arg Thr Leu
1               5                   10                  15

Glu Asp Leu Leu Met Gly Thr Leu Gly Ile Val Cys Pro Ile Cys Ser
                20                  25                  30

Gln Lys Pro
        35

<210> SEQ ID NO 395
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 395

Ala Leu Pro Phe Gly Phe Ile Leu Val
1               5

<210> SEQ ID NO 396
<211> LENGTH: 9
<212> TYPE: PRT
```

```
<213> ORGANISM: Artificial Sequence
<220> FEATURE:
<223> OTHER INFORMATION: Synthetic Immunogen

<400> SEQUENCE: 396

Thr Leu Ala Asp Phe Asp Pro Arg Val
1               5

<210> SEQ ID NO 397
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 397

Ile Met Asp Gln Val Pro Phe Ser Val
1               5

<210> SEQ ID NO 398
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 398

Ser Ile Met Thr Tyr Asp Phe His Gly Ala
1               5                   10

<210> SEQ ID NO 399
<211> LENGTH: 16
<212> TYPE: PRT
<213> ORGANISM: Artificial Sequence
<220> FEATURE:
<223> OTHER INFORMATION: Synthetic Immunogen

<400> SEQUENCE: 399

Ala Gln Tyr Ile Lys Ala Asn Ser Lys Phe Ile Gly Ile Thr Glu Leu
1               5                   10                  15

<210> SEQ ID NO 400
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 400

Phe Leu Tyr Asp Asp Asn Gln Arg Val
1               5

<210> SEQ ID NO 401
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 401

Tyr Leu Ile Glu Leu Ile Asp Arg Val
1               5

<210> SEQ ID NO 402
<211> LENGTH: 9
<212> TYPE: PRT
<213> ORGANISM: Artificial Sequence
```

```
<220> FEATURE:
<223> OTHER INFORMATION: Synthetic Immunogen

<400> SEQUENCE: 402

Asn Leu Met Glu Gln Pro Ile Lys Val
1               5

<210> SEQ ID NO 403
<211> LENGTH: 10
<212> TYPE: PRT
<213> ORGANISM: Artificial Sequence
<220> FEATURE:
<223> OTHER INFORMATION: Synthetic Immunogen

<400> SEQUENCE: 403

Phe Leu Ala Glu Asp Ala Leu Asn Thr Val
1               5                   10

<210> SEQ ID NO 404
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 404

Ala Leu Met Glu Gln Gln His Tyr Val
1               5

<210> SEQ ID NO 405
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 405

Ile Leu Asp Asp Ile Gly His Gly Val
1               5

<210> SEQ ID NO 406
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 406

Lys Leu Asp Val Gly Asn Ala Glu Val
1               5

<210> SEQ ID NO 407
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 407

Thr Phe Glu Phe Thr Ser Phe Phe Tyr
1               5

<210> SEQ ID NO 408
<211> LENGTH: 10
<212> TYPE: PRT
<213> ORGANISM: Artificial Sequence
<220> FEATURE:
```

```
<223> OTHER INFORMATION: Synthetic Immunogen

<400> SEQUENCE: 408

Ser Trp Pro Asp Gly Ala Glu Leu Pro Phe
1               5                   10

<210> SEQ ID NO 409
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 409

Gly Ile Leu Gly Phe Val Phe Thr Leu
1               5

<210> SEQ ID NO 410
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 410

Gly Ile Leu Gly Phe Val Phe Thr Leu
1               5

<210> SEQ ID NO 411
<211> LENGTH: 23
<212> TYPE: PRT
<213> ORGANISM: Artificial Sequence
<220> FEATURE:
<223> OTHER INFORMATION: Synthetic Immunogen

<400> SEQUENCE: 411

Ser Val Tyr Asp Phe Phe Val Trp Leu Lys Phe Phe His Arg Thr Cys
1               5                   10                  15

Lys Cys Thr Gly Asn Phe Ala
            20

<210> SEQ ID NO 412
<211> LENGTH: 15
<212> TYPE: PRT
<213> ORGANISM: Artificial Sequence
<220> FEATURE:
<223> OTHER INFORMATION: Synthetic Immunogen

<400> SEQUENCE: 412

Asp Leu Ala Gln Met Phe Phe Cys Phe Lys Glu Leu Glu Gly Trp
1               5                   10                  15

<210> SEQ ID NO 413
<211> LENGTH: 20
<212> TYPE: PRT
<213> ORGANISM: Artificial Sequence
<220> FEATURE:
<223> OTHER INFORMATION: Synthetic Immunogen

<400> SEQUENCE: 413

Ala Val Gly Ala Leu Glu Gly Pro Arg Asn Gln Asp Trp Leu Gly Val
1               5                   10                  15

Pro Arg Gln Leu
            20
```

```
<210> SEQ ID NO 414
<211> LENGTH: 9
<212> TYPE: PRT
<213> ORGANISM: Artificial Sequence
<220> FEATURE:
<223> OTHER INFORMATION: Synthetic Immunogen

<400> SEQUENCE: 414

Arg Ala His Tyr Asn Ile Val Thr Phe
1               5

<210> SEQ ID NO 415
<211> LENGTH: 12
<212> TYPE: PRT
<213> ORGANISM: Artificial Sequence
<220> FEATURE:
<223> OTHER INFORMATION: Modified peptide

<400> SEQUENCE: 415

Phe Phe Arg Lys Ser Ile Ile Asn Phe Glu Lys Leu
1               5                   10
```

AMINO SPHINGOGLYCOLIPID ANALOGUES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 930170_403USPC_SEQUENCE_LISTING.txt. The text file is 89 KB, was created on Dec. 1, 2016, and is being submitted electronically via EFS-Web.

FIELD OF INVENTION

This invention relates generally to certain sphingoglycolipid analogues and peptide derivatives thereof, compositions comprising these compounds, including pharmaceutical compositions and adjuvant compositions, processes for preparing the compounds, and methods of treating or preventing diseases or conditions using such compounds, especially diseases or conditions relating to cancer, infection, atopic disorders, autoimmune disease or diabetes.

BACKGROUND

Invariant natural killer T-cells (NKT) are a subset of T-cells that are implicated in a broad range of diseases. In some circumstances they can enhance the response to infection (Kinjo, Illarionov et al. 2011) and cancer (Wu, Lin et al. 2011) but also possess the ability to suppress autoimmune disease (Hong, Wilson et al. 2001) and type II diabetes. Activation of NKT cells can also lead to undesirable immune responses as related to allergy, (Wingender, Rogers et al. 2011) autoimmunity (Zeng, Liu et al. 2003) and atherosclerosis (Tupin, Nicoletti et al. 2004).

Unlike conventional T-cells that are restricted by major histocompatibility complex (MHC) molecules that present peptide antigens, NKT cells are uniquely restricted by CD1d proteins (Bendelac, Savage et al. 2007). CD1d proteins belong to the CD1 family that contains five members, CD1a-e. Like MHC molecules, the CD1 family members all contain an antigen binding region that is flanked by two anti-parallel α-helices that sit above a β-sheet. Unlike MHC molecules, the binding region of the CD1 protein contains two large hydrophobic binding pockets that are suited to bind lipid antigens rather than peptide-based antigens (Li, Girardi et al. 2010). α-Galactosylceramide (α-GalCer) potently activates human and mouse NKT cells (Kawano, Cui et al. 1997). In animal studies, α-GalCer is reported to be useful in the treatment of a number of diseases including cancer, (Morita, Motoki et al. 1995; Motoki, Morita et al. 1995) and autoimmune disease (Hong, Wilson et al. 2001). The compound has also been shown to function as a potent vaccine adjuvant in the treatment and prophylaxis of cancer and infectious disease (Silk, Hermans et al. 2004). This adjuvant activity has been attributed to stimulatory interactions between activated NKT cells and dendritic cells (DCs), the most potent antigen-presenting cells in the body. As a consequence, the DCs are rendered capable of promoting strong adaptive immune responses (Fujii, Shimizu et al. 2003; Hermans, Silk et al. 2003).

There is considerable interest in therapeutic vaccines for the treatment of cancer. The aim is to stimulate clonal expansion of T cells within a host that are capable of recognising and killing tumour cells, leaving normal tissues intact. This specificity relies on recognition of unique, tumour-derived, protein fragments presented by MHC molecules on the tumour cell surface. Vaccines used in this context typically involve injection of the defined tumour-associated "tumour antigens", or their peptide fragments, together with immune adjuvants capable of driving an immune response. In the absence of such adjuvants, the opposite outcome may ensue, with the tumour antigens actually being "tolerated" by the immune system rather than provoking tumour rejection. Advances in this therapy are therefore dependent on appropriate combinations of antigen and adjuvant (Speiser and Romero 2010).

When incorporated into a vaccine, α-GalCer must first be acquired by antigen-presenting cells in the host, and then presented to NKT cells within the local environment (Fujii, Shimizu et al. 2003; Hermans, Silk et al. 2003). This process brings the two cell-types into close association, permitting stimulatory signals to be passed from NKT cell to antigen-presenting cell.

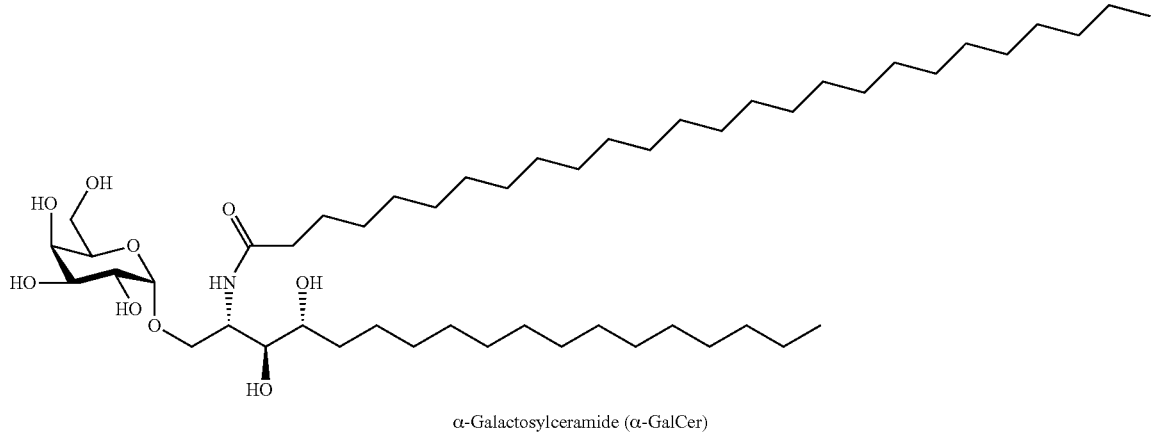

α-Galactosylceramide (α-GalCer)

Importantly, if the same antigen-presenting cells acquire the defined antigens of the vaccine, the stimulatory signals received through interaction with NKT cells can be translated directly into a superior capacity to provoke clonal proliferation of antigen-specific T cells with capacity to kill (Hermans, Silk et al. 2003; Semmling, Lukacs-Kornek et al. 2010). One way to achieve this is to load antigen-presenting cells ex vivo with antigenic material and NKT cell ligands (Petersen, Sika-Paotonu et al. 2010). Although a promising approach, in the clinic this requires leukapheresis and the ex vivo culturing of peripheral blood mononuclear cells (PBMC) over 7 days in a highly controlled sterile facility to generate sufficient antigen-presenting cells, which is a cumbersome and costly process. An alternative is to target antigen-presenting cells in vivo, with covalent attachment of antigen to NKT cell ligand ensuring entry into the same cell. Although used successfully with other immune adjuvant compounds, including the covalent attachment of a TLR2 agonist to MUC1 peptides (Cai, Huang et al. 2011), the approach has not been regarded as easily applicable to α-GalCer because the chemical attachment of peptide will result in a conjugate with significantly diminished, or no, capacity to stimulate NKT cells. In particular, the specific lipid moieties of α-GalCer are required for optimal binding into the A and F pockets of CD1d, and the polar head-group is required to be positioned appropriately for interaction with the T-cell receptor of the NKT cell (Borg, Wun et al. 2007), placing particularly tight constraints on the whole glycolipid structure for activity.

Although α-GalCer has considerable biological activity it does have limitations such as poor solubility, (Ebensen, Link et al. 2007) lack of efficacy in human clinical trials, (Giaccone, Punt et al. 2002) promotion of T-cell anergy (Parekh, Wilson et al. 2005) and the generation of both Th1 and Th2 cytokines which may contribute to mixed results in model studies.

It is an object of the invention to provide novel compounds or vaccines useful as agents for treating diseases or conditions relating to cancer, infection, autoimmune disease, atopic disorders or cancer, or to at least provide a useful alternative.

STATEMENTS OF INVENTION

In a first aspect, the invention provides a compound of formula (I):

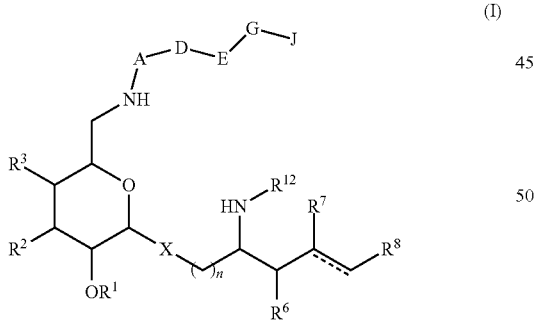

(I)

wherein:
A is a self-immolative linker group;
D is selected from the group consisting of:

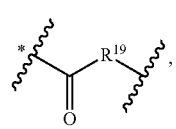

D1

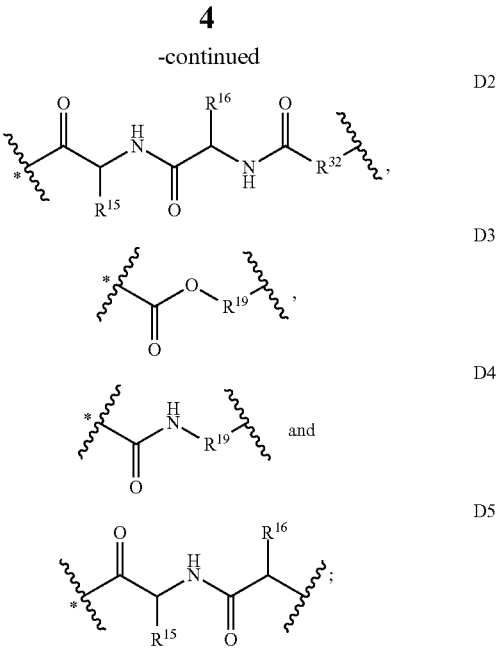

wherein * denotes a point of attachment of group D to group A;

$R^{15}$ is a side chain of one of the following amino acids: L-lysine, L-citrulline, L-arginine, L-glutamine or L-threonine;

$R^{16}$ is a side chain of a hydrophobic amino acid;

$R^{19}$ is an alkylene group;

$R^{32}$ is an alkylene group or an O-alkylene group wherein the O is attached to the carbonyl group of D2;

E is selected from the group consisting of:

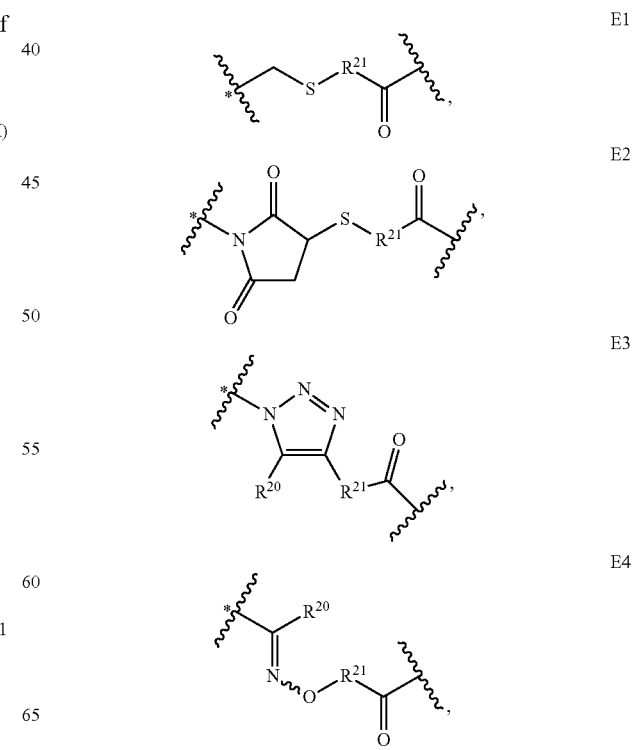

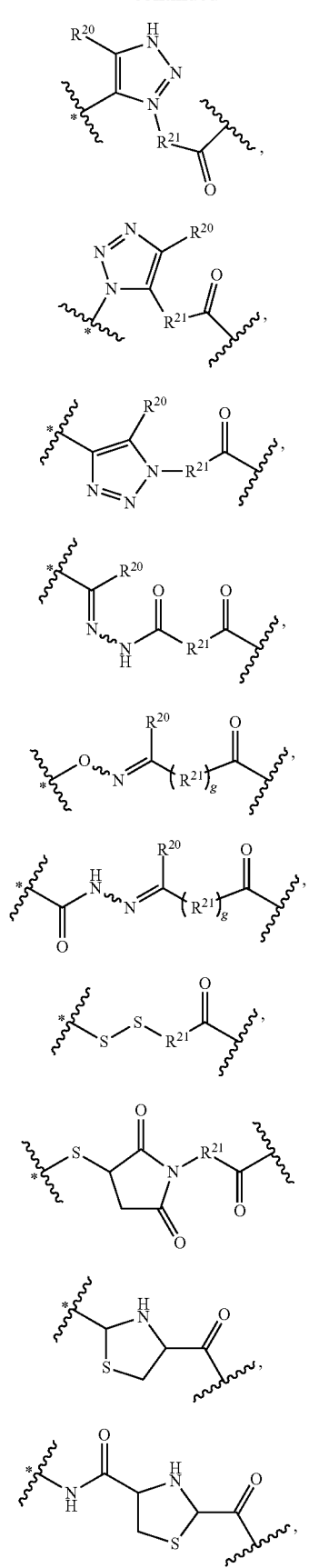
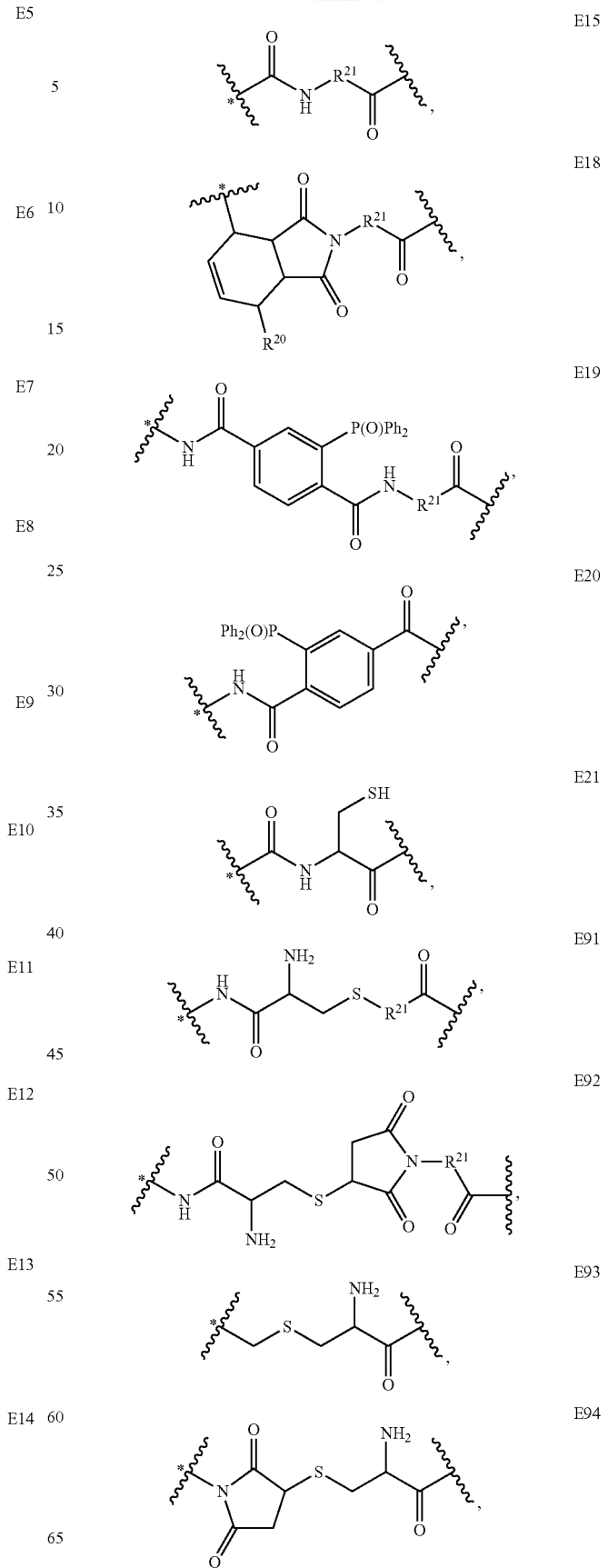

-continued

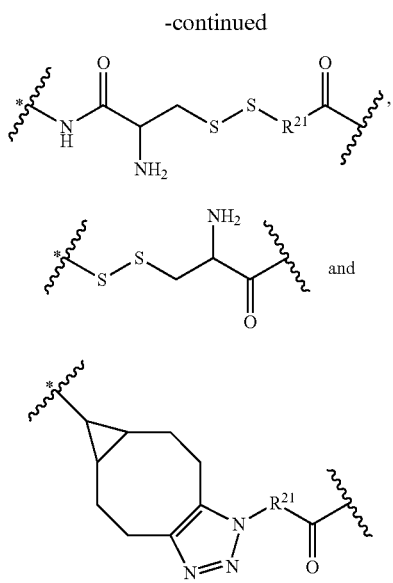

wherein * denotes a point of attachment of group E to group D;

$R^{20}$ is H or lower alkyl;

$R^{21}$ is an alkylene group;

g is 0 when $R^{20}$ is H or g is 1 when $R^{20}$ is lower alkyl;

provided that E is E18 only when D is D1, D2 or D3 and provided that E is E1, E2, E3, E4, E5, E6, E7, E8, E9, E10, E11, E12, E13, E15, E20, E21, E93, E94 or E96 only when D is D1, D2, D3 or D4; and provided that E is E91, E92 or E95 only when D is D5 and provided that E is E97 only when D is D2;

G is absent or G is an amino acid sequence of up to 6 amino acids, attached through its N-terminus to group E and through its C-terminus to group J;

J is a peptidic antigen, optionally substituted at its N and/or C-termini with up to 6 amino acids selected from the group of natural flanking residues for the antigen, and optionally terminated with $NH_2$ at the C-terminus so as to provide a C-terminal amide, and attached to group G through its N-terminus or, wherein G is absent, attached to group E through its N-terminus;

$R^1$ is H or glycosyl, provided that if $R^1$ is glycosyl then $R^2$ and $R^3$ are both OH;

$R^2$ is selected from the group consisting of H, OH, F and $OR^{10}$; provided that if $R^2$ is H, F or $OR^{10}$, then $R^1$ is H and $R^3$ is OH;

$R^3$ is selected from the group consisting of H, OH, F and $OR^{10}$; provided that if $R^3$ is H, F or $OR^{10}$, then $R^1$ is H and $R^2$ is OH;

$R^6$ is OH or H;

$R^7$ is OH or H;

when $R^7$ is H, ═══ denotes an optional double bond linking the carbon adjacent to $R^7$ with the carbon adjacent to $R^8$;

$R^8$ is H or $C_1$-$C_{15}$ alkyl having a straight or branched carbon chain, wherein the carbon chain optionally incorporates one or more double bonds, one or more triple bonds, one or more oxygen atoms and/or a terminal or non-terminal optionally substituted aryl group;

$R^{10}$ is glycosyl;

$R^{12}$ is $C_6$-$C_{30}$ acyl having a straight or branched carbon chain optionally substituted with one or more hydroxy groups at positions 2 and/or 3 of the acyl group and/or an optionally substituted chain terminating aryl group and which optionally incorporates one or more double bonds, one or more triple bonds, and/or one or more optionally substituted arylene groups and wherein the carbon chain is optionally substituted with one or more deuterium atoms; wherein the optional substituents on the aryl and arylene groups may be selected from halogen, cyano, dialkylamino, $C_1$-$C_6$ amide, nitro, $C_1$-$C_6$ alkoxy, $C_1$-$C_6$ acyloxy and $C_1$-$C_6$ thioalkyl;

X is O, $CH_2$ or S; wherein when X is $CH_2$ then the following must all be true: the stereochemistry of the 6-membered sugar ring in formula (I) is α-D-galacto; $R^1$ is H; $R^2$ and $R^3$ are both OH; and: either $R^6$ is OH and $R^7$ is OH and the stereochemistry at carbon atoms 2, 3 and 4 is (2S, 3S, 4R), (2S, 3S, 4S), (2R, 3S, 4S), (2R, 3S, 4R) or (2S, 3R, 4S); or $R^6$ is OH and $R^7$ is H, and $R^8$ is $C_{13}H_{27}$ and the stereochemistry at carbon atoms 2 and 3 is (2S, 3S); when X is S then the following must all be true: the stereochemistry of the 6-membered sugar ring in formula (I) is α-D-galacto; $R^1$ is H; $R^2$ and $R^3$ are both OH; and:

either $R^6$ is OH and $R^7$ is OH and the stereochemistry at carbon atoms 2, 3 and 4 is (2S, 3S, 4R); or $R^6$ is OH and $R^7$ is H and the stereochemistry at the carbon atoms 2 and 3 is (2S, 3S);

n is 1 when X is O or S; or n is 0 or 1 when X is $CH_2$;

or a pharmaceutically acceptable salt thereof.

Preferably, the compound of formula (I) is a compound of formula (Ia):

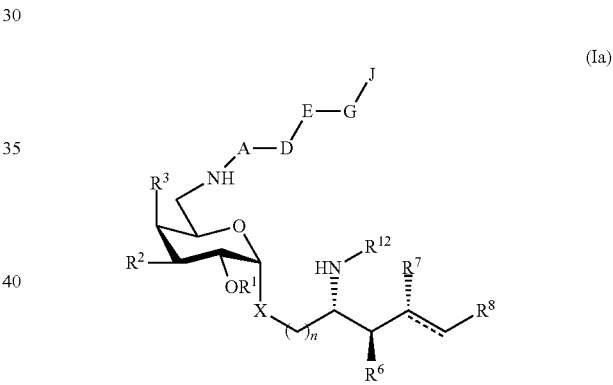

wherein X, $R^1$, $R^2$, $R^3$, $R^6$, $R^7$, $R^8$, $R^{10}$, $R^{12}$, $R^{15}$, $R^{16}$, $R^{19}$, $R^{20}$, $R^{21}$, $R^{32}$, n, g, A, D, E, G and J are all as defined above for formula (I);

or a pharmaceutically acceptable salt thereof.

Preferably the compound of formula (I) is a compound of formula (Ib):

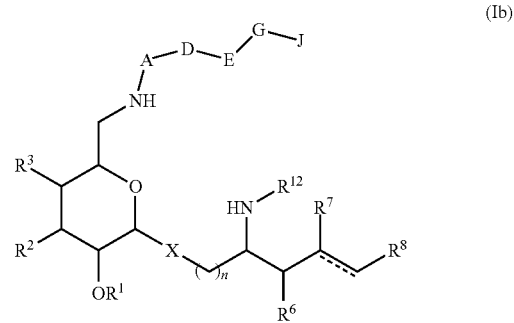

wherein:

A is a self-immolative linker group;

D is selected from the group consisting of:

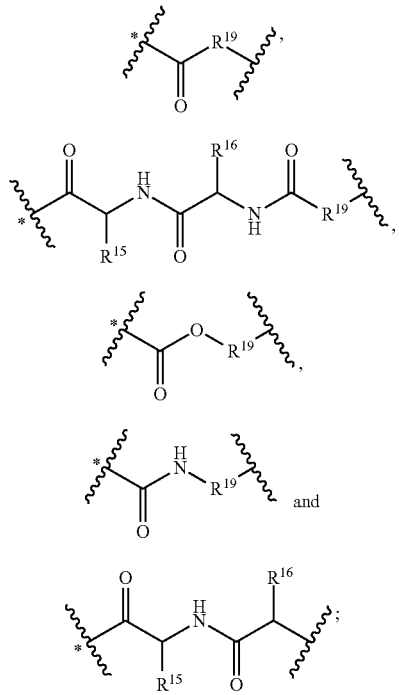

wherein * denotes a point of attachment of group D to group A;

$R^{15}$ is a side chain of one of the following amino acids: L-lysine, L-citrulline, L-arginine, L-glutamine or L-threonine;

$R^{16}$ is a side chain of a hydrophobic amino acid;

$R^{19}$ is an alkylene group;

E is selected from the group consisting of:

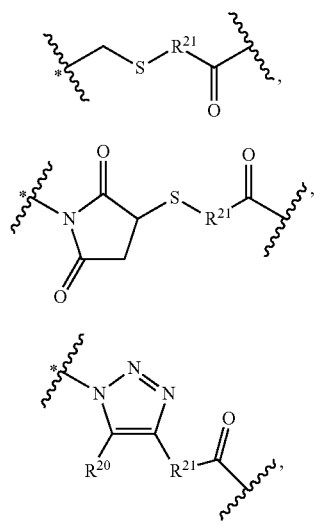

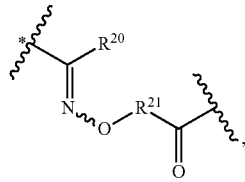

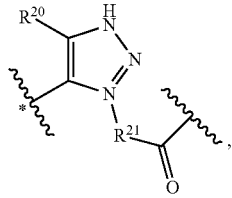

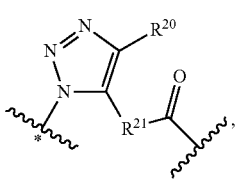

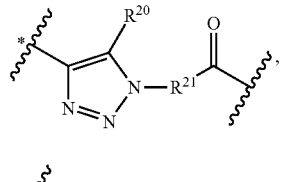

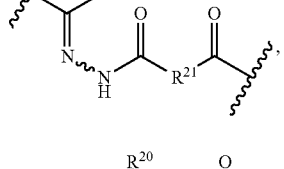

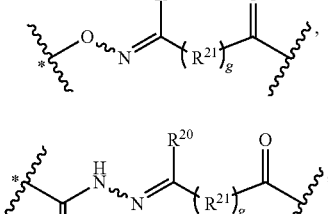

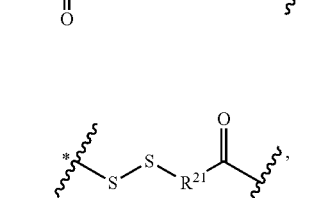

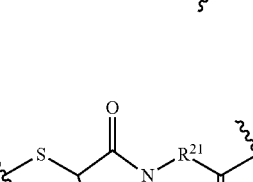

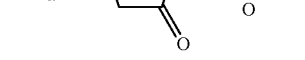

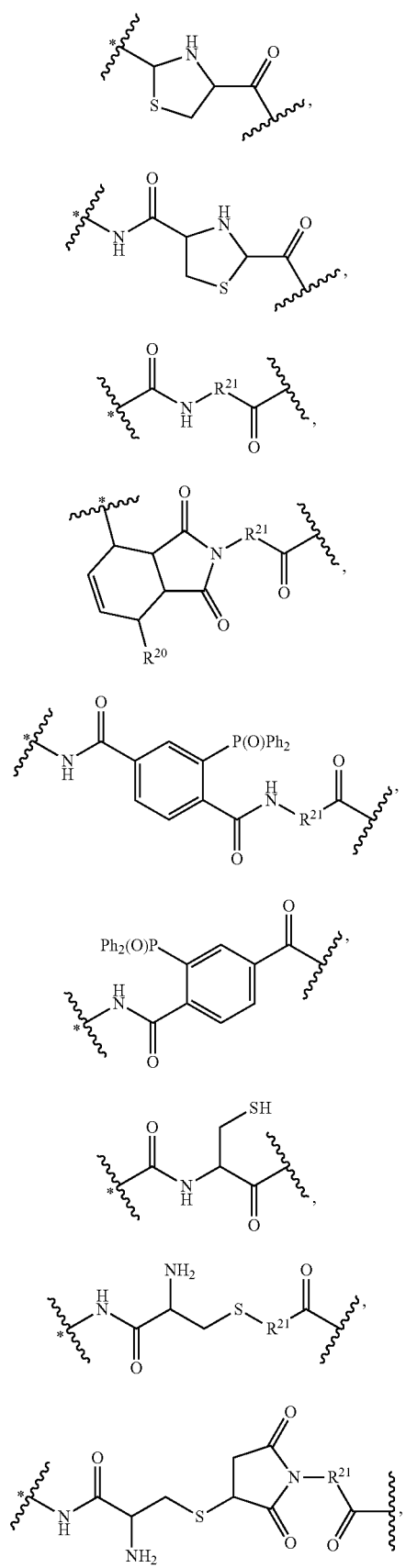

wherein * denotes a point of attachment of group E to group D;

$R^{20}$ is H or lower alkyl;

$R^{21}$ is an alkylene group;

g is 0 when $R^{20}$ is H or g is 1 when $R^{20}$ is lower alkyl;

provided that E is E18 only when D is D1, D2 or D3 and provided that E is E1, E2, E3, E4, E5, E6, E7, E8, E9, E10, E11, E12, E13, E15, E20, E21, E93, E94 or E96 only when D is D1, D2, D3 or D4; and provided that E is E91, E92 or E95 only when D is D5;

G is absent or G is an amino acid sequence of up to 6 amino acids, attached through its N-terminus to group E and through its C-terminus to group J;

J is a peptidic antigen, optionally substituted at its N and/or C-termini with up to 6 amino acids selected from the group of natural flanking residues for the antigen, and optionally terminated with $NH_2$ at the C-terminus so as to provide a C-terminal amide, and attached to group G through its N-terminus or, wherein G is absent, attached to group E through its N-terminus;

$R^1$ is H or glycosyl, provided that if $R^1$ is glycosyl then $R^2$ and $R^3$ are both OH;

$R^2$ is selected from the group consisting of H, OH, F and $OR^{10}$; provided that if $R^2$ is H, F or $OR^{10}$, then $R^1$ is H and $R^3$ is OH;

$R^3$ is selected from the group consisting of H, OH, F and $OR^{10}$; provided that if $R^3$ is H, F or $OR^{10}$, then $R^1$ is H and $R^2$ is OH;

$R^6$ is OH or H;

$R^7$ is OH or H;

when $R^7$ is H, ═══ denotes an optional double bond linking the carbon adjacent to $R^7$ with the carbon adjacent to $R^8$;

$R^8$ is H or $C_1$-$C_{15}$ alkyl having a straight or branched carbon chain, wherein the carbon chain optionally incorporates one or more double bonds, one or more triple bonds, one or more oxygen atoms and/or a terminal or non-terminal optionally substituted aryl group;

$R^{10}$ is glycosyl;

$R^{12}$ is $C_6$-$C_{30}$ acyl having a straight or branched carbon chain optionally substituted with one or more hydroxy groups at positions 2 and/or 3 of the acyl group and/or an optionally substituted chain terminating aryl group and which optionally incorporates one or more double bonds, one or more triple bonds, and/or one or more optionally substituted arylene groups and wherein the carbon chain is optionally substituted with one or more deuterium atoms; wherein the optional substituents on the aryl and arylene groups may be selected from halogen, cyano, dialkylamino, $C_1$-$C_6$ amide, nitro, $C_1$-$C_6$ alkoxy, $C_1$-$C_6$ acyloxy and $C_1$-$C_6$ thioalkyl;

X is O, $CH_2$ or S; wherein when X is $CH_2$ then the following must all be true: the stereochemistry of the 6-membered sugar ring in formula (I) is α-D-galacto; $R^1$ is H; $R^2$ and $R^3$ are both OH; and:

either $R^6$ is OH and $R^7$ is OH and the stereochemistry at carbon atoms 2, 3 and 4 is (2S, 3S, 4R), (2S, 3S, 4S), (2R, 3S, 4S), (2R, 3S, 4R) or (2S, 3R, 4S); or $R^6$ is OH and $R^7$ is H, and $R^8$ is $C_{13}H_{27}$ and the stereochemistry at carbon atoms 2 and 3 is (2S, 3S);

when X is S then the following must all be true: the stereochemistry of the 6-membered sugar ring in formula (I) is α-D-galacto; $R^1$ is H; $R^2$ and $R^3$ are both OH; and:

either $R^6$ is OH and $R^7$ is OH and the stereochemistry at carbon atoms 2, 3 and 4 is (2S, 3S, 4R); or $R^6$ is OH and $R^7$ is H and the stereochemistry at the carbon atoms 2 and 3 is (2S, 3S);

n is 1 when X is O or S; or n is 0 or 1 when X is $CH_2$;

or a pharmaceutically acceptable salt thereof.

In another aspect, the invention provides a compound of formula (II):

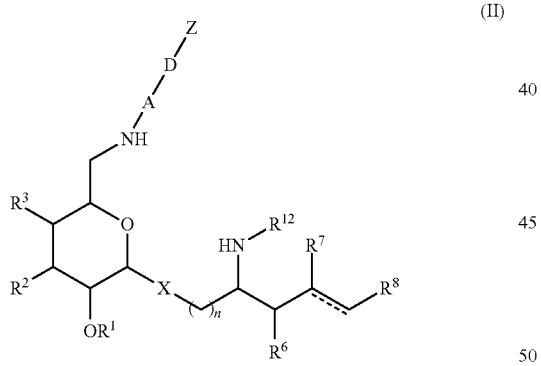

(II)

wherein A, D, X, $R^1$, $R^2$, $R^3$, $R^6$, $R^7$, $R^8$, $R^{10}$, $R^{12}$, $R^{15}$, $R^{16}$, $R^{32}$, and n are all as defined above for formula (I);

Z is selected from the group consisting of:

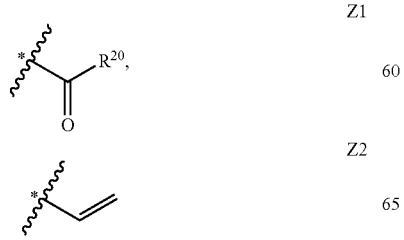

Z1

Z2

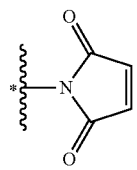

Z3

Z4

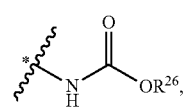

Z5

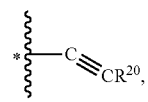

Z7

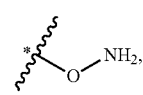

Z8

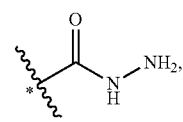

Z9

Z10

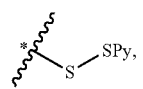

Z11

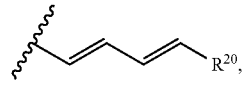

Z12

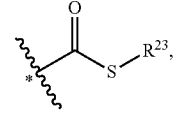

Z13

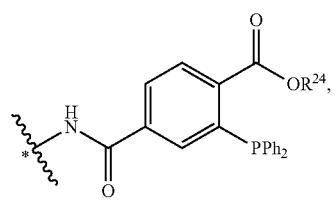

Z14

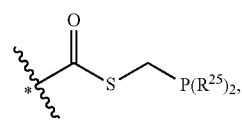

Z15

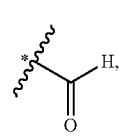

Z16

-continued

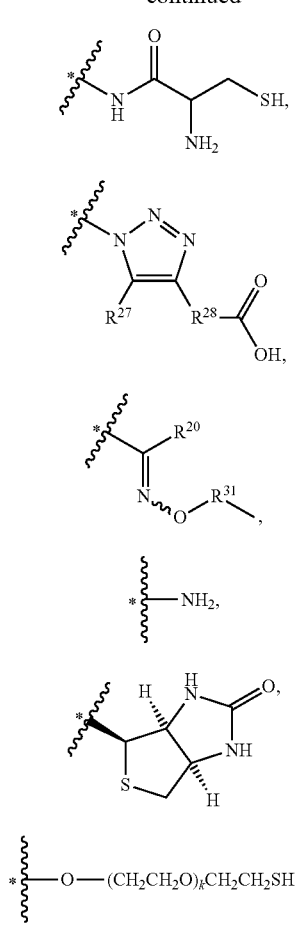

Z17

Z18

Z19

Z20

Z21

Z22

Z23 wherein * denotes a point of attachment of group Z to group D, except as defined for Z23;
$R^{20}$ is as defined above for formula (I);
$R^{23}$ is aryl, aralkyl or optionally substituted alkyl;
$R^{24}$ is lower alkyl;
$R^{25}$ is p-$C_6H_4$L wherein L is H, methoxy, COOH, C(O)NHCH$_2$COOH or CH$_2$CH$_2$NMe$_2$;
$R^{26}$ is aralkyl;
$R^{27}$ is H or lower alkyl;
$R^{28}$ is alkylene;
$R^{31}$ is (CH$_2$CH$_2$O)$_k$
k is an integer from 2 to 100;
W is an optionally substituted cyclooctynyl ring; or W is a fused bicyclic or tricyclic ring system comprising an optionally substituted cyclooctynyl ring fused to one or more aryl groups or one or more cycloalkyl groups; wherein the cyclooctynyl ring optionally contains a N atom within the ring, which N atom is optionally substituted with an acyl group; and wherein the cyclooctynyl ring is optionally substituted with one or more substituents selected from the group consisting of halogen, hydroxyl, alkoxy and aralkyl wherein the aryl part of this group is optionally substituted with a carboxylic acid; and wherein * or one of the optional substituents comprises a point of attachment of Z23 to group D;

provided that Z is Z1, Z2, Z3, Z4, Z7, Z8, Z9, Z10, Z11, Z13, Z15, Z16, Z17 or Z18 only when D is D1, D2, D3 or D4 and provided that Z is Z12 only when D is D1, D2 or D3 and provided that Z is Z5 or Z20 only when D is D5, and provided that Z is Z21, Z22 or Z23 only when D is D2;

or a pharmaceutically acceptable salt thereof.

Preferably, the compound of formula (II) is a compound of formula (IIa):

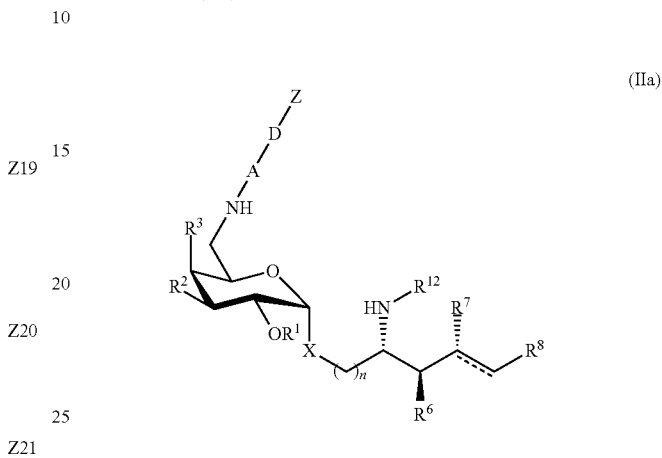

(IIa)

wherein A, D, X, Z, $R^1$, $R^2$, $R^3$, $R^6$, $R^7$, $R^8$, $R^{10}$, $R^{12}$, $R^{15}$, $R^{16}$, $R^{19}$, $R^{20}$, $R^{21}$, $R^{23}$, $R^{24}$, $R^{25}$, $R^{26}$, $R^{27}$, $R^{28}$, $R^{31}$, W, k and n are all as defined above for formula (II);

or a pharmaceutically acceptable salt thereof.

Preferably, the compound of formula (II) is a compound of formula (IIb):

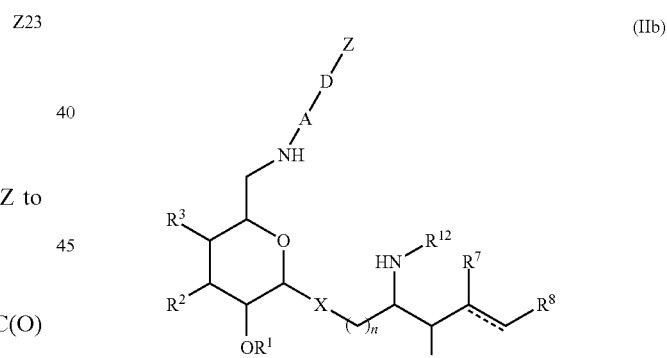

(IIb)

wherein A, D, X, $R^1$, $R^2$, $R^3$, $R^6$, $R^7$, $R^8$, $R^{10}$, $R^{12}$, $R^{15}$, $R^{16}$, $R^{19}$ and n are all as defined above for formula (Ib);

Z is selected from the group consisting of:

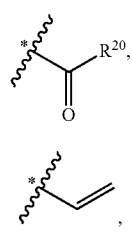

Z1

Z2

-continued

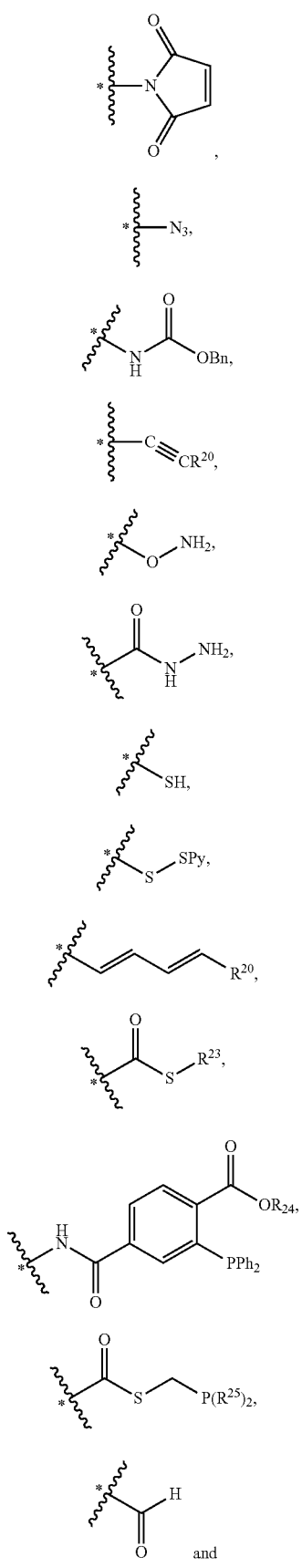

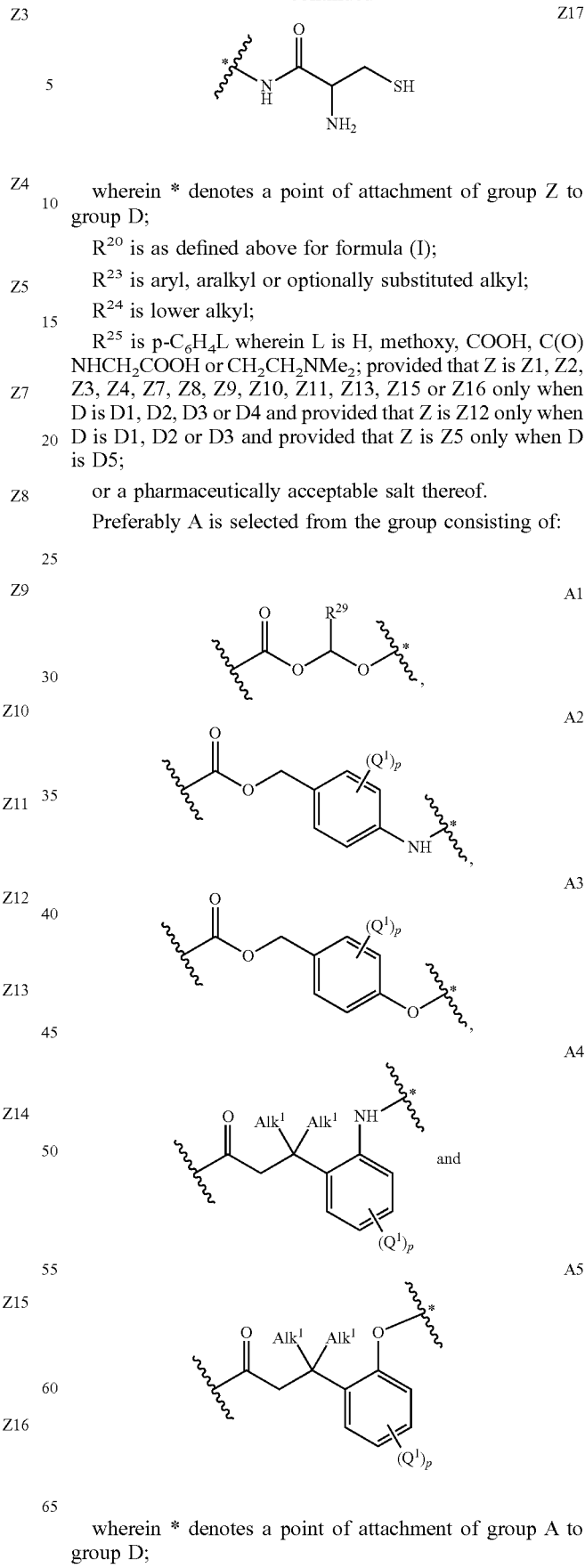

wherein * denotes a point of attachment of group Z to group D;

R²⁰ is as defined above for formula (I);

R²³ is aryl, aralkyl or optionally substituted alkyl;

R²⁴ is lower alkyl;

R²⁵ is p-C₆H₄L wherein L is H, methoxy, COOH, C(O)NHCH₂COOH or CH₂CH₂NMe₂; provided that Z is Z1, Z2, Z3, Z4, Z7, Z8, Z9, Z10, Z11, Z13, Z15 or Z16 only when D is D1, D2, D3 or D4 and provided that Z is Z12 only when D is D1, D2 or D3 and provided that Z is Z5 only when D is D5;

or a pharmaceutically acceptable salt thereof.

Preferably A is selected from the group consisting of:

wherein * denotes a point of attachment of group A to group D;

each $Q^1$, the same or different, is independently selected from the group consisting of H, alkyl, alkoxy, halogen, nitro, aryl; or, together with the ring to which it is attached, forms a fused bicyclic aryl group;

p is an integer from 1 to 4;

$Alk^1$ is $C_1$-$C_4$ straight chain alkyl; and $R^{29}$ is H or lower alkyl;

provided that A is A1 only when D is D1 and provided that A is A2 only when D is D2, D3 or D5 and provided that A is A3 only when D is D1, D3 or D4 and provided that A is A4 only when D is D2, D3 or D5 and provided that A is A5 only when D is D1, D3 or D4.

More preferably, A is A1 or A2. Still more preferably, A is A1 wherein $R^{29}$ is H, or A is A2 wherein $Q^1$ is H.

Preferably, $Q^1$ in A2 or A3 is H. More preferably $Q^1$ in A2 or A3 is H and p is 4. Alternatively preferably, $Q^1$ in A2 or A3 is Me or OMe and p is 2, wherein the Me or OMe groups are situated ortho- to the heteroatom on the aromatic ring.

Preferably D is D1.

Alternatively preferably D is D2.

Alternatively preferably D is D3.

Alternatively preferably D is D4.

Alternatively preferably D is D5.

Preferably $R^{15}$ is selected from the group consisting of:

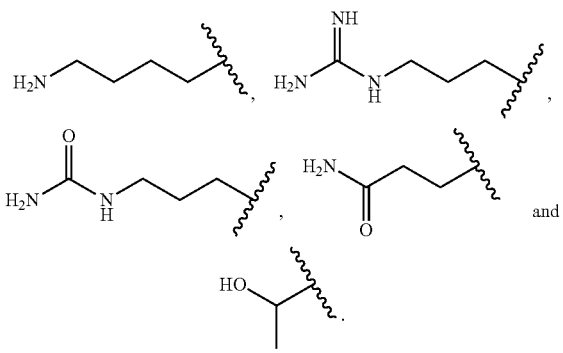

More preferably $R^{15}$ is selected from the group consisting of:

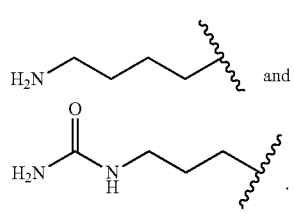

Still more preferably $R^{15}$ is

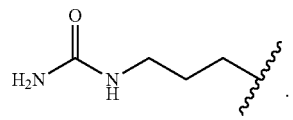 [SMILES: *CCCNC(N)=O]

Preferably $R^{16}$ is a side chain of one of the following amino acids: L-phenylalanine, L-valine, L-leucine, L-isoleucine, L-norleucine, L-methionine, L-tryptophan or L-tyrosine; that is, preferably $R^{16}$ is selected from the group consisting of:

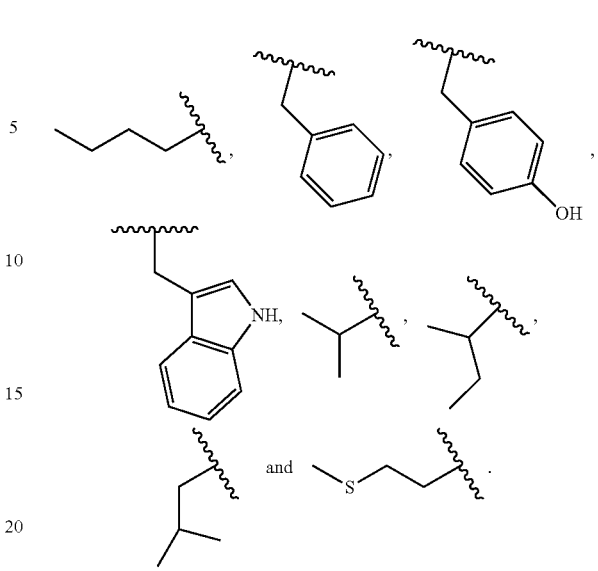

More preferably $R^{16}$ is selected from the group consisting of:

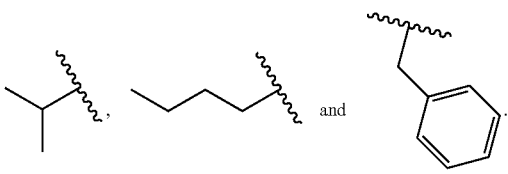

Still more preferably $R^{15}$ is

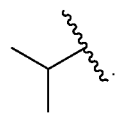

Preferably E is any one of E1 to E8, E93 or E94. More preferably E is any one of E1 to E4, E93 or E94.

Preferably E is E3 wherein $R^{20}$ is H. Alternatively preferably E is E4 wherein $R^{20}$ is methyl.

Alternatively preferably E is E7 wherein $R^{20}$ is H.

Alternatively preferably E is E97.

Preferably E is E97 when D is D2, wherein $R^{32}$ is O-alkylene, preferably $OCH_2$.

Most preferably E is:

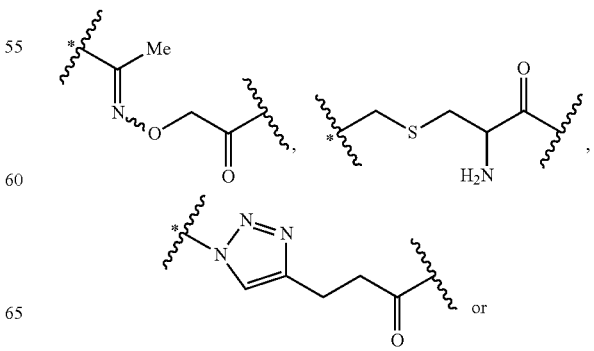

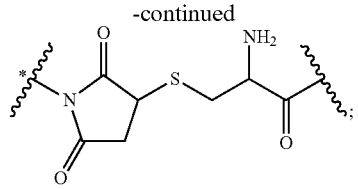

wherein * denotes a point of attachment of group E to group D.

Preferably Z is Z23, Z22, Z21, Z20, Z19, Z18, Z4, Z3 or Z1. Most preferably Z is Z4.

Preferably W is a cyclooctynyl ring fused to a cycloalkyl ring, preferably a cyclopropyl ring.

Preferably Z23 is

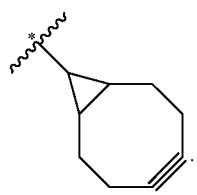 [SMILES: *C1C2CCC#CCCC12]

Preferably k is an integer from 10 to 32. More preferably k is an integer from 19 to 32. More preferably k is 10.

Preferably G is

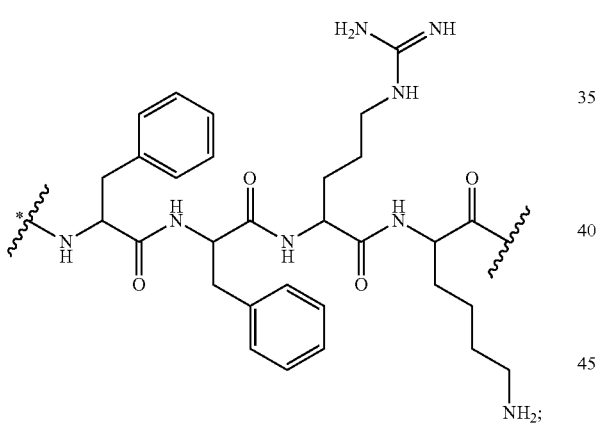

wherein * denotes a point of attachment of group G to group E.

Alternatively preferably G is absent.

Preferably J is a peptide that contains within its sequence one or more epitopes that bind to MHC molecules and induce T cell responses.

More preferably J is selected from the group consisting of:

| | |
|---|---|
| AMLGTHTMEV, | (SEQ ID NO: 1) |
| MLGTHTMEV, | (SEQ ID NO: 2) |
| EAAGIGILTV, | (SEQ ID NO: 3) |
| AAGIGILTV, | (SEQ ID NO: 4) |
| AADHRQLQLSISSCLQQL, | (SEQ ID NO: 5) |
| AAGIGILTVILGVL, | (SEQ ID NO: 6) |
| AARAVFLAL, | (SEQ ID NO: 7) |
| ACDPHSGHFV, | (SEQ ID NO: 8) |
| ACYEFLWGPRALVETS, | (SEQ ID NO: 9) |
| ADHRQLQLSISSCLQQL, | (SEQ ID NO: 10) |
| AEEAAGIGILT, | (SEQ ID NO: 11) |
| AEEAAGIGIL, | (SEQ ID NO: 12) |
| AELVHFLLL, | (SEQ ID NO: 13) |
| AELVHFLLLKYRAR, | (SEQ ID NO: 14) |
| AEPINIQTW, | (SEQ ID NO: 15) |
| AFLPWHRLF, | (SEQ ID NO: 16) |
| AGATGGRGPRGAGA, | (SEQ ID NO: 17) |
| ALCRWGLLL, | (SEQ ID NO: 18) |
| ALDVYNGLL, | (SEQ ID NO: 19) |
| ALFDIESKV, | (SEQ ID NO: 20) |
| ALGGHPLLGV, | (SEQ ID NO: 21) |
| ALIHHNTHL, | (SEQ ID NO: 22) |
| ALKDVEERV, | (SEQ ID NO: 23) |
| ALLAVGATK, | (SEQ ID NO: 24) |
| ALLEIASCL, | (SEQ ID NO: 25) |
| ALNFPGSQK, | (SEQ ID NO: 26) |
| ALPYWNFATG, | (SEQ ID NO: 27) |
| ALSVMGVYV, | (SEQ ID NO: 28) |
| ALWPWLLMAT, | (SEQ ID NO: 29) |
| ALWPWLLMA, | (SEQ ID NO: 30) |

ALYVDSLFFL, (SEQ ID NO: 31)

ANDPIFVVL, (SEQ ID NO: 32)

APPAYEKLSAEQ, (SEQ ID NO: 33)

APRGPHGGAASGL, (SEQ ID NO: 34)

APRGVRMAV, (SEQ ID NO: 35)

ARGPESRLL, (SEQ ID NO: 36)

ASGPGGGAPR, (SEQ ID NO: 37)

ATGFKQSSKALQRPVAS, (SEQ ID NO: 38)

AVCPWTWLR, (SEQ ID NO: 39)

AWISKPPGV, (SEQ ID NO: 40)

AYVCGIQNSVSANRS, (SEQ ID NO: 41)

CATWKVICKSCISQTPG, (SEQ ID NO: 42)

CEFHACWPAFTVLGE, (SEQ ID NO: 43)

CLSRRPWKRSWSAGSCPGMPHL, (SEQ ID NO: 44)

CMTWNQMNL, (SEQ ID NO: 45)

CQWGRLWQL, (SEQ ID NO: 46)

CTACRWKKACQR, (SEQ ID NO: 47)

DPARYEFLW, (SEQ ID NO: 48)

DTGFYTLHVIKSDLVNEEATGQFRV, (SEQ ID NO: 49)

DVTFNIICKKCG, (SEQ ID NO: 50)

EAAGIGILTV, (SEQ ID NO: 51)

EADPTGHSY, (SEQ ID NO: 52)

EAFIQPITR, (SEQ ID NO: 53)

EDLTVKIGDFGLATEKSRWSGSHQFEQLS, (SEQ ID NO: 54)

EEAAGIGILTVI, (SEQ ID NO: 55)

EEKLIVVLF, (SEQ ID NO: 56)

EFYLAMPFATPM, (SEQ ID NO: 57)

EGDCAPEEK, (SEQ ID NO: 58)

EIIYPNASLLIQN, (SEQ ID NO: 59)

EKIQKAFDDIAKYFSK, (SEQ ID NO: 60)

ELTLGEFLKL, (SEQ ID NO: 61)

ELVRRILSR, (SEQ ID NO: 62)

ESRLLEFYLAMPF, (SEQ ID NO: 63)

ETVSEQSNV, (SEQ ID NO: 64)

EVDPASNTY, (SEQ ID NO: 65)

EVDPIGHLY, (SEQ ID NO: 66)

EVDPIGHVY, (SEQ ID NO: 67)

EVISCKLIKR, (SEQ ID NO: 68)

EVYDGREHSA, (SEQ ID NO: 69)

EYLQLVFGI, (SEQ ID NO: 70)

EYLSLSDKI, (SEQ ID NO: 71)

EYSKECLKEF, (SEQ ID NO: 72)

EYVIKVSARVRF, (SEQ ID NO: 73)

FIASNGVKLV, (SEQ ID NO: 74)

FINDEIFVEL, (SEQ ID NO: 75)

FLDEFMEGV, (SEQ ID NO: 76)

FLEGNEVGKTY, (SEQ ID NO: 77)

FLFLLFFWL, (SEQ ID NO: 78)

FLIIWQNTM, (SEQ ID NO: 79)

FLLHHAFVDSIFEQWLQRHRP, (SEQ ID NO: 80)

FLLLKYRAREPVTKAE, (SEQ ID NO: 81)

FLTPKKLQCV, (SEQ ID NO: 82)

FLWGPRALV, (SEQ ID NO: 83)

FMNKFIYEI, (SEQ ID NO: 84)

FMVEDETVL, (SEQ ID NO: 85)

FPSDSWCYF, (SEQ ID NO: 86)

FRSGLDSYV, (SEQ ID NO: 87)

FSWAMDLDPKGA, (SEQ ID NO: 88)

GARGPESRLLEFYLAMPFATPMEAELARRSLAQDAPPL, (SEQ ID NO: 89)

GDNQIMPKAGLLIIV, (SEQ ID NO: 90)

GELIGILNAAKVPAD, (SEQ ID NO: 91)

GFKQSSKAL, (SEQ ID NO: 92)

GLASFKSFLK, (SEQ ID NO: 93)

GLCTLVAML, (SEQ ID NO: 94)

GLPPDVQRV, (SEQ ID NO: 95)

GLYDGMEHLI, (SEQ ID NO: 96)

GRAMLGTHTMEVTVY, (SEQ ID NO: 97)

GVALQTMKQ, (SEQ ID NO: 98)

GVGSPYVSRLLGICL, (SEQ ID NO: 99)

AKFVAAWTLKAAA, (SEQ ID NO: 100)

GVLLKEFTVSGNILTIRLT, (SEQ ID NO: 101)

GVLVGVALI, (SEQ ID NO: 102)

GVYDGREHTV, (SEQ ID NO: 103)

HLFGYSWYK, (SEQ ID NO: 104)

HLIRVEGNLRVE, (SEQ ID NO: 105)

HLSTAFARV, (SEQ ID NO: 106)

HLYQGCQVV, (SEQ ID NO: 107)

HQQYFYKIPILVINK, (SEQ ID NO: 108)

HTMEVTVYHR, (SEQ ID NO: 109)

IALNFPGSQK, (SEQ ID NO: 110)

IGRIAECILGMNPSR, (SEQ ID NO: 111)

IISAVVGIL, (SEQ ID NO: 112)

ILAKFLHWL, (SEQ ID NO: 113)

ILDSSEEDK, (SEQ ID NO: 114)

ILDTAGREEY, (SEQ ID NO: 115)

ILHNGAYSL, (SEQ ID NO: 116)

ILSRDAAPLPRPG, (SEQ ID NO: 117)

ILTVILGVL, (SEQ ID NO: 118)

IMDQVPFFS, (SEQ ID NO: 119)

IMDQVPFSV, (SEQ ID NO: 120)

IMIGVLVGV, (SEQ ID NO: 121)

INKTSGPKRGKHAWTHRLRE, (SEQ ID NO: 122)

ISGGPRISY, (SEQ ID NO: 123)

ISPNSVFSQWRVVCDSLEDYD, (SEQ ID NO: 124)

ISQAVHAAHAEINEAGR, (SEQ ID NO: 125)

ITDQVPFSV, (SEQ ID NO: 126)

ITKKVADLVGF, (SEQ ID NO: 127)

KASEKIFYV, (SEQ ID NO: 128)

KAVYNFATM, (SEQ ID NO: 129)

KCDICTDEY, (SEQ ID NO: 130)

KEFTVSGNILT, (SEQ ID NO: 131)

KEFTVSGNILTI, (SEQ ID NO: 132)

KELEGILLL, (SEQ ID NO: 133)

KHAWTHRLRERKQLVVYEEI, (SEQ ID NO: 134)

KIFGSLAFL, (SEQ ID NO: 135)

KIFSEVTLK, (SEQ ID NO: 136)

KIFYVYMKRKYEAM, (SEQ ID NO: 137)

KIFYVYMKRKYEAMT, (SEQ ID NO: 138)

KILDAVVAQK, (SEQ ID NO: 139)

KINKNPKYK, (SEQ ID NO: 140)

KISQAVHAAHAEINEAGRESIINFEKLTEWT, (SEQ ID NO: 141)

KKLLTQHFVQENYLEY, (SEQ ID NO: 142)

KMDAEHPEL, (SEQ ID NO: 143)

KNCEPVVPNAPPAYEKLSAE, (SEQ ID NO: 144)

KRYFKLSHLQMHSRKH, (SEQ ID NO: 145)

KSSEKIVYVYMKLNYEVMTK, (SEQ ID NO: 146)

KTWGQYWQV, (SEQ ID NO: 147)

KVAELVHFL, (SEQ ID NO: 148)

KVHPVIWSL, (SEQ ID NO: 149)

KVLEYVIKV, (SEQ ID NO: 150)

KYDCFLHPF, (SEQ ID NO: 151)

KYVGIEREM, (SEQ ID NO: 152)

LAALPHSCL, (SEQ ID NO: 153)

LAAQERRVPR, (SEQ ID NO: 154)

LAGIGILTV, (SEQ ID NO: 155)

LAMPFATPM, (SEQ ID NO: 156)

LGFKVTLPPFMRSKRAADFH, (SEQ ID NO: 157)

LGPGRPYR, (SEQ ID NO: 158)

LHHAFVDSIF, (SEQ ID NO: 159)

LIYRRRLMK, (SEQ ID NO: 160)

LKEFTVSGNILTIRL, (SEQ ID NO: 161)

LKLSGVVRL, (SEQ ID NO: 162)

LLANGRMPTVLQCVN, (SEQ ID NO: 163)

LLDGTATLRL, (SEQ ID NO: 164)

LLEFYLAMPFATPM, (SEQ ID NO: 165)

LLEFYLAMPFATPMEAELARRSLAQ, (SEQ ID NO: 166)

LLFGLALIEV, (SEQ ID NO: 167)

LLGATCMFV, (SEQ ID NO: 168)

LLGPGRPYR, (SEQ ID NO: 169)

LLGRNSFEV, (SEQ ID NO: 170)

LLKYRAREPVTKAE, (SEQ ID NO: 171)

LLLDDLLVSI, (SEQ ID NO: 172)

LLLLTVLTV, (SEQ ID NO: 173)

LLWSFQTSA, (SEQ ID NO: 174)

LLYKLADLI, (SEQ ID NO: 175)

LMLQNALTTM, (SEQ ID NO: 176)

LPAVVGLSPGEQEY, (SEQ ID NO: 177)

LPHSSSHWL, (SEQ ID NO: 178)

LPRWPPPQL, (SEQ ID NO: 179)

LPSSADVEF, (SEQ ID NO: 180)

LSHLQMHSRKH, (SEQ ID NO: 181)

LSRLSNRLL, (SEQ ID NO: 182)

LTDLQPYMRQFVAHL, (SEQ ID NO: 183)

LWWVNNQSLPVSP, (SEQ ID NO: 184)

LYATVIHDI, (SEQ ID NO: 185)

LYSACFWWL, (SEQ ID NO: 186)

LYVDSLFFL, (SEQ ID NO: 187)

MEVDPIGHLY, (SEQ ID NO: 188)

MIAVFLPIV, (SEQ ID NO: 189)

MIFEKHGFRRTTPP, (SEQ ID NO: 190)

MKLNYEVMTKLGFKVTLPPF, (SEQ ID NO: 191)

MLAVISCAV, (SEQ ID NO: 192)

MLLAVLYCL, (SEQ ID NO: 193)

MLMAQEALAFL, (SEQ ID NO: 194)

MPFATPMEA, (SEQ ID NO: 195)

MPREDAHFIYGYPKKGHGHS, (SEQ ID NO: 196)

MSLQRQFLR, (SEQ ID NO: 197)

MVKISGGPR, (SEQ ID NO: 198)

NLVPMVATV, (SEQ ID NO: 199)

NPPSMVAAGSVVAAV, (SEQ ID NO: 200)

NSIVKSITVSASG, (SEQ ID NO: 201)

NSNHVASGAGEAAIETQSSSSEEIV, (SEQ ID NO: 202)

NSQPVWLCL, (SEQ ID NO: 203)

NTYASPRFK, (SEQ ID NO: 204)

NYARTEDFF, (SEQ ID NO: 205)

NYKRCFPVI, (SEQ ID NO: 206)

NYNNFYRFL, (SEQ ID NO: 207)

PDTRPAPGSTAPPAHGVTSA, (SEQ ID NO: 208)

PFATPMEAELARR, (SEQ ID NO: 209)

PGSTAPPAHGVT, (SEQ ID NO: 210)

PGTRVRAMAIYKQ, (SEQ ID NO: 211)

PGVLLKEFTVSGNILTIRLTAADHR, (SEQ ID NO: 212)

PLLENVISK, (SEQ ID NO: 213)

PLPPARNGGL, (SEQ ID NO: 214)

PLQPEQLQV, (SEQ ID NO: 215)

PLTSIISAV, (SEQ ID NO: 216)

PRALAETSYVKVLEY, (SEQ ID NO: 217)

PVTWRRAPA, (SEQ ID NO: 218)

PYYFAAELPPRNLPEP, (SEQ ID NO: 219)

QCSGNFMGF, (SEQ ID NO: 220)

QCTEVRADTRPWSGP, (SEQ ID NO: 221)

QGAMLAAQERRVPRAAEVPR, (SEQ ID NO: 222)

QGQHFLQKV, (SEQ ID NO: 223)

QLAVSVILRV, (SEQ ID NO: 224)

QNILLSNAPLGPQFP, (SEQ ID NO: 225)

QQITKTEV, (SEQ ID NO: 226)

QRPYGYDQIM, (SEQ ID NO: 227)

QYSWFVNGTF, (SEQ ID NO: 228)

RAGLQVRKNK, (SEQ ID NO: 229)

REPFTKAEMLGSVIR, (SEQ ID NO: 230)

REPVTKAEML, (SEQ ID NO: 231)

RIAECILGM, (SEQ ID NO: 232)

RKVAELVHFLLLKYR, (SEQ ID NO: 233)

RKVAELVHFLLLKYRA, (SEQ ID NO: 234)

RLLEFYLAMPFA, (SEQ ID NO: 235)

RLLQETELV, (SEQ ID NO: 236)

RLMKQDFSV, (SEQ ID NO: 237)

RLPRIFCSC, (SEQ ID NO: 238)

RLSSCVPVA, (SEQ ID NO: 239)

RLVDDFLLV, (SEQ ID NO: 240)

RMPEAAPPV, (SEQ ID NO: 241)

RMPTVLQCVNVSVVS, (SEQ ID NO: 242)

RNGYRALMDKS, (SEQ ID NO: 243)

RNGYRALMDKSLHVGTQCALTRR, (SEQ ID NO: 244)

RPGLLGASVLGLDDI, (SEQ ID NO: 245)

RPHVPESAF, (SEQ ID NO: 246)

| | |
|---|---|
| RQKRILVNL, | (SEQ ID NO: 247) |
| RSDSGQQARY, | (SEQ ID NO: 248) |
| RTKQLYPEW, | (SEQ ID NO: 249) |
| RVIKNSIRLTL, | (SEQ ID NO: 250) |
| RVRFFFPSL, | (SEQ ID NO: 251) |
| RYQLDPKFI, | (SEQ ID NO: 252) |
| SAFPTTINF, | (SEQ ID NO: 253) |
| SAWISKPPGV, | (SEQ ID NO: 254) |
| SAYGEPRKL, | (SEQ ID NO: 255) |
| SEIWRDIDF, | (SEQ ID NO: 256) |
| SELFRSGLDSY, | (SEQ ID NO: 257) |
| SESIKKKVL, | (SEQ ID NO: 258) |
| SESLKMIF, | (SEQ ID NO: 259) |
| SFSYTLLSL, | (SEQ ID NO: 260) |
| SHETVIIEL, | (SEQ ID NO: 261) |
| SIINFEKL, | (SEQ ID NO: 262) |
| SLADTNSLAV, | (SEQ ID NO: 263) |
| SLFEGIDIYT, | (SEQ ID NO: 264) |
| SLFPNSPKWTSK, | (SEQ ID NO: 265) |
| SLFRAVITK, | (SEQ ID NO: 266) |
| SLGWLFLLL, | (SEQ ID NO: 267) |
| SLLMWITQC, | (SEQ ID NO: 268) |
| SLLMWITQCFLPVF, | (SEQ ID NO: 269) |
| SLLQHLIGL, | (SEQ ID NO: 270) |
| SLPYWNFATG, | (SEQ ID NO: 271) |
| SLSKILDTV, | (SEQ ID NO: 272) |
| SLYKFSPFPL, | (SEQ ID NO: 273) |
| SLYSFPEPEA, | (SEQ ID NO: 274) |
| SNDGPTLI, | (SEQ ID NO: 275) |
| SPRWWPTCL, | (SEQ ID NO: 276) |
| SPSSNRIRNT, | (SEQ ID NO: 277) |
| SQKTYQGSY, | (SEQ ID NO: 278) |
| SRFGGAVVR, | (SEQ ID NO: 279) |
| SSALLSIFQSSPE, | (SEQ ID NO: 280) |
| SSDYVIPIGTY, | (SEQ ID NO: 281) |
| SSKALQRPV, | (SEQ ID NO: 282) |
| SSPGCQPPA, | (SEQ ID NO: 283) |
| STAPPVHNV, | (SEQ ID NO: 284) |
| SVASTITGV, | (SEQ ID NO: 285) |
| SVDYFFVWL, | (SEQ ID NO: 286) |
| SVSESDTIRSISIAS, | (SEQ ID NO: 287) |
| SVYDFFVWL, | (SEQ ID NO: 288) |
| SYLDSGIHF, | (SEQ ID NO: 289) |
| SYLQDSDPDSFQD, | (SEQ ID NO: 290) |
| TFPDLESEF, | (SEQ ID NO: 291) |
| TGRAMLGTHTMEVTVYH, | (SEQ ID NO: 292) |
| TLDSQVMSL, | (SEQ ID NO: 293) |
| TLDWLLQTPK, | (SEQ ID NO: 294) |
| TLEEITGYL, | (SEQ ID NO: 295) |
| TLMSAMTNL, | (SEQ ID NO: 296) |
| TLNDECWPA, | (SEQ ID NO: 297) |
| TLPGYPPHV, | (SEQ ID NO: 298) |
| TLYQDDTLTLQAAG, | (SEQ ID NO: 299) |
| TMKQICKKEIRRLHQY, | (SEQ ID NO: 300) |

-continued

TMNGSKSPV, (SEQ ID NO: 301)

TPRLPSSADVEF, (SEQ ID NO: 302)

TSCILESLFRAVITK, (SEQ ID NO: 303)

TSEKRPFMCAY, (SEQ ID NO: 304)

TSYVKVLHHMVKISG, (SEQ ID NO: 305)

TTEWVETTARELPIPEPE, (SEQ ID NO: 306)

TVSGNILTIR, (SEQ ID NO: 307)

TYACFVSNL, (SEQ ID NO: 308)

TYLPTNASL, (SEQ ID NO: 309)

TYYRPGVNLSLSC, (SEQ ID NO: 310)

VAELVHFLL, (SEQ ID NO: 311)

VFGIELMEVDPIGHL, (SEQ ID NO: 312)

VGQDVSVLFRVTGALQ, (SEQ ID NO: 313)

VIFSKASSSLQL, (SEQ ID NO: 314)

VISNDVCAQV, (SEQ ID NO: 315)

VLDGLDVLL, (SEQ ID NO: 316)

VLFYLGQY, (SEQ ID NO: 317)

VLHWDPETV, (SEQ ID NO: 318)

VLLKEFTVSG, (SEQ ID NO: 319)

VLLQAGSLHA, (SEQ ID NO: 320)

VLPDVFIRCV, (SEQ ID NO: 321)

VLPDVFIRC, (SEQ ID NO: 322)

VLRENTSPK, (SEQ ID NO: 323)

VLYRYGSFSV, (SEQ ID NO: 324)

VPGVLLKEFTVSGNILTIRLTAADHR, (SEQ ID NO: 325)

VPLDCVLYRY, (SEQ ID NO: 326)

VRIGHLYIL, (SEQ ID NO: 327)

-continued

VSSFFSYTL, (SEQ ID NO: 328)

VVLGVVFGI, (SEQ ID NO: 329)

VVPCEPPEV, (SEQ ID NO: 330)

VVVGAVGVG, (SEQ ID NO: 331)

VYFFLPDHL, (SEQ ID NO: 332)

WEKMKASEKIFYVYMKRK, (SEQ ID NO: 333)

WLPFGFILI, (SEQ ID NO: 334)

WNRQLYPEWTEAQRLD, (SEQ ID NO: 335)

WQYFFPVIF, (SEQ ID NO: 336)

WRRAPAPGA, (SEQ ID NO: 337)

YACFVSNLATGRNNS, (SEQ ID NO: 338)

YFSKKEWEKMKSSEKIVYVY, (SEQ ID NO: 339)

YLEPGPVTA, (SEQ ID NO: 340)

YLEPGPVTV, (SEQ ID NO: 341)

YLNDHLEPWI, (SEQ ID NO: 342)

YLQLVFGIEV, (SEQ ID NO: 343)

YLSGANLNL, (SEQ ID NO: 344)

YLVPQQGFFC, (SEQ ID NO: 345)

YMDGTMSQV, (SEQ ID NO: 346)

YMIMVKCWMI, (SEQ ID NO: 347)

YRPRPRRY, (SEQ ID NO: 348)

YSVYFNLPADTIYTN, (SEQ ID NO: 349)

YSWRINGIPQQHTQV, (SEQ ID NO: 350)

YVDFREYEYY, (SEQ ID NO: 351)

YYWPRPRRY, (SEQ ID NO: 352)

IMDQVPFFS, (SEQ ID NO: 353)

SVDYFFVWL, (SEQ ID NO: 354)

-continued

ALFDIESKV, (SEQ ID NO: 355)

NLVPMVATV (SEQ ID NO: 356)
and

GLCTLVAML, (SEQ ID NO: 357)

SVASTITGV, (SEQ ID NO: 358)

VMAGDIYSV, (SEQ ID NO: 359)

ALADGVQKV, (SEQ ID NO: 360)

LLGATCMFV, (SEQ ID NO: 361)

SVFAGVVGV, (SEQ ID NO: 362)

ALFDGDPHL, (SEQ ID NO: 363)

YVDPVITSI, (SEQ ID NO: 364)

STAPPVHNV, (SEQ ID NO: 365)

LAALPHSCL, (SEQ ID NO: 366)

SQDDIKGIQKLYGKRS, (SEQ ID NO: 367)

FLPSDFFPSV (SEQ ID NO: 368)

FLPSDFFPSV, (SEQ ID NO: 369)

TLGEFLKLDRERAKN, (SEQ ID NO: 370)

TFSYVDPVITSISPKYGMET, (SEQ ID NO: 371)

AMTQLLAGV, (SEQ ID NO: 372)

KVFAGIPTV, (SEQ ID NO: 373)

AIIDGVESV, (SEQ ID NO: 374)

GLWHHQTEV, (SEQ ID NO: 375)

NLDTLMTYV, (SEQ ID NO: 376)

KIQEILTQV, (SEQ ID NO: 377)

LTFGDVVAV, (SEQ ID NO: 378)

TMLARLASA, (SEQ ID NO: 379)

IMDQVPFSV, (SEQ ID NO: 380)

MHQKRTAMFQDPQERPRKLPQLCTELQTTIHD, (SEQ ID NO: 381)

-continued

LPQLCTELQTTI, (SEQ ID NO: 382)

HDIILECVYCKQQLLRREVY, (SEQ ID NO: 383)

KQQLLRREVYDFAFRDLCIVYRDGN, (SEQ ID NO: 384)

RDLCIVYRDGNPYAVCDKCLKFYSKI, (SEQ ID NO: 385)

DKCLKFYSKISEYRHYCYSLYGTTL, (SEQ ID NO: 386)

HYCYSLYGTTLEQQYNKPLCDLLIR, (SEQ ID NO: 387)

YGTTLEQQYNKPLCDLLIRCINCQKPLCPEEK, (SEQ ID NO: 388)

RCINCQKPLCPEEKQRHLDKKQRFHNIRGRWT, (SEQ ID NO: 389)

DKKQRFHNIRGRWTGRCMSCCRSSRTRRETQL, (SEQ ID NO: 390)

MHGDTPTLHEYMLDLQPETTDLYCYEQLNDSSEEE, (SEQ ID NO: 391)

LYCYEQLNDSSEEEDEIDGPAGQAEPDRAHYNIVT, (SEQ ID NO: 392)

GQAEPDRAHYNIVTFCCKCDSTLRLCVQSTHVDIR, (SEQ ID NO: 393)

TLRLCVQSTHVDIRTLEDLLMGTLGIVCPICSQKP, (SEQ ID NO: 394)

ALPFGFILV, (SEQ ID NO: 395)

TLADFDPRV, (SEQ ID NO: 396)

IMDQVPFSV, (SEQ ID NO: 397)

SIMTYDFHGA, (SEQ ID NO: 398)

AQYIKANSKFIGITEL, (SEQ ID NO: 399)

FLYDDNQRV, (SEQ ID NO: 400)

YLIELIDRV, (SEQ ID NO: 401)

NLMEQPIKV, (SEQ ID NO: 402)

FLAEDALNTV, (SEQ ID NO: 403)

ALMEQQHYV, (SEQ ID NO: 404)

ILDDIGHGV, (SEQ ID NO: 405)

KLDVGNAEV, (SEQ ID NO: 406)

TFEFTSFFY, (SEQ ID NO: 407)

SWPDGAELPF, (SEQ ID NO: 408)

```
                           (SEQ ID NO: 409)
    GILGFVFTL, (SEQ ID NO: 410)
    ILRGSVAHK (SEQ ID NO: 411)
    SVYDFFVWLKFFHRTCKCTGNFA, (SEQ ID NO: 412)
    DLAQMFFCFKELEGW, (SEQ ID NO: 413)
    AVGALEGPRNQDWLGVPRQL
    and (SEQ ID NO: 414)
    RAHYNIVTF.
```

Still more preferably J is selected from the group consisting of:

```
                           (SEQ ID NO: 397)
    IMDQVPFSV, (SEQ ID NO: 341)
    YLEPGPVTV, (SEQ ID NO: 155)
    LAGIGILTV, (SEQ ID NO: 346)
    YMDGTMSQV, (SEQ ID NO: 262)
    SIINFEKL, (SEQ ID NO: 125)
    ISQAVHAAHAEINEAGR, (SEQ ID NO: 141)
    KISQAVHAAHAEINEAGRESIINFEKLTEWT, (SEQ ID NO: 129)
    KAVYNFATM, (SEQ ID NO: 194)
    MLMAQEALAFL, (SEQ ID NO: 268)
    SLLMWITQC, (SEQ ID NO: 89)
    GARGPESRLLEFYLAMPFATPMEAELARRSLAQDAPPL, (SEQ ID NO: 325)
    VPGVLLKEFTVSGNILTIRLTAADHR, (SEQ ID NO: 63)
    ESRLLEFYLAMPF, (SEQ ID NO: 269)
    SLLMWITQCFLPVF, (SEQ ID NO: 116)
    ILHNGAYSL, (SEQ ID NO: 99)
    GVGSPYVSRLLGICL, (SEQ ID NO: 100)
    AKFVAAWTLKAAA, (SEQ ID NO: 353)
    IMDQVPFFS, (SEQ ID NO: 354)
    SVDYFFVWL, (SEQ ID NO: 355)
    ALFDIESKV, (SEQ ID NO: 356)
    NLVPMVATV
    and (SEQ ID NO: 357)
    GLCTLVAML.
```

Alternatively more preferably J is selected from the group consisting of:

```
                           (SEQ ID NO: 358)
    SVASTITGV, (SEQ ID NO: 359)
    VMAGDIYSV, (SEQ ID NO: 360)
    ALADGVQKV, (SEQ ID NO: 361)
    LLGATCMFV, (SEQ ID NO: 362)
    SVFAGVVGV, (SEQ ID NO: 363)
    ALFDGDPHL, (SEQ ID NO: 364)
    YVDPVITSI, (SEQ ID NO: 365)
    STAPPVHNV, (SEQ ID NO: 366)
    LAALPHSCL, (SEQ ID NO: 367)
    SQDDIKGIQKLYGKRS, (SEQ ID NO: 368)
    FLPSDFFPSV, (SEQ ID NO: 369)
    FLPSDFFPSV, (SEQ ID NO: 370)
    TLGEFLKLDRERAKN, (SEQ ID NO: 371)
    TFSYVDPVITSISPKYGMET, (SEQ ID NO: 372)
    AMTQLLAGV, (SEQ ID NO: 373)
    KVFAGIPTV, (SEQ ID NO: 374)
    AIIDGVESV, (SEQ ID NO: 375)
    GLWHHQTEV, (SEQ ID NO: 376)
    NLDTLMTYV, (SEQ ID NO: 377)
    KIQEILTQV, (SEQ ID NO: 378)
    LTFGDVVAV, (SEQ ID NO: 379)
    TMLARLASA,
```

```
                                         (SEQ ID NO: 380)
IMDQVPFSV, (SEQ ID NO: 381)
MHQKRTAMFQDPQERPRKLPQLCTELQTTIHD, (SEQ ID NO: 382)
LPQLCTELQTTI, (SEQ ID NO: 383)
HDIILECVYCKQQLLRREVY, (SEQ ID NO: 384)
KQQLLRREVYDFAFRDLCIVYRDGN, (SEQ ID NO: 385)
RDLCIVYRDGNPYAVCDKCLKFYSKI, (SEQ ID NO: 386)
DKCLKFYSKISEYRHYCYSLYGTTL, (SEQ ID NO: 387)
HYCYSLYGTTLEQQYNKPLCDLLIR, (SEQ ID NO: 388)
YGTTLEQQYNKPLCDLLIRCINCQKPLCPEEK, (SEQ ID NO: 389)
RCINCQKPLCPEEKQRHLDKKQRFHNIRGRWT, (SEQ ID NO: 390)
DKKQRFHNIRGRWTGRCMSCCRSSRTRRETQL, (SEQ ID NO: 391)
MHGDTPTLHEYMLDLQPETTDLYCYEQLNDSSEEE, (SEQ ID NO: 392)
LYCYEQLNDSSEEEDEIDGPAGQAEPDRAHYNIVT, (SEQ ID NO: 393)
GQAEPDRAHYNIVTFCCKCDSTLRLCVQSTHVDIR, (SEQ ID NO: 394)
TLRLCVQSTHVDIRTLEDLLMGTLGIVCPICSQKP, (SEQ ID NO: 395)
ALPFGFILV, (SEQ ID NO: 396)
TLADFDPRV, (SEQ ID NO: 397)
IMDQVPFSV, (SEQ ID NO: 398)
SIMTYDFHGA, (SEQ ID NO: 400)
FLYDDNQRV, (SEQ ID NO: 401)
YLIELIDRV, (SEQ ID NO: 402)
NLMEQPIKV, (SEQ ID NO: 403)
FLAEDALNTV, (SEQ ID NO: 404)
ALMEQQHYV, (SEQ ID NO: 405)
ILDDIGHGV,
and (SEQ ID NO: 406)
KLDVGNAEV.
```

Preferably Z is any one of Z1 to Z5. Still more preferably Z is Z1. Still more preferably Z is Z1 wherein $R^{20}$ is methyl.

Preferably the stereochemistry of the 6-membered sugar ring of formula (I) or formula (II) is α-D-galacto.

Preferably $R^6$ is OH and $R^7$ is OH and the stereochemistry at carbon atoms 2, 3 and 4 is (2S, 3S, 4R). More preferably the stereochemistry of the 6-membered sugar ring of formula (I) or formula (II) is α-D-galacto and $R^6$ is OH and $R^7$ is OH and the stereochemistry at carbon atoms 2, 3 and 4 is (2S, 3S, 4R).

Preferably X is O. More preferably X is O and the stereochemistry of the 6-membered sugar ring of formula (I) or formula (II) is α-D-galacto and $R^6$ is OH and $R^7$ is OH and the stereochemistry at carbon atoms 2, 3 and 4 is (2S, 3S, 4R).

Preferably $R^{23}$ is 2-sulfoethyl.

Preferably $R^{12}$ is $C_{26}$ acyl having a straight or branched carbon chain optionally substituted with one or more hydroxy groups at positions 2 and/or 3 of the acyl group and/or an optionally substituted chain terminating aryl group and which optionally incorporates one or more double bonds, one or more triple bonds, and/or one or more optionally substituted arylene groups and wherein the carbon chain is optionally substituted with one or more deuterium atoms; wherein the optional substituents on the aryl and arylene groups may be selected from halogen, cyano, dialkylamino, $C_1$-$C_6$ amide, nitro, $C_1$-$C_6$ alkoxy, $C_1$-$C_6$ acyloxy and $C_1$-$C_6$ thioalkyl. More preferably, $R^{12}$ is $C_{26}$ acyl.

Alternatively preferably $R^{12}$ is $C_{11}$ acyl having a straight or branched carbon chain optionally substituted with one or more hydroxy groups at positions 2 and/or 3 of the acyl group and/or an optionally substituted chain terminating aryl group and which optionally incorporates one or more double bonds, one or more triple bonds, and/or one or more optionally substituted arylene groups and wherein the carbon chain is optionally substituted with one or more deuterium atoms; wherein the optional substituents on the aryl and arylene groups may be selected from halogen, cyano, dialkylamino, $C_1$-$C_6$ amide, nitro, $C_1$-$C_6$ alkoxy, $C_1$-$C_6$ acyloxy and $C_1$-$C_6$ thioalkyl. More preferably, $R^{12}$ is $C_{11}$ acyl.

Preferably $R^8$ is $C_{10}$ to $C_{14}$ alkyl having a straight or branched carbon chain, wherein the carbon chain optionally incorporates one or more double bonds, one or more triple bonds, one or more oxygen atoms and/or a terminal or non-terminal optionally substituted aryl group. More preferably, $R^8$ is $C_{10}$ to $C_{14}$ alkyl.

Even more preferably, $R^8$ is $C_{13}$ alkyl having a straight or branched carbon chain, wherein the carbon chain optionally incorporates one or more double bonds, one or more triple bonds, one or more oxygen atoms and/or a terminal or non-terminal optionally substituted aryl group. Most preferably, $R^8$ is $C_{13}$ alkyl.

Preferably, n in formula (I) or formula (II) is 1, the stereochemistry of the 6-membered sugar ring of formula (I) or formula (II) is α-D-galacto, $R^6$ is OH and $R^7$ is OH. It is further preferred that n in formula (I) or formula (II) is 1, the stereochemistry of the 6-membered sugar ring of formula (I) or formula (II) is α-D-galacto, $R^6$ is OH, $R^7$ is OH and the stereochemistry at carbon atoms 2, 3 and 4 is (2S, 3S, 4R).

Alternatively preferably, n in formula (I) or formula (II) is 0, X is $CH_2$, the stereochemistry of the 6-membered sugar ring of formula (I) or formula (II) is α-D-galacto, $R^6$ is OH and $R^7$ is OH. It is further preferred that n in formula (I) or formula (II) is 0, the stereochemistry of the 6-membered sugar ring of formula (I) or formula (II) is α-D-galacto, $R^6$ is OH, $R^7$ is OH and the stereochemistry at carbon atoms 2, 3 and 4 is (2S, 3S, 4R).

Preferably, in formula (I) or formula (II) when X is O, $R^6$ is OH, $R^7$ is H, $R^8$ is $C_1$-$C_{15}$ alkyl and ═══ is a double bond linking the carbon adjacent to $R^7$ with the carbon adjacent to $R^8$, then the stereochemistry at the carbon atoms 2, 3 is (2S, 3R).

Preferably $R^1$ is H.

It is also preferred that $R^2$ is OH. More preferably $R^1$ is H and $R^2$ is OH.

Preferably $R^3$ is OH.

Preferably $R^6$ is OH.

Preferably $R^7$ is OH. More preferably $R^6$ and $R^7$ are both OH.

Alternatively it is preferred that one of $R^6$ and $R^7$ is H.

Preferably, $R^8$ is $C_1$-$C_{15}$ alkyl having a straight or branched carbon chain, wherein the carbon chain optionally incorporates one or more double bonds, one or more triple bonds, one or more oxygen atoms and/or a terminal or non-terminal optionally substituted aryl group.

More preferably, $R^8$ is $C_1$-$C_{15}$ alkyl. Most preferably, $R^8$ is $C_1$-$C_{15}$ alkyl having a straight or branched carbon chain.

Preferably $R^8$ is $C_{13}$ alkyl having a straight or branched carbon chain, wherein the carbon chain optionally incorporates one or more double bonds, one or more triple bonds, one or more oxygen atoms and/or a terminal or non-terminal optionally substituted aryl group.

More preferably $R^8$ is $C_{13}$ alkyl. Most preferably, $R^8$ is $C_{13}$ alkyl having a straight carbon chain.

Alternatively preferably $R^8$ is $C_5$ alkyl having a straight or branched carbon chain, wherein the carbon chain optionally incorporates one or more double bonds, one or more triple bonds, one or more oxygen atoms and/or a terminal or non-terminal optionally substituted aryl group.

More preferably $R^8$ is $C_5$ alkyl. Most preferably, $R^8$ is $R_5$ alkyl having a straight carbon chain.

Still more preferably $R^8$ is $C_1$-$C_{15}$ alkyl, $R^7$ is $OR^{12}$ and $R^6$ is OH. Still more preferably $R^8$ is $C_1$-$C_{15}$ alkyl, $R^7$ is $OR^{12}$, $R^6$ is OH and X is O.

Preferably $R^{12}$ is acyl having a straight carbon chain from 6 to 30 carbon atoms long. More preferably $R^{12}$ is $C_{26}$ acyl. More preferably $R^{12}$ is $C_{26}$ acyl having a straight carbon chain. More preferably X is O and $R^{12}$ is acyl having a straight carbon chain from 6 to 30 carbon atoms long.

Alternatively preferably $R^{12}$ is acyl having a straight carbon chain from 6 to 30 carbon atoms long and having an optionally substituted chain terminating aryl group.

More preferably $R^{12}$ is $C_{11}$ acyl having an optionally substituted chain terminating aryl group.

Still more preferably the optionally substituted aryl group is phenyl, optionally substituted with a halogen, e.g. a fluorine, e.g. the optionally substituted aryl group is p-fluorophenyl. More preferably X is O and $R^{12}$ is acyl having a straight carbon chain from 6 to 30 carbon atoms long and having an optionally substituted chain terminating aryl group.

Preferably $R^{26}$ is benzyl.

Preferably any halogen in the compound of formula (I) or (II) is fluorine.

Preferably the compound of formula (I) is a compound selected from the group consisting of:

(a) 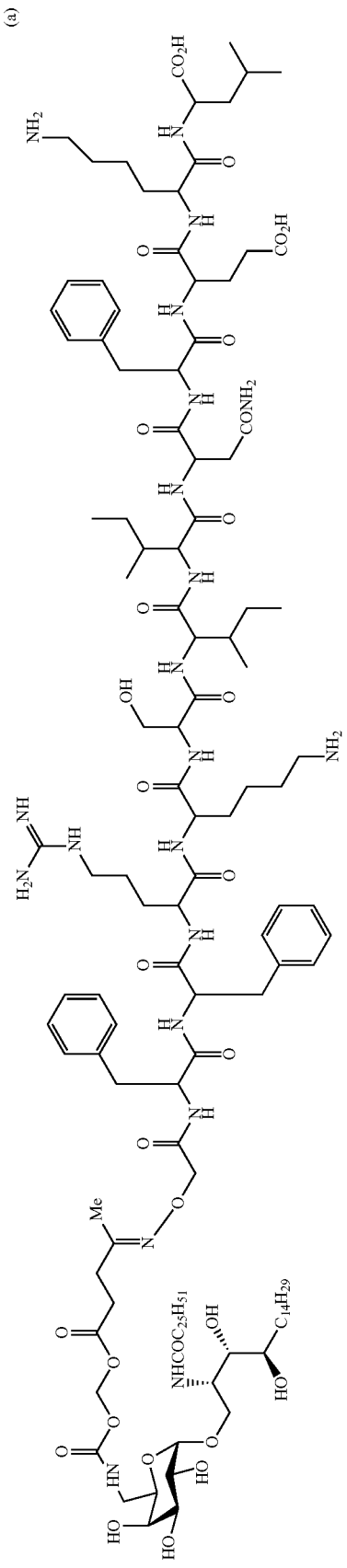
(b) 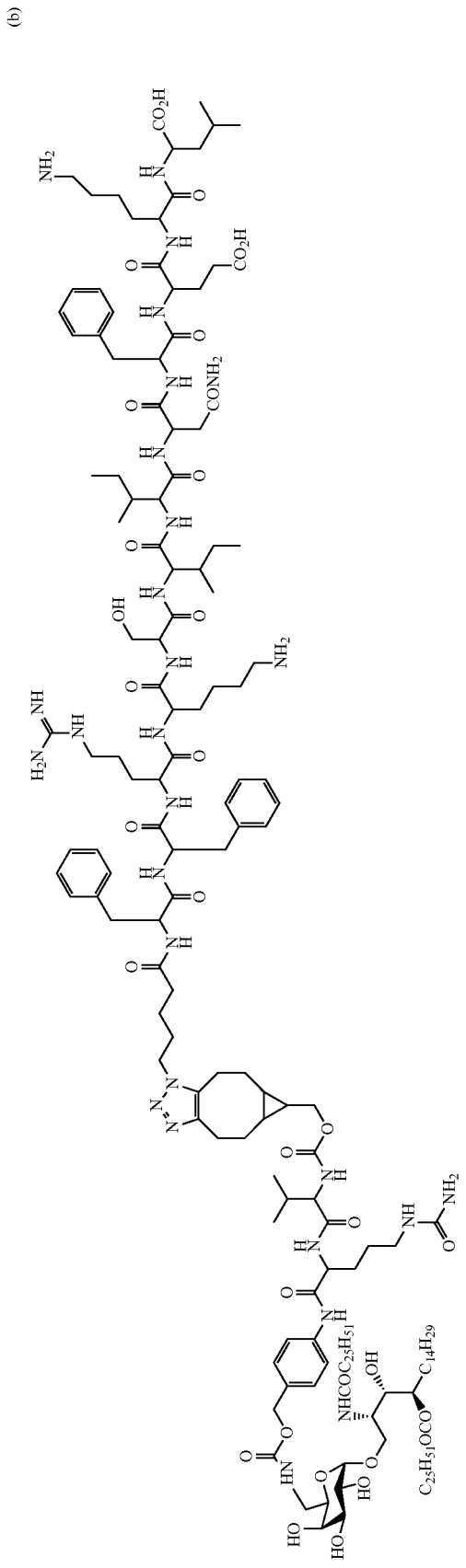

-continued
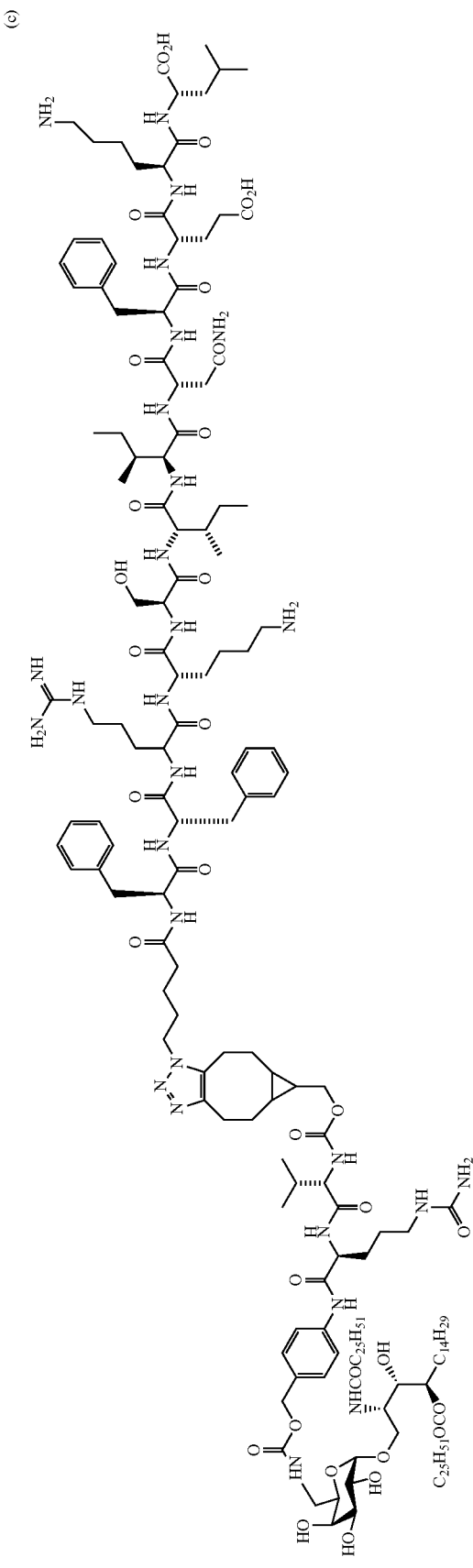
(c)
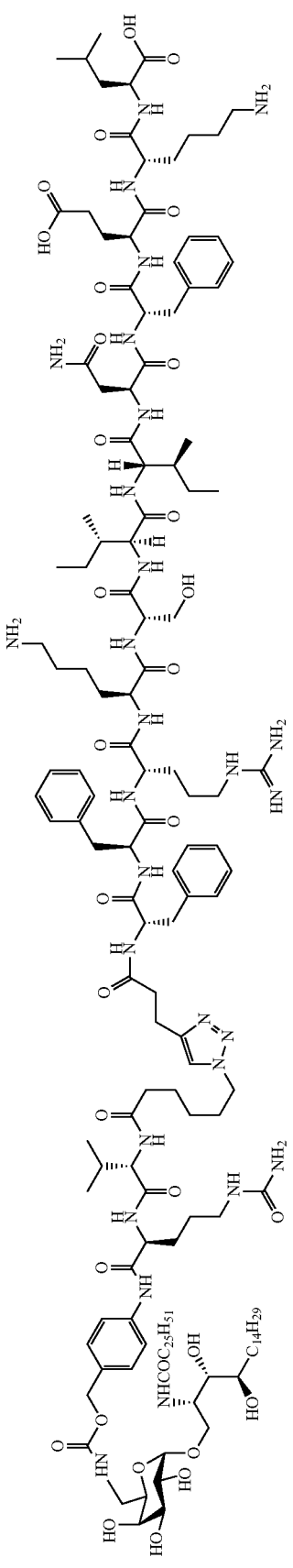
(d)
and or a pharmaceutically acceptable salt thereof.
Preferably the compound of formula (II) is a compound selected from the group consisting of:
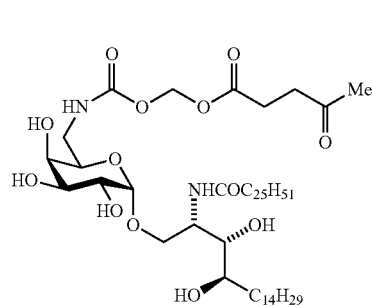
(e)
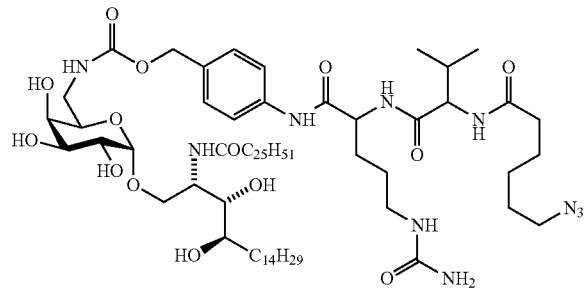
(f)
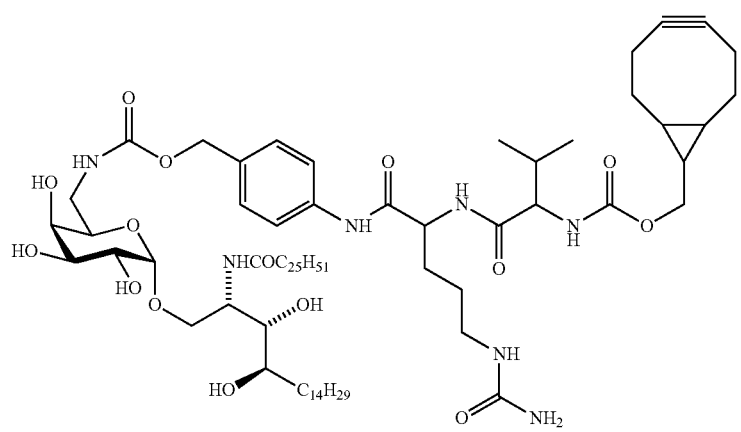
(g)
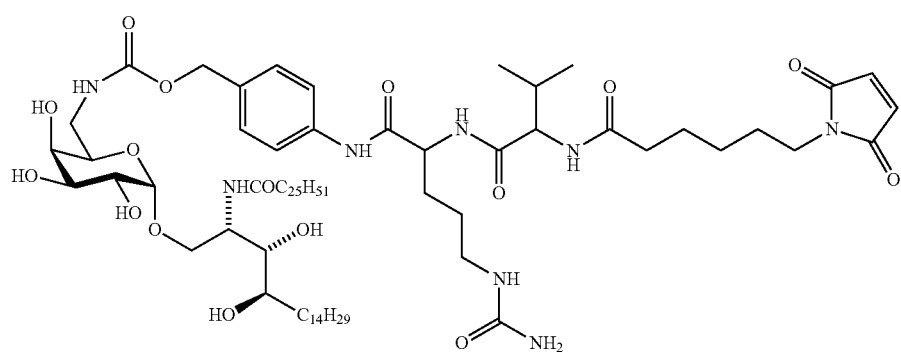
(h)
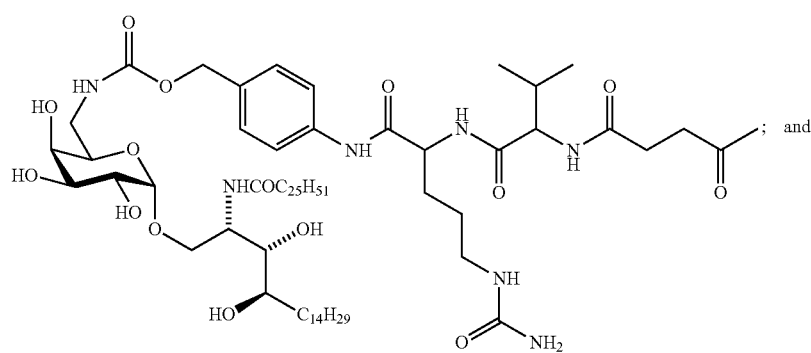
; and (j)

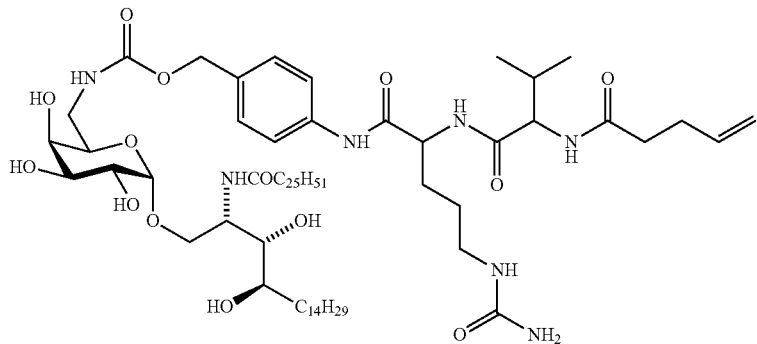

(k)

or a pharmaceutically acceptable salt thereof.

In another aspect the invention provides a pharmaceutical composition comprising a pharmaceutically effective amount of a compound of formula (I) or a compound of formula (II) and optionally a pharmaceutically acceptable carrier.

In another aspect the invention provides an immunogenic composition comprising a compound of formula (I) or a compound of formula (II) or CN168 (as defined below) and a pharmaceutically acceptable diluent and optionally an antigen.

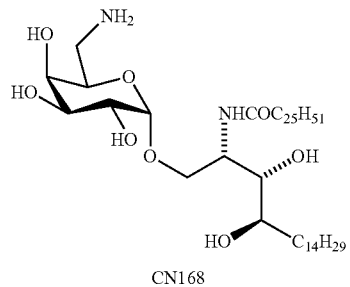

CN168

In another aspect the invention provides a vaccine comprising a compound of formula (I) or a compound of formula (II) or CN168 and a pharmaceutically acceptable diluent and optionally an antigen.

In another aspect the invention provides a compound of formula (I) or a compound of formula (II) or CN168, and optionally an antigen, for use in the preparation of a vaccine.

In another aspect, the invention provides a pharmaceutical composition comprising a compound of formula (I) or a compound of formula (II) or CN168 and a pharmaceutically acceptable exipient.

In another aspect, the invention provides a pharmaceutical composition comprising a compound of formula (I) or a compound of formula (II) and a pharmaceutically acceptable exipient.

In one embodiment, the pharmaceutical composition is an immunogenic composition optionally comprising an antigen.

In another embodiment, the pharmaceutical composition is a vaccine optionally comprising an antigen.

The antigen may be, or may be a combination of, a bacterium such as *Bacillus Calmette-Guérin* (BCG), a virus, a protein or peptide. Examples of suitable antigens include, but are not limited to, Wilms' Tumor 1 (WT1), (Li, Oka et al. 2008) tumor-associated antigen MUC1, (Brossart, Heinrich et al. 1999) latent membrane protein 2 (LMP2), (Lu, Liang et al. 2006) HPV E6E7, (Davidson, Faulkner et al. 2004) NY-ESO-1 (Karbach, Gnjatic et al. 2010), tyrosinase-related protein (Trp)-2 (Noppen, Levy et al. 2000; Chang 2006), survivin (Schmitz, Diestelkoetter et al. 2000; Friedrichs, Siegel et al. 2006; Ciesielski, Kozbor et al. 2008), MART-1 (Bettinotti, Kim et al. 1998; Jager, Hohn et al. 2002), CEA691 (Huarte, Sarobe et al. 2002) and glycoprotein 100 (gp100) (Levy, Pitcovski et al. 2007), helper epitopes (Alexander, Sidney et al 1994), Topoisomerase II α, Integrin β8 subunit precursor, Abl-binding protein C3, TACE/ADAM 17, Junction plakoglobin, EDDR1 and BAP31 (Berinstein, Karkada et al 2012).

In still another aspect the invention provides a compound of formula (I) or formula (II) in combination with at least one other compound, e.g. a second drug compound, e.g. an anti-bacterial agent or an anti-cancer agent such as Vemurafenib (PLX4032), Imatinib or Carfilzomib.

In yet another aspect the invention provides the use of a compound of formula (I) or formula (II) as a medicament.

In another aspect the invention provides the use of a compound of formula (I) or a compound of formula (II) or CN168 for treating or preventing an infectious disease, an atopic disorder, an autoimmune disease, diabetes or cancer.

In another aspect the invention provides the use of a pharmaceutical composition comprising a pharmaceutically effective amount of a compound of formula (I) or a compound of formula (II) or CN168, for treating or preventing an infectious disease, an atopic disorder, an autoimmune disease, diabetes or cancer.

In another aspect the invention provides a compound of formula (I) or formula (II) for use in the manufacture of a medicament.

In another aspect the invention provides a pharmaceutical composition for treating or preventing an infectious disease, an atopic disorder, an autoimmune disease, diabetes or cancer, comprising a compound of formula (I) or a compound of formula (II) or CN168.

In another aspect the invention provides a compound of formula (I) or a compound of formula (II) or CN168 for treating or preventing an infectious disease, an atopic disorder, an autoimmune disease, diabetes or cancer.

In another aspect the invention provides the use of a compound of formula (I) or a compound of formula (II) or CN168 in the manufacture of a medicament for treating or preventing an infectious disease, an atopic disorder, an autoimmune disease, diabetes or cancer.

In another aspect the invention provides a method of treating or preventing an infectious disease, an atopic disorder, an autoimmune disease, diabetes or cancer comprising administering a pharmaceutically effective amount of a compound of formula (I) or a compound of formula (II) or CN168 to a patient requiring treatment.

In another aspect the invention provides a method of treating or preventing an infectious disease, an atopic disorder, an autoimmune disease, diabetes or cancer comprising sequential administration of pharmaceutically effective amounts of one or more compounds of formula (I) or formula (II) and/or CN168 to a patient requiring treatment. The compounds of formula (I) or (II) or CN168 may be formulated as a vaccine, for separate, sequential administration. The sequential administration may include two or more administration steps, preferably wherein the compounds of formula (I) or (II) or CN168 are administered 1 to 90 days apart, preferably 14 to 28 days apart. The sequential administration may include administering the same compound of formula (I) or (II) or CN168 two or more times. Alternatively, the sequential administration may include administering differing compounds of formula (I) or (II) or CN168 two or more times. Alternatively, the sequential administration may include administering a compound of formula (I) or (II) or CN168 one or more times, and administering α-galactosylceramide one or more times.

In another aspect the invention provides the use of a compound of formula (I) or formula (II) in combination with at least one other compound, e.g. a second drug compound, e.g. an anti-bacterial agent or an anti-cancer agent such as Vemurafenib (PLX4032), Imatinib or Carfilzomib for treating or preventing an infectious disease, an atopic disorder, an autoimmune disease, diabetes or cancer.

In another aspect the invention provides a method of treating or preventing an infectious disease, an atopic disorder, an autoimmune disease, diabetes or cancer comprising administering to a patient a pharmaceutically effective amount of a compound of formula (I) or a compound of formula (II) or CN168 in combination with at least one other compound, e.g. a second drug compound, e.g. an antibacterial agent or an anti-cancer agent such as Vemurafenib (PLX4032), Imatinib or Carfilzomib. The compound of formula (I) or formula (II) and the other compound may be administered separately, simultaneously or sequentially.

The diseases or conditions include cancer, e.g. melanoma, prostate, breast, lung, glioma, lymphoma, colon, head and neck and nasopharyngeal carcinoma (NPV); infectious diseases, e.g. HIV; bacterial infections; atopic diseases, e.g. asthma; or autoimmune diseases.

In another aspect the invention provides a method of treating or preventing asthma comprising administering a pharmaceutically effective amount of a compound of formula (I) or a compound of formula (II) or CN168 to a patient requiring treatment.

In another aspect the invention provides a vaccine for preventing asthma comprising administering a pharmaceutically effective amount of a compound of formula (I) or a compound of formula (II) or CN168.

In another aspect the invention provides a method of modifying an immune response in a patient, comprising administering a compound of formula (I) or a compound of formula (II) or CN 168, and optionally an antigen, to the patient.

Preferably the patient is a human.

Preferably the compound is a compound of formula (I). The compound of formula (I) may be selected from the group consisting of compounds (a), (b), (c) and (d), as defined above.

Alternatively preferably the compound is a compound of formula (II). The compound of formula (II) may be selected from the group consisting of compounds (e), (f), (g), (h), (j) and (k), as defined above.

Compounds of formula (I) and formula (II) are described herein as "compounds of the invention". A compound of the invention includes a compound in any form, e.g. in free form or in the form of a salt or a solvate.

It will be appreciated that any of the sub-scopes disclosed herein, e.g. with respect to X, $R^1$, $R^2$, $R^3$, $R^6$, $R^7$, $R^8$, $R^{10}$, $R^{12}$, $R^{15}$, $R^{16}$, $R^{19}$, $R^{20}$, $R^{21}$, $R^{23}$, $R^{24}$, $R^{25}$, $R^{26}$, $R^{27}$, $R^{28}$, $R^{29}$, $R^{31}$, $R^{32}$, n, k, g, W, $Alk^1$, $Q^1$, Z, A, D, E, G and J may be combined with any of the other sub-scopes disclosed herein to produce further sub-scopes.

DETAILED DESCRIPTION

Definitions

The term "cancer" and like terms refer to a disease or condition in a patient that is typically characterized by abnormal or unregulated cell growth. Cancer and cancer pathology can be associated, for example, with metastasis, interference with the normal functioning of neighbouring cells, release of cytokines or other secretory products at abnormal levels, cell proliferation, tumour formation or growth, suppression or aggravation of inflammatory or immunological response, neoplasia, premalignancy, malignancy, invasion of surrounding or distant tissues or organs, such as lymph nodes, etc. Particular cancers are described in detail herein. Examples include lung, glioma, lymphoma, colon, head and neck and nasopharyngeal carcinoma (NPV), melanoma, chronic myelogenous leukemia (CML), myeloma, prostate, breast, glioblastoma, renal cell carcinoma, hepatic cancers.

"Infections" and like terms refer to diseases or conditions of a patient comprising internal and/or external growth or establishment of microbes. Microbes include all living forms too small to be seen by eye, including bacteria, viruses, fungi, and protozoa. Included are aerobic and anaerobic bacteria, and gram positive and gram negative bacteria such as cocci, bacilli, spirochetes, and mycobacteria. Particular infectious disorders are described in detail herein. Examples include bacterial or viral infections, e.g. HIV.

"Atopic disorders" and like terms refer to a disease or condition of a patient that is typically characterized by an abnormal or up-regulated immune response, for example, an IgE-mediated immune response, and/or Th2-cell immune response. This can include hypersensitivity reactions (e.g., Type I hypersensitivity), in particular, as associated with allergic rhinitis, allergic conjunctivitis, atopic dermatitis, and allergic (e.g. extrinsic) asthma. Typically, atopic disorders are associated with one or more of rhinorrhea, sneezing, nasal congestion (upper respiratory tract), wheezing, dyspnea (lower respiratory tract), itching (e.g., eyes, skin), nasal turbinate edema, sinus pain on palpation, conjunctival hyperemia and edema, skin lichenification, stridor, hypotension, and anaphylaxis. Particular atopic disorders are described in detail herein.

The term "patient" includes human and non-human animals. Non-human animals include, but are not limited to birds and mammals, in particular, mice, rabbits, cats, dogs, pigs, sheep, goats, cows, horses, and possums.

"Treatment" and like terms refer to methods and compositions to prevent, cure, or ameliorate a medical disease, disorder, or condition, and/or reduce at least a symptom of such disease or disorder. In particular, this includes methods and compositions to prevent or delay onset of a medical disease, disorder, or condition; to cure, correct, reduce, slow, or ameliorate the physical or developmental effects of a medical disease, disorder, or condition; and/or to prevent, end, reduce, or ameliorate the pain or suffering caused by the medical disease, disorder, or condition.

The term "amino acid" includes both natural and non-natural amino acids.

The term "antigen" refers to a molecule that contains one or more epitopes (linear, overlapping, conformational or a combination of these) that, upon exposure to a subject, will induce an immune response that is specific for that antigen. The term "antigen" includes neoantigens. Typical neoantigens are small proteins resulting from mutations in cancer cells, that may activate the immune system.

The term "self-immolative linker" means any chemical group that, by covalent attachment, bridges a second and a third chemical group, wherein the covalent bond between the self-immolative linker and the second chemical group is metabolically cleavable in vivo and wherein, upon cleavage of this covalent bond in vivo, the self-immolative linker is detached from the third chemical group through spontaneous chemical bond rearrangements. At least one, preferably both, of the second and third chemical groups is a biologically active, e.g. pharmaceutically active, agent or prodrug thereof. Most preferably, each of the second and third chemical groups is independently an immune stimulant (e.g. pattern recognition receptor agonist, TLR agonist or NKT-cell agonist), an antigen (e.g. peptide, protein or carbohydrate) or a targeting group (e.g. antibody or glycan). In some examples, upon detachment of the self-immolative linker from the second chemical group, the self-immolative linker fragments and detaches from the third chemical group. Examples of self-immolative linkers are described in Philip L. Carl, Prasun K. Chakravarty, John A. Katzenellenbogen, Journal of Medicinal Chemistry, 1981, Vol. 24, No. 5, pg 479; and Simplicio et al., Molecules, 2008, vol. 13, pg 519. The covalent bond between the self-immolative linker and the second chemical group may be cleaved by, for example, an esterase, a peptidase, a phosphatase, a phospholipase or a hydrolase, or by way of a redox or pH-dependent process.

The term "alkyl", unless otherwise defined, means any saturated hydrocarbon radical having up to 30 carbon atoms and includes any $C_1$-$C_{25}$, $C_1$-$C_{20}$, $C_1$-$C_{15}$, $C_1$-$C_{10}$, or $C_1$-$C_6$ alkyl group, and is intended to include cyclic (including fused bicyclic) alkyl groups (sometimes referred to herein as "cycloalkyl"), straight-chain and branched-chain alkyl groups, and straight or branched chain alkyl groups substituted with cyclic alkyl groups. Examples of alkyl groups include: methyl group, ethyl group, n-propyl group, iso-propyl group, cyclopropyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, cyclohexyl group, cyclooctyl group, and 1-methyl-2-ethylpropyl group.

The term "alkylene" means a diradical corresponding to an alkyl group. Examples of alkylene groups include methylene group, cyclohexylene group, ethylene group. An alkylene group can incorporate one or more cyclic alkylene group(s) in the alkylene chain, for example, "alkylene" can include a cyclohexylene group attached to a methylene group. Any alkylene group may be optionally substituted with one or more substituents selected from the group consisting of hydroxyl, halogen, e.g. fluorine, alkyl, e.g. methyl, and aryl. Any alkylene may optionally include one or more arylene moieties within the alkylene chain, for example, a phenylene group may be included within an alkylene chain.

The term "lower alkyl" means any saturated hydrocarbon radical having from 1 to 6 carbon atoms and is intended to include both straight- and branched-chain alkyl groups.

Any alkyl group may optionally be substituted with one or more substituents selected from the group consisting of $SO_3H$ (or a salt thereof), hydroxy and halogen, e.g. fluorine.

The term "alkenyl" means any hydrocarbon radical having at least one double bond, and having up to 30 carbon atoms, and includes any $C_2$-$C_{25}$, $C_2$-$C_{20}$, $C_2$-$C_{15}$, $C_2$-$C_{10}$, or $C_2$-$C_6$ alkenyl group, and is intended to include both straight- and branched-chain alkenyl groups. Examples of alkenyl groups include: ethenyl group, n-propenyl group, iso-propenyl group, n-butenyl group, iso-butenyl group, sec-butenyl group, t-butenyl group, n-pentenyl group, 1,1-dimethylpropenyl group, 1,2-dimethylpropenyl group, 2,2-dimethylpropenyl group, 1-ethylpropenyl group, 2-ethylpropenyl group, n-hexenyl group and 1-methyl-2-ethylpropenyl group.

The term "lower alkenyl" means any hydrocarbon radical having at least one double bond, and having from 2 to 6 carbon atoms, and is intended to include both straight- and branched-chain alkenyl groups.

Any alkenyl group may optionally be substituted with one or more substituents selected from the group consisting of alkoxy, hydroxy and halogen, e.g. fluorine.

The term "aryl" means an aromatic radical having 4 to 18 carbon atoms and includes heteroaromatic radicals. Examples include monocyclic groups, as well as fused groups such as bicyclic groups and tricyclic groups. Examples include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group, pyridyl group, pyrrolyl group, pyridazinyl group, pyrimidinyl group, pyrazinyl group, triazolyl group (including a 1-H-1,2,3-triazol-1-yl and a 1-H-1,2,3-triazol-4-yl group), tetrazolyl group, benzotriazolyl group, pyrazolyl group, imidazolyl group, benzimidazolyl group, indolyl group, isoindolyl group, indolizinyl group, purinyl group, indazolyl group, furyl group, pyranyl group, benzofuryl group, isobenzofuryl group, thienyl group, thiazolyl group, isothiazolyl group, benzothiazolyl group, oxazolyl group, and isoxazolyl group.

The term "arylene" means a diradical corresponding to an aryl group. Examples include phenylene group.

The term "aralkyl" means an aryl group which is attached to an alkylene moiety, where aryl and alkylene are as defined above. Examples include benzyl group.

Any aryl or aralkyl group may optionally be substituted with one or more substituents selected from the group consisting of alkyl, halogen, cyano, dialkylamino, amide (both N-linked and C-linked: —NHC(O)R and —C(O)NHR), nitro, alkoxy, acyloxy and thioalkyl.

The term "alkoxy" means an OR group, where R is alkyl as defined above. The term "lower alkoxy" means an OR group, where R is "lower alkyl" as defined above.

The term "acyl", unless otherwise defined, means C(=O)R' group, where R' is alkyl as defined above.

The term "acyloxy" means OR" group, where R" is acyl as defined above.

The term "glycosyl" means a radical derived from a cyclic monosaccharide, disaccharide or oligosaccharide by removal of the hemiacetal hydroxy group. Examples include α-D-glucopyranosyl, α-D-galactopyranosyl, β-D-galactopyranosyl, α-D-2-deoxy-2-acetamidogalactopyranosyl.

The term "amide" includes both N-linked (—NHC(O)R) and C-linked (—C(O)NHR) amides.

The term "pharmaceutically acceptable salt" is intended to apply to non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

For the purposes of the invention, any reference to the disclosed compounds includes all possible formulations, configurations, and conformations, for example, in free form (e.g. as a free acid or base), in the form of salts or hydrates, in the form of isomers (e.g. cis/trans isomers), stereoisomers such as enantiomers, diastereomers and epimers, in the form of mixtures of enantiomers or diastereomers, in the form of racemates or racemic mixtures, or in the form of individual enantiomers or diastereomers. Specific forms of the compounds are described in detail herein.

As used in this specification, the words "comprises", "comprising", and similar words, are not to be interpreted in an exclusive or exhaustive sense. In other words, they are intended to mean "including, but not limited to".

Any reference to prior art documents in this specification is not to be considered an admission that such prior art is widely known or forms part of the common general knowledge in the field.

THE COMPOUNDS OF THE INVENTION

The compounds of the invention, particularly those exemplified, are useful as pharmaceuticals, particularly for the treatment or prevention of diseases or conditions relating to cancer, infection, atopic disorders or autoimmune disease. The compounds of the invention are also useful as vaccine adjuvants or simple vaccines. For example, a compound of the invention may be formulated in a vaccine together with one or more antigens.

The compounds of the invention are useful in both free base form and in the form of salts and/or solvates.

The carbon atoms of the acyclic moiety of the compounds of formula (I) and formula (II) are numbered as shown below. This is the numbering used herein to denote these carbon atoms.

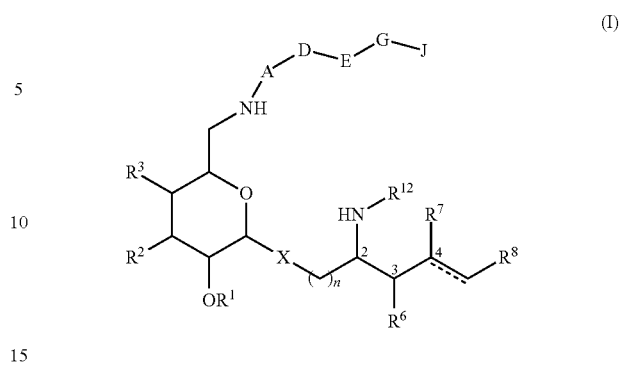

The applicants have surprisingly found that 6-amino-6-deoxy-α-galactosylceramide peptide conjugates of formula (I) (such as CN169) can induce an increased antigen-specific T cell response as compared to admixed controls comprising of α-GalCer and peptide in in vivo models.

Compounds of formula (I) of the invention are useful as simple synthetic vaccines, vaccine adjuvants or immunomodulatory drugs. Without wishing to be bound by theory, the applicants propose that such compounds are chemically stable, but can be cleaved enzymatically or at specific sites in vivo. The compounds of formula (I) constitute antigen-adjuvant conjugates (AAC) that can serve as precursors to amines (I'), Scheme 1 (e.g. CN168) and an antigen-containing component. The antigen component may then be further processed by the antigen-presenting cell and ultimately loaded and displayed by MHC molecules.

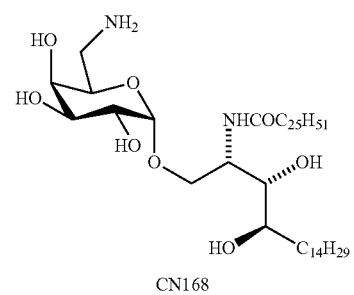

CN168

Advantageously, this approach provides for the incorporation of a range of "trigger" groups to allow control of the rate of release of amines (e.g. CN168) and peptide antigens.

Scheme 1

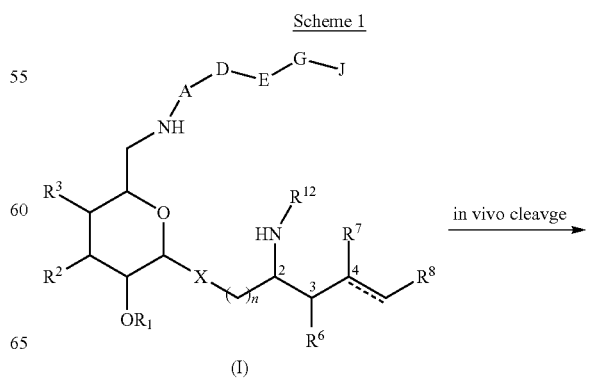

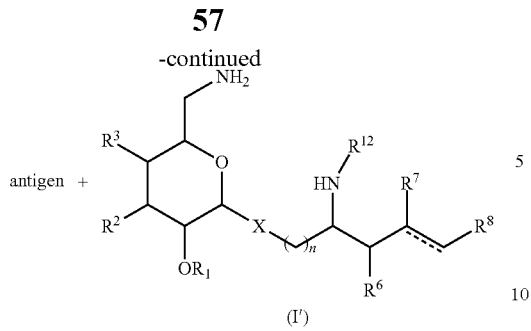
In particular the 6-azido α-GalCer derivative 2 can be reduced to the amine CN168 and reacted in situ with (4-nitrophenoxy)carbonyloxymethyl 4-oxopentanoate to afford the ketone 3. The ketone 3 can then be coupled with N-terminally modified peptides such as AoAA-FFRKSIIN-FEKL (SEQ ID NO: 415) (Scheme 2).
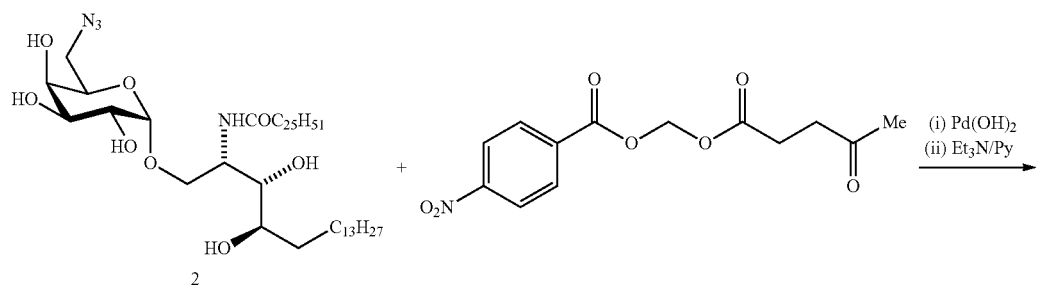
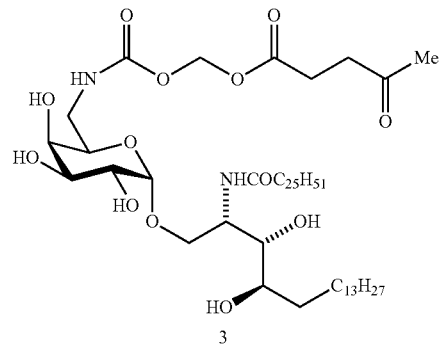
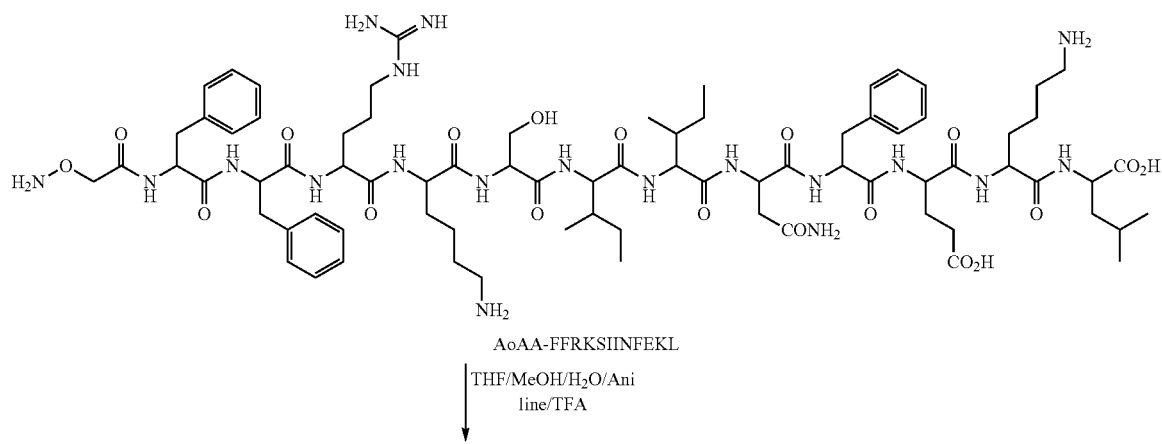

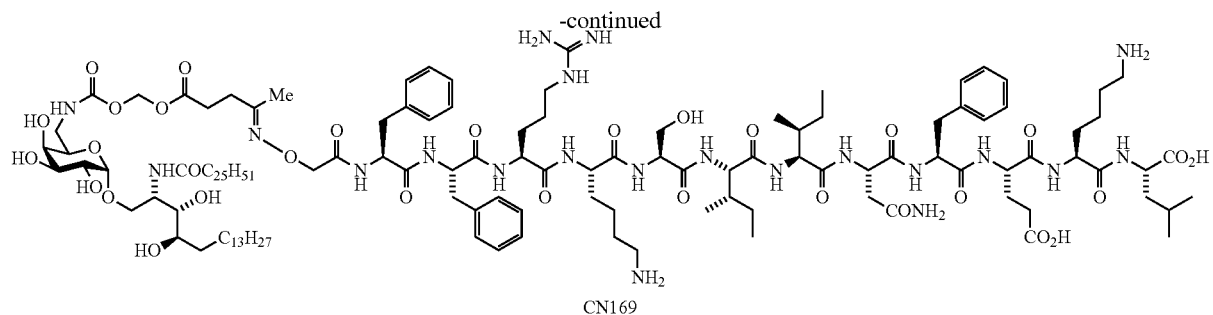

CN169

Levulinic acid is coupled with AoAA-FFRKSIINFEKL (SEQ ID NO: 415) to afford CN159, a presumed in vivo breakdown product of CN169 (Scheme 3).

Scheme 3

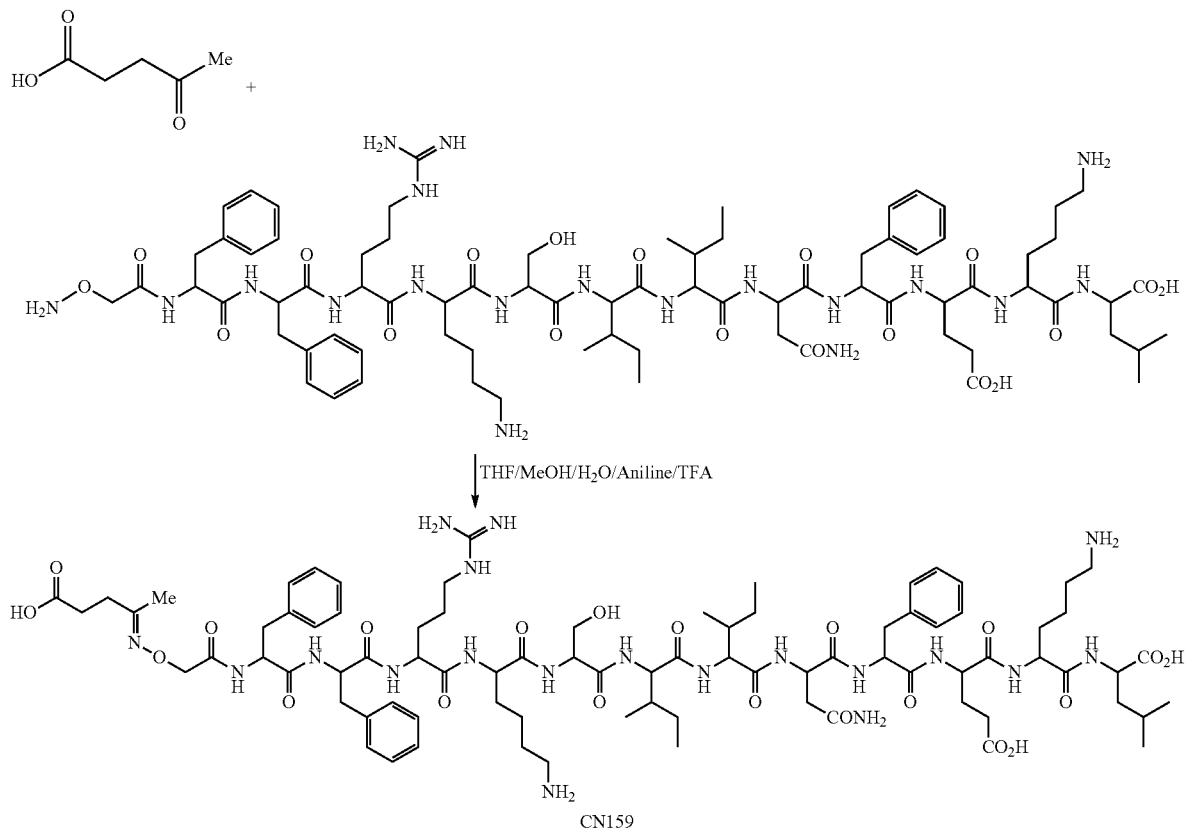

CN159

When injected into mice CN169 is able to potently activate B cells, as measured in the blood (FIG. 1). Without wishing to be bound by theory, the applicants hypothesise that CN169 is cleaved enzymatically to release a peptide component and ultimately the glycolipid CN168 that is hypothesised to be responsible for the observed activity.

Advantageously, vaccination of mice with CN169 (which contains the peptide SIINFEKL—an epitope of chicken ovalbumin protein that binds the MHC molecule H-2K$^b$) is immunologically superior to vaccination with α-GalCer and peptide. For example, vaccination with CN169 results in a larger population of peptide-specific T cells (defined as Vα2$^+$ CD45.1$^+$ cells by flow cytometry) as compared with vaccination with admixed α-GalCer and SIINFEKL (SEQ ID NO: 262) peptide, or α-GalCer and CN159, the same peptide further comprising the N-terminal substitution required for linkage (FIG. 2).

When injected into mice, the amine CN168 is able to potently activated dendritic cells (DC) as measured by an up-regulation of CD86 (FIG. 3).

Other Aspects

The compounds of the invention may be administered to a patient by a variety of routes, including orally, parenterally, by inhalation spray, topically, rectally, nasally, buccally, intravenously, intra-muscularly, intra-dermally, subcutaneously or via an implanted reservoir, preferably intravenously. The amount of compound to be administered will vary widely according to the nature of the patient and the nature and extent of the disorder to be treated. Typically the dosage for an adult human will be in the range 50-15000 µg/m². The specific dosage required for any particular patient will depend upon a variety of factors, including the patient's age, body weight, general health, sex, etc.

For oral administration the compounds of the invention can be formulated into solid or liquid preparations, for example tablets, capsules, powders, solutions, suspensions and dispersions. Such preparations are well known in the art as are other oral dosage regimes not listed here. In the tablet form the compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid, and the lubricant may be magnesium stearate. For oral administration in the form of capsules, diluents such as lactose and dried corn-starch may be employed. Other components such as colourings, sweeteners or flavourings may be added.

When aqueous suspensions are required for oral use, the active ingredient may be combined with carriers such as water and ethanol, and emulsifying agents, suspending agents and/or surfactants may be used. Colourings, sweeteners or flavourings may also be added.

The compounds may also be administered by injection in a physiologically acceptable diluent such as water or saline. The diluent may comprise one or more other ingredients such as ethanol, propylene glycol, an oil or a pharmaceutically acceptable surfactant. In one preferred embodiment, the compounds are administered by intravenous injection, where the diluent comprises an aqueous solution of sucrose, L-histidine and a pharmaceutically acceptable surfactant, e.g. Tween 20.

The compounds may also be administered topically. Carriers for topical administration of the compounds include mineral oil, liquid petrolatum, white petrolatum, propylene glycol, polyoxyethylene, polyoxypropylene compound, emulsifying wax and water. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyldodecanol, benzyl alcohol and water.

The compounds may further be administered by means of sustained release systems. For example, they may be incorporated into a slowly dissolving tablet or capsule.

Synthesis of the Compounds of the Invention

CN169 is synthesized from 6-azido-6-deoxy-α-galactosylceramide (Jervis, Cox et al. 2011) which is turn is derived from diol 1 (Lee, Farrand et al. 2006).

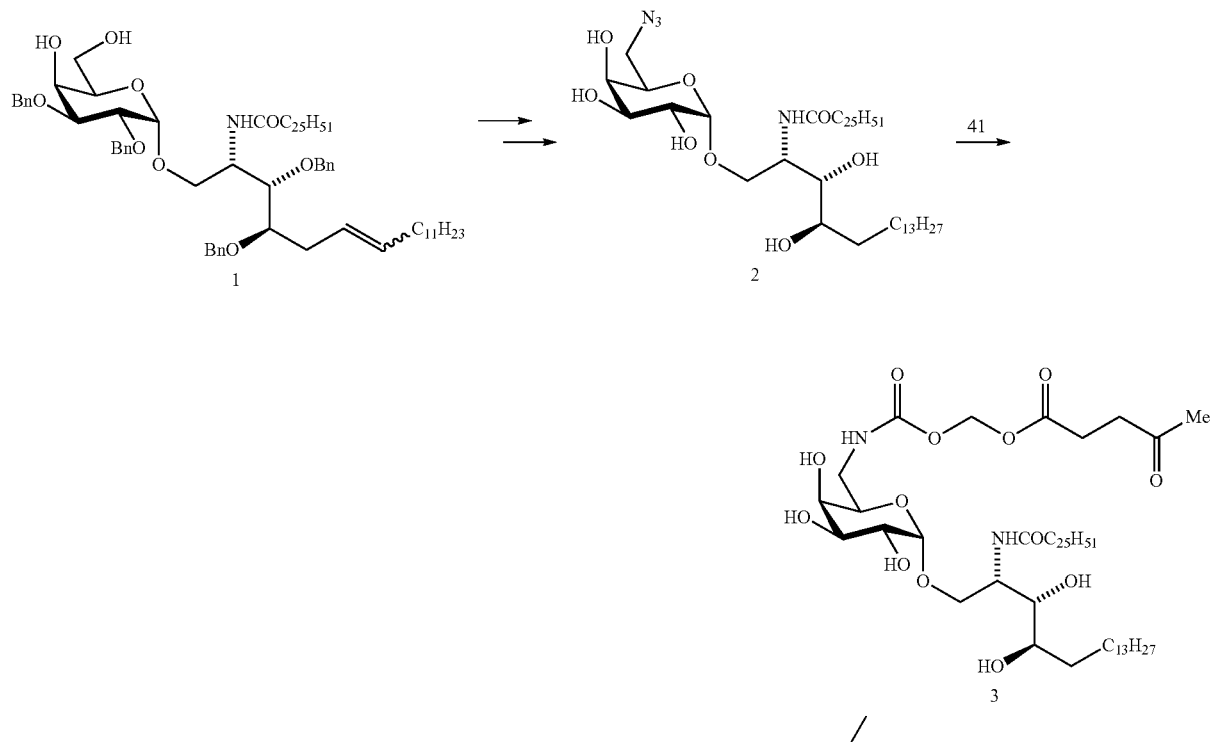

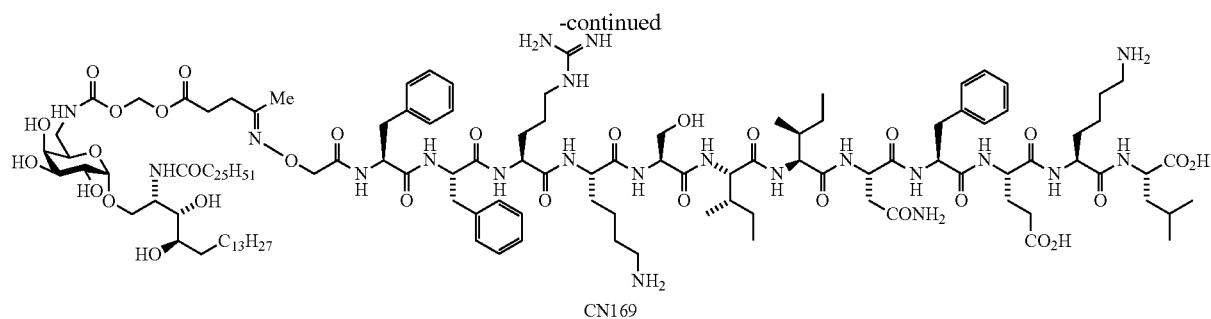

CN169

Synthesis of Compounds of Formula (I')

A variety of synthetic methods are reported in the literature, some of which are referenced herein. Those skilled in the art will appreciate that these methods can be adapted for the synthesis of compounds of formula (I'). For a recent review of α-GalCer analogues synthesized that includes some of these methods, see Banchet-Cadeddu et al. (Banchet-Cadeddu, Henon et al. 2011). The reported methods all involve a key coupling or glycosylation step that brings together the sugar and phytosphingosine components.

General Method (1) for the Synthesis of Compounds of Formula (I')

In case of compounds of formula (I') there are two general methods. The first includes the incorporation of the azido or amino functional group before glycosylation. Routine protecting group manipulation provides access to compounds of formula (XI) where $R^1$=H and L represents a leaving group suitable for glycosylation with compounds of formula (XII). When N is amino it is protected until the final stages of the synthetic strategy.

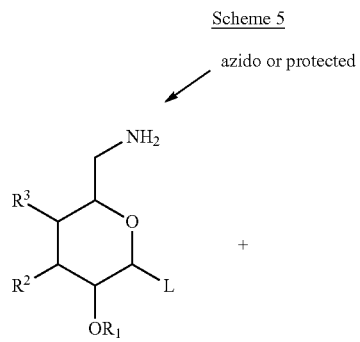

Scheme 5

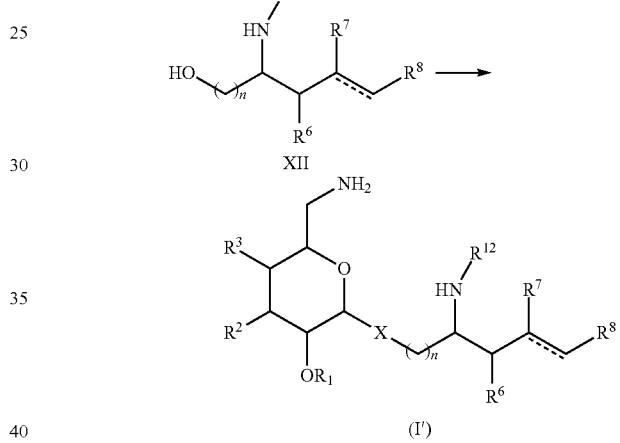

Starting materials include diacetonide 4 that is used to synthesize glycosyl donor 5 (Zhou, Forestier et al. 2002). Glycosylation with 6 and deprotection affords 6-amino-6-deoxy-α-GalCer (Scheme 7). In the case where $R^1$=glycosyl an initial glycosylation is required to form the disaccharide that is subsequently glycosylated with 7 (Liu, Deng et al. 2008). When $R^6$ and/or $R^7$ are OH suitable protecting groups include silyl (see 7), benzyl (Scheme 6) (Trappeniers, Van Beneden et al. 2008), acetonide or benzoate. When $R^6$ and/or $R^7$ are OH epimers are synthesized from D-ribo-phytosphingosine by protecting group manipulation and epimerisation under Mitsunobu conditions (Scheme 6) (Trappeniers, Goormans et al. 2008). For example, all 8 stereoisomers of a protected phytosphingosine acceptor have been synthesized in an approach that also allows modification of the group $R^8$ (Park, Lee et al. 2008; Baek, Seo et al. 2011). Furthermore, 3-deoxy (Baek, Seo et al. 2011) and 4-deoxy phytosphingosine (Morita, Motoki et al. 1995; Howell, So et al. 2004; Du, Kulkarni et al. 2007) derivatives have also been described. Methods for the synthesis of donors where $R^1$ is glycosyl, (Veerapen, Brigl et al. 2009) $R^2$ or $R^3$ is O-glycosyl, (Kawano, Cui et al. 1997) $R^2$ or $R^3$ is either H or F, (Raju, Castillo et al. 2009) have also been reported and can be used for for the pepraration of compounds of formula (I').

Scheme 6
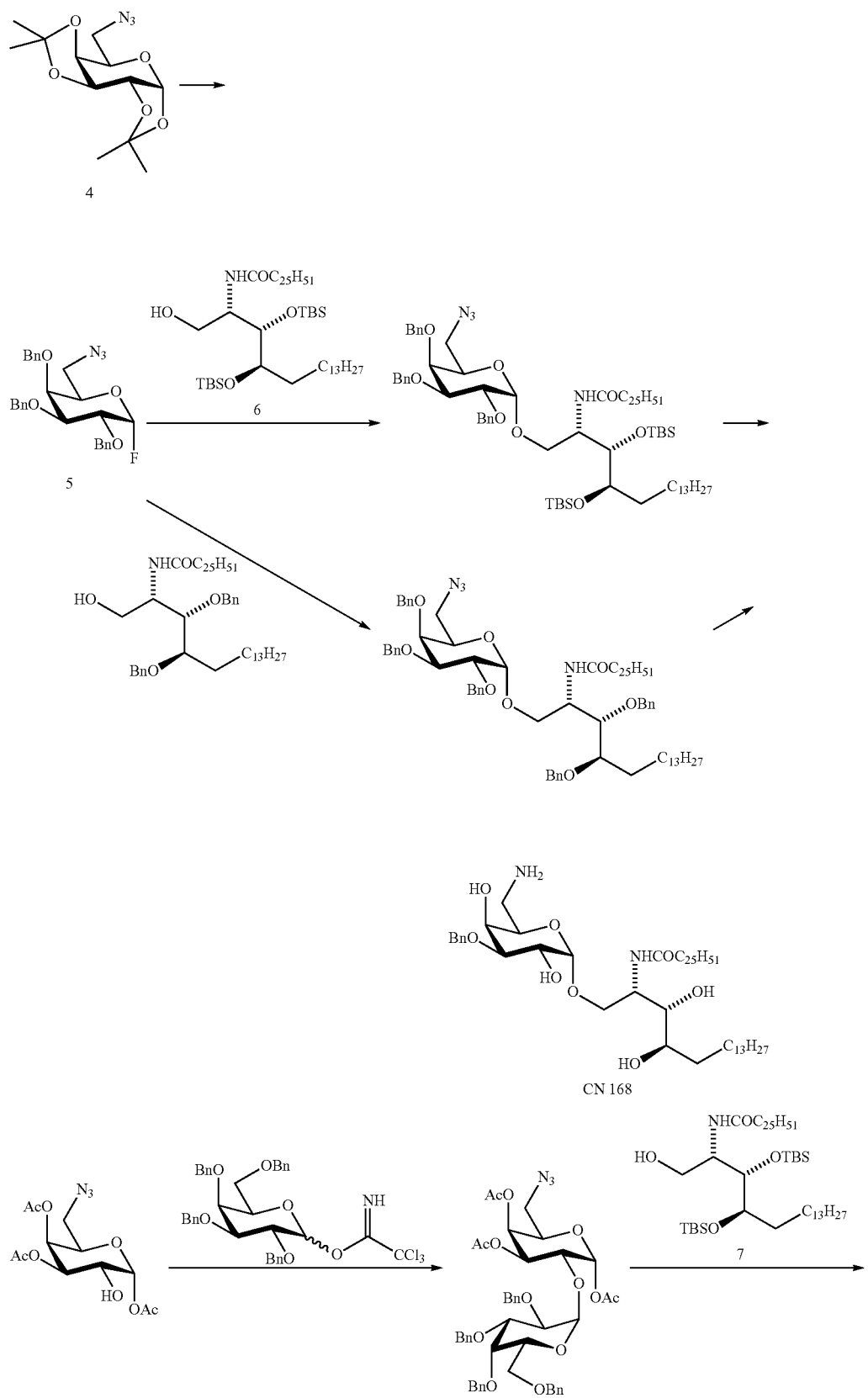

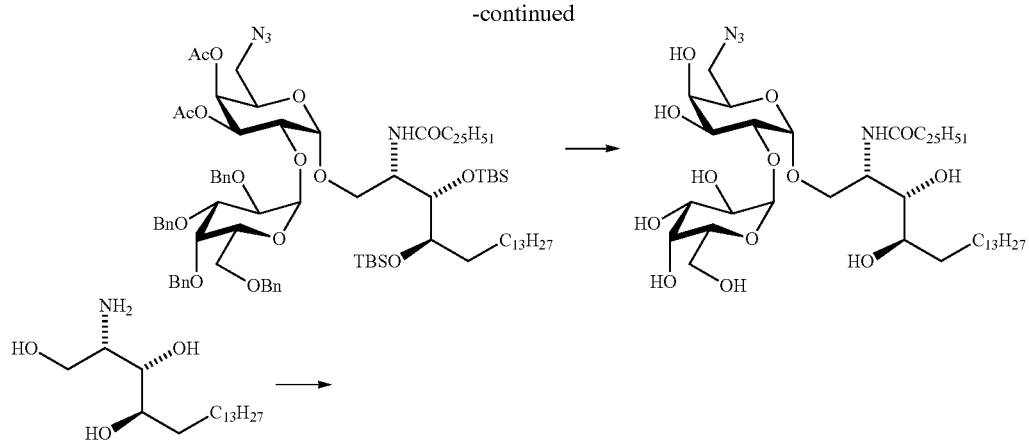

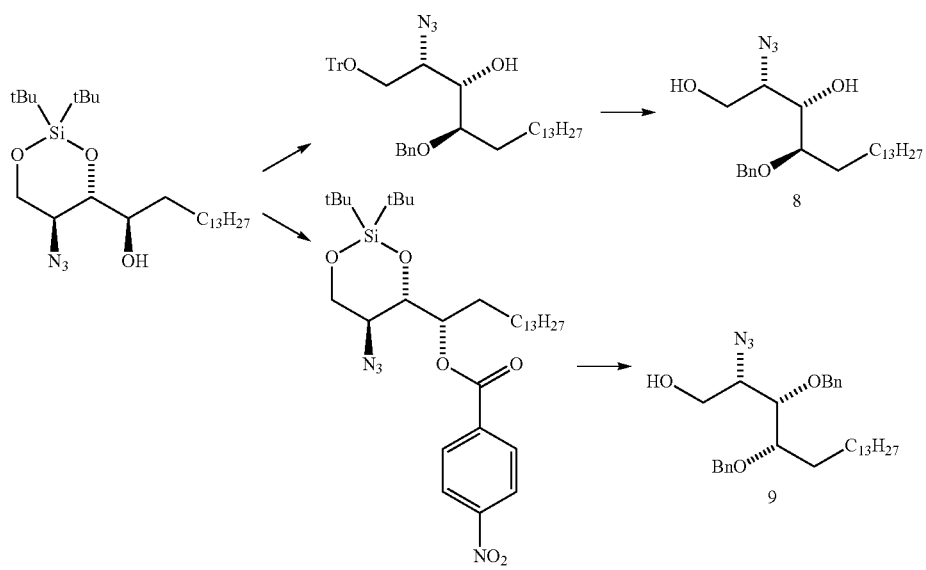

General Method (2) for the Synthesis of Compounds of Formula (I')

Scheme 7

An alternative general approach for the synthesis of compounds of formula (I') is introduction of the amino functional group after glycosylation. Examples include the glycosylation of a TMS-protected galactosyl donor with a protected phtyoshingosine precursor followed by selective removal of the primary silyl group with acid and subsequent introduction of an azido functional group (Scheme 8) (Jervis, Cox et al. 2011). Another approach includes the regioselective opening of benzylidene acetal 9a and subsequent introduction of the azido group (Pauwels, Aspeslagh et al. 2012).

Scheme 8

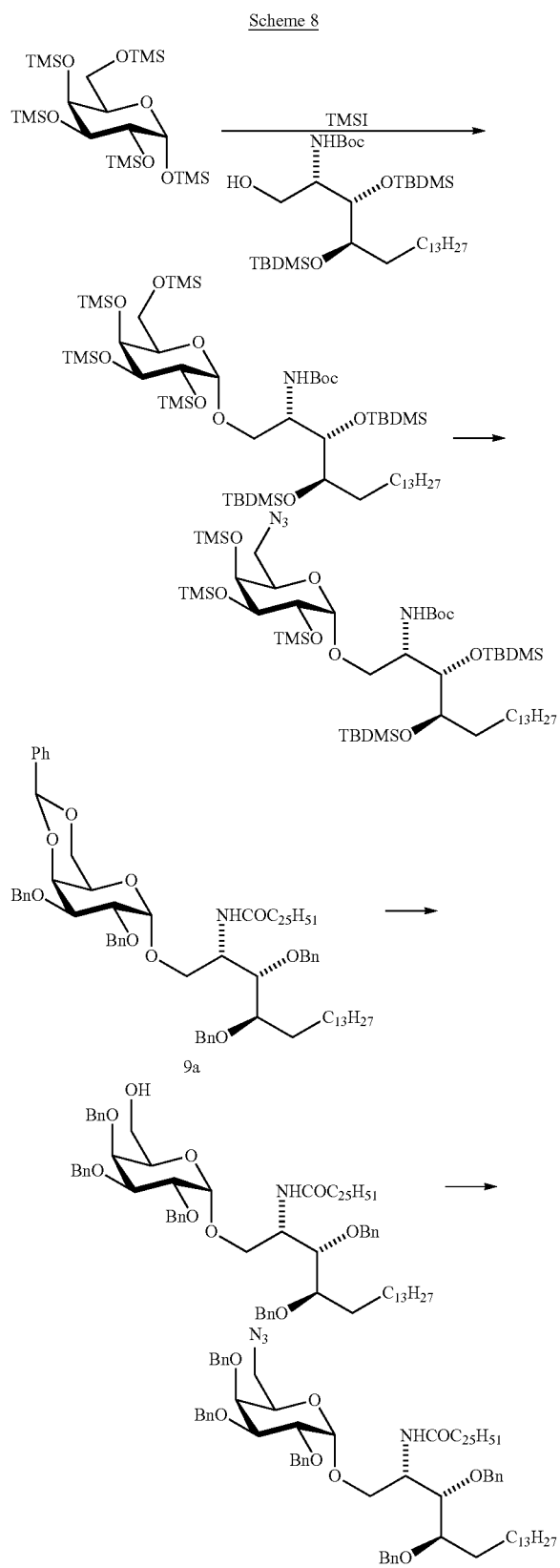

For starting materials (I') where X is CH₂ and R⁷ is H, these are synthesized according to reported methods for analogous compounds (Chen, Schmieg et al. 2004) using sphingosine as the starting material in place of phytosphingosine. For starting materials (I') in which X is S, syntheses of analogous compounds have been described (Dere and Zhu 2008; O'Reilly and Murphy 2011).

Amines (I') are further transformed into compounds of formula (II) (as shown below in General Method 3) according to the following general procedures:

General Method (3) for Synthesis of Compounds of Formula (II)

Scheme 9

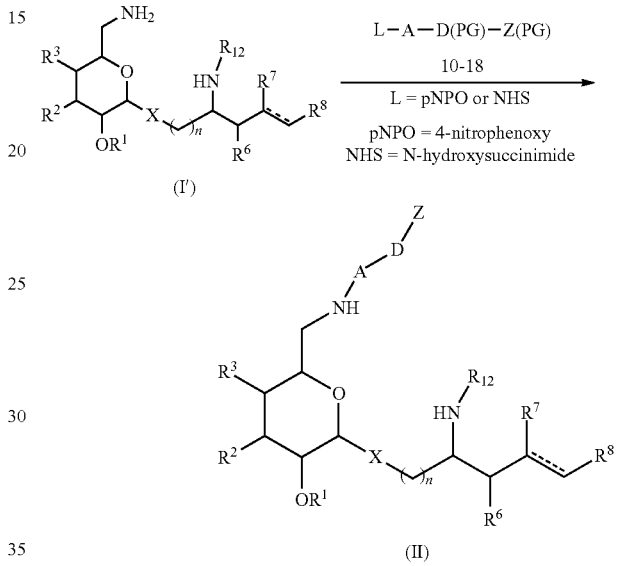

For the preparation of compounds of formula (II) (Scheme 9), a mixture of amine (I'), potentially prepared in situ from the azide, (0.05-0.1 M), activated carbonate or ester 10-18 (where D(PG) may be D as defined herein for formula (I) and (II) or a protected form of D, and where Z(PG) may be Z as defined herein for formula (II) or a protected form of Z) (1.05-2 equiv) and NEt₃ (0-10 equiv) are stirred in a suitable solvent (e.g. pyridine, pyridine-CHC₃, CHC₃-MeOH, DMF, DMSO) at ambient temperature until the reaction is essentially complete (TLC). Diethylamine may be added to quench excess reagent. After concentration of the mixture, the residue is purified by column chromatography on silica gel and/or C18 silica gel. Any protecting groups in D(PG) and/or Z(PG) are subsequently removed, by standard methods, (Isidro-Llobet, Alvarez et al. 2009). The deprotected products are purified by chromatography on silica gel and/or C18 silica gel.

Scheme 9a

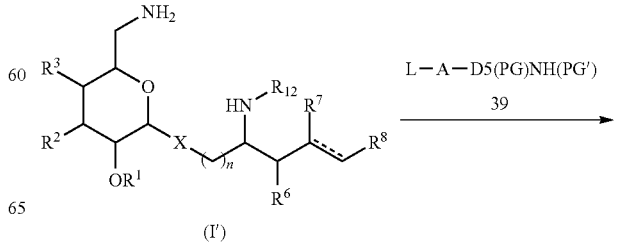

-continued

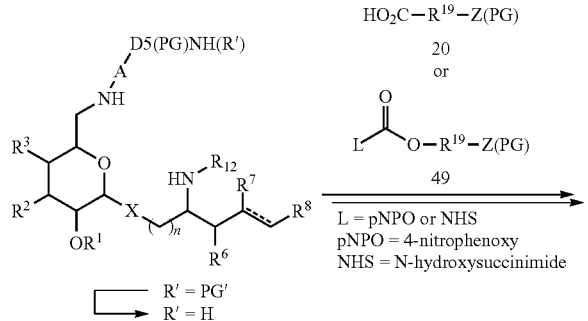

Alternatively (Scheme 9a), amine (1') (0.05-0.1 M) is reacted with activated carbonate or ester 39 (Dubowchik, Firestone et al. 2002) (where PG' is defined as an amine protecting group, e.g. Fmoc, Boc, Alloc, preferably Fmoc) under similar conditions to the reaction shown in Scheme 9). PG' is removed by standard methods, (Isidro-Llobet, Alvarez et al. 2009), e.g. piperidine/DMF for removal of the Fmoc group, and the resulting amine is coupled with a reagent containing the component Z(PG), where Z(PG) may be Z as defined herein for formula (II) or a protected form of Z. The reagent may be a) a carboxylic acid (20), in which case standard peptide coupling activators (e.g. HBTU, HATU) are employed; or b) an activated ester (e.g. NHS ester, pNP ester, mixed carbonic anhydride) which is derived from carboxylic acid 20 by standard methods; or c) an activated carbonate 49 (preferably pNP carbonate) which is derived from the corresponding alcohol. Any protecting groups in D(PG) and/or Z(PG) are subsequently removed, by standard methods, (Isidro-Llobet, Alvarez et al. 2009). The deprotected products are purified by chromatography on silica gel and/or C18 silica gel.

General Method (4) for Synthesis of Reagents 10

Scheme 10

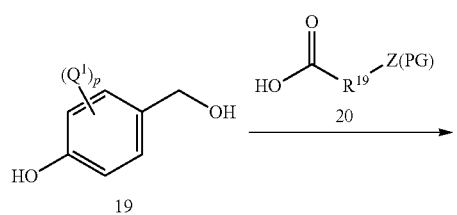

-continued

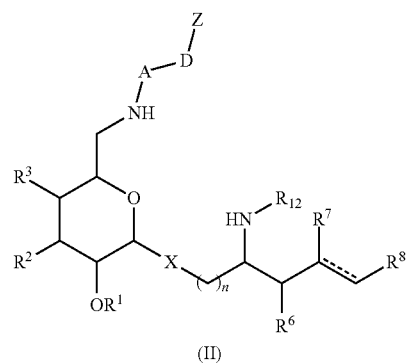

Esters 10 (where Z(PG) may be Z as defined herein for formula (II) or a protected form of Z) are synthesized by the reaction of 4-hydroxybenzylic alcohols 19 with carboxylic acids 20 or their activated esters in accordance with or by adapting literature procedures (Greenwald, Pendri et al. 1999). In some cases, it may be advantageous to use a protected form of 19, eg, 4-hydroxybenzyl THP ether or 4-hydroxybenzyaldehyde. The benzylic alcohol products are subsequently converted to the corresponding p-nitrophenyl carbonates 10 by reaction with bis(p-nitrophenyl carbonate) and Hünig's base in DMF (Dubowchik, Firestone et al. 2002). Benzylic alcohols 19 are commercially available or obtained by simple derivatisation of commercially available 4-hydroxybenzyl alcohols. Acids 20 are commercially available, or accessed by standard chemical transformations of common starting materials (e.g. terminal alkenoic acids, hydroxyalkanoic acids, haloalkanoic acids, aminoalkanoic acids, alkanedioic acids), or by following literature methods: (Iha, van Horn et al. 2010) for Z=Z8; (Hudlicky, Koszyk et al. 1980) for Z=Z12; (Saxon and Bertozzi 2000) for Z=Z14; (Tam, Soellner et al. 2007) for Z=Z15. Acids 20 containing a keto group (Z=Z1), may also be accessed by coupling of 2-metallated alkenyl reagents with haloalkanoic esters (Hatakeyama, Nakagawa et al. 2009), followed by ozonolysis of the double bond. In certain cases, groups Z in 20 may be used in protected form Z(PG) (eg, phthalimides for Z8 and Z9, thioester or disulfide for Z10, acetal or alkene for Z16, Tbeoc-Thz for Z17 (Fang, Wang et al. 2012).

General Method (5) for Synthesis of Reagents 11

Scheme 11

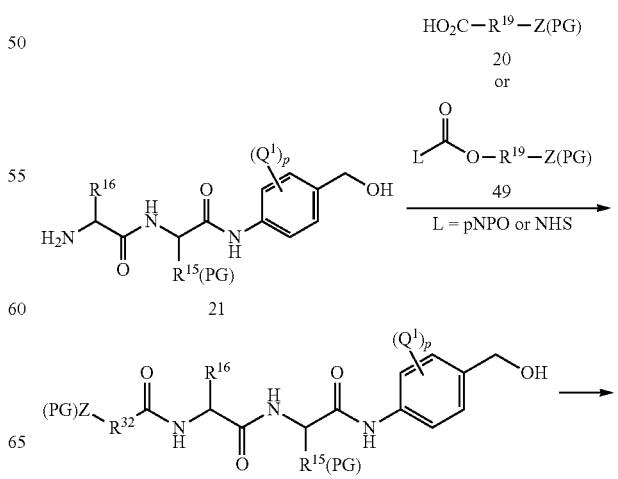

-continued

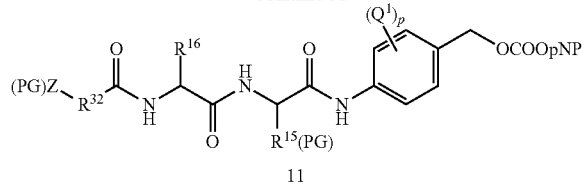

11

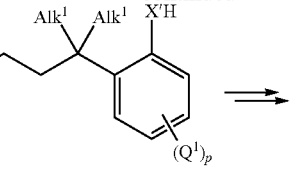

23 X' = O
24 X' = NH

Dipeptides 11 (where $R^{15}$(PG) may be $R^{15}$ as defined herein for formula (I) or a protected form of $R^{15}$ and where Z(PG) may be Z as defined herein for formula (II) or a protected form of Z) are prepared by reaction of amines 21 (Dubowchik, Firestone et al. 2002) with the appropriate acid 20 using the chloroformate method (Chaudhary, Girgis et al. 2003) to give amide products. Briefly, 20 (1.3 equiv) is dissolved in solvent (eg, in $CH_2Cl_2$, THF, ether) and treated at 0° C. with $NEt_3$ (1.4 equiv) followed by isobutyl chloroformate (1.25 equiv) and, after −30 min, the resulting solution is transferred to a solution of the amine 21 in $CH_2Cl_2$/MeOH. The reaction is generally complete within 2 h at room temperature. An alternative method involves reaction of 21 with the NHS ester of 20 in a polar aprotic solvent (eg, DMF, NMP) (Dubowchik, Firestone et al. 2002). Amines 21 may also be reacted with activated carbonates 49 (preferably pNP carbonate) derived from the corresponding alcohol, to give carbamate products. The hydroxyl group of the resulting amide or carbamate products is subsequently converted to the corresponding p-nitrophenyl carbonates 11 by reaction with bis(p-nitrophenyl carbonate) and Hünig's base in DMF (Dubowchik, Firestone et al. 2002).

General Method (6) for Synthesis of Carbonate and Carbamate Reagents 12-15

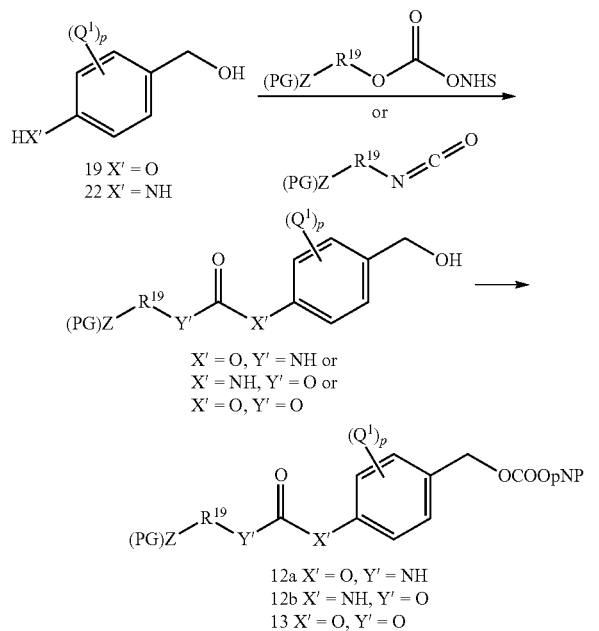

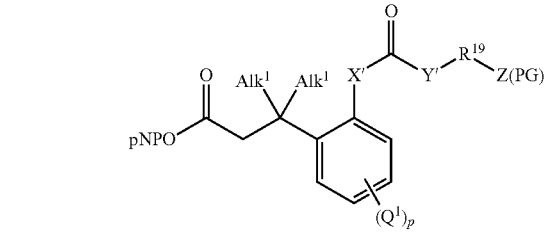

14a X' = O, Y' = NH
14b X' = NH, Y' = O
15 X' = O, Y' = O

Carbamates 12 and carbonates 13 (where Z(PG) may be Z as defined herein for formula (II) or a protected form of Z) are prepared by reaction of 4-hydroxybenzylic alcohols 19 or 4-aminobenzylic alcohols 22 with isocyanates or activated NHS carbonates as reported (Greenwald, Pendri et al. 1999). In some cases, it may be advantageous to use a protected form of 19, eg, 4-hydroxybenzyl THP ether or 4-hydroxybenzyaldehyde. The benzylic alcohol products are subsequently converted to the corresponding p-nitrophenyl carbonates 12, 13 by reaction with bis(p-nitrophenyl carbonate) and Hünig's base in DMF (Dubowchik, Firestone et al. 2002).

Carbamates 14 and carbonates 15 are prepared in a similar manner, from phenols 23 or anilines 24, with standard manipulations for conversion of the silyl ether group into an active ester (see General Methods 8 and 9).

General Method (7) for Synthesis of Reagents 16

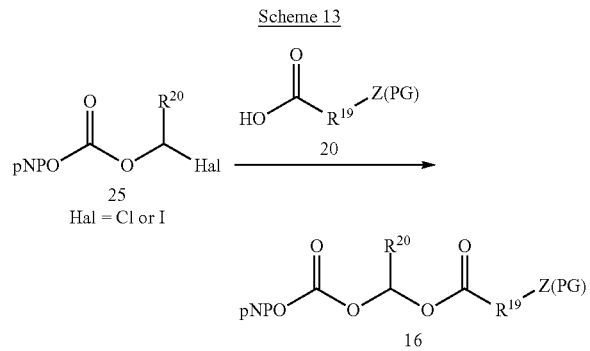

Esters 16 (where Z(PG) may be Z as defined herein for formula (II) or a protected form of Z) are prepared by reaction of α-haloalkyl 4-nitrophenyl carbonates 25, eg, iodomethyl 4-nitrophenyl carbonate (Gangwar, Pauletti et al. 1997) or α-chloroethyl 4-nitrophenyl carbonate) (Alexander, Cargill et al. 1988), with a carboxylic acid 20, either in the presence of $Ag_2O$ or $Cs_2CO_3$, or as the preformed salt, in an anhydrous solvent (e.g. MeCN, toluene, dioxane, DMF), at a temperature between 20 and 80° C.

General Method (8) for Synthesis of Reagents 17

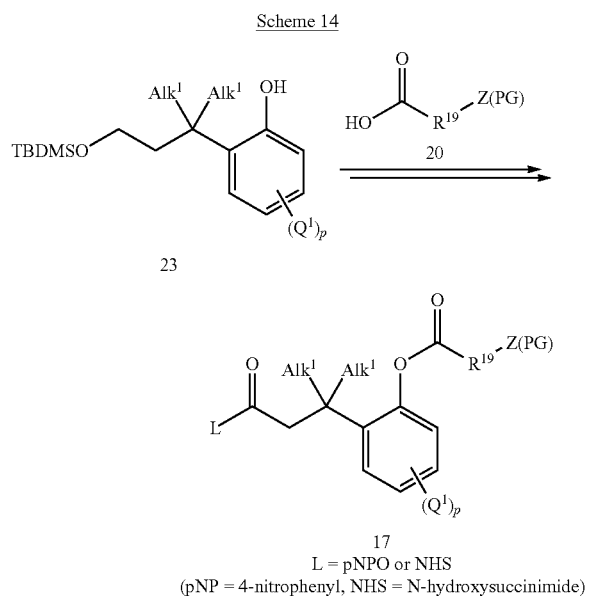

Scheme 14

17
L = pNPO or NHS
(pNP = 4-nitrophenyl, NHS = N-hydroxysuccinimide)

Esters 17 (where Z(PG) may be Z as defined herein for formula (II) or a protected form of Z) are synthesised from phenols 23 in accordance with or by adapting literature procedures, (Carpino, Triolo et al. 1989; Amsberry and Borchardt 1991; Amsberry, Gerstenberger et al. 1991; Nicolaou, Yuan et al. 1996; Greenwald, Choe et al. 2000).

General Method (9) for Synthesis of Reagents 18

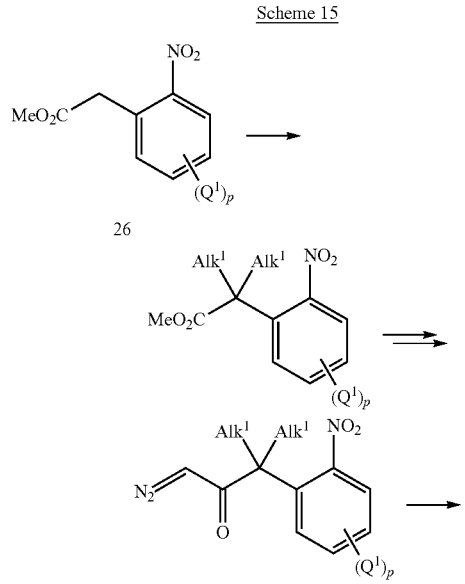

Scheme 15

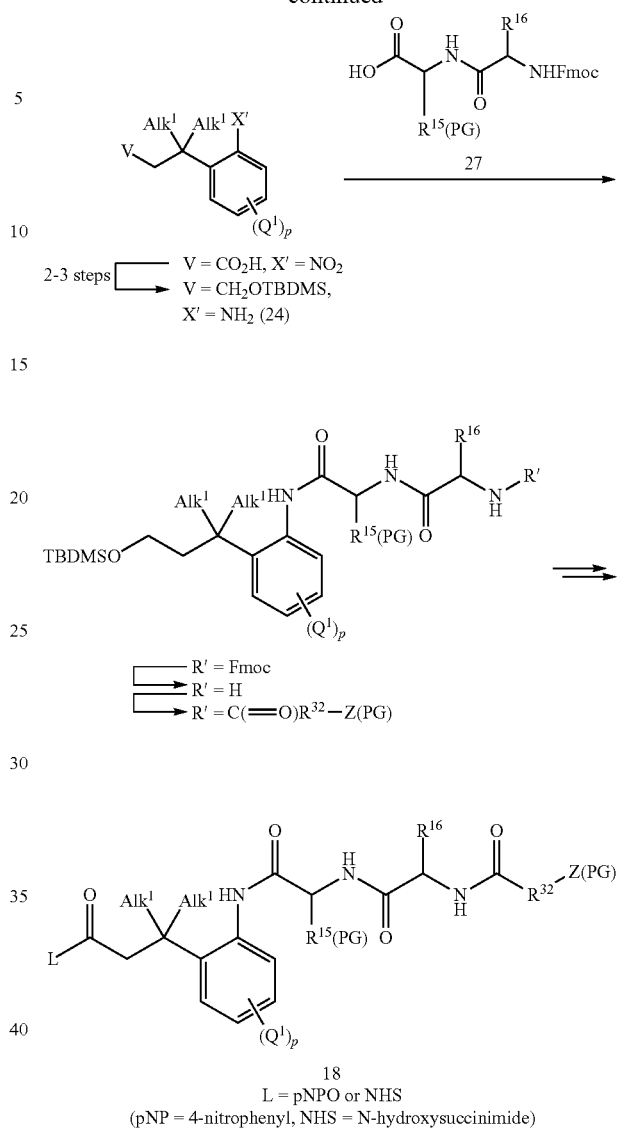

18
L = pNPO or NHS
(pNP = 4-nitrophenyl, NHS = N-hydroxysuccinimide)

Dipeptides 18 (where Z(PG) may be Z as defined herein for formula (II) or a protected form of Z) are synthesised from o-nitrophenylacetic acid esters 26 (Scheme 15), obtained from commercial sources, or by known procedures, or by Ardnt-Eistert homologation of the corresponding 6-nitrobenzoic acid esters (Atwell, Sykes et al. 1994)). The esters 26 are gem-dialkylated with an alkyl iodide and a suitable base (e.g. NaH, KO$^t$Bu, n-BuLi), optionally in the presence of 18-crown-6. The dialkylated product is, via the acid chloride, subjected to Arndt-Eistert homologation ($CH_2N_2$; then heat or Ag(II)). The carboxyl group is reduced to the alcohol oxidation level to prevent premature lactamization and the resulting alcohol is protected as the TBDMS ether. After reduction of the nitro group, the resulting amine 24 is coupled with dipeptides 27 (Dubowchik, Firestone et al. 2002). Fmoc cleavage is followed by amide or carbamate formation (see General Method 5). Finally, desilylation, oxidation and activation of the resulting carboxylic acid by standard methods gives reagents 18.

General Method (10) for Coupling of Antigen to Compounds of Formula (II) by Thiolene Ligation where Z is Z2, Z10 or Z17

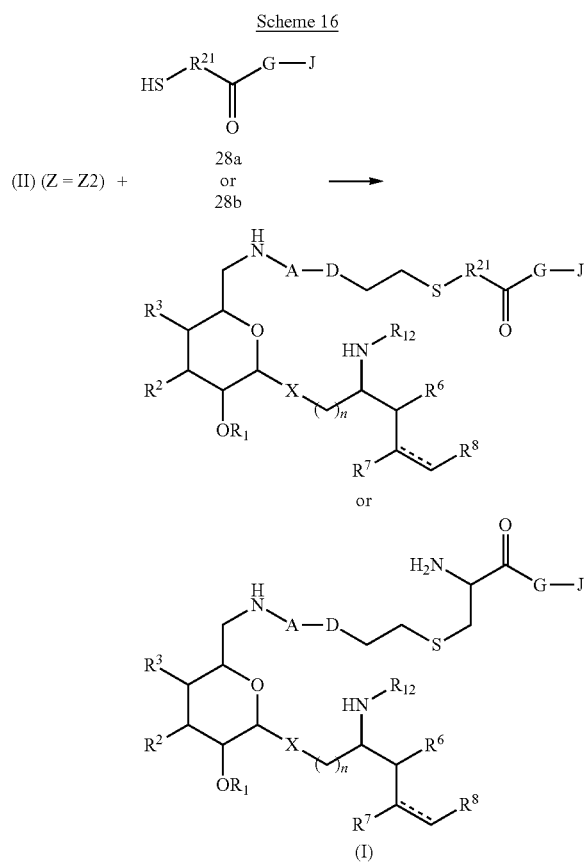

Scheme 16

Z is Z2: The compound of formula (II) and peptide-thiol 28a or N-terminal cysteinyl peptide 28b are dissolved in an appropriate solvent. Suitable solvent systems may include chloroform, THF, methanol, DMF, DMSO, tert-butanol, water, or mixtures thereof. After purging with Ar, the mixture is stirred in the presence of a radical initiator under photochemical conditions (Campos, Killops et al. 2008), or alternatively, under thermal conditions (Dondoni 2008). After completion of the reaction, the product is purified by chromatography on the appropriate solid phase (e.g. silica gel, C4, and/or C18 silica).

Scheme 17

Z is Z10 or Z17: The compound of formula (II) is reacted with N-terminal alkenoyl peptide 29 under the conditions described above.

General Method (11) for Coupling of Antigen to Compounds of Formula (II) by Azide-Alkyne Cycloaddition where Z is Z4, Z7 or Z23

Scheme 18

Z is Z4: The compound of formula (II) and N-terminal alkynoyl peptide 30 are stirred with copper (II) sulfate (up to 0.1 mM), a coordinating ligand (e.g. TBTA, THPTA or Bim(Py)₂, preferably TBTA) (Presolski, Hong et al. 2010) and a reducing agent (e.g., copper metal, ascorbic acid or TCEP, preferably copper metal) in a deoxygenated aqueous-organic solvent system (Rostovtsev, Green et al. 2002). Suitable organic solvents may include chloroform, THF, methanol, DMF, DMSO, tert-butanol, or mixtures thereof. After completion of the reaction, the crude product may be isolated from the catalyst by precipitation into aq EDTA (pH 7.7) and separation of the pellet by centrifugation. Alternatively, pentamethylcyclopentadienyl ruthenium catalysts may be employed to provide regioisomeric products (Zhang, Chen et al. 2005; Majireck and Weinreb 2006). The product is purified by chromatography on the appropriate solid phase (e.g. silica gel, C4, and/or C18 silica).

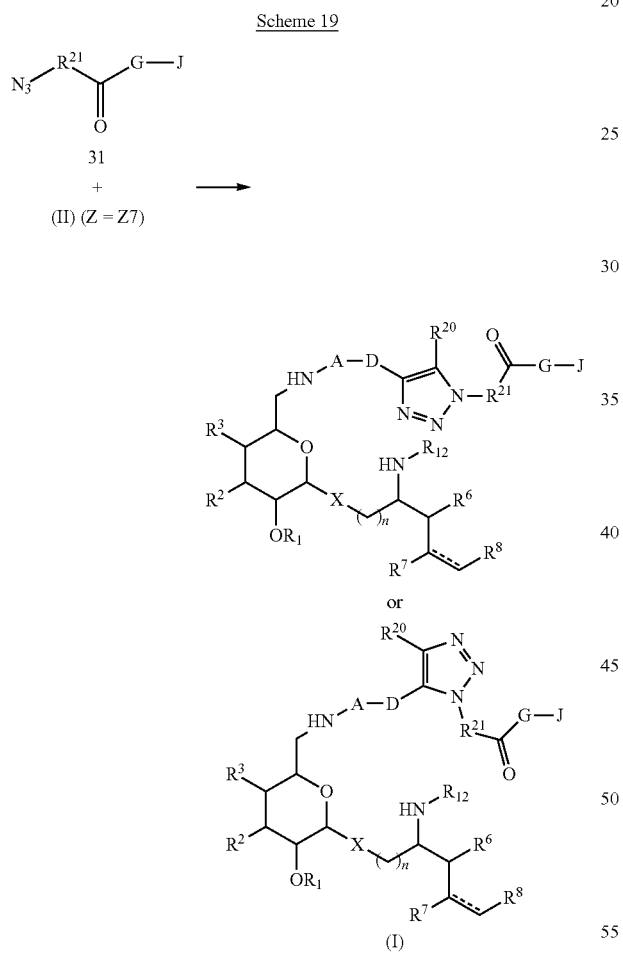

Scheme 19

Z is Z7: The compound of formula (II) is reacted with azido-functionalized peptide 31 under the conditions described above.

Z is Z23: The compound of formula (II) is mixed with azido-functionalized peptide 31 in an appropriate solvent at rt. After completion of the reaction, the solvent is removed and the product is purified by chromatography on the appropriate solid phase (e.g. silica gel, C4, and/or C18 silica).

General Method (12) for Coupling of Antigen to Compounds of Formula (II) by Thiol-Maleimide Conjugate Addition where Z is Z3, Z10 or Z17

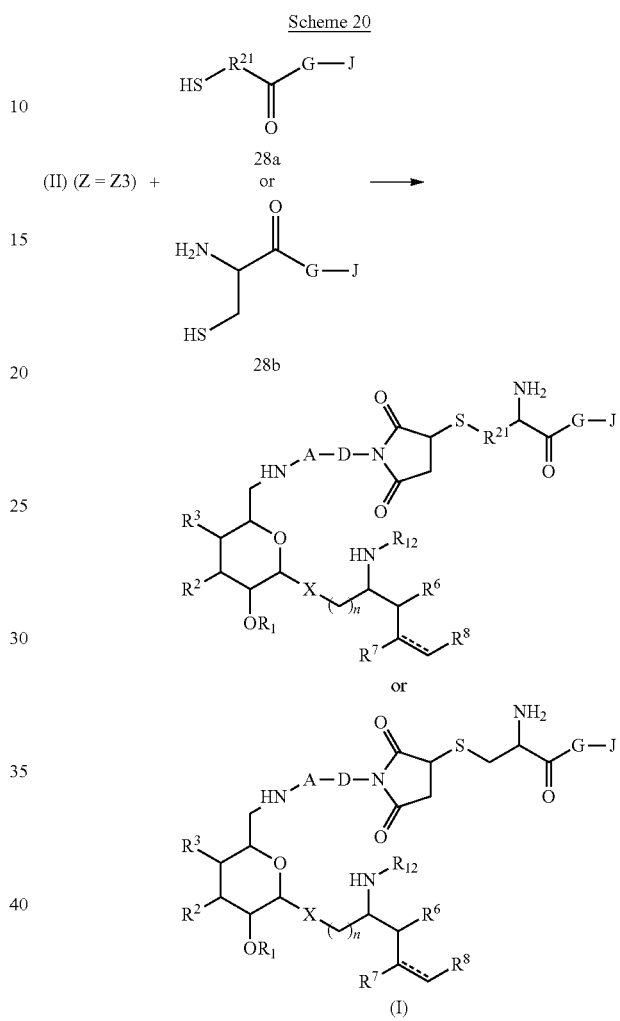

Scheme 20

Z is Z3: The compound of formula (II) and peptide-thiol 28a or N-terminal cysteinyl peptide 28b are dissolved in an appropriate solvent system, optionally in the presence of excess TCEP to ensure the thiol remains in the reduced state. Suitable solvents may include chloroform, THF, methanol, DMF, DMSO, tert-butanol, water, or mixtures thereof. The mixture is stirred at 4° C. to rt. After completion of the reaction, the product is purified by chromatography on the appropriate solid phase (e.g. silica gel, C4, and/or C18 silica).

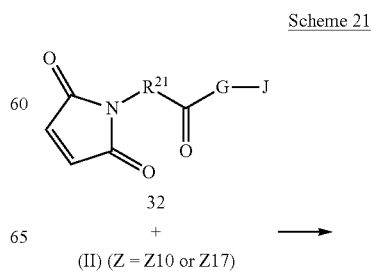

Scheme 21

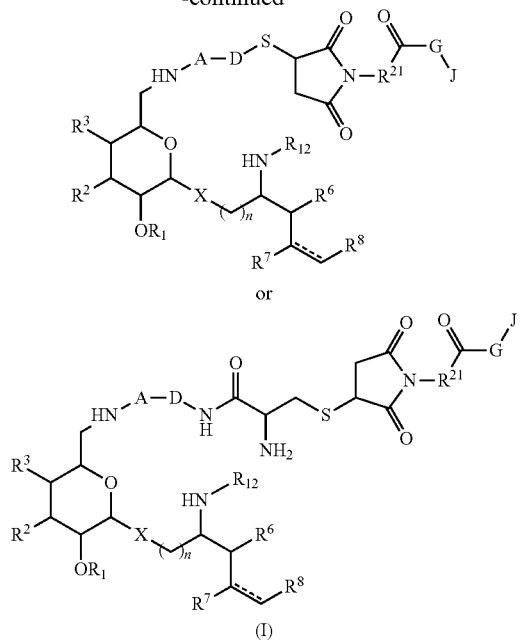

(I)

Z is Z10 or Z17: The compound of formula (II) is reacted with maleimido-functionalized peptide 32 under the conditions described above.

General Method (13) for Coupling of Antigen to Compounds of Formula (II) by Oxime or Hydrazone Formation where Z is Z1, Z8 or Z9

Scheme 22

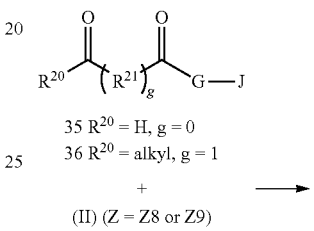

33 X = —ONH$_2$
34 X = —C(O)NHNH$_2$

+

(II) (Z = Z1)

Z is Z1: The compound of formula (II) and either aminooxy-functionalised peptide 33 or hydrazide derivative 34 are stirred at room temperature in the minimum amount of an aqueous-organic solvent system required for dissolution of both components. Suitable organic solvents may include chloroform, THF, methanol, DMF, DMSO, tert-butanol, or mixtures thereof. Anilinium acetate (Dirksen, Hackeng et al. 2006) or anilinium trifluoroacetate (up to 200 mM) may be incorporated as both buffer (pH 3.5-5.0) and catalyst for the reaction. After completion of the reaction, the product is purified by chromatography on the appropriate solid phase (i.e. silica gel, C4, and/or C18 silica).

Scheme 23

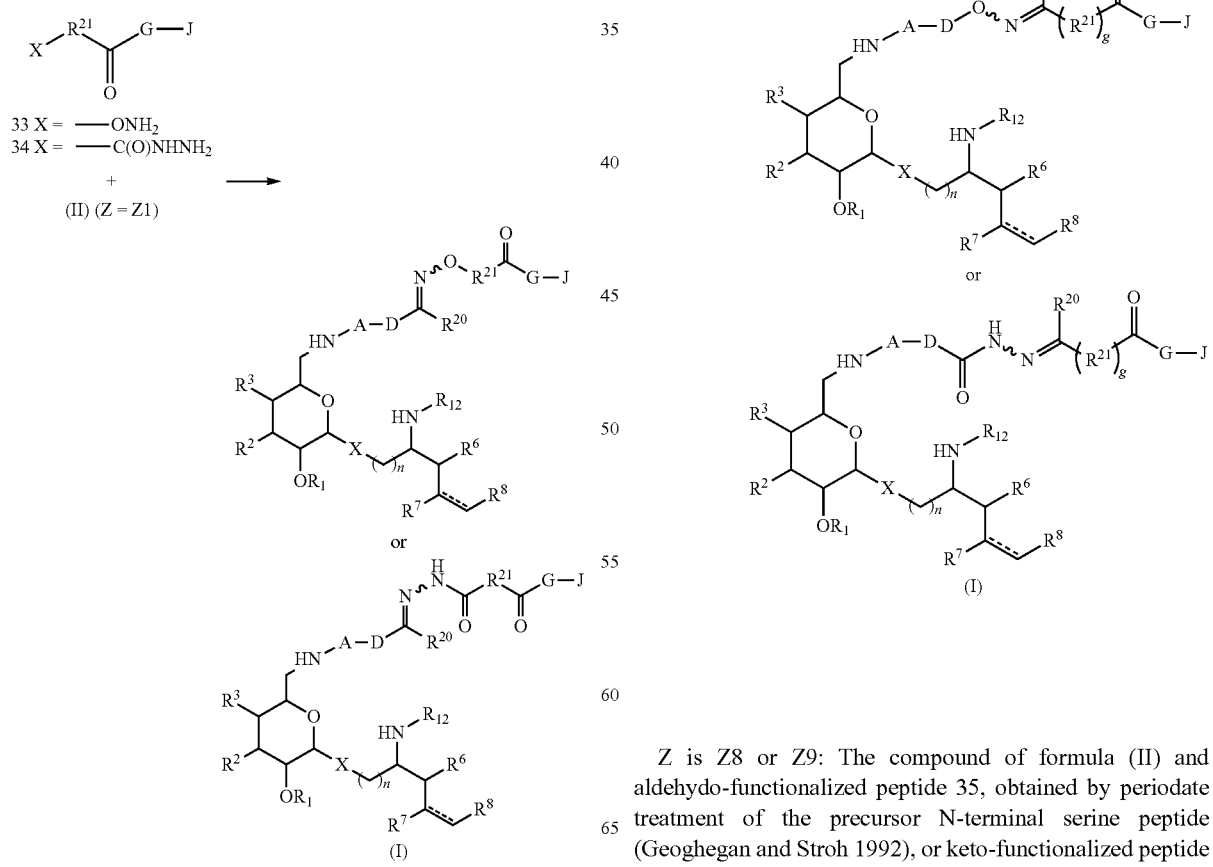

35 R$^{20}$ = H, g = 0
36 R$^{20}$ = alkyl, g = 1

+

(II) (Z = Z8 or Z9)

Z is Z8 or Z9: The compound of formula (II) and aldehydo-functionalized peptide 35, obtained by periodate treatment of the precursor N-terminal serine peptide (Geoghegan and Stroh 1992), or keto-functionalized peptide 36 are reacted under the conditions described above.

General Method (14) for Coupling of Antigen to Compounds of Formula (II) by Disulfide Exchange where Z is Z10 or Z11

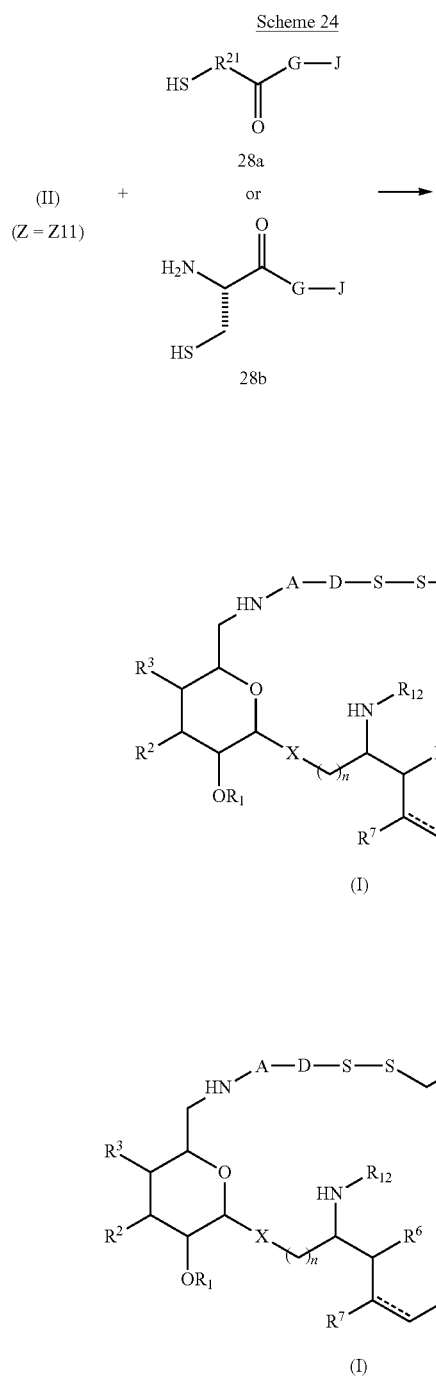

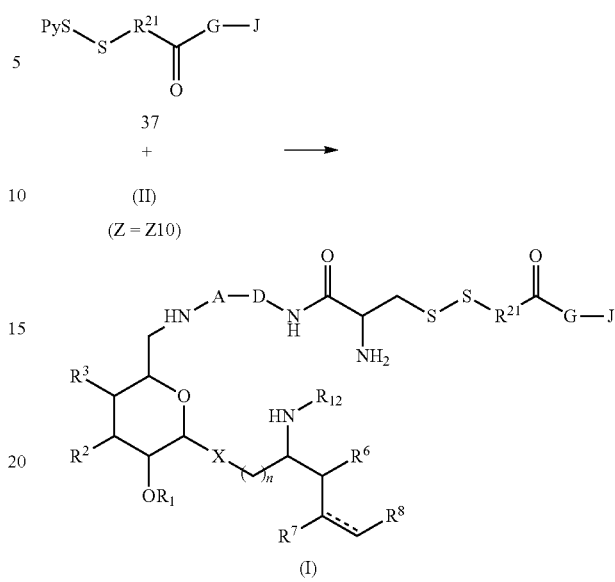

Z is Z10: The compound of formula (II) and disulfide-functionalized peptide 37 are reacted under the conditions described above.

General Method (15) for Coupling of Antigen to Compounds of Formula (II) by Diels-Alder Cycloaddition where Z is Z12

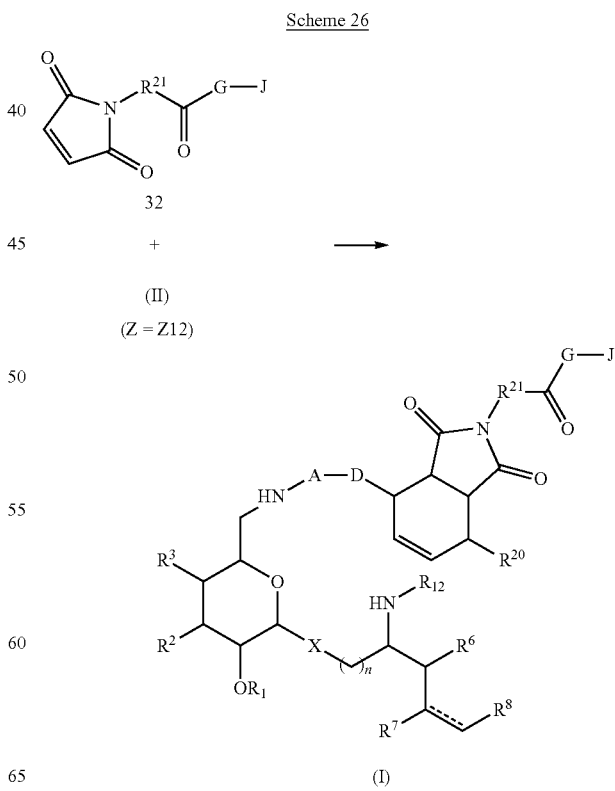

Z is Z11: The compound of formula (II) (prepared by reaction of a precursor thiol with dipyridyl disulfide) and either peptide thiol 28a or N-terminal cysteinyl peptide 28b are allowed to react at room temperature under an inert atmosphere in an appropriate solvent system buffered to pH 6.5-7.5 (Widdison, Wilhelm et al. 2006). Suitable solvents may include chloroform, THF, methanol, DMF, DMSO, tert-butanol, water or mixtures thereof.

Z is Z12: The compound of formula (II), the diene moiety of which is either commercially available or obtained following literature methods (Hudlicky, Koszyk et al. 1980; Choi, Ha et al. 1989), and maleimido-functionalized peptide 32 are allowed to react in an appropriate solvent system (e.g., chloroform, THF, methanol, DMF, DMSO, tert-butanol, water or mixtures thereof) at pH≤6.5 (de Araujo, Palomo et al. 2006).

General Method (16) for Coupling of Antigen to Compounds of Formula (II) by Native Chemical Ligation where Z is Z13

Scheme 27

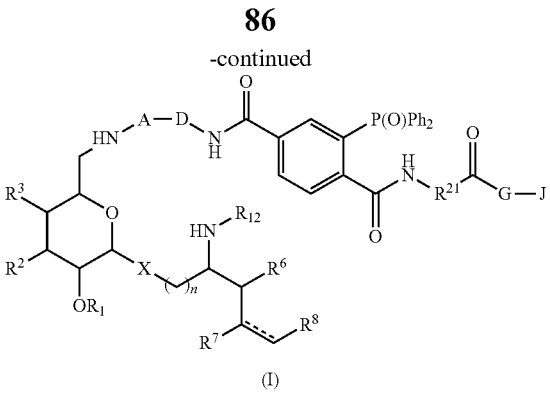

The compound of formula (II) and N-terminal cysteinyl peptide 28b are allowed to react in an appropriate solvent system (e.g., chloroform, THF, methanol, DMF, DMSO, tert-butanol, water or mixtures thereof) following literature protocols (Hackenberger and Schwarzer 2008).

General Method (17) for Coupling of Antigen to Compounds of Formula (II) by Staudinger Ligation where Z is Z14 or Z4

Scheme 28

Z is Z14: The compound of formula (II) and azido peptide 31 are allowed to react in an appropriate solvent system (e.g., chloroform, THF, methanol, DMF, DMSO, tert-butanol, water or mixtures thereof) following literature protocols (Saxon and Bertozzi 2000).

Scheme 29

Z is Z4: The compound of formula (II) and peptide 38 (prepared following literature protocols) (Kiick, Saxon et al. 2002) are allowed to react as described above.

General Method (18) for Coupling of Antigen to Compounds of Formula (II) by Traceless Staudinger Ligation where Z is Z15 or Z4

Scheme 30

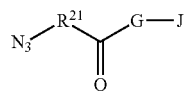

31

+

(II)
(Z = Z15)

→

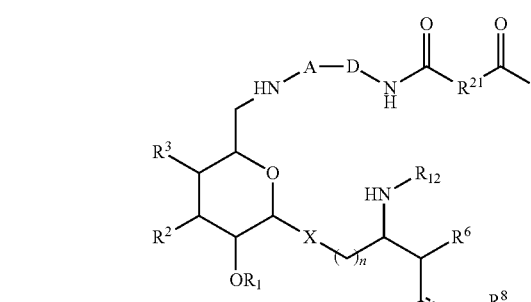

(I)

Z is Z15: The compound of formula (II), wherein the thioester group Z15 is prepared following literature procedures (Soellner, Tam et al. 2006), and azido peptide 31 are allowed to react in an appropriate solvent system (e.g. chloroform, THF, methanol, DMF, DMSO, tert-butanol, water or mixtures thereof) following literature protocols (Soellner, Tam et al. 2006; Tam, Soellner et al. 2007).

General Method (19) for Coupling of Antigen to Compounds of Formula (II) where Z is Z16 or Z17

Scheme 31

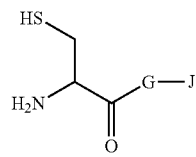

28b

+

(II)
(Z = Z16)

→

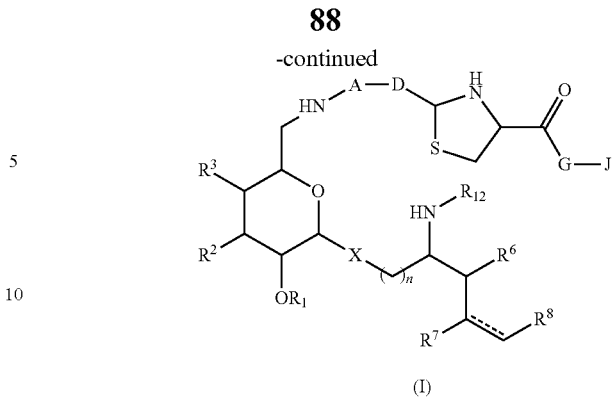

(I)

Z is Z16: The compound of formula (II), wherein the aldehyde group Z16 is obtained from ozonolytic cleavage of a precursor alkene, or acidic deprotection of a precursor acetal, and N-terminal cysteinyl peptide 28b are allowed to react in an appropriate solvent system (e.g., chloroform, THF, methanol, DMF, DMSO, tert-butanol, water or mixtures thereof) at pH 5-7, following literature protocols (Liu and Tam 1994; Liu, Rao et al. 1996).

Scheme 32

OHC—⟨ ⟩—G—J

35

+

(II)
(Z = Z17)

→

(I)

Z is Z17: The compound of formula (II) and aldehyde-terminated peptide 35, are allowed to react as described above.

General Method (20) for the Synthesis of Peptidic Antigen G-J

Functionalised peptides are synthesised according to reported methods that utilize solid phase peptide synthesis (SPPS) (Amblard, Fehrentz et al. 2006). In particular, the Fmoc protection approach (Atherton, Fox et al. 1978; Fields and Noble 1990) on an appropriately functionalised resin (e.g. trityl chloride resin, 2-chlorotrityl chloride resin, Wang resin, Sasrin resin, HMPB resin) can be employed for the synthesis of functionalised peptides. Peptides with C-terminal amides are constructed on Rink amide, Pal, MBHA or Sieber resins. A brief description, using trityl chloride resin, follows:

Trityl chloride resin (1 g) is swollen in dry DCM for 30 mins. After this time Fmoc-AA-OH (1.131 g, 3.20 mmol) and DIPEA (0.669 ml, 3.84 mmol) are added with dry DCM under an argon atmosphere and the reaction stirred for 1 h. The resin is transferred to a sintered reaction vessel and washed with DCM. A solution containing HBTU (7.59 g) and 4.18 mL DIPEA (4.18 mL) in dry DMF (50 mL) is prepared and 8 mL of this solution is used for each coupling. The reaction sequence for coupling is as follows; swell resin in DCM for 30 mins, for each iteration (i), wash thoroughly with DMF (ii), deprotect with 20% piperidine in DMF for 5 mins (×2) (iii), wash with DMF (iv), swell with DCM (v), wash with DMF (vi), add amino acid and 8 mL of coupling solution and shake for 30 mins. Steps (i)-(vi) are repeated to end of peptide. Finally, while the peptide is still attached to the resin, an appropriately functionalised acid is coupled to the free N-terminus to give the fully protected, resin-bound, functionalized peptides 28-38.

Cleavage from the resin: the beads are treated with 95:2.5:2.5 TFA:TIS:water for 3 h, during this time the beads turn a bright red colour. After 3 h the beads are filtered and washed with TFA. The TFA is evaporated and the peptide precipitated and washed with ether to afford the crude peptide. The material is purified via reverse phase preparative HPLC, eluting with 10-50% acetonitrile water with 0.1% TFA. The material is characterised by LC-MS.

ABBREVIATIONS

Figure 1:
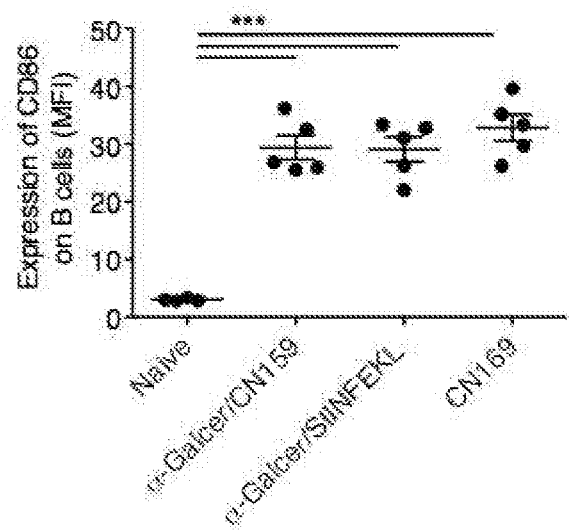
FIG. 1 shows CD86 expression on B cells in the peripheral blood as a readout of NKT cell activity in response to injection of compounds of the invention. Groups of C57BL/6 mice (n=3) are injected intravenously with 0.23 nmol of the indicated glycolipid compounds and then the blood samples collected 20 h later for the analysis of CD86 expression on CD45 (B220)+B cells by antibody labelling and flow cytometry. Mean fluorescence index (MFI)±SEM are presented, *P<0.05, *P<0.01, ***P<0.001. The data show that injection of the conjugate CN169 induces activation of NKT cells resulting in levels of CD86 expression on B cells that are similar to injection of admixed α-GalCer and SIINFEKL (SEQ ID NO: 262), or admixed α-GalCer and CN159, an N-terminal extended peptide derivative that is a presumed in vivo breakdown product of CN169.
Figure 2:
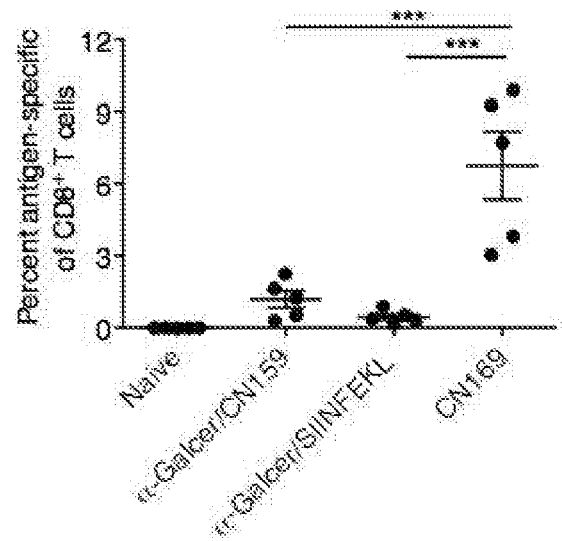
FIG. 2 shows enumeration of T cells with specificity for the peptide antigen SIINFEKL (SEQ ID NO: 262) following intravenous administration of compounds of the invention as vaccines into mice. The compounds are injected to give the equivalent molar dose of SIINFEKL (SEQ ID NO: 262) peptide in each case. To increase sensitivity of the assay, all mice are initially donated a cohort of 10,000 SIINFEKL-specific T cells from a transgenic mouse encoding a T cell receptor for this antigen (OT-1 mice) by intravenous injection of the cells one day before the vaccines are administered. To discriminate the donated T cells from those of the host, the donated cells exhibit congenic expression of the CD45.1 variant of the CD45 molecule. It is therefore possible to enumerate SIINFEKL-specific T cells in blood by flow cytometry using antibodies for CD45.1 together with antibodies for the transgenic T cell receptor (Vα2). Control animals (naïve) are injected with the diluent phosphate-buffered saline (PBS). The data show that injection of the conjugate CN169 induces a larger population of SIINFEKL-specific T cells than injection of admixed components α-GalCer and SIINFEKL (SEQ ID NO: 262), or admixed α-GalCer and CN159. Each dot represents a different animal; mean per treatment group±SEM are presented. *P<0.05, *P<0.01, ***P<0.001
Figure 3:
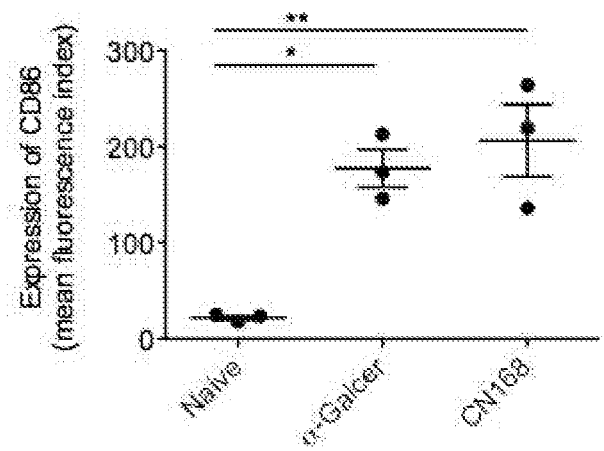
FIG. 3 shows CD86 expression on dendritic cells. The data show that injection of compounds of the invention induces activation of iNKT cells and subsequent maturation of dendritic cells, as indicated by up-regulation of expression of the activation marker CD86. Groups of C57BL/6 mice (n=3) are injected intravenously with 0.571 nmol of the indicated compounds and then the spleens removed 20 h later for the analysis of CD86 expression on CD11c$^+$ dendritic cells by antibody labelling and flow cytometry. Mean fluorescence index (MFI)±SEM are presented. *P<0.05, *P<0.01, ***P<0.001
Figure 4:
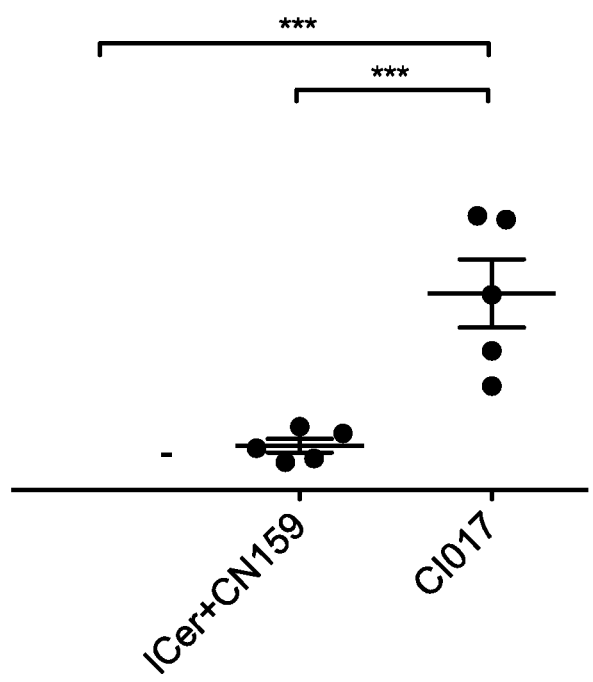
FIG. 4 shows the cytotoxic capacity of T cells with specificity for the peptide antigen SIINFEKL (SEQ ID NO: 262) following intravenous administration of compounds of the invention as vaccines into wild type mice. The compounds are injected to give the equivalent molar dose of SIINFEKL (SEQ ID NO: 262) peptide, in each case of 0.571 nmol. Flow cytometry is used to assess the killing of target cells comprised of syngeneic splenocytes loaded ex vivo with 5 μM SIINFEKL (SEQ ID NO: 262) injected intravenously 7 days after vaccination. To discriminate the targets from host tissue, the injected cells are labelled with the fluorescent dye carboxyfluorescein succinimidyl ester (CFSE). A cohort syngeneic splenocytes (without peptide) labelled with the fluorescent dye cell tracker orange are also injected to serve as controls. Killing is defined as the percentage of peptide-loaded targets killed relative to control cells. Each treatment group contained 5 animals. Control animals are injected with the diluent phosphate-buffered saline (PBS). The data show that injection of CI-017 induces greater SIINFEKL (SEQ ID NO: 262)-specific cytotoxicity compared to injection of PBS, or injection of α-GalCer mixed with CN159, which is an N-terminal extended SIINFEKL (SEQ ID NO: 262) peptide (including the protease cleavage sequence FFRK) that is used in manufacture of the conjugate. Mean percentage of killing per group±SEM are shown. ***p<0.001
Figure 5:
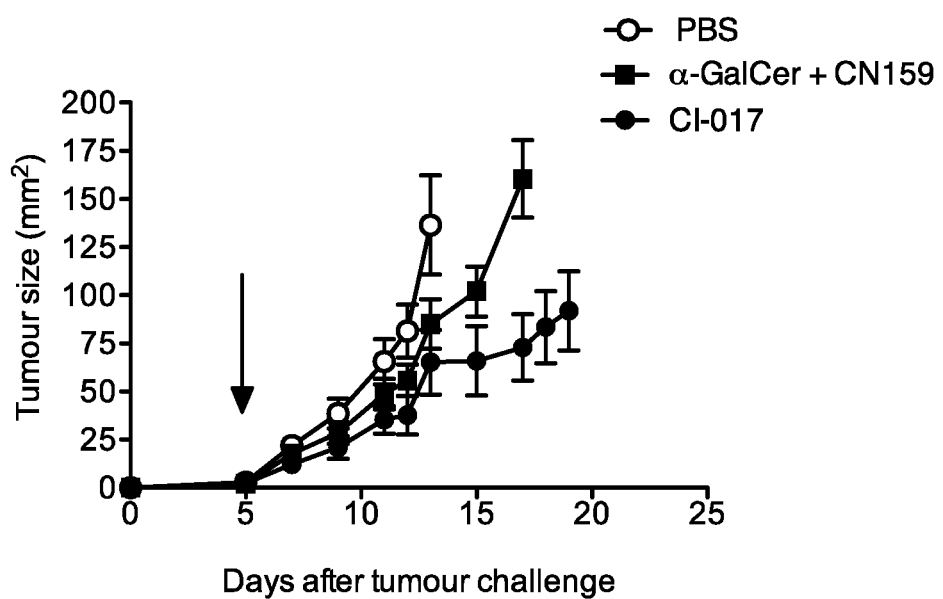
FIG. 5 shows the antitumour effect of vaccination with conjugate vaccine CI-017 (0.571 nmol) compared to vaccination with peptide CN159 (0.571 nmol) mixed with α-GalCer (0.571 nmol). Progression of subcutaneous B16.OVA tumours is monitored in animals treated five days after tumour challenge with intravenous CI-017 or CN159 peptide and α-GalCer or with PBS. The mean tumour sizes per group (n=5)±SEM are shown. These data show that vaccination with CI-017 results in superior anti-tumour activity as compared to the control groups.

NMR Nuclear magnetic resonance spectrometry
HRMS High resolution mass spectrometry
ESI Electrospray ionisation
RT Room temperature
THF Tetrahydrofuran
PBS Phosphate-buffered saline
HPLC High performance liquid chromatography
FCS Fetal calf serum
MS Mass spectrometry
LC-MS Liquid chromatography-mass spectrometry
TFA Trifluoroacetic acid
TLC Thin layer chromatography
DMF Dimethylformamide DMSO Dimethylsulfoxide
DCM Dichloromethane
NMP N-methyl-2-pyrrolidone
DDQ 2,3-Dichloro-5,6-dicyano-1,4-benzoquinone
PMB p-Methoxybenzyl
DMAP 4-Dimethylaminopyridine
TMS Trimethylsilyl
DCC N,N'-dicyclohexylcarbodiimide
DIPEA N,N-diisopropylethylamine
TBDPS tert-Butyldiphenylsilyl
TBAF Tetra-n-butylammonium fluoride
THP Tetrahydropyranyl
EDCI 1-Ethyl-3-β-dimethylaminopropyl)carbodiimide
CAN Ceric ammonium nitrate
Tbeoc-Thz N-(2-(tert-Butyldisulfanyl)ethoxycarbonyl)-L-thiazolidine-4-carboxylic acid
HBTU 2-(1H-benzotriazol-1-yl)-1,1,3,3-tetramethyluronium hexaflurophosphate.
TCEP Tris(2-carboxyethyl)phosphine)
TBTA Tris(benzyltriazolylmethyl)amine

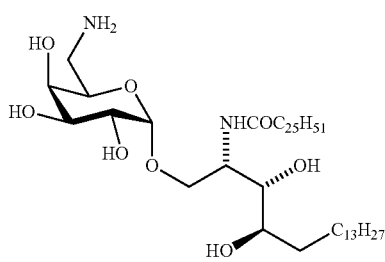

CN168

THPTA Tris(3-hydroxypropyltriazolylmethyl)amine
Bim(Py)₂ ((2-Benzimidazolyl)methyl)-bis-((2-pyridyl)methyl)amine
EDTA Ethylenediaminetetraacetic acid

EXAMPLES

The examples described herein are for purposes of illustrating embodiments of the invention. Other embodiments, methods, and types of analyses are within the capabilities of persons of ordinary skill in the art and need not be described in detail herein. Other embodiments within the scope of the art are considered to be part of this invention.

Anhydrous solvents are obtained commercially. Air sensitive reactions are carried out under Ar. Thin layer chromatography (TLC) is performed on aluminium sheets coated with 60 $F_{254}$ silica. Flash column chromatography is performed on Merck or SiliCycle silica gel (40-63 μm) or SiliCycle reversed phase (C18) silica gel (40-63 μm). NMR spectra are recorded on a Bruker 500 MHz spectrometer. $^1$H NMR spectra are referenced to tetramethylsilane at 0 ppm (internal standard) or to residual solvent peak (CHCl₃ 7.26 ppm, CHD₂OD 3.31 ppm, CHD₂S(O)CD₃ 2.50 ppm). $^{13}$C NMR spectra are referenced to tetramethylsilane at 0 ppm (internal standard) or to the deuterated solvent peak (CDCl₃ 77.0 ppm, CD₃OD 49.0 ppm, CD₃S(O)CD₃ 39.52 ppm). CDCl₃-CD₃OD solvent mixtures are always referenced to the methanol peak. High resolution electrospray ionization mass spectra are recorded on a Q-Tof Premier mass spectrometer.

Example 1—Synthesis of (2S,3S,4R)-1-O-α-6-Amino-6-deoxy-D-Galactopyranosyl-4-hexacosanoyl-2-((4-oxopentanoyloxy)methoxycarbonylamino)octadecane-1,3,4-triol (CN300)

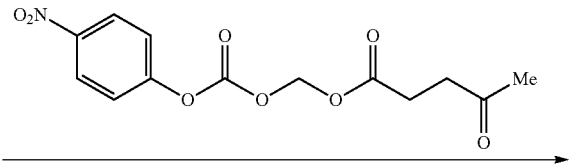

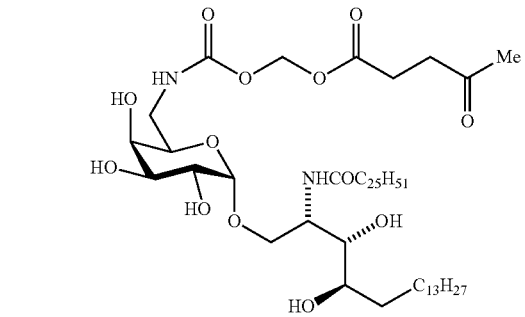

CN300

Example 1.1—(4-Nitrophenoxy)carbonyloxymethyl 4-oxopentanoate (41)

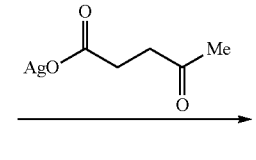

-continued

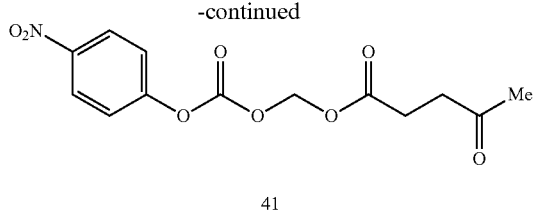

41

The silver salt of levulinic acid is prepared by adding a solution of AgNO₃ (700 mg, 4.1 mmol) in water (10 mL) to the sodium salt of levulinic acid (4.3 mmol in ~10 mL water, prepared by basification of levulinic acid with 1 M aq NaOH to pH 7-8). After 30 min, the resultant precipitate is isolated by filtration and washed with cold water followed by Et₂O. The product is dried under vacuum to afford the silver salt as a white solid (636 mg, 69%). A mixture of iodomethyl 4-nitrophenyl carbonate (Gangwar, Pauletti et al. 1997) (105 mg, 0.325 mmol, dried by azeotropic distillation with toluene), 4 Å molecular sieves (~250 mg) and silver levulinate (89 mg, 0.40 mmol) in dry toluene (1.5 mL) is protected from light and stirred at 40° C. After 4 h, the mixture is diluted with Et₂O, filtered through celite, and concentrated under reduced pressure. The crude residue is purified by silica gel chromatography (30% to 40% EtOAc/petroleum ether) to afford the title compound (41) (85 mg, 84%) as a colourless oil. ¹H NMR (500 MHz, CDCl₃) δ 2.20 (s, 3H), 2.67-2.70 (m, 2H), 2.80-2.83 (m, 2H), 5.88 (s, 2H), 7.38-7.48 (m, 2H), 8.24-8.34 (m, 2H); ¹³C NMR (126 MHz, CDCl₃) δ 27.7, 29.7, 37.6, 82.5, 121.8, 125.4, 145.7, 151.5, 155.1, 171.2, 206.0; HRMS (ESI): m/z calcd for C₁₃H₁₃NO₈Na [M+Na]⁺ 334.0539, found 334.0544.

Example 1.2—(2S,3S,4R)-1-(2,3-Di-O-benzyl-6-O-(4-toluenesulfonyl)-α-D-galactopyranosyloxy)-3,4-di(benzyloxy)-2-hexacosanoylamino-octadeca-6-ene (CN301)

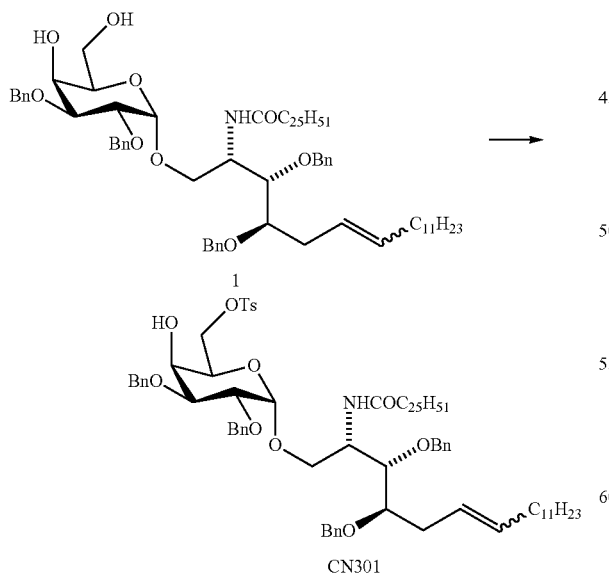

Tosyl chloride (0.091 g, 0.476 mmol) is added to diol 1 (0.276 g, 0.227 mmol) (which is prepared as described in Lee, A., K. J. Farrand, et al. (2006) "Novel synthesis of alpha-galactosyl-ceramides and confirmation of their powerful NKT cell agonist activity." Carbohydr Res 341(17): 2785-2798.) stirring in pyridine (2.76 ml, 34.1 mmol) at 0° C. and the mixture left to warm to r.t. over 18 h. Over the following 8 h, the reaction mixture is warmed to 35° C. and more tosyl chloride added in aliquots (total added: 0.300 g, 1.57 mmol) until the starting material has disappeared by TLC. Once cool, the solution is diluted with EtOAc, H₂O is added and allowed to stir for 30 mins. The layers are then separated, the organic layer dried (MgSO₄) and the solvent removed. Purification of the resulting residue by silica gel chromatography (10% EtOAc/petroleum ether changing to 20% EtOAc/petroleum ether) gave the mono-tosylated material CN301 (0.246 g, 0.179 mmol, 79%) as a colourless oil. [α]_D²⁰=+16.4 (c 0.005, CHCl₃); ¹H NMR (500 MHz, CDCl₃) δ 0.88 (t, J=6.8 Hz, 6H), 1.22-1.32 (m, 62H), 1.47-1.51 (m, 2H), 1.86-1.95 (m, 2H), 2.02-2.06 (m, 2H), 2.40 (s, 3H), 2.43-2.53 (m, 2H), 3.60-3.63 (m, 1H), 3.74-3.77 (m, 4H), 3.80 (dd, J=9.7, 3.2 Hz, 1H), 3.93-3.94 (m, 1H), 3.97-3.99 (m, 1H), 4.09-4.17 (m, 2H), 4.33-4.38 (m, 1H), 4.51-4.54 (m, 2H), 4.58 (d, J=11.7 Hz, 1H), 4.60 (d, J=11.6 Hz, 1H), 4.66 (d, J=11.6 Hz, 1H), 4.70 (d, J=11.7 Hz, 2H), 4.74 (d, J=11.5 Hz, 1H), 4.77 (d, J=3.4 Hz, 1H), 5.43-5.52 (m, 2H), 5.68-5.72 (m, 1H), 7.22-7.32 (m, 22H), 7.74 (d, J=8.3 Hz, 2H); ¹³C NMR (125 MHz, CDCl₃) δ 14.1, 22.7, 25.6, 27.6, 27.8, 29.3, 29.4, 29.6, 29.7, 31.9), 36.7, 49.8, 67.1, 67.9, 68.5, 68.9, 71.5, 72.7, 73.3, 75.7, 77.0, 79.29, 79.31, 98.5, 125.4, 127.5, 127.6, 127.68, 127.72, 127.76, 127.8, 128.0, 128.3, 128.4, 128.5, 129.8, 132.1, 137.8, 138.2, 138.5, 138.6, 144.8, 172.8; HRMS (ESI): m/z calcd for C₈₅H₁₂₇NO₁₁SNa [M+Na]⁺ 1392.9028, found 1392.9031.

Example 1.2—(2S,3S,4R)-2-Hexacosanoylamino-1-(6-O-(4-toluenesulfonyl)-α-D-galactopyranosyloxy)-3,4-octadecandiol (CN302)

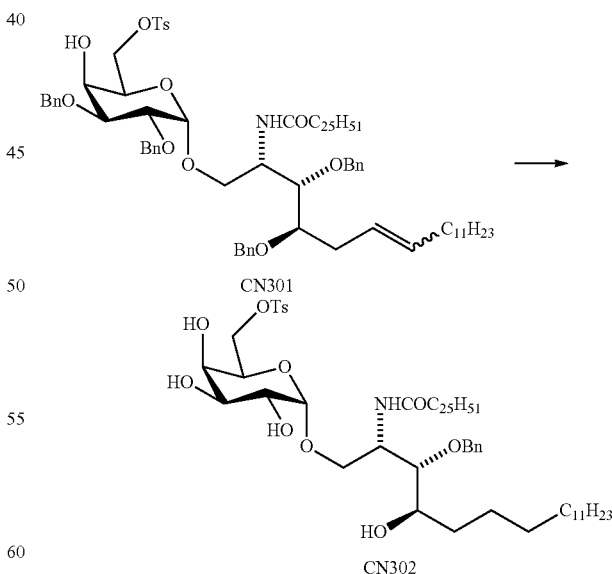

Pd(OH)₂/C (20% Pd; ~5 mg) is added to protected tosylate CN301 (0.040 g, 0.029 mmol) stirring in anhydrous CH₂Cl₂:MeOH (4 mL; 1:1). The reaction vessel is evacuated and flushed with hydrogen and stirred at r.t. for 24 h. The product mixture is filtered through celite, washed repeatedly with CHCl$_3$:MeOH (3:1) and then concentrated. Purification by silica gel chromatography (100% CHCl$_3$ changing to 10% MeOH/CHC$_3$) gives the target CN302 (23 mg, 0.023 mmol, 79%) as a white solid. $^1$H NMR (500 MHz, CDCl$_3$/CD$_3$OD 3:1) δ 0.88 (t, J=6.9 Hz, 6H), 1.23-1.42 (m, 68H), 1.52-1.68 (m, 4H), 2.16-2.26 (m, 2H), 2.46 (s, 3H), 3.35-3.36 (m, 1H), 3.52-3.58 (m, 2H), 3.64 (dd, J=10.7, 4.0 Hz, 1H), 3.70-3.76 (m, 2H), 3.83-3.87 (m, 2H), 4.03-4.06 (m, 1H), 4.13-4.23 (m, 2H), 4.85 (d, J=3.4 Hz, 1H), 7.58 (d, J=8.1 Hz, 2H), 7.79 (d, J=8.1 Hz, 2H); $^{13}$C NMR (125 MHz, CDCl$_3$/CD$_3$OD 3:1) δ 14.2, 21.7, 22.9, 26.1, 29.59, 29.63, 29.7, 29.8, 29.92, 29.95, 30.04, 32.2, 32.8, 36.8, 50.4, 68.1, 68.9, 69.2, 69.6, 70.1, 72.4, 74.9, 77.8, 99.9, 128.2, 130.2, 132.8, 145.5, 174.6; HRMS (ESI): m/z calcd for C57H$_{105}$NO$_{11}$SNa [M+Na]$^+$ 1034.7306, found 1034.7317.

Example 1.3—(2S,3S,4R)-2-Hexacosanoylamino-1-(2,3,4-tri-O-acetyl-6-O-(4-toluenesulfonyl)-α-D-galactopyranosyloxy)-3,4-di(acetyloxy)octadecane (CN303)

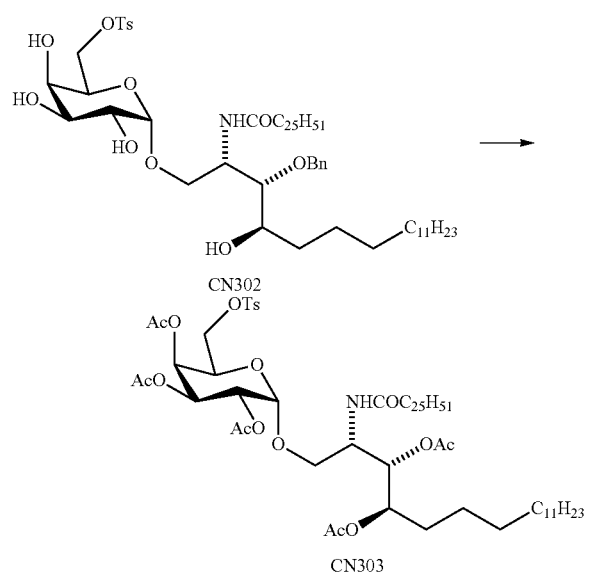

Tosylate CN302 (10 mg, 9.9 µmol) is dissolved in pyridine (0.10 mL, 1.2 mmol) and cooled to 0° C. Acetic anhydride (0.10 mL, 1.0 mmol) and 4-(dimethylamino)pyridine (1.0 mg, 8.1 µmol) are then added and stirred at r.t. for 5 h. The product mixture is diluted with CH$_2$Cl$_2$, and is washed with 1M HCl, saturated NaHCO$_3$, brine, dried (MgSO$_4$) and the solvent removed in vacuo. Purification by silica gel chromatography (20% EtOAc/petroleum ether changing to 30% EtOAc/petroleum ether) affords the acetylated compound CN303 (10 mg, 8.2 µmol, 83%) as a colourless oil. $^1$H NMR (500 MHz, CDCl$_3$) δ 0.88 (t, J=6.9 Hz, 6H), 1.22-1.33 (m, 68H), 1.62-1.75 (m, 4H), 1.97 (s, 3H), 1.99 (s, 3H), 2.05 (s, 3H), 2.07 (s, 3H), 2.08 (s, 3H), 2.23-2.29 (m, 2H), 2.45 (s, 3H), 3.37 (dd, J=10.8, 2.7 Hz, 1H), 3.62 (dd, J=10.8, 2.9 Hz, 1H), 3.98 (dd, J$_{A,B}$=10.3, J$_{A,X}$=5.9 Hz, 1H), 4.04 (dd, J$_{B,A}$=10.2, J$_{B,X}$=6.7 Hz, 1H), 4.16 (t, J=6.9 Hz, 1H), 4.36 (tt, J=9.7, 2.7 Hz, 1H), 4.87-4.90 (m, 2H), 5.10 (dd, J=10.9, 3.6 Hz, 1H), 5.23 (dd, J=9.8, 2.5 Hz, 1H), 5.29 (dd, J=10.9, 3.4 Hz, 1H), 5.41 (br d, J=2.8 Hz, 1H), 6.24 (d, J=9.7 Hz, 1H), 7.34 (d, J=8.2 Hz, 2H), 7.75 (d, J=8.2 Hz, 2H); HRMS (ESI): m/z calcd for C$_{67}$H$_{115}$NO$_{16}$SNa [M+Na]$^+$ 1244.7834, found 1244.7844.

Example 1.4—(2S,3S,4R)-1-(6-Deoxy-6-azido-α-D-galactopyranosyloxy)-2-hexacosanoylamino-3,4-octadecandiol (CN304)

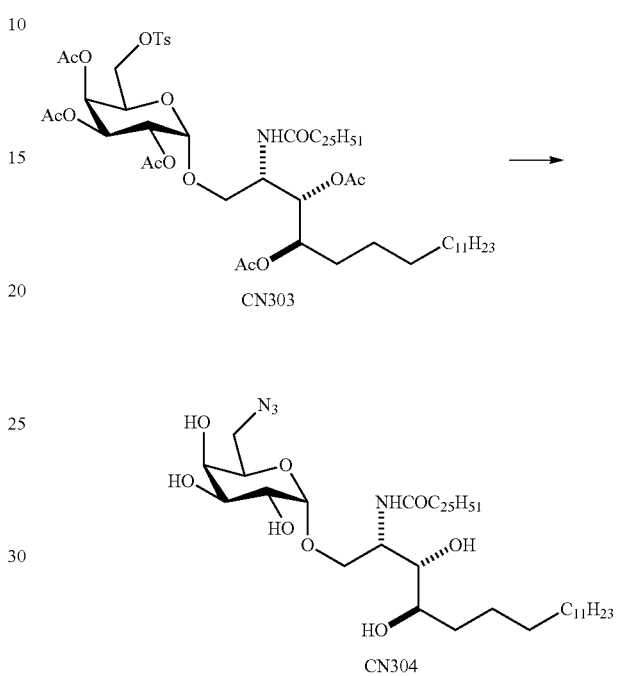

To a stirred solution of the tosylate CN303 (140 mg, 0.115 mmol) in DMF (5 mL) is added sodium azide (150 mg, 2.28 mmol) and 15-crown-5 ether (20 mg, 0.089 mol). The mixture is heated to 90° C. for 18 hr at which time further sodium azide (50 mg, 0.041 mmol) is added and heating continued at 100° C. for 2 hrs. After cooling, the mixture is diluted with DCM (50 mL) and water (50 mL). The aqueous phase is re-extracted with ethyl acetate (2×50 mL) and the combined organic extract is dried over MgSO$_4$ and filtered. The solvent is removed via reduced pressure and the crude residue is purified by silica gel chromatography (0% to 20% to 40% to 100% EtOAc/toluene) to afford the azide (115 mg, 96%). The azide is dissolved in DCM/MeOH (3:3 mL) to which 30% NaOMe in MeOH (3 drops) is added and is stirred for 3 hrs. The solvents are removed via reduced pressure and the crude solid is purified by chromatography eluting with MeOH/CHCl$_3$ (0% to 20% to 40%) to afford the title compound CN304 (80 mg, 86%) as a thin film. $^1$H NMR (500 MHz, CDCl$_3$) δ 0.88 (t, J=7.0 Hz, 6H), 1.22-1.41 (m, 68H), 1.50-1.69 (m, 4H), 2.18-2.22 (m, 2H), 3.30-3.38 (m, 2H), 3.50-3.52 (m, 3H), 3.70-3.78 (m, 2H), 3.79-3.84 (m, 1H), 3.85 (brs, 1H), 3.90 (m, 1H), 4.19-4.23 (m, 1H), 4.92 (d, J=3.4 Hz, 1H); $^{13}$C NMR (126 MHz, CDCl$_3$) δ 15.3, 24.0, 27.2, 30.6, 30.7, 30.9, 31.0, 33.3, 33.9, 37.9, 51.4, 52.6, 69.2, 70.1, 71.0, 71.3, 71.4, 73.5, 76.1, 101.0, 175.6; HRMS (ESI): m/z calcd for C$_{50}$H$_{99}$N$_4$O$_8$ [M+H]$^+$ 883.7463, found 883.7465.

Example 1.5—(2S,3S,4R)-1-(6-Deoxy-6-(4-(oxo-pentanoyloxy)methoxycarbonylamino)-α-D-galacto-pyranosyloxy)-2-hexacosanoylamino-3,4-octadecan-diol (CN300)

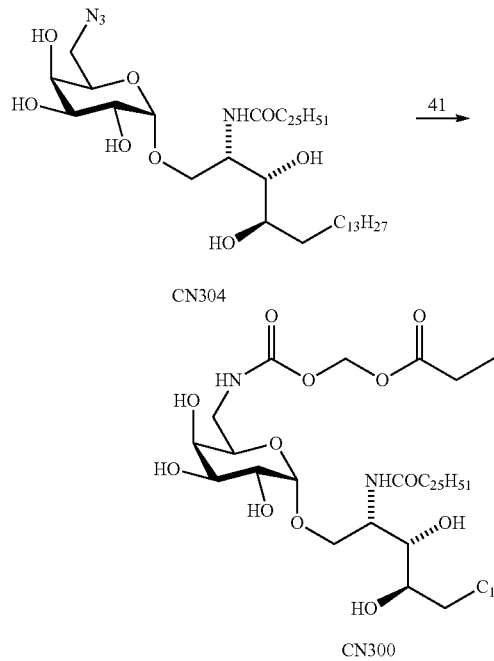

To a solution of the azide CN304 (18 mg, 0.020 mmol) in DCM/MeOH (1:2, 2 mL) is added 20% Pd(OH)$_2$ (20 mg) and the mixture is stirred under hydrogen for 2 hrs. After the hydrogen is removed, the mixture is filtered through celite, and washed CHCl$_3$/MeOH/H$_2$O (30 mL) and hot ethanol (30 mL). The volatiles are concentrated under reduced pressure and pyridine (2 mL) is added followed by a solution of the pNP-carbonate 41 (9.8 mg, 0.032 mmol) in DCM (200 µL) followed by the further addition of triethylamine (1 mL). After stirring at 30° C. for 1 hr, the mixture is diluted with chloroform and the volatiles are removed under reduced pressure. The crude residue is purified by silica gel chromatography (1.5:40:60 to 1.5:45:55 MeOH/dioxane/CHCl$_3$) to afford the title compound CN300 (3 mg, 0.0029 mmol, 15%) as a thin film. $^1$H NMR (500 MHz, 1:1 CDCl$_3$/CD$_3$OD) δ 0.88-0.90 (m, 6H), 1.24-1.34 (m, 68H), 1.55-1.72 (m, 4H), 2.20 (s, 3H), 2.17-2.24 (m, 2H), 2.59-2.63 (m, 2H), 2.79-2.83 (m, 2H), 3.30-3.83 (m, 11H), 4.90-4.93 (m, 1H), 5.69-5.75 (m, 2H); $^{13}$C NMR (126 MHz, 1:1 CDCl$_3$/CD$_3$OD) δ 14.2, 22.8, 26.1, 28.1, 29.5, 29.9, 32.1, 33.0, 36.7, 37.8, 41.4, 50.6, 67.5, 69.1, 69.6, 70.4, 72.4, 75.1, 80.4, 99.9, 156.1, 172.3, 174.7, 208.0; HRMS (ESI): m/z calcd for C$_{57}$H$_{108}$N$_2$O$_{13}$Na [M+Na]$^+$ 1051.7749, found 1051.7750.

Example 1.6—(2S,3S,4R)-1-(6-Deoxy-6-amino)-α-D-galactopyranosyloxy)-2-hexacosanoylamino-3,4-octadecandiol (CN168)

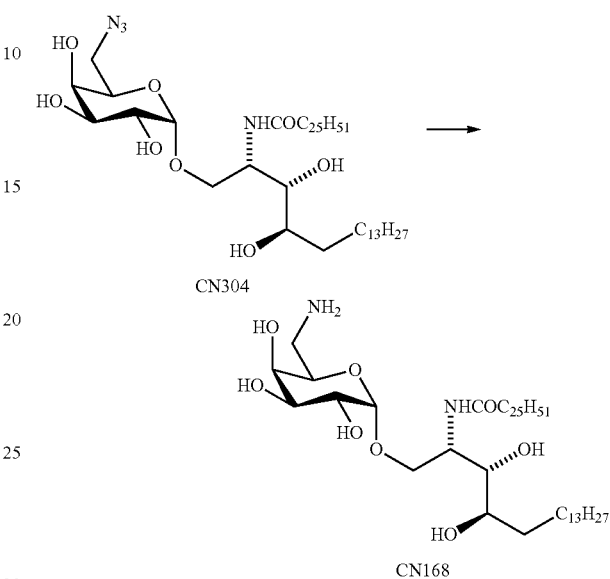

To a solution of the azide CN304 (18 mg, 0.020 mmol) in DCM/MeOH (1:2, 2 mL) is added 20% Pd(OH)$_2$ (20 mg) and the mixture is stirred under hydrogen for 2 hrs. After the hydrogen is removed, the mixture is filtered through celite, and washed with CHCl$_3$/MeOH (30 mL) and hot ethanol (30 mL). The volatiles are concentrated under reduced pressure to afford the title compound CN168 (Zhou, Forestier et al. 2002) (13 mg, 0.015 mmol, 74%) as a white solid. $^1$H NMR (500 MHz, 3:1 CDCl$_3$/CD$_3$OD) δ 0.82-0.85 (m, 6H), 1.18-1.328 (m, 68H), 1.43-1.67 (m, 4H), 2.13-2.20 (m, 2H), 3.07 (dd J=3.8, 13.3 Hz, 1H), 3.20-3.24 (m, 1H), 3.46-3.52 (m, 2H), 3.58-3.62 (m, 1H), 3.68-3.76 (m, 4H), 3.85-3.89 (m, 1H), 3.99-4.02 (m, 1H), 4.92 (d, J=3.5 Hz, 1H), 7.49 (d, J=8.7 Hz, 1H); HRMS (ESI): m/z calcd for C$_{50}$H$_{101}$N$_2$O$_8$ [M+H]$^+$ 857.758, found 857.7559.

Example 2—(2S,3S,4R)-1-(6-Deoxy-6-(4-((2-(FFRKSIINFEKL)-2-(oxo)ethoxyimino)pentanoy-loxy)methoxycarbonylamino)-α-D-galactopyranosy-loxy)-2-hexacosanoylamino-3,4-octadecandiol (CN169)

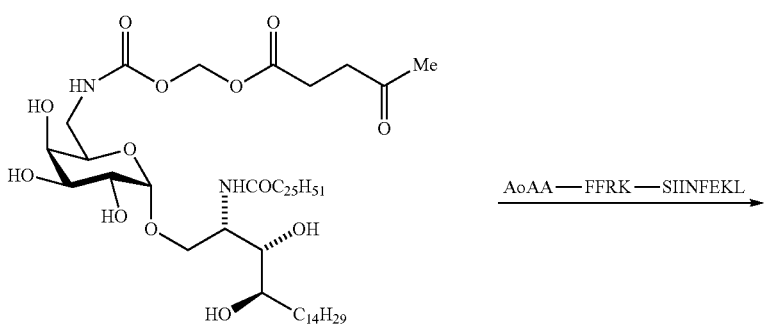 AoAA—FFRK—SIINFEKL

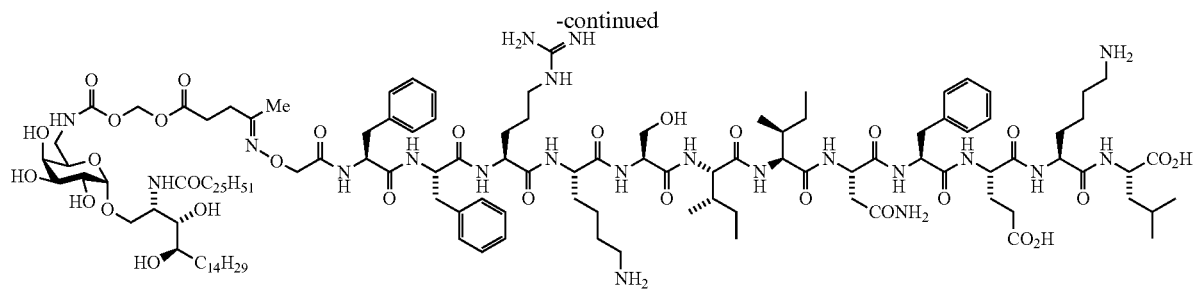

Peptide 2-(aminooxy)acetyl-FFRKSIINFEKL (SEQ ID NO: 415) (12.2 mg, 7.55 mmol) and ketone CN300 (4.20 mg, 4.08 μmol) are stirred together in a mixture of THF (0.71 mL), MeOH (0.35 mL) and water/aniline/TFA (200:6:3, 0.4 mL) at 30-40° C. for 48 h. The solvent is removed and the crude product purified by preparative HPLC (Phenomenex Luna C18(2), 5 μm, 250×30 mm, 35° C., 50 mL/min; Mobile phase A=20:80:0.05 water/MeOH/TFA; Mobile phase B=100:0.05 MeOH/TFA; 0-10 min: 100% A-100% B; 10-15 min: 100% B; 15-16 min: 100% B-100% A; 16-17 min: 100% A) to give the title compound CN169 (5.6 mg, 52%). $^1$H NMR (500 MHz, $d_6$-DMSO) δ 0.69-0.96 (m, 24H), 1.00-1.45 (m, 74H), 1.70-1.50 (m, 27H), 1.79 (s, 3H), 1.90-2.13 (m, 6H), 2.20-2.30 (m, 2H), 2.35-2.49 (m, 6H), 2.72-2.89 (m, 7H), 2.92-2.98 (m, 1H), 3.03-3.21 (m, 8H), 3.53-3.73 (m, 6H), 3.93-4.00 (m, 2H), 4.12-4.47 (m, 13H), 4.48-4.64 (m, 6H), 4.72 (s, 1H), 5.35 (t, J=4.8 Hz, 1H), 5.61-5.66 (m, 2H), 6.95 (s, 1H); 7.12-7.30 (m, 15H), 7.35-8.22 (m, 22H); HRMS (ESI): m/z calcd for $C_{134}H_{227}N_{21}O_{31}$ $[(M+2H)/2]^+$ 1313.3416, found 1313.3412.

Example 2.1 (2S,3S,4R)-1-(6-Deoxy-6-(N-(6-azido-hexanoyl)-Val-Cit-4-aminobenzyloxycarbonylamino)-α-D-galactopyranosyloxy)-2-hexacosanoylamino-3,4-octadecandiol (CI1022)

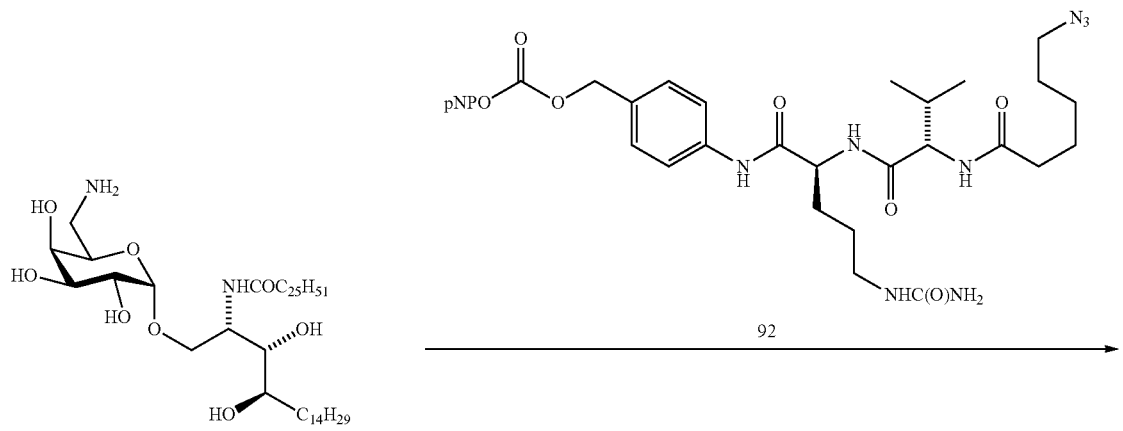

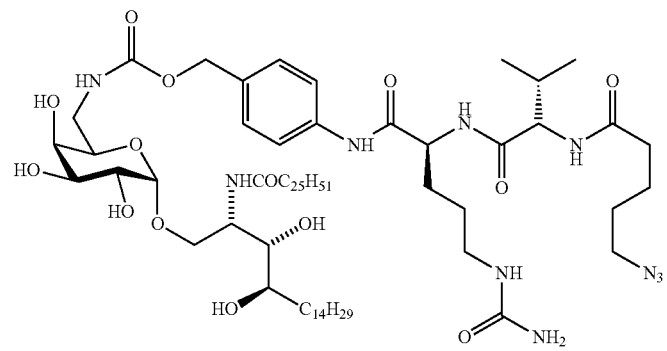

To a mixture of CN168 (20 mg, 0.023 mmol) and pNP-carbonate 92 (20 mg, 0.029 mmol) in anhydrous pyridine (600 μL) under Ar is added Et$_3$N (20 μL, 0.28 mmol) and the mixture is stirred at rt. After 26 h, the mixture is concentrated to dryness under high vacuum, and the crude residue is purified by column chromatography on silica gel (MeOH/CHCl$_3$=0:1 to 1:1) to afford the title compound CI1022 as a white solid (20 mg, 61%). $^1$H NMR (500 MHz, d6-DMSO) δ 0.82-0.87 (m, 12H), 1.21-1.32 (m, 70H), 1.40-1.56 (m, 10H), 1.57-1.63 (m, 1H), 1.66-1.75 (m, 1H), 1.95-2.01 (m, 1H), 2.04-2.10 (m, 2H), 2.12-2.24 (m, 2H), 2.90-2.97 (m, 1H), 2.97-3.03 (m, 1H), 3.11-3.16 (m, 2H), 3.20-3.46 (m, 5H), 3.46-3.73 (m, 7H), 3.97 (br s, 1H), 4.17-4.27 (m, 2H), 4.33-4.61 (m, 4H), 4.69 (s, 1H), 4.90-4.95 (m, 2H), 5.39 (s, 2H), 5.97-6.01 (m, 1H), 7.03-7.08 (m, 1H), 7.26 (d, J=8.3 Hz, 2H), 7.55-7.61 (m, 3H), 7.81 (d, J=8.4 Hz, 1H), 8.04 (d, J=7.7 Hz, 1H), 9.96 (s, 1H); HRMS-ESI [M+Na]$^+$ calcd for C$_{75}$H$_{136}$N$_{10}$NaO$_{14}$: 1424.0135; found 1424.0134.

Example 2.2—(2S,3S,4R)-1-(6-Deoxy-6-(4-β-(FFRKSIINFEKL)-3-oxopropyl)-1H-1,2,3-triazol-1-yl)hexanoyl)-(N-Val-Cit-4-aminobenzyloxycarbonylamino)-1-(α-D-galactopyranosyloxy))-2-hexacosanoylamino-3,4-octadecandiol (CI-017)

CI022 →

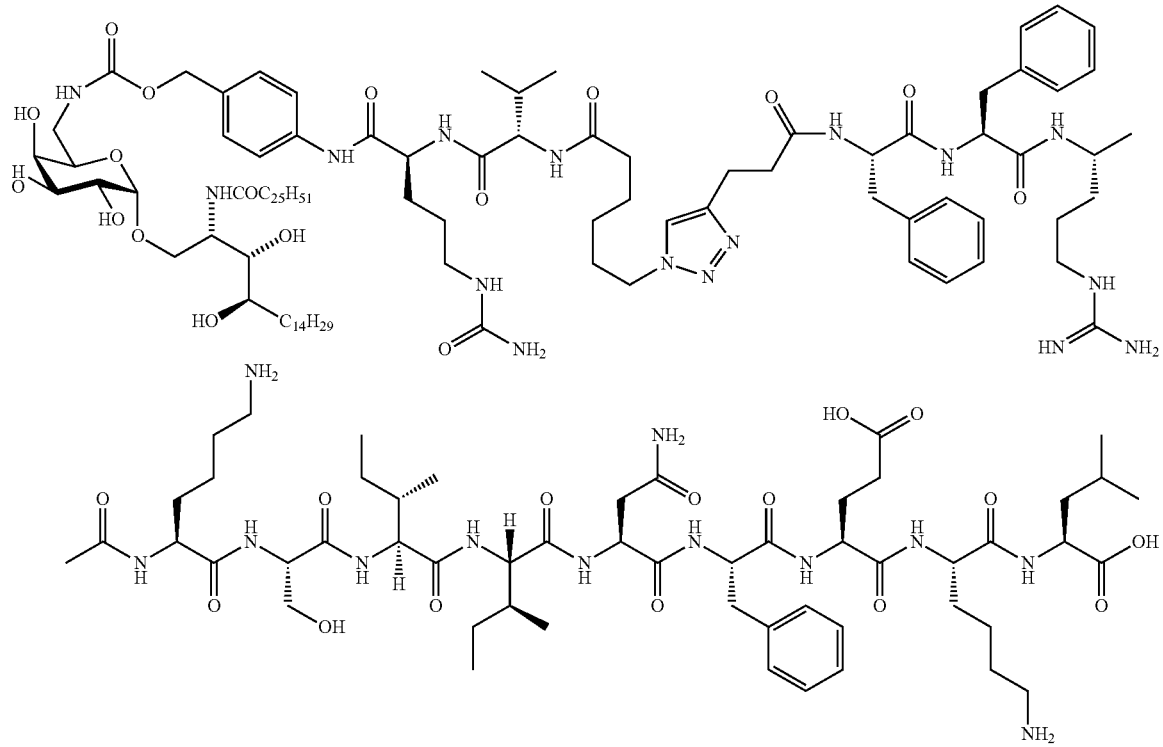

CI017

To a stirred solution of peptide 4-pentynoyl-FFRKSIIN-FEKL (SEQ ID NO: 415) (4.2 mg, 2.6 μmol), CI1022 (1.3 mg, 0.93 μmol) and TBTA (0.35 mg, 0.66 μmol) in DMSO (280 μL) is added CHCl$_3$ (280 μL) and MeOH (280 μL) followed by a small amount of copper foil (5 mm×2 mm) and the reaction mixture is stirred at 20° C. for 15 h then at 30° C. for 24 h. The volatiles are removed under reduced pressure to give a residue which is centrifuged with an aqueous solution of 0.05 M EDTA (pH 11) (2×10 mL), water (2×10 mL) and the remaining pellet is dried under high vacuum. The crude product is purified by preparative HPLC (Phenomenex Luna C18(1), 5 μm, 250×10 mm, 40° C., 3.0 mL/min; Mobile phase A=100:0.05 water/TFA; Mobile phase B=100:0.0.05 MeOH/TFA; 0-5 min: 80-100% B; 5-12 min: 100% B; 12-13 min: 100-80% B; 13-15 min: 80% B) to give the title compound CI017 (1.30 mg, 46%, 97% pure by HPLC); HRMS-ESI m/z calcd for C$_{155}$H$_{258}$N$_{28}$O$_{32}$ [M+2H]$^{2+}$ 1511.9633, found 1511.9722.

Example 3—4-((2-(FFRKSIINFEKL)-2-oxoethoxy)imino)pentanoic acid (CN159)

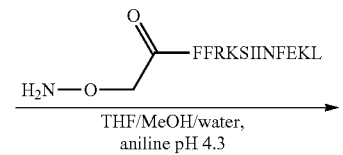

-continued

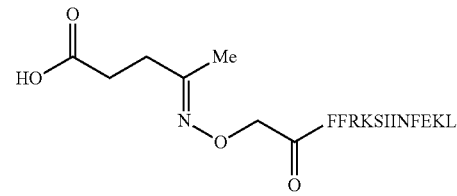

CN159

Peptide 2-(aminooxy)acetyl-FFRKSIINFEKL (6.0 mg, 3.72 mmol) is dissolved in THF/MeOH (2:1, 600 μL) and added to an aqueous mixture of water/aniline/TFA (200:6:4, 300 μL, pH 4.3). A solution of levulinic acid (100 mg, 0.86 mmol) dissolved in MeOH (200 μL) is added and the reaction mixture stirred at 25° C. for 48 h. The solvent is removed and the crude product purified by preparative HPLC (Phenomenex Luna C18(1), 5 μm, 250×10 mm, 40° C., 1.4 mL/min; Mobile phase A=100:0.1 water/TFA; Mobile phase B=100:0.1 MeOH/TFA; 0-10 min: 50-100% B; 10-15 min: 100% B; 15-16 min: 100-50% B; 16-20 min: 50% B) to give the title compound CN159 (3.9 mg, 62%, 96% pure by HPLC). $^1$H NMR (500 MHz, d6-DMSO) δ 0.70-0.88 (m, 18H), 0.99-1.11 (m, 2H), 1.24-1.43 (m, 7H), 1.44-1.60 (m, 12H), 1.60-1.577 (m, 8H), 1.79 (s, 2H), 1.91 (s, 1H), 2.17-2.30 (m, 2H), 2.31-2.40 m, 3H), 2.67-2.96 (m, 9H), 2.98-3.16 (m, 4H), 3.54-3.62 (m, 4H), 4.11-4.62 (m, 15H), 5.00 (br s, 1H), 6.92 (s, 1H), 7.11-7.29 (m, 17H), 7.36 (d, J=7.9 Hz, 1H), 7.41 (s, 1H), 7.45-7.53 (m, 1H), 7.57-7.87 (m, 8H), 7.91-8.21 (m, 8H); HRMS (ESI): m/z calcd for $C_{82}H_{126}N_{19}O_{21}$ [M+H]$^+$ 1712.9376, found 1712.9366.

Example 4—Formulating Compounds of the Invention for Intravenous Injection

Compounds of the invention are formulated analogously to reported methods for α-GalCer. Briefly, solubilisation is based on excipient proportions described by Giaccone et al (Giaccone, Punt et al. 2002). Thus, 100 μL of a 10 mg/mL solution of α-GalCer or a compound of the invention in 9:1 THF/MeOH is added to 1.78 mL of an aqueous solution of Tween 20 (15.9 mg), sucrose (177 mg) and L-histidine (23.8 mg). This homogeneous mixture is freeze dried and the resulting foam is stored under Ar at −18° C. This material is reconstituted with 1.0 mL of PBS or water prior to serial dilutions in PBS to achieve final injectable solutions of α-GalCer or compounds of the invention.

Example 5—Biological Studies

Mice:
C57BL/6 are from breeding pairs originally obtained from Jackson Laboratories, Bar Harbor, Me., and used according to institutional guidelines with approval from the Victoria University of Wellington Animal Ethics Committee.

Administration of Compounds of the Invention:
Each compound of the invention is supplied as formulated product (see example 3), and diluted in phosphate-buffered saline (PBS) for injection (0.23 nmol/mouse) by intravenous injection into the lateral tail vein. In humans the expected therapeutic dose lies in the 50-4800 (μg/m$^2$) range (Giaccone, Punt et al. 2002). Note, 0.23 nmol in a mouse is a human equivalent dose of 30 μg/m$^2$ for α-GalCer.

All antibody labelling is performed on ice in FACS buffer (PBS supplemented with 1% FCS, 0.05% sodium azide, and 2 mM EDTA). Non-specific FcR-mediated antibody staining is blocked by incubation for 10 min with anti-CD16/32 Ab (24G2, prepared in-house from hybridoma supernatant). Flow cytometry is performed on a BD Biosciences FACSCalibur or BD LSRII SORP flow cytometer with data analysis using FlowJo software (Tree Star, Inc., OR, USA).

Phenotyping B Cells from Peripheral Blood:
Antibody staining and flow cytometry are used to examine the expression of the maturation markers CD86 on peripheral blood B cells following injection of compounds of the invention. Blood was collected from the lateral tail vein, followed by lysis of red blood cells with RBC lysis buffer (Puregene, Gentra Systems, Minneapolis, Minn., USA). Antibody staining is performed in PBS 2% fetal bovine serum and 0.01% sodium azide. The anti-FcgRII monoclonal antibody 2.4G2 is used at 10 mg/ml to inhibit non-specific staining. Monoclonal antibodies (all BD Biosciences Pharmingen, San Jose, Calif., USA) are used to examine expression of CD86 on gated CD45 (B220)+B cells.

Analysis of Peptide-Specific T Cell Proliferation In Vivo:
Pooled lymph node cell suspensions are prepared from animals of a cross between OT-1 mice, which express a transgenic T cell receptor (TCR) specific for the ovalbumin epitope SIINFEKL (SEQ ID NO: 262)-in the context of H-2K$^b$ molecules, and B6.SJL-Ptprc$^a$ Pepc$^b$/BoyJ mice, which are congenic with C57BL/6 mice for the CD45.1$^+$ marker. The samples are enriched for CD8$^+$ cells using antibody coated magnetic beads (Miltenyi), and then transferred into C57BL/6 mice (1×10$^4$ per mouse). Groups of recipient animals (n=5) are immunized with compounds of the invention one day later. Doses are chosen to provide equivalent molar values of SIINFEKL peptide. Control animals received PBS. After seven days, blood samples are collected from the lateral tail vein and stained directly ex vivo with antibodies for TCR Vα2, CD45.1 and CD8 to detect the SIINFEKL (SEQ ID NO: 262)-specific CD8$^+$ T cells by flow cytometry.

Phenotyping DC from Spleen:
Antibody staining and flow cytometry is used to examine the expression of maturation markers on dendritic cells in the spleen following injection of compounds of the invention (0.23 nmol). Splenocyte preparations are prepared by gentle teasing of splenic tissue through gauze in Iscove's Modified Dulbecco's Medium with 2 mM glutamine, 1% penicillin-streptomycin, 5×10-5 M 2-mercapto-ethanol and 5% fetal bovine serum (all Invitrogen, Auckland, New Zealand), followed by lysis of red blood cells with RBC lysis buffer (Puregene, Gentra Systems, Minneapolis, Minn., USA). Antibody staining is performed in PBS 2% fetal bovine serum and 0.01% sodium azide. The anti-FcgRII monoclonal antibody 2.4G2 is used at 10 mg/ml to inhibit non-specific staining. Monoclonal antibodies (all BD Biosciences Pharmingen, San Jose, Calif., USA) are used to examine expression of the maturation markers CD40, CD80 and CD86 on CD11c+ dendritic cells.

Analysis of Peptide-Specific T Cell-Mediated Cytotoxicity In Vivo:
The cytotoxic capacity of induced CD8$^+$ T cell responses is measured by VITAL assay (Hermans, Silk et al. 2004). Mice are immunized with the compounds of the invention, or PBS, and then injected intravenously seven days later with two populations of syngeneic splenocytes; those loaded with 500 nM, SIINFEKL-peptide and labelled with 1.65 nM carboxyfluorescein succinimidyl ester (CFSE), or those loaded with peptide and labelled with 10 μM cell tracker orange (CTO). Specific lysis of the peptide-loaded targets is monitored by flow cytometry of blood or spleen samples 24 h later. Mean percent survival of peptide-pulsed (CFSE+) targets is calculated relative to that of the control population (CTO+), and cytotoxic activity is expressed as percent specific lysis (100−mean percent survival of peptide-pulsed targets).

Analysis of Anti-Tumour Activity:
Groups of C57BL/6 mice (n=5) receive a subcutaneous injection into the flank of 1×10$^5$ B16.OVA melanoma cells, which express a cDNA encoding the chicken ovalbumin (OVA) sequence. The different groups are treated five days later by intravenous injection of one of the following;

CI-017 (0.571 nmol), peptide CN159 (0.571 nmol) mixed with α-GalCer (0.571 nmol), or PBS. Mice are monitored for tumour growth every 3-4 days, and tumour size for each group calculated as the mean of the products of bisecting diameters (±SEM). Measurements are terminated for each group when the first animal develops a tumour exceeding 200 mm$^2$.

Where the foregoing description reference has been made to integers having known equivalents thereof, those equivalents are herein incorporated as if individually set forth.

Although the invention has been described in connection with specific preferred embodiments, it should be understood that the invention as claimed should not be unduly limited to such specific embodiments.

It is appreciated that further modifications may be made to the invention as described herein without departing from the spirit and scope of the invention.

The examples described herein are for purposes of illustrating embodiments of the invention. Other embodiments, methods, and types of analyses are within the capabilities of persons of ordinary skill in the art and need not be described in detail herein. Other embodiments within the scope of the art are considered to be part of this invention.

Although the invention has been described in connection with specific preferred embodiments, it should be understood that the invention as claimed should not be unduly limited to such specific embodiments.

It is appreciated that further modifications may be made to the invention as described herein without departing from the spirit and scope of the invention.

INDUSTRIAL APPLICABILITY

The invention relates to sphingoglycolipid analogues and peptide derivatives thereof, which are useful in treating or preventing diseases or such as those relating to infection, atopic disorders, autoimmune diseases or cancer.

REFERENCES

Alexander, J., R. Cargill, et al. (1988). "(Acyloxy)alkyl carbamates as novel bioreversible prodrugs for amines: increased permeation through biological membranes." *J Med Chem* 31(2): 318-322.

Alexander, J., J Sidney, et al. (1994) "Development of high potency universal DR-restricted helper epitopes by modification of high affinity DR-blocking peptides." *Immunity* 1 (9), 751-61.

Amblard, M., J. A. Fehrentz, et al. (2006). "Methods and protocols of modern solid phase Peptide synthesis." *Mol Biotechnol* 33(3): 239-254.

Amsberry, K. L. and R. T. Borchardt (1991). "Amine prodrugs which utilize hydroxy amide lactonization. I. A potential redox-sensitive amide prodrug." *Pharm Res* 8(3): 323-330.

Amsberry, K. L., A. E. Gerstenberger, et al. (1991). "Amine prodrugs which utilize hydroxy amide lactonization. II. A potential esterase-sensitive amide prodrug." *Pharm Res* 8(4): 455-461.

Atherton, E., H. Fox, et al. (1978). "A mild procedure for solid phase peptide synthesis: use of fluorenylmethoxycarbonylamino-acids." *Journal of the Chemical Society, Chemical Communications* (13): 537-539.

Atwell, G. J., B. M. Sykes, et al. (1994). "Relationships between structure and kinetics of cyclization of 2-aminoaryl amides: potential prodrugs of cyclization-activated aromatic mustards." *J Med Chem* 37(3): 371-380.

Baek, D. J., J.-H. Seo, et al. (2011). "The 3-Deoxy Analogue of α-GalCer: Disclosing the Role of the 4-Hydroxyl Group for CD1d-Mediated NKT Cell Activation." *ACS Medicinal Chemistry Letters* 2(7): 544-548.

Banchet-Cadeddu, A., E. Henon, et al. (2011). "The stimulating adventure of KRN 7000." *Org Biomol Chem* 9(9): 3080-3104.

Bendelac, A., P. B. Savage, et al. (2007). "The biology of NKT cells." *Annu Rev Immunol* 25: 297-336.

Berinstein, N. L., M. Karkada, et al. (2012). "First-in-man application of a novel therapeutic cancer vaccine formulation with the capacity to induce multi-functional T cell responses in ovarian, breast and prostate cancer patients." *Journal of translational medicine* 10, 156.

Bettinotti, M. P., C. J. Kim, et al. (1998). "Stringent allele/epitope requirements for MART-1/Melan A immunodominance: implications for peptide-based immunotherapy." *J Immunol* 161(2): 877-889.

Borg, N. A., K. S. Wun, et al. (2007). "CD1d-lipid-antigen recognition by the semi-invariant NKT T-cell receptor." *Nature* 448(7149): 44-49.

Brossart, P., K. S. Heinrich, et al. (1999). "Identification of HLA-A2-restricted T-cell epitopes derived from the MUC1 tumor antigen for broadly applicable vaccine therapies." *Blood* 93(12): 4309-4317.

Cai, H., Z. H. Huang, et al. (2011). "Towards a fully synthetic MUC1-based anticancer vaccine: efficient conjugation of glycopeptides with mono-, di-, and tetravalent lipopeptides using click chemistry." *Chemistry* 17(23): 6396-6406.

Campos, L. M., K. L. Killops, et al. (2008). "Development of Thermal and Photochemical Strategies for Thiol-Ene Click Polymer Functionalization." *Macromolecules* 41(19): 7063-7070.

Carpino, L. A., S. A. Triolo, et al. (1989). "Reductive lactonization of strategically methylated quinone propionic acid esters and amides." *The Journal of Orqanic Chemistry* 54(14): 3303-3310.

Chang, J. (2006). "Efficient amplification of melanoma-specific CD8+ T cells using artificial antigen presenting complex." *Exp Mol Med* 38(6): 591-598.

Chaudhary, A., M. Girgis, et al. (2003). "Using mixed anhydrides from amino acids and isobutyl chloroformate in N-acylations: a case study on the elucidation of mechanism of urethane formation and starting amino acid liberation using carbon dioxide as the probe." *Tetrahedron Lett* 44(29): 5543-5546.

Chen, G., J. Schmieg, et al. (2004). "Efficient synthesis of alpha-C-galactosyl ceramide immunostimulants: use of ethylene-promoted olefin cross-metathesis." *Org Lett* 6(22): 4077-4080.

Choi, J. K., D. C. Ha, et al. (1989). ".alpha.-acylamino radical cyclizations: application to the synthesis of a tetracyclic substructure of gelsemine." *The Journal of Orqanic Chemistry* 54(2): 279-290.

Ciesielski, M. J., D. Kozbor, et al. (2008). "Therapeutic effect of a T helper cell supported CTL response induced by a survivin peptide vaccine against murine cerebral glioma." *Cancer Immunol Immunother* 57(12): 1827-1835.

Davidson, E. J., R. L. Faulkner, et al. (2004). "Effect of TA-CIN (HPV 16 L2E6E7) booster immunisation in vulval intraepithelial neoplasia patients previously vaccinated with TA-HPV (vaccinia virus encoding HPV 16/18 E6E7)." *Vaccine* 22(21-22): 2722-2729.

de Araujo, A. D., J. M. Palomo, et al. (2006). "Diels-Alder ligation of peptides and proteins." *Chemistry* 12(23): 6095-6109.

Deng, S., J. Mattner, et al. (2011). "Impact of sugar stereochemistry on natural killer T cell stimulation by bacterial glycolipids." *Org Biomol Chem* 9(22): 7659-7662.

Dere, R. T. and X. Zhu (2008). "The first synthesis of a thioglycoside analogue of the immunostimulant KRN7000." *Org Lett* 10(20): 4641-4644.

Dirksen, A., T. M. Hackeng, et al. (2006). "Nucleophilic catalysis of oxime ligation." *Angew Chem Int Ed Engl* 45(45): 7581-7584.

Dondoni, A. (2008). "The emergence of thiol-ene coupling as a click process for materials and bioorganic chemistry." *Anqew Chem Int Ed* 47: 8995-8997

Du, W., S. S. Kulkarni, et al. (2007). "Efficient, one-pot syntheses of biologically active alpha-linked glycolipids." *Chem Commun (Camb)*(23): 2336-2338.

Dubowchik, G. M., R. A. Firestone, et al. (2002). "Cathepsin B-labile dipeptide linkers for lysosomal release of doxorubicin from internalizing immunoconjugates: model studies of enzymatic drug release and antigen-specific in vitro anticancer activity." *Bioconjug Chem* 13(4): 855-869.

Ebensen, T., C. Link, et al. (2007). "A pegylated derivative of alpha-galactosylceramide exhibits improved biological properties." *J Immunol* 179(4): 2065-2073.

Fang, G. M., J. X. Wang, et al. (2012). "Convergent chemical synthesis of proteins by ligation of Peptide hydrazides." *Anqew Chem Int Ed Engl* 51(41): 10347-10350.

Fields, G. B. and R. L. Noble (1990). "Solid phase peptide synthesis utilizing 9-fluorenylmethoxycarbonyl amino acids." *Int J Pept Protein Res* 35(3): 161-214.

Friedrichs, B., S. Siegel, et al. (2006). "Survivin-derived peptide epitopes and their role for induction of antitumor immunity in hematological malignancies." *Leuk Lymphoma* 47(6): 978-985.

Fujii, S., K. Shimizu, et al. (2003). "Activation of natural killer T cells by alpha-galactosylceramide rapidly induces the full maturation of dendritic cells in vivo and thereby acts as an adjuvant for combined CD4 and CD8 T cell immunity to a coadministered protein." *J Exp Med* 198 (2): 267-279.

Gangwar, S., G. M. Pauletti, et al. (1997). "Synthesis of a Novel Esterase-Sensitive Cyclic Prodrug of a Hexapeptide Using an (Acyloxy)alkoxy Promoiety." *The Journal of Organic Chemistry* 62(5): 1356-1362.

Geoghegan, K. F. and J. G. Stroh (1992). "Site-directed conjugation of nonpeptide groups to peptides and proteins via periodate oxidation of a 2-amino alcohol. Application to modification at N-terminal serine." *Bioconjug Chem* 3(2): 138-146.

Giaccone, G., C. J. Punt, et al. (2002). "A phase I study of the natural killer T-cell ligand alpha-galactosylceramide (KRN7000) in patients with solid tumors." *Clin Cancer Res* 8(12): 3702-3709.

Greenwald, R. B., Y. H. Choe, et al. (2000). "Drug delivery systems based on trimethyl lock lactonization: poly(ethylene glycol) prodrugs of amino-containing compounds." *J Med Chem* 43(3): 475-487.

Greenwald, R. B., A. Pendri, et al. (1999). "Drug delivery systems employing 1,4- or 1,6-elimination: poly(ethylene glycol) prodrugs of amine-containing compounds." *J Med Chem* 42(18): 3657-3667.

Hackenberger, C. P. and D. Schwarzer (2008). "Chemoselective ligation and modification strategies for peptides and proteins." *Anqew Chem Int Ed Engl* 47(52): 10030-10074.

Hatakeyama, T., N. Nakagawa, et al. (2009). "lIron-Catalyzed Negishi Coupling Toward an Effective Olefin Synthesis." *Orqanic letters* 11(20): 4496-4499.

Hermans, I. F., J. D. Silk, et al. (2003). "NKT cells enhance CD4+ and CD8+ T cell responses to soluble antigen in vivo through direct interaction with dendritic cells." *J Immunol* 171(10): 5140-5147.

Hong, S., M. T. Wilson, et al. (2001). "The natural killer T-cell ligand alpha-galactosylceramide prevents autoimmune diabetes in non-obese diabetic mice." *Nat Med* 7(9): 1052-1056.

Howell, A. R., R. C. So, et al. (2004). "Approaches to the preparation of sphinganines." *Tetrahedron* 60(50): 11327-11347.

Huarte, E., P. Sarobe, et al. (2002). "Enhancing immunogenicity of a CTL epitope from carcinoembryonic antigen by selective amino acid replacements." *Clin Cancer Res* 8(7): 2336-2344.

Hudlicky, T., F. F. Koszyk, et al. (1980). "Cyclopentene annulation via intramolecular addition of diazoketones to 1,3-dienes. Applications to the synthesis of cyclopentanoid terpenes." *The Journal of Orqanic Chemistry* 45(25): 5020-5027.

Iha, R. K., B. A. van Horn, et al. (2010). "Complex, degradable polyester materials via ketoxime ether-based functionalization: Amphiphilic, multifunctional graft copolymers and their resulting solution-state aggregates." *Journal of Polymer Science Part A: Polymer Chemistry* 48(16): 3553-3563.

Isidro-Llobet, A., M. Alvarez, et al. (2009). "Amino acid-protecting groups." *Chem Rev* 109(6): 2455-2504.

Jager, E., H. Hohn, et al. (2002). "Peptide-specific CD8+ T-cell evolution in vivo: response to peptide vaccination with Melan-A/MART-1." *Int J Cancer* 98(3): 376-388.

Jervis, P. J., L. R. Cox, et al. (2011). "Synthesis of a Versatile Building Block for the Preparation of 6-N-Derivatized α-Galactosyl Ceramides: Rapid Access to Biologically Active Glycolipids." *J. Or. Chem.* 76, 320-323.

Karbach, J., S. Gnjatic, et al. (2010). "Tumor-reactive CD8+ T-cell responses after vaccination with NY-ESO-1 peptide, CpG 7909 and Montanide ISA-51: association with survival." *Int J Cancer* 126(4): 909-918.

Kawano, T., J. Cui, et al. (1997). "CD1d-restricted and TCR-mediated activation of valpha14 NKT cells by glycosylceramides." *Science* 278(5343): 1626-1629.

Kiick, K. L., E. Saxon, et al. (2002). "Incorporation of azides into recombinant proteins for chemoselective modification by the Staudinger ligation." *Proc Natl Acad Sci USA* 99(1): 19-24.

Kinjo, Y., P. Illarionov, et al. (2011). "lInvariant natural killer T cells recognize glycolipids from pathogenic Gram-positive bacteria." *Nature Immunology*: 1-10.

Kreiter, S., Vormehr, M., et al. (2015). "Mutant MHC class II epitopes drive therapeutic immune responses to cancer." *Nature* 7549: 692-696.

Lee, A., K. J. Farrand, et al. (2006). "Novel synthesis of alpha-galactosyl-ceramides and confirmation of their powerful NKT cell agonist activity." *Carbohydr Res* 341(17): 2785-2798.

Lennerz, V.; Fatho, M.; et al. "The response of autologous T cells to a human melanoma is dominated by mutated neoantigens." *P.N.A.S.*, 102 (44), 16013-8.

Levy, A., J. Pitcovski, et al. (2007). "A melanoma multi-epitope polypeptide induces specific CD8+ T-cell response." *Cell Immunol* 250(1-2): 24-30.

Li, Y., E. Girardi, et al. (2010). "The Vα14 invariant natural killer T cell TCR forces microbial glycolipids and CD1d into a conserved binding mode." *Journal of Experimental Medicine* 207(11): 2383-2393.

Li, X., Fujio, M. et al. (2010). "Design of a potent CD1d-binding NKT cell ligand as a vaccine adjuvant." *PNAS* 107(29): 13010-13015.

Li, Z., Y. Oka, et al. (2008). "Identification of a WT1 protein-derived peptide, WT1, as a HLA-A 0206-restricted, WT1-specific CTL epitope." *Microbiol Immunol* 52(11): 551-558.

Liu, Y., S. Deng, et al. (2008). "Synthesis of diglycosylceramides and evaluation of their iNKT cell stimulatory properties." *Bioorg Med Chem Lett* 18(10): 3052-3055.

Liu, C.-F., C. Rao, et al. (1996). "Orthogonal Ligation of Unprotected Peptide Segments through Pseudoproline Formation for the Synthesis of HIV-1 Protease Analogs." *Journal of the American Chemical Society* 118(2): 307-312.

Liu, C.-F. and J. P. Tam (1994). "Chemical Ligation Approach To Form a Peptide Bond between Unprotected Peptide Segments. Concept and Model Study." *Journal of the American Chemical Society* 116(10): 4149-4153.

Lu, X.-L., Z.-H. Liang, et al. (2006). "Induction of the Epstein-Barr Virus Latent Membrane Protein 2 Antigen-specific Cytotoxic T Lymphocytes Using Human Leukocyte Antigen Tetramer-based Artificial Antigen-presenting Cells." *Acta Biochimica et Biophysica Sinica* 38(3): 157-163.

Majireck, M. M. and S. M. Weinreb (2006). "A study of the scope and regioselectivity of the ruthenium-catalyzed [3+2]-cycloaddition of azides with internal alkynes." *J Org Chem* 71(22): 8680-8683.

Morita, M., K. Motoki, et al. (1995). "Structure-activity relationship of alpha-galactosylceramides against B16-bearing mice." *J Med Chem* 38(12): 2176-2187.

Motoki, K., M. Morita, et al. (1995). "lImmunostimulatory and antitumor activities of monoglycosylceramides having various sugar moieties." *Biol Pharm Bull* 18(11): 1487-1491.

Nicolaou, M. G., C.-S. Yuan, et al. (1996). "Phosphate Prodrugs for Amines Utilizing a Fast Intramolecular Hydroxy Amide Lactonization." *The Journal of Orqanic Chemistry* 61(24): 8636-8641.

Noppen, C., F. Levy, et al. (2000). "Naturally processed and concealed HLA-A2.1-restricted epitopes from tumor-associated antigen tyrosinase-related protein-2." *Int J Cancer* 87(2): 241-246.

O'Reilly, C. and P. V. Murphy (2011). "Synthesis of alpha-S-glycosphingolipids based on uronic acids." *Org Lett* 13(19): 5168-5171.

Parekh, V. V., M. T. Wilson, et al. (2005). "Glycolipid antigen induces long-term natural killer T cell anergy in mice." *J Clin Invest* 115(9): 2572-2583.

Park, J. J., J. H. Lee, et al. (2008). "Synthesis of all stereoisomers of KRN7000, the CD1d-binding NKT cell ligand." *Bioorg Med Chem Lett* 18(14): 3906-3909.

Pauwels, N., S. Aspeslagh, et al. (2012). "Synthesis of 6"-triazole-substituted alpha-GalCer analogues as potent iNKT cell stimulating ligands." *Bioorg Med Chem* 20(24): 7149-7154.

Petersen, T. R., D. Sika-Paotonu, et al. (2010). "Potent anti-tumor responses to immunization with dendritic cells loaded with tumor tissue and an NKT cell ligand." *Immunol Cell Biol* 88(5): 596-604.

Plettenburg, O., V. Bodmer-Narkevitch, et al. (2002). "Synthesis of alpha-galactosyl ceramide, a potent immunostimulatory agent." *J Org Chem* 67(13): 4559-4564.

Presolski, S. I.; Hong, V. et al. (2010). "Tailored ligand acceleration of the Cu-catalyzed azide-alkyne cycloaddition reaction: practical and mechanistic implications." *J Am Chem Soc* 132: 14570-14576.

Raju, R., B. F. Castillo, et al. (2009). "Synthesis and evaluation of 3"- and 4"-deoxy and -fluoro analogs of the immunostimulatory glycolipid, KRN7000." *Bioorg Med Chem Lett* 19(15): 4122-4125.

Rostovtsev, V. V., L. G. Green, et al. (2002). "A stepwise huisgen cycloaddition process: copper(I)-catalyzed regioselective "ligation" of azides and terminal alkynes." *Anqew Chem Int Ed Engl* 41(14): 2596-2599.

Saxon, E. and C. R. Bertozzi (2000). "Cell surface engineering by a modified Staudinger reaction." *Science* 287(5460): 2007-2010.

Schmitz, M., P. Diestelkoetter, et al. (2000). "Generation of survivin-specific CD8+ T effector cells by dendritic cells pulsed with protein or selected peptides." *Cancer Res* 60(17): 4845-4849.

Semmling, V., V. Lukacs-Kornek, et al. (2010). "Alternative cross-priming through CCL17-CCR4-mediated attraction of CTLs toward NKT cell-licensed DCs." *Nat Immunol* 11(4): 313-320.

Silk, J. D., I. F. Hermans, et al. (2004). "Utilizing the adjuvant properties of CD1d-dependent NK T cells in T cell-mediated immunotherapy." *J Clin Invest* 114(12): 1800-1811.

Soellner, M. B., A. Tam, et al. (2006). "Staudinger ligation of peptides at non-glycyl residues." *J Org Chem* 71(26): 9824-9830.

Speiser, D. E. and P. Romero (2010). "Molecularly defined vaccines for cancer immunotherapy, and protective T cell immunity." *Semin Immunol* 22(3): 144-154.

Tam, A., M. B. Soellner, et al. (2007). "Water-soluble phosphinothiols for traceless staudinger ligation and integration with expressed protein ligation." *J Am Chem Soc* 129(37): 11421-11430.

Trappeniers, M., K. Van Beneden, et al. (2008). "6'-derivatised alpha-GalCer analogues capable of inducing strong CD1d-mediated Th1-biased NKT cell responses in mice." *J Am Chem Soc* 130(49): 16468-16469.

Trappeniers, M., S. Goormans, et al. (2008). "Synthesis and in vitro evaluation of alpha-GalCer epimers." *ChemMedChem* 3(7): 1061-1070.

Tupin, E., A. Nicoletti, et al. (2004). "CD1d-dependent activation of NKT cells aggravates atherosclerosis." *J Exp Med* 199(3): 417-422.

Veerapen, N., M. Brigl, et al. (2009). "Synthesis and biological activity of alpha-galactosyl ceramide KRN7000 and galactosyl (alpha1-->2) galactosyl ceramide." *Bioorg Med Chem Lett* 19(15): 4288-4291.

Widdison, W. C., S. D. Wilhelm, et al. (2006). "Semisynthetic maytansine analogues for the targeted treatment of cancer." *J Med Chem* 49(14): 4392-4408.

Wingender, G., P. Rogers, et al. (2011). "lInvariant NKT cells are required for airway inflammation induced by environmental antigens." *J Exp Med* 208(6): 1151-1162.

Wu, T.-N., K.-H. Lin, et al. (2011). "Avidity of CD1d-ligand-receptor ternary complex contributes to T-helper 1 (Th1) polarization and anticancer efficacy." *Proc Natl Acad Sci USA* 108(42): 17275-17280.

Zeng, D., Y. Liu, et al. (2003). "Activation of natural killer T cells in NZB/W mice induces Th1-type immune responses exacerbating lupus." *J Clin Invest* 112(8): 1211-1222.

Zhang, L., X. Chen, et al. (2005). "Ruthenium-catalyzed cycloaddition of alkynes and organic azides." *J Am Chem Soc* 127(46): 15998-15999.

Zhou, X. T., C. Forestier, et al. (2002). "Synthesis and NKT cell stimulating properties of fluorophore- and biotin-appended 6"-amino-6"-deoxy-galactosylceramides." *Org Lett* 4(8): 1267-1270.

The invention claimed is:

1. A compound of formula (I):

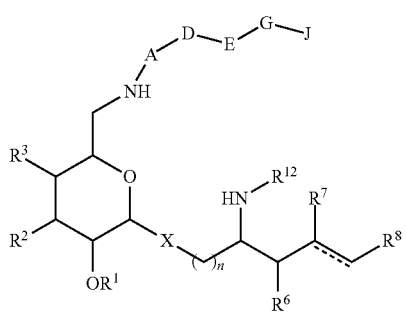

(I)

wherein:

A is a self-immolative linker group;

D is selected from the group consisting of:

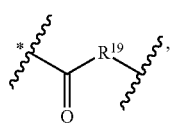

D1

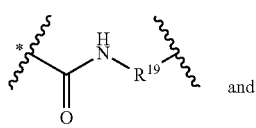

D2

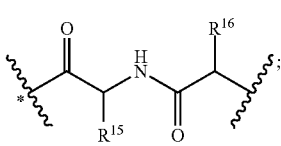

D3

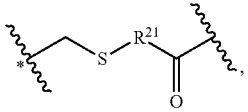

D4

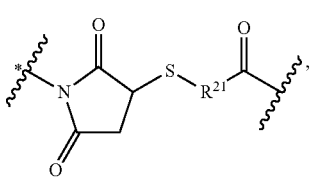

D5 wherein * denotes a point of attachment of group D to group A;

$R^{15}$ is a side chain of one of the following amino acids: L-lysine, L-citrulline, L-arginine, L-glutamine or L-threonine;

$R^{16}$ is a side chain of a hydrophobic amino acid;

$R^{19}$ is an alkylene group;

$R^{32}$ is an alkylene group or an O-alkylene group wherein the O is attached to the carbonyl group of D2;

E is selected from the group consisting of:

E1

E2

-continued

-continued

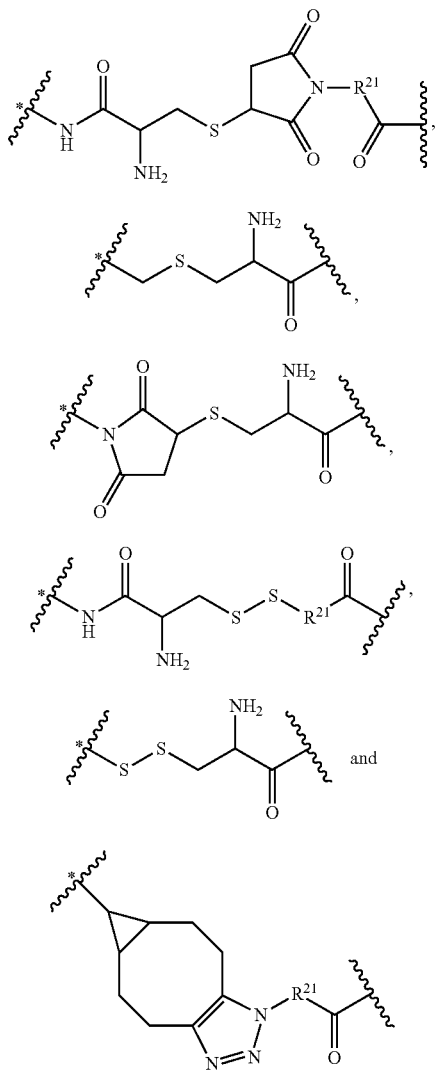

wherein * denotes a point of attachment of group E to group D;
$R^{20}$ is H or lower alkyl;
$R^{21}$ is an alkylene group;
g is 0 when $R^{20}$ is H or g is 1 when $R^{20}$ is lower alkyl;
provided that E is E18 only when D is D1, D2 or D3 and provided that E is E1, E2, E3, E4, E5, E6, E7, E8, E9, E10, E11, E12, E13, E15, E20, E21, E93, E94 or E96 only when D is D1, D2, D3 or D4; and provided that E is E91, E92 or E95 only when D is D5 and provided that E is E97 only when D is D2;
G is absent or G is an amino acid sequence of up to 6 amino acids, attached through its N-terminus to group E and through its C-terminus to group J;
J is a peptidic antigen, optionally substituted at its N and/or C-termini with up to 6 amino acids selected from the group of natural flanking residues for the antigen, and optionally terminated with $NH_2$ at the C-terminus so as to provide a C-terminal amide, and attached to group G through its N-terminus or, wherein G is absent, attached to group E through its N-terminus;
$R^1$ is H or glycosyl, provided that if $R^1$ is glycosyl then $R^2$ and $R^3$ are both OH;

$R^2$ is selected from the group consisting of H, OH, F and $OR^{10}$; provided that if $R^2$ is H, F or $OR^{10}$, then $R^1$ is H and $R^3$ is OH;
$R^3$ is selected from the group consisting of H, OH, F and $OR^{10}$; provided that if $R^3$ is H, F or $OR^{10}$, then $R^1$ is H and $R^2$ is OH;
$R^6$ is OH or H;
$R^7$ is OH or H;
when $R^7$ is H, ===== denotes an optional double bond linking the carbon adjacent to $R^7$ with the carbon adjacent to $R^8$;
$R^8$ is H or $C_1$-$C_{15}$ alkyl having a straight or branched carbon chain, wherein the carbon chain optionally incorporates one or more double bonds, one or more triple bonds, one or more oxygen atoms and/or a terminal or non-terminal optionally substituted aryl group;
$R^{10}$ is glycosyl;
$R^{12}$ is $C_6$-$C_{30}$ acyl having a straight or branched carbon chain optionally substituted with one or more hydroxy groups at positions 2 and/or 3 of the acyl group and/or an optionally substituted chain terminating aryl group and which optionally incorporates one or more double bonds, one or more triple bonds, and/or one or more optionally substituted arylene groups and wherein the carbon chain is optionally substituted with one or more deuterium atoms; wherein the optional substituents on the aryl and arylene groups may be selected from halogen, cyano, dialkylamino, $C_1$-$C_6$ amide, nitro, $C_1$-$C_6$ alkoxy, $C_1$-$C_6$ acyloxy and $C_1$-$C_6$ thioalkyl;
X is O, $CH_2$ or S; wherein
when X is $CH_2$ then the following must all be true: the stereochemistry of the 6-membered sugar ring in formula (I) is α-D-galacto; $R^1$ is H; $R^2$ and $R^3$ are both OH; and:
either $R^6$ is OH and $R^7$ is OH and the stereochemistry at carbon atoms 2, 3 and 4 is (2S, 3S, 4R), (2S, 3S, 4S), (2R, 3S, 4S), (2R, 3S, 4R) or (2S, 3R, 4S); or $R^6$ is OH and $R^7$ is H, and $R^8$ is $C_{13}H_{27}$ and the stereochemistry at carbon atoms 2 and 3 is (2S, 3S);
when X is S then the following must all be true: the stereochemistry of the 6-membered sugar ring in formula (I) is α-D-galacto; $R^1$ is H; $R^2$ and $R^3$ are both OH; and:
either $R^6$ is OH and $R^7$ is OH and the stereochemistry at carbon atoms 2, 3 and 4 is (2S, 3S, 4R); or $R^6$ is OH and $R^7$ is H and the stereochemistry at the carbon atoms 2 and 3 is (2S, 3S);
n is 1 when X is O or S; or n is 0 or 1 when X is $CH_2$;
or a pharmaceutically acceptable salt thereof.

2. The compound of claim 1 which is a compound of formula (Ia):

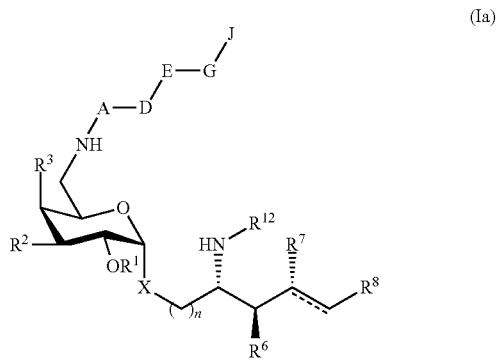

wherein X, $R^1$, $R^2$, $R^3$, $R^6$, $R^7$, $R^8$, $R^{10}$, $R^{12}$, $R^{15}$, $R^{16}$, $R^{19}$, $R^{20}$, $R^{21}$, $R^{32}$, n, g, A, D, E, G and J are all as defined in claim 1;
or a pharmaceutically acceptable salt thereof.

3. A compound of formula (II):

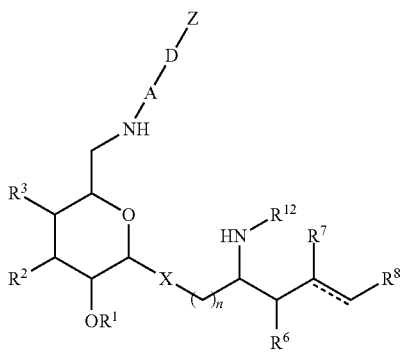

(II)

wherein A, D, X, $R^1$, $R^2$, $R^3$, $R^6$, $R^7$, $R^8$, $R^{10}$, $R^{12}$, $R^{15}$, $R^{16}$, $R^{32}$, and n are all as defined above for formula (I);
Z is selected from the group consisting of:

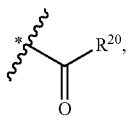

Z1

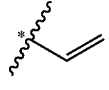

Z2

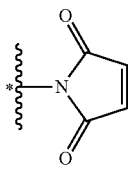

Z3

Z4

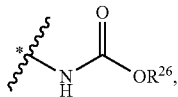

Z5

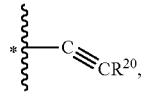

Z7

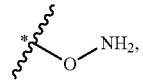

Z8

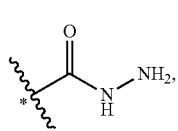

Z9

Z10

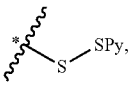

Z11

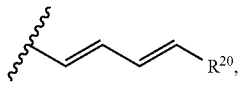

Z12

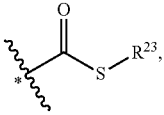

Z13

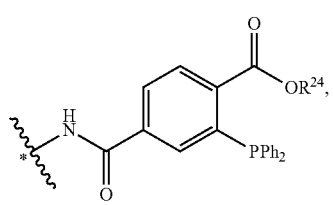

Z14

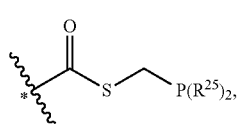

Z15

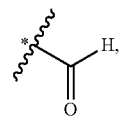

Z16

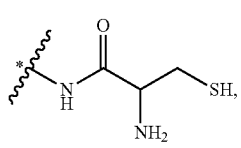

Z17

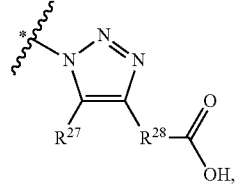

Z18

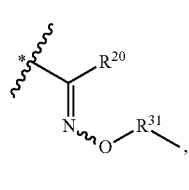

Z19

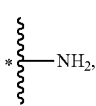

Z20

-continued

Z21
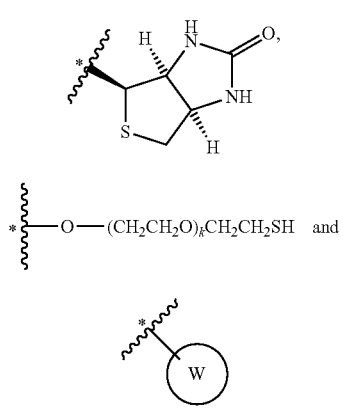

Z22
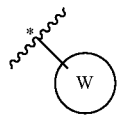*—O—(CH₂CH₂O)$_k$CH₂CH₂SH and

Z23
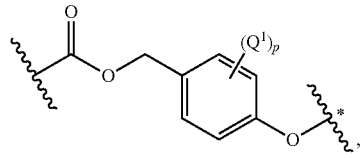

wherein * denotes a point of attachment of group Z to group D, except as defined for Z23;
$R^{20}$ is as defined above for formula (I);
$R^{23}$ is aryl, aralkyl or optionally substituted alkyl;
$R^{24}$ is lower alkyl;
$R^{25}$ is p-C₆H₄L wherein L is H, methoxy, COOH, C(O)NHCH₂COOH or CH₂CH₂NMe₂;
$R^{26}$ is aralkyl;
$R^{27}$ is H or lower alkyl;
$R^{28}$ is alkylene;
$R^{31}$ is (CH₂CH₂O)$_k$
k is an integer from 2 to 100;
W is an optionally substituted cyclooctynyl ring; or W is a fused bicyclic or tricyclic ring system comprising an optionally substituted cyclooctynyl ring fused to one or more aryl groups or one or more cycloalkyl groups; wherein the cyclooctynyl ring optionally contains a N atom within the ring, which N atom is optionally substituted with an acyl group; and wherein the cyclooctynyl ring is optionally substituted with one or more substituents selected from the group consisting of halogen, hydroxyl, alkoxy and aralkyl wherein the aryl part of this group is optionally substituted with a carboxylic acid; and wherein * or one of the optional substituents comprises a point of attachment of Z23 to group D;
provided that Z is Z1, Z2, Z3, Z4, Z7, Z8, Z9, Z10, Z11, Z13, Z15, Z16, Z17 or Z18 only when D is D1, D2, D3 or D4 and provided that Z is Z12 only when D is D1, D2 or D3 and provided that Z is Z5 or Z20 only when D is D5, and provided that Z is Z21, Z22 or Z23 only when D is D2;
or a pharmaceutically acceptable salt thereof.

4. The compound of claim 1, wherein A is selected from the group consisting of:

A1
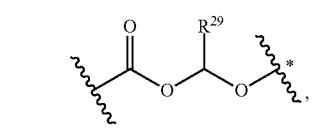

A2
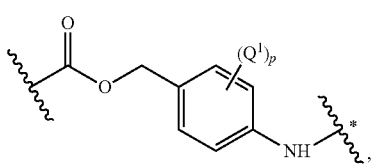

-continued

A3
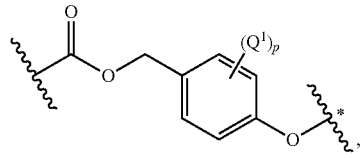

A4
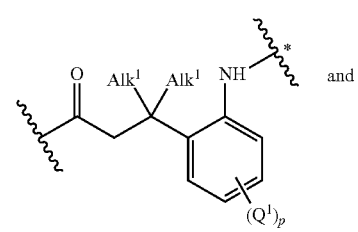

A5
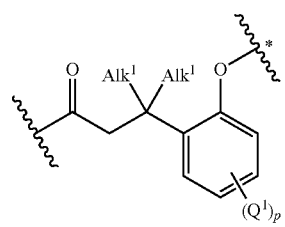

wherein * denotes a point of attachment of group A to group D;
each $Q^1$, the same or different, is independently selected from the group consisting of H, alkyl, alkoxy, halogen, nitro, aryl; or, together with the ring to which it is attached, forms a fused bicyclic aryl group;
p is an integer from 1 to 4;
$Alk^1$ is $C_1$-$C_4$ straight chain alkyl; and
$R^{29}$ is H or lower alkyl;
provided that A is A1 only when D is D1 and provided that A is A2 only when D is D2, D3 or D5 and provided that A is A3 only when D is D1, D3 or D4 and provided that A is A4 only when D is D2, D3 or D5 and provided that A is A5 only when D is D1, D3 or D4.

5. The compound as of claim 4, wherein A is A1 or A2.

6. The compound of claim 5, wherein A is A1 wherein $R^{28}$ is H, or wherein A is A2 wherein $Q^1$ is H.

7. The compound of claim 1, wherein D is D1.

8. The compound of claim 1, wherein D is D2.

9. The compound of claim 1, wherein D is D5.

10. The compound of claim 1, wherein $R^{15}$ is selected from the group consisting of:

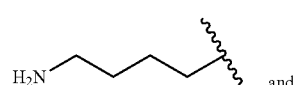 and

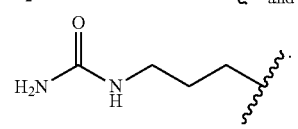

11. The compound of claim 1, wherein $R^{16}$ is selected from the group consisting of:

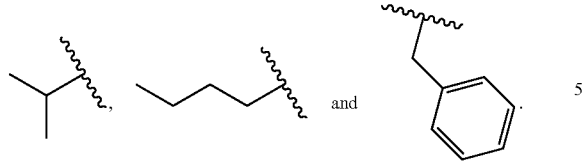

12. The compound of claim 1, wherein J is selected from the group consisting of:

AMLGTHTMEV, (SEQ ID NO: 1)
MLGTHTMEV, (SEQ ID NO: 2)
EAAGIGILTV, (SEQ ID NO: 3)
AAGIGILTV, (SEQ ID NO: 4)
AADHRQLQLSISSCLQQL, (SEQ ID NO: 5)
AAGIGILTVILGVL, (SEQ ID NO: 6)
AARAVFLAL, (SEQ ID NO: 7)
ACDPHSGHFV, (SEQ ID NO: 8)
ACYEFLWGPRALVETS, (SEQ ID NO: 9)
ADHRQLQLSISSCLQQL, (SEQ ID NO: 10)
AEEAAGIGILT, (SEQ ID NO: 11)
AEEAAGIGIL, (SEQ ID NO: 12)
AELVHFLLL, (SEQ ID NO: 13)
AELVHFLLLKYRAR, (SEQ ID NO: 14)
AEPINIQTW, (SEQ ID NO: 15)
AFLPWHRLF, (SEQ ID NO: 16)
AGATGGRGPRGAGA, (SEQ ID NO: 17)
ALCRWGLLL, (SEQ ID NO: 18)
ALDVYNGLL, (SEQ ID NO: 19)
ALFDIESKV, (SEQ ID NO: 20)
ALGGHPLLGV, (SEQ ID NO: 21)
ALIHHNTHL, (SEQ ID NO: 22)

-continued

ALKDVEERV, (SEQ ID NO: 23)
ALLAVGATK, (SEQ ID NO: 24)
ALLEIASCL, (SEQ ID NO: 25)
ALNFPGSQK, (SEQ ID NO: 26)
ALPYWNFATG, (SEQ ID NO: 27)
ALSVMGVYV, (SEQ ID NO: 28)
ALWPWLLMAT, (SEQ ID NO: 29)
ALWPWLLMA, (SEQ ID NO: 30)
ALYVDSLFFL, (SEQ ID NO: 31)
ANDPIFVVL, (SEQ ID NO: 32)
APPAYEKLSAEQ, (SEQ ID NO: 33)
APRGPHGGAASGL, (SEQ ID NO: 34)
APRGVRMAV, (SEQ ID NO: 35)
ARGPESRLL, (SEQ ID NO: 36)
ASGPGGGAPR, (SEQ ID NO: 37)
ATGFKQSSKALQRPVAS, (SEQ ID NO: 38)
AVCPWTWLR, (SEQ ID NO: 39)
AWISKPPGV, (SEQ ID NO: 40)
AYVCGIQNSVSANRS, (SEQ ID NO: 41)
CATWKVICKSCISQTPG, (SEQ ID NO: 42)
CEFHACWPAFTVLGE, (SEQ ID NO: 43)
CLSRRPWKRSWSAGSCPGMPHL, (SEQ ID NO: 44)
CMTWNQMNL, (SEQ ID NO: 45)
CQWGRLWQL, (SEQ ID NO: 46)
CTACRWKKACQR, (SEQ ID NO: 47)
DPARYEFLW, (SEQ ID NO: 48)
DTGFYTLHVIKSDLVNEEATGQFRV, (SEQ ID NO: 49)

DVTFNIICKKCG, (SEQ ID NO: 50)

EAAGIGILTV, (SEQ ID NO: 51)

EADPTGHSY, (SEQ ID NO: 52)

EAFIQPITR, (SEQ ID NO: 53)

EDLTVKIGDFGLATEKSRWSGSHQFEQLS, (SEQ ID NO: 54)

EEAAGIGILTVI, (SEQ ID NO: 55)

EEKLIVVLF, (SEQ ID NO: 56)

EFYLAMPFATPM, (SEQ ID NO: 57)

EGDCAPEEK, (SEQ ID NO: 58)

EIIYPNASLLIQN, (SEQ ID NO: 59)

EKIQKAFDDIAKYFSK, (SEQ ID NO: 60)

ELTLGEFLKL, (SEQ ID NO: 61)

ELVRRILSR, (SEQ ID NO: 62)

ESRLLEFYLAMPF, (SEQ ID NO: 63)

ETVSEQSNV, (SEQ ID NO: 64)

EVDPASNTY, (SEQ ID NO: 65)

EVDPIGHLY, (SEQ ID NO: 66)

EVDPIGHVY, (SEQ ID NO: 67)

EVISCKLIKR, (SEQ ID NO: 68)

EVYDGREHSA, (SEQ ID NO: 69)

EYLQLVFGI, (SEQ ID NO: 70)

EYLSLSDKI, (SEQ ID NO: 71)

EYSKECLKEF, (SEQ ID NO: 72)

EYVIKVSARVRF, (SEQ ID NO: 73)

FIASNGVKLV, (SEQ ID NO: 74)

FINDEIFVEL, (SEQ ID NO: 75)

FLDEFMEGV, (SEQ ID NO: 76)

FLEGNEVGKTY, (SEQ ID NO: 77)

FLFLLFFWL, (SEQ ID NO: 78)

FLIIWQNTM, (SEQ ID NO: 79)

FLLHHAFVDSIFEQWLQRHRP, (SEQ ID NO: 80)

FLLLKYRAREPVTKAE, (SEQ ID NO: 81)

FLTPKKLQCV, (SEQ ID NO: 82)

FLWGPRALV, (SEQ ID NO: 83)

FMNKFIYEI, (SEQ ID NO: 84)

FMVEDETVL, (SEQ ID NO: 85)

FPSDSWCYF, (SEQ ID NO: 86)

FRSGLDSYV, (SEQ ID NO: 87)

FSWAMDLDPKGA, (SEQ ID NO: 88)

GARGPESRLLEFYLAMPFATPMEAELARRSLAQDAPPL, (SEQ ID NO: 89)

GDNQIMPKAGLLIIV, (SEQ ID NO: 90)

GELIGILNAAKVPAD, (SEQ ID NO: 91)

GFKQSSKAL, (SEQ ID NO: 92)

GLASFKSFLK, (SEQ ID NO: 93)

GLCTLVAML, (SEQ ID NO: 94)

GLPPDVQRV, (SEQ ID NO: 95)

GLYDGMEHLI, (SEQ ID NO: 96)

GRAMLGTHTMEVTVY, (SEQ ID NO: 97)

GVALQTMKQ, (SEQ ID NO: 98)

GVGSPYVSRLLGICL, (SEQ ID NO: 99)

AKFVAAWTLKAAA, (SEQ ID NO: 100)

GVLLKEFTVSGNILTIRLT, (SEQ ID NO: 101)

GVLVGVALI, (SEQ ID NO: 102)

GVYDGREHTV, (SEQ ID NO: 103)

HLFGYSWYK, (SEQ ID NO: 104)

HLIRVEGNLRVE, (SEQ ID NO: 105)

HLSTAFARV, (SEQ ID NO: 106)

HLYQGCQVV, (SEQ ID NO: 107)

HQQYFYKIPILVINK, (SEQ ID NO: 108)

HTMEVTVYHR, (SEQ ID NO: 109)

IALNFPGSQK, (SEQ ID NO: 110)

IGRIAECILGMNPSR, (SEQ ID NO: 111)

IISAVVGIL, (SEQ ID NO: 112)

ILAKFLHWL, (SEQ ID NO: 113)

ILDSSEEDK, (SEQ ID NO: 114)

ILDTAGREEY, (SEQ ID NO: 115)

ILHNGAYSL, (SEQ ID NO: 116)

ILSRDAAPLPRPG, (SEQ ID NO: 117)

ILTVILGVL, (SEQ ID NO: 118)

IMDQVPFFS, (SEQ ID NO: 119)

IMDQVPFSV, (SEQ ID NO: 120)

IMIGVLVGV, (SEQ ID NO: 121)

INKTSGPKRGKHAWTHRLRE, (SEQ ID NO: 122)

ISGGPRISY, (SEQ ID NO: 123)

ISPNSVFSQWRVVCDSLEDYD, (SEQ ID NO: 124)

ISQAVHAAHAEINEAGR, (SEQ ID NO: 125)

ITDQVPFSV, (SEQ ID NO: 126)

ITKKVADLVGF, (SEQ ID NO: 127)

KASEKIFYV, (SEQ ID NO: 128)

KAVYNFATM, (SEQ ID NO: 129)

KCDICTDEY, (SEQ ID NO: 130)

KEFTVSGNILT, (SEQ ID NO: 131)

KEFTVSGNILTI, (SEQ ID NO: 132)

KELEGILLL, (SEQ ID NO: 133)

KHAWTHRLRERKQLVVYEEI, (SEQ ID NO: 134)

KIFGSLAFL, (SEQ ID NO: 135)

KIFSEVTLK, (SEQ ID NO: 136)

KIFYVYMKRKYEAM, (SEQ ID NO: 137)

KIFYVYMKRKYEAMT, (SEQ ID NO: 138)

KILDAVVAQK, (SEQ ID NO: 139)

KINKNPKYK, (SEQ ID NO: 140)

KISQAVHAAHAEINEAGRESIINFEKLTEWT, (SEQ ID NO: 141)

KKLLTQHFVQENYLEY, (SEQ ID NO: 142)

KMDAEHPEL, (SEQ ID NO: 143)

KNCEPVVPNAPPAYEKLSAE, (SEQ ID NO: 144)

KRYFKLSHLQMHSRKH, (SEQ ID NO: 145)

KSSEKIVYVYMKLNYEVMTK, (SEQ ID NO: 146)

KTWGQYWQV, (SEQ ID NO: 147)

KVAELVHFL, (SEQ ID NO: 148)

KVHPVIWSL, (SEQ ID NO: 149)

KVLEYVIKV, (SEQ ID NO: 150)

KYDCFLHPF, (SEQ ID NO: 151)

KYVGIEREM, (SEQ ID NO: 152)

LAALPHSCL, (SEQ ID NO: 153)

LAAQERRVPR, (SEQ ID NO: 154)

LAGIGILTV, (SEQ ID NO: 155)

LAMPFATPM, (SEQ ID NO: 156)

LGFKVTLPPFMRSKRAADFH, (SEQ ID NO: 157)

LGPGRPYR, (SEQ ID NO: 158)

LHHAFVDSIF, (SEQ ID NO: 159)

LIYRRRLMK, (SEQ ID NO: 160)

LKEFTVSGNILTIRL, (SEQ ID NO: 161)

LKLSGVVRL, (SEQ ID NO: 162)

LLANGRMPTVLQCVN, (SEQ ID NO: 163)

LLDGTATLRL, (SEQ ID NO: 164)

LLEFYLAMPFATPM, (SEQ ID NO: 165)

LLEFYLAMPFATPMEAELARRSLAQ, (SEQ ID NO: 166)

LLFGLALIEV, (SEQ ID NO: 167)

LLGATCMFV, (SEQ ID NO: 168)

LLGPGRPYR, (SEQ ID NO: 169)

LLGRNSFEV, (SEQ ID NO: 170)

LLKYRAREPVTKAE, (SEQ ID NO: 171)

LLLDDLLVSI, (SEQ ID NO: 172)

LLLLTVLTV, (SEQ ID NO: 173)

LLWSFQTSA, (SEQ ID NO: 174)

LLYKLADLI, (SEQ ID NO: 175)

LMLQNALTTM, (SEQ ID NO: 176)

LPAVVGLSPGEQEY, (SEQ ID NO: 177)

LPHSSSHWL, (SEQ ID NO: 178)

LPRWPPPQL, (SEQ ID NO: 179)

LPSSADVEF, (SEQ ID NO: 180)

LSHLQMHSRKH, (SEQ ID NO: 181)

LSRLSNRLL, (SEQ ID NO: 182)

LTDLQPYMRQFVAHL, (SEQ ID NO: 183)

LWWVNNQSLPVSP, (SEQ ID NO: 184)

LYATVIHDI, (SEQ ID NO: 185)

LYSACFWWL, (SEQ ID NO: 186)

LYVDSLFFL, (SEQ ID NO: 187)

MEVDPIGHLY, (SEQ ID NO: 188)

MIAVFLPIV, (SEQ ID NO: 189)

MIFEKHGFRRTTPP, (SEQ ID NO: 190)

MKLNYEVMTKLGFKVTLPPF, (SEQ ID NO: 191)

MLAVISCAV, (SEQ ID NO: 192)

MLLAVLYCL, (SEQ ID NO: 193)

MLMAQEALAFL, (SEQ ID NO: 194)

MPFATPMEA, (SEQ ID NO: 195)

MPREDAHFIYGYPKKGHGHS, (SEQ ID NO: 196)

MSLQRQFLR, (SEQ ID NO: 197)

MVKISGGPR, (SEQ ID NO: 198)

NLVPMVATV, (SEQ ID NO: 199)

NPPSMVAAGSVVAAV, (SEQ ID NO: 200)

NSIVKSITVSASG, (SEQ ID NO: 201)

NSNHVASGAGEAAIETQSSSSEEIV, (SEQ ID NO: 202)

NSQPVWLCL, (SEQ ID NO: 203)

NTYASPRFK, (SEQ ID NO: 204)

NYARTEDFF, (SEQ ID NO: 205)

NYKRCFPVI, (SEQ ID NO: 206)

NYNNFYRFL, (SEQ ID NO: 207)

PDTRPAPGSTAPPAHGVTSA, (SEQ ID NO: 208)

PFATPMEAELARR, (SEQ ID NO: 209)

PGSTAPPAHGVT, (SEQ ID NO: 210)

PGTRVRAMAIYKQ, (SEQ ID NO: 211)

-continued

PGVLLKEFTVSGNILTIRLTAADHR, (SEQ ID NO: 212)

PLLENVISK, (SEQ ID NO: 213)

PLPPARNGGL, (SEQ ID NO: 214)

PLQPEQLQV, (SEQ ID NO: 215)

PLTSIISAV, (SEQ ID NO: 216)

PRALAETSYVKVLEY, (SEQ ID NO: 217)

PVTWRRAPA, (SEQ ID NO: 218)

PYYFAAELPPRNLPEP, (SEQ ID NO: 219)

QCSGNFMGF, (SEQ ID NO: 220)

QCTEVRADTRPWSGP, (SEQ ID NO: 221)

QGAMLAAQERRVPRAAEVPR, (SEQ ID NO: 222)

QGQHFLQKV, (SEQ ID NO: 223)

QLAVSVILRV, (SEQ ID NO: 224)

QNILLSNAPLGPQFP, (SEQ ID NO: 225)

QQITKTEV, (SEQ ID NO: 226)

QRPYGYDQIM, (SEQ ID NO: 227)

QYSWFVNGTF, (SEQ ID NO: 228)

RAGLQVRKNK, (SEQ ID NO: 229)

REPFTKAEMLGSVIR, (SEQ ID NO: 230)

REPVTKAEML, (SEQ ID NO: 231)

RIAECILGM, (SEQ ID NO: 232)

RKVAELVHFLLLKYR, (SEQ ID NO: 233)

RKVAELVHFLLLKYRA, (SEQ ID NO: 234)

RLLEFYLAMPFA, (SEQ ID NO: 235)

RLLQETELV, (SEQ ID NO: 236)

RLMKQDFSV, (SEQ ID NO: 237)

RLPRIFCSC, (SEQ ID NO: 238)

RLSSCVPVA, (SEQ ID NO: 239)

RLVDDFLLV, (SEQ ID NO: 240)

RMPEAAPPV, (SEQ ID NO: 241)

RMPTVLQCVNVSVVS, (SEQ ID NO: 242)

RNGYRALMDKS, (SEQ ID NO: 243)

RNGYRALMDKSLHVGTQCALTRR, (SEQ ID NO: 244)

RPGLLGASVLGLDDI, (SEQ ID NO: 245)

RPHVPESAF, (SEQ ID NO: 246)

RQKRILVNL, (SEQ ID NO: 247)

RSDSGQQARY, (SEQ ID NO: 248)

RTKQLYPEW, (SEQ ID NO: 249)

RVIKNSIRLTL, (SEQ ID NO: 250)

RVRFFFPSL, (SEQ ID NO: 251)

RYQLDPKFI, (SEQ ID NO: 252)

SAFPTTINF, (SEQ ID NO: 253)

SAWISKPPGV, (SEQ ID NO: 254)

SAYGEPRKL, (SEQ ID NO: 255)

SEIWRDIDF, (SEQ ID NO: 256)

SELFRSGLDSY, (SEQ ID NO: 257)

SESIKKKVL, (SEQ ID NO: 258)

SESLKMIF, (SEQ ID NO: 259)

SFSYTLLSL, (SEQ ID NO: 260)

SHETVIIEL, (SEQ ID NO: 261)

SIINFEKL, (SEQ ID NO: 262)

SLADTNSLAV, (SEQ ID NO: 263)

SLFEGIDIYT, (SEQ ID NO: 264)

SLFPNSPKWTSK, (SEQ ID NO: 265)

-continued

| | |
|---|---|
| SLFRAVITK, | (SEQ ID NO: 266) |
| SLGWLFLLL, | (SEQ ID NO: 267) |
| SLLMWITQC, | (SEQ ID NO: 268) |
| SLLMWITQCFLPVF, | (SEQ ID NO: 269) |
| SLLQHLIGL, | (SEQ ID NO: 270) |
| SLPYWNFATG, | (SEQ ID NO: 271) |
| SLSKILDTV, | (SEQ ID NO: 272) |
| SLYKFSPFPL, | (SEQ ID NO: 273) |
| SLYSFPEPEA, | (SEQ ID NO: 274) |
| SNDGPTLI, | (SEQ ID NO: 275) |
| SPRWWPTCL, | (SEQ ID NO: 276) |
| SPSSNRIRNT, | (SEQ ID NO: 277) |
| SQKTYQGSY, | (SEQ ID NO: 278) |
| SRFGGAVVR, | (SEQ ID NO: 279) |
| SSALLSIFQSSPE, | (SEQ ID NO: 280) |
| SSDYVIPIGTY, | (SEQ ID NO: 281) |
| SSKALQRPV, | (SEQ ID NO: 282) |
| SSPGCQPPA, | (SEQ ID NO: 283) |
| STAPPVHNV, | (SEQ ID NO: 284) |
| SVASTITGV, | (SEQ ID NO: 285) |
| SVDYFFVWL, | (SEQ ID NO: 286) |
| SVSESDTIRSISIAS, | (SEQ ID NO: 287) |
| SVYDFFVWL, | (SEQ ID NO: 288) |
| SYLDSGIHF, | (SEQ ID NO: 289) |
| SYLQDSDPDSFQD, | (SEQ ID NO: 290) |
| TFPDLESEF, | (SEQ ID NO: 291) |
| TGRAMLGTHTMEVTVYH, | (SEQ ID NO: 292) |

-continued

| | |
|---|---|
| TLDSQVMSL, | (SEQ ID NO: 293) |
| TLDWLLQTPK, | (SEQ ID NO: 294) |
| TLEEITGYL, | (SEQ ID NO: 295) |
| ZTLMSAMTNL, | (SEQ ID NO: 296) |
| TLNDECWPA, | (SEQ ID NO: 297) |
| TLPGYPPHV, | (SEQ ID NO: 298) |
| TLYQDDTLTLQAAG, | (SEQ ID NO: 299) |
| TMKQICKKEIRRLHQY, | (SEQ ID NO: 300) |
| TMNGSKSPV, | (SEQ ID NO: 301) |
| TPRLPSSADVEF, | (SEQ ID NO: 302) |
| TSCILESLFRAVITK, | (SEQ ID NO: 303) |
| TSEKRPFMCAY, | (SEQ ID NO: 304) |
| TSYVKVLHHMVKISG, | (SEQ ID NO: 305) |
| TTEWVETTARELPIPEPE, | (SEQ ID NO: 306) |
| TVSGNILTIR, | (SEQ ID NO: 307) |
| TYACFVSNL, | (SEQ ID NO: 308) |
| TYLPTNASL, | (SEQ ID NO: 309) |
| TYYRPGVNLSLSC, | (SEQ ID NO: 310) |
| VAELVHFLL, | (SEQ ID NO: 311) |
| VFGIELMEVDPIGHL, | (SEQ ID NO: 312) |
| VGQDVSVLFRVTGALQ, | (SEQ ID NO: 313) |
| VIFSKASSSLQL, | (SEQ ID NO: 314) |
| VISNDVCAQV, | (SEQ ID NO: 315) |
| VLDGLDVLL, | (SEQ ID NO: 316) |
| VLFYLGQY, | (SEQ ID NO: 317) |
| VLHWDPETV, | (SEQ ID NO: 318) |
| VLLKEFTVSG, | (SEQ ID NO: 319) |

VLLQAGSLHA, (SEQ ID NO: 320)

VLPDVFIRCV, (SEQ ID NO: 321)

VLPDVFIRC, (SEQ ID NO: 322)

VLRENTSPK, (SEQ ID NO: 323)

VLYRYGSFSV, (SEQ ID NO: 324)

VPGVLLKEFTVSGNILTIRLTAADHR, (SEQ ID NO: 325)

VPLDCVLYRY, (SEQ ID NO: 326)

VRIGHLYIL, (SEQ ID NO: 327)

VSSFFSYTL, (SEQ ID NO: 328)

VVLGVVFGI, (SEQ ID NO: 329)

VVPCEPPEV, (SEQ ID NO: 330)

VVVGAVGVG, (SEQ ID NO: 331)

VYFFLPDHL, (SEQ ID NO: 332)

WEKMKASEKIFYVYMKRK, (SEQ ID NO: 333)

WLPFGFILI, (SEQ ID NO: 334)

WNRQLYPEWTEAQRLD, (SEQ ID NO: 335)

WQYFFPVIF, (SEQ ID NO: 336)

WRRAPAPGA, (SEQ ID NO: 337)

YACFVSNLATGRNNS, (SEQ ID NO: 338)

YFSKKEWEKMKSSEKIVYVY, (SEQ ID NO: 339)

YLEPGPVTA, (SEQ ID NO: 340)

YLEPGPVTV, (SEQ ID NO: 341)

YLNDHLEPWI, (SEQ ID NO: 342)

YLQLVFGIEV, (SEQ ID NO: 343)

YLSGANLNL, (SEQ ID NO: 344)

YLVPQQGFFC, (SEQ ID NO: 345)

YMDGTMSQV, (SEQ ID NO: 346)

YMIMVKCWMI, (SEQ ID NO: 347)

YRPRPRRY, (SEQ ID NO: 348)

YSVYFNLPADTIYTN, (SEQ ID NO: 349)

YSWRINGIPQQHTQV, (SEQ ID NO: 350)

YVDFREYEYY, (SEQ ID NO: 351)

YYWPRPRRY, (SEQ ID NO: 352)

IMDQVPFFS, (SEQ ID NO: 353)

SVDYFFVWL, (SEQ ID NO: 354)

ALFDIESKV, (SEQ ID NO: 355)

NLVPMVATV and (SEQ ID NO: 356)

GLCTLVAML, (SEQ ID NO: 357)

SVASTITGV, (SEQ ID NO: 358)

VMAGDIYSV, (SEQ ID NO: 359)

ALADGVQKV, (SEQ ID NO: 360)

LLGATCMFV, (SEQ ID NO: 361)

SVFAGVVGV, (SEQ ID NO: 362)

ALFDGDPHL, (SEQ ID NO: 363)

YVDPVITSI, (SEQ ID NO: 364)

STAPPVHNV, (SEQ ID NO: 365)

LAALPHSCL, (SEQ ID NO: 366)

SQDDIKGIQKLYGKRS, (SEQ ID NO: 367)

FLPSDFFPSV (SEQ ID NO: 368)

FLPSDFFPSV, (SEQ ID NO: 369)

TLGEFLKLDRERAKN, (SEQ ID NO: 370)

TFSYVDPVITSISPKYGMET, (SEQ ID NO: 371)

AMTQLLAGV, (SEQ ID NO: 372)

KVFAGIPTV, (SEQ ID NO: 373)

AIIDGVESV, (SEQ ID NO: 374)

GLWHHQTEV, (SEQ ID NO: 375)

NLDTLMTYV, (SEQ ID NO: 376)

KIQEILTQV, (SEQ ID NO: 377)

LTFGDVVAV, (SEQ ID NO: 378)

TMLARLASA, (SEQ ID NO: 379)

IMDQVPFSV, (SEQ ID NO: 380)

MHQKRTAMFQDPQERPRKLPQLCTELQTTIHD, (SEQ ID NO: 381)

LPQLCTELQTTI, (SEQ ID NO: 382)

HDIILECVYCKQQLLRREVY, (SEQ ID NO: 383)

KQQLLRREVYDFAFRDLCIVYRDGN, (SEQ ID NO: 384)

RDLCIVYRDGNPYAVCDKCLKFYSKI, (SEQ ID NO: 385)

DKCLKFYSKISEYRHYCYSLYGTTL, (SEQ ID NO: 386)

HYCYSLYGTTLEQQYNKPLCDLLIR, (SEQ ID NO: 387)

YGTTLEQQYNKPLCDLLIRCINCQKPLCPEEK, (SEQ ID NO: 388)

RCINCQKPLCPEEKQRHLDKKQRFHNIRGRWT, (SEQ ID NO: 389)

DKKQRFHNIRGRWTGRCMSCCRSSRTRRETQL, (SEQ ID NO: 390)

MHGDTPTLHEYMLDLQPETTDLYCYEQLNDSSEEE, (SEQ ID NO: 391)

LYCYEQLNDSSEEEDEIDGPAGQAEPDRAHYNIVT, (SEQ ID NO: 392)

GQAEPDRAHYNIVTFCCKCDSTLRLCVQSTHVDIR, (SEQ ID NO: 393)

TLRLCVQSTHVDIRTLEDLLMGTLGIVCPICSQKP, (SEQ ID NO: 394)

ALPFGFILV, (SEQ ID NO: 395)

TLADFDPRV, (SEQ ID NO: 396)

IMDQVPFSV, (SEQ ID NO: 397)

SIMTYDFHGA, (SEQ ID NO: 398)

AQYIKANSKFIGITEL, (SEQ ID NO: 399)

FLYDDNQRV, (SEQ ID NO: 400)

YLIELIDRV, (SEQ ID NO: 401)

NLMEQPIKV, (SEQ ID NO: 402)

FLAEDALNTV, (SEQ ID NO: 403)

ALMEQQHYV, (SEQ ID NO: 404)

ILDDIGHGV, (SEQ ID NO: 405)

KLDVGNAEV, (SEQ ID NO: 406)

TFEFTSFFY, (SEQ ID NO: 407)

SWPDGAELPF, (SEQ ID NO: 408)

GILGFVFTL, (SEQ ID NO: 409)

ILRGSVAHK (SEQ ID NO: 410)

SVYDFFVWLKFFHRTCKCTGNFA, (SEQ ID NO: 411)

DLAQMFFCFKELEGW, (SEQ ID NO: 412)

AVGALEGPRNQDWLGVPRQL (SEQ ID NO: 413)
and

RAHYNIVTF. (SEQ ID NO: 414)

13. The compound of claim 1, wherein the stereochemistry of the 6-membered sugar ring of formula (I) is α-D-galacto.

14. The compound of claim 1, wherein X is O.

15. The compound of claim 1, wherein n is 1, the stereochemistry of the 6-membered sugar ring of formula (I) is α-D-galacto, $R^6$ is OH and $R^7$ is OH.

16. The compound of claim 1 which is selected from the group consisting of:

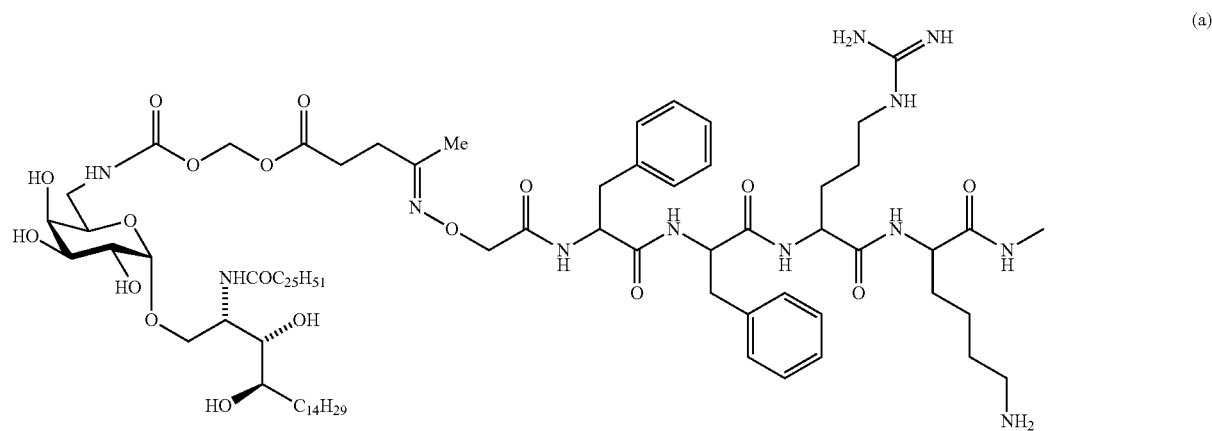
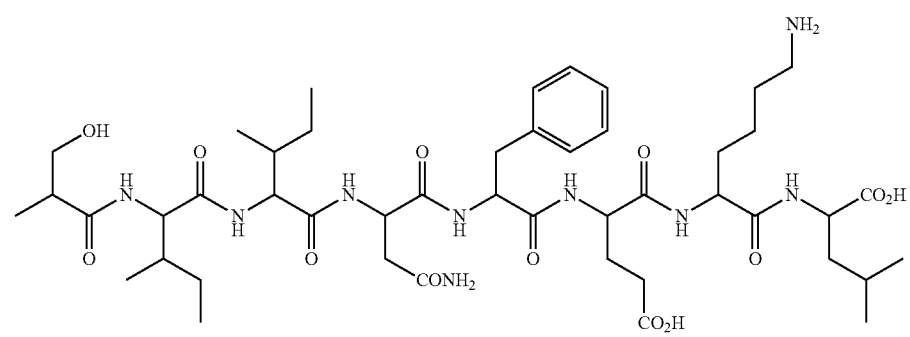
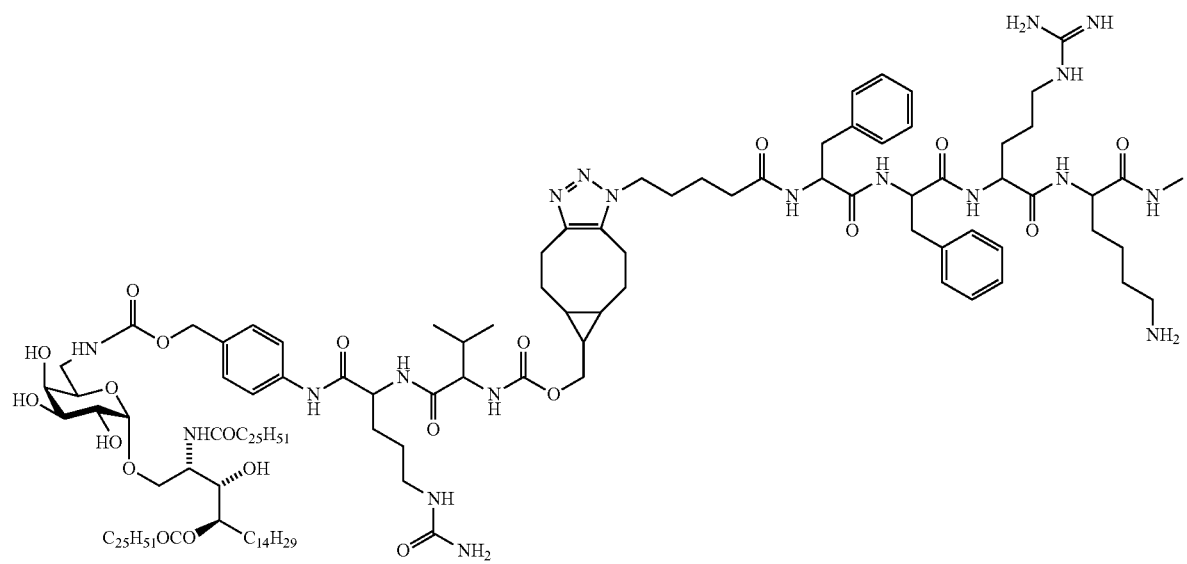
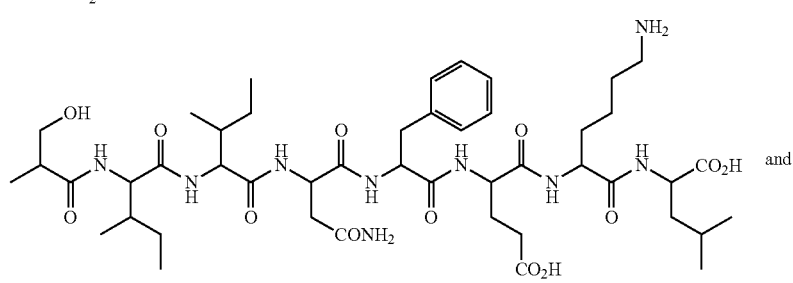
and

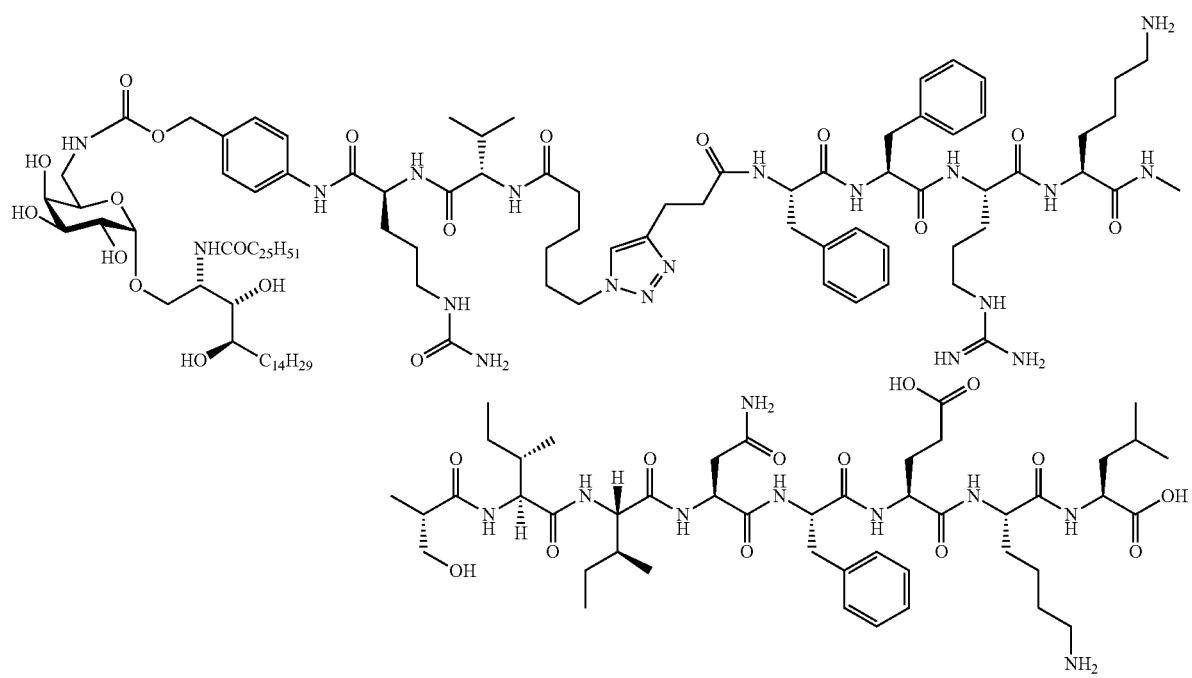
or a pharmaceutically acceptable salt thereof.
17. The compound of claim 3 which is selected from the group consisting of:
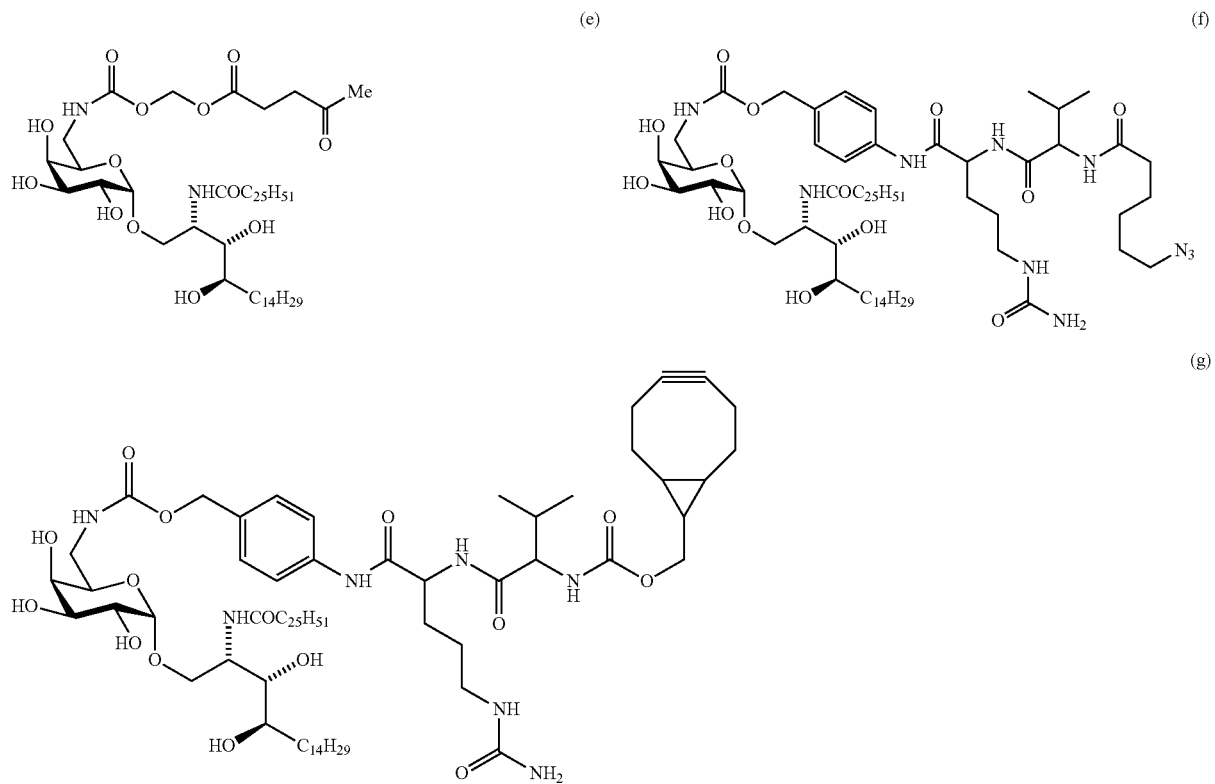

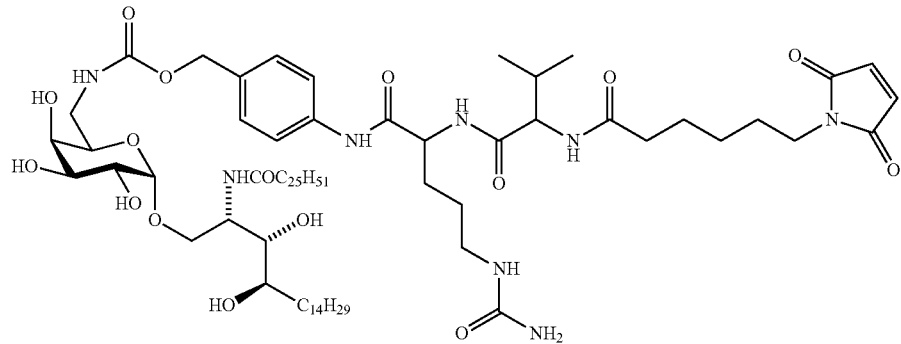

(h)

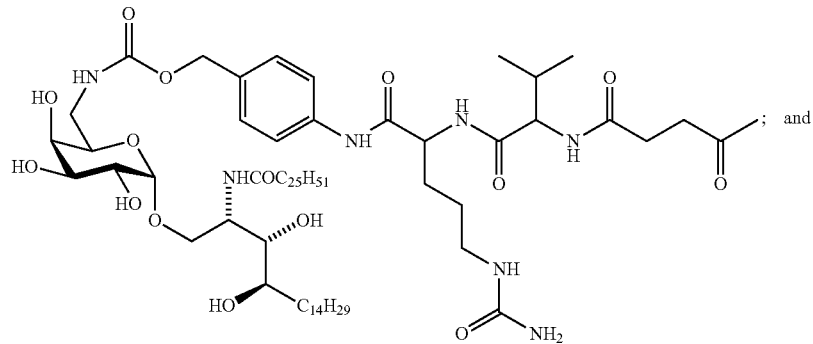

; and (j)

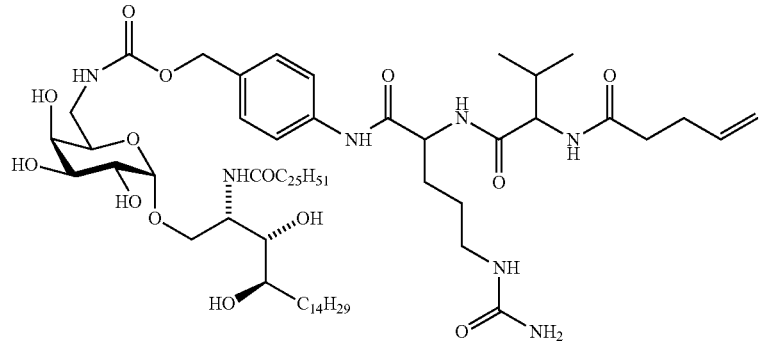

(k)

or a pharmaceutically acceptable salt thereof.

18. A pharmaceutical composition, comprising the compound of claim 1; and a pharmaceutically acceptable exipient.

19. A vaccine, comprising (i) the compound of claim 1 and a pharmaceutically acceptable diluent, or (ii) the compound of claim 1, a pharmaceutically acceptable diluent, and an antigen.

20. The compound of claim 3, wherein the stereochemistry of the 6-membered sugar ring of formula (ii) is α-D-galacto.

21. The compound of claim 3, wherein n is 1, the stereochemistry of the 6-membered sugar ring of formula (ii) is α-D-galacto, $R^6$ is OH and $R^7$ is OH.

* * * * *

UNITED STATES PATENT AND TRADEMARK OFFICE
CERTIFICATE OF CORRECTION

PATENT NO. : 10,046,046 B2  
APPLICATION NO. : 15/316124  
DATED : August 14, 2018  
INVENTOR(S) : Anderson et al.

Page 1 of 1

It is certified that error appears in the above-identified patent and that said Letters Patent is hereby corrected as shown below:

In the Claims

Column 272, Claim 12, Line 10:
"ZTLMSAMTNL" should read, --TLMSAMTNL--.

Signed and Sealed this
Twenty-fourth Day of December, 2019

Andrei Iancu
*Director of the United States Patent and Trademark Office*